US006518237B1

(12) United States Patent
Yuqiu et al.

(10) Patent No.: US 6,518,237 B1
(45) Date of Patent: Feb. 11, 2003

(54) COMPOSITIONS FOR TREATMENT AND DIAGNOSIS OF BREAST CANCER AND METHODS FOR THEIR USE

(75) Inventors: Jiang Yuqiu, Kent, WA (US); Davin C. Dillon, Redmond, WA (US); Jennifer L. Mitcham, Redmond, WA (US); Jiangchun Xu, Bellevue, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/389,681

(22) Filed: Sep. 2, 1999

Related U.S. Application Data

(63) Continuation-in-part of application No. 09/339,338, filed on Jun. 23, 1999, which is a continuation-in-part of application No. 09/285,480, filed on Apr. 2, 1999, which is a continuation-in-part of application No. 09/222,575, filed on Dec. 28, 1998, now Pat. No. 6,387,697.

(51) Int. Cl.[7] .......................... C12Q 1/68; A61K 38/00; A01N 37/18; C07H 21/02

(52) U.S. Cl. ............................... 514/2; 435/6; 530/300; 536/23.1

(58) Field of Search ........................ 530/300; 536/23.1; 435/6; 514/2

(56) References Cited

U.S. PATENT DOCUMENTS

| | | | |
|---|---|---|---|
| 5,215,926 | A | 6/1993 | Etchells, III et al. |
| 5,240,856 | A | 8/1993 | Goffe et al. |
| 5,891,857 | A | 4/1999 | Holt et al. |
| 5,986,170 | A | 11/1999 | Subjeck |

FOREIGN PATENT DOCUMENTS

| | | |
|---|---|---|
| WO | WO 89/06280 | 7/1989 |
| WO | WO 98/21331 | 5/1998 |
| WO | WO 98/33915 | 8/1998 |
| WO | WO 98/54963 | 12/1998 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

GenBank Accession No. AC069200, May 24, 2000.

Sulston et al., "Toward a complete human genome sequence," *Genome Research* 8(11):1097–1108, 1998.

GenBank Accession No. AF269087, Mar. 28, 2001.

GenBank Accession No. AAK27325, Mar. 28, 2001.

Chang and Shu, "Current status of adoptive immunotherapy of cancer," *Critical Reviews in Oncology/Hematology* 22(3):213–228, Apr. 1996.

Cheever and Chen, "Therapy with cultured T cells: principles revisited," *Immunological Reviews*, 157: 177–194, 1997.

Cheever et al., "Potential uses of interleukin 2 in cancer therapy," *Immunobiol*, 172:365–382, 1986.

(List continued on next page.)

*Primary Examiner*—Jeffrey Siew
*Assistant Examiner*—Young Kim
(74) *Attorney, Agent, or Firm*—Seed Intellectual Property Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

18 Claims, 1 Drawing Sheet-

OTHER PUBLICATIONS

Figure 1:
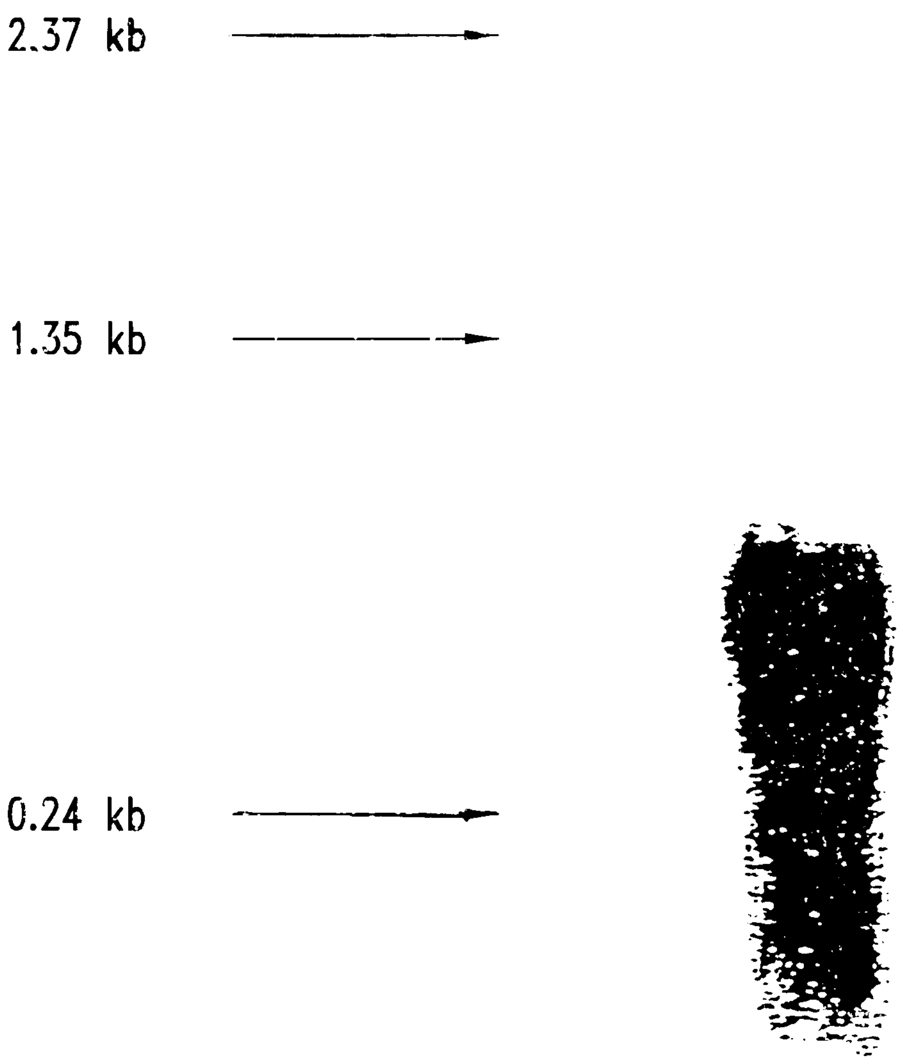

Cole et al., "Characterization of the functional specificity of a cloned T–cell receptor heterodimer recognizing the MART–melanoma antigent," *Cancer Research*, 55:748–752, Feb. 15, 1995.

Durrant L., "Cancer vaccines," *Anti–Cancer Drugs*, 8:727–733, 1997.

Eshhar Z., "Tumor–specific T–bodies: toward clinical application," *Cancer Immunol Immunother*, 45:131–136, 1997.

Hwu et al., "In vivo antitumor activity of T cells redirected with chimeric antibody/T–cell receptor genes," *Cancer Research*, 55:3369–3373, Aug. 1, 1995.

Porter–Jordan and Lippman, "Overview of the biologic markers of breast cancer," *Breast Cancer* 8:(1):73–100, Feb. 1994.

Wei et al., "Protection against mammary tumor growth by vaccination with full–length, modified human *ErbB*–2 DNA," *Int. J. Cancer*, 81:748–754, 1999.

GenBank Accession No. AA864891, Feb. 20, 1998.

GenBank Accession No. AA398925, Apr. 25, 1997.

COMPOSITIONS FOR TREATMENT AND DIAGNOSIS OF BREAST CANCER AND METHODS FOR THEIR USE

CROSS-REFERENCE TO RELATED APPLICATIONS

This application is a continuation-in-part of U.S. application Ser. No. 09/339,338, filed on Jun. 23, 1999, which is a continuation-in-part of U.S. application Ser. No. 09/285,480, filed on Apr. 2, 1999, which is a continuation-in-part of U.S. application Ser. No. 09/222,575, filed Dec. 28, 1998, U.S. Pat. No. 6,387,697.

TECHNICAL FIELD

The present invention relates generally to compositions and methods for the treatment of breast cancer. The invention is more particularly related to polypeptides comprising at least a portion of a protein that is preferentially expressed in breast tumor tissue and to polynucleotides encoding such polypeptides. Such polypeptides and polynucleotides may be used in vaccines and pharmaceutical compositions for treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g. Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

The present invention provides compounds and methods for the treatment and diagnosis of cancer, such as breast cancer. In one aspect, isolated polypeptides are provided comprising at least a portion of a breast tumor protein or a variant thereof. Certain portions and other variants are immunogenic, such that the ability of the variant to react with protein-specific antisera is not substantially diminished With certain embodiments, the polypeptide comprises an amino acid sequence encoded by a polynucleotide selected from the group consisting of: (a) nucleotide sequences recited in SEQ ID NO: 1–61, 63–175, 178, 180, 182–313, 320–324, 342, 353, 366–368, 377, 382, 385, 389, 395, 397, 400, 408, 411, 413, 414, 416, 417, 419–423, 426, 427, 429, 431, 435–438, 441, 443–446, 450, 453 and 454; (b) complements of said nucleotide sequences; and (c) variants of a sequence of (a) or (b). In specific embodiments, the inventive polypeptides comprise at least a portion of a tumor antigen that comprises an amino acid sequence selected from the group consisting of SEQ ID NO: 62, 176, 179 and 181.

In related aspects, isolated polynucleotides encoding the above polypeptides, or a portion thereof (such as a portion encoding at least 15 contiguous amino acid residues of a breast tumor protein), are provided. In specific embodiments, such polynucleotides comprise a sequence selected from the group consisting of sequences provided in SEQ ID NO: 1–61, 63–175, 178, 180, 182–313, 320–324, 342, 353, 366–368, 377, 382, 385, 389, 395, 397, 400, 408, 411, 413, 414, 416, 417, 419–423, 426, 427, 429, 431, 435–438, 441, 443–446, 450, 453 and 454 and variants thereof The present invention further provides expression vectors comprising the above polynucleotides, together with host cells transformed or transfected with such expression vectors. In preferred embodiments, the host cells are selected from the group consisting of *E. coli*, yeast and mammalian cells.

In another aspect, the present invention provides fusion proteins comprising a first and a second inventive polypeptide or, alternatively, an inventive polypeptide and a known breast tumor antigen.

The present invention also provides pharmaceutical compositions comprising at least one of the above polypeptides, or a polynucleotide encoding such a polypeptide, and a physiologically acceptable carrier, together with vaccines comprising at least one such polypeptide or polynucleotide in combination with a non-specific immune response enhancer. Pharmaceutical compositions and vaccines comprising one or more of the above fusion proteins are also provided.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) a non-specific immune response enhancer.

In yet another aspect, methods are provided for inhibiting the development of breast cancer in a patient, comprising administering an effective amount of at least one of the above pharmaceutical compositions and/or vaccines.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

The polypeptides disclosed herein may be usefully employed in the diagnosis and monitoring of breast cancer. In one aspect of the present invention, methods are provided for detecting a cancer in a patient, comprising: (a) contacting a biological sample obtained from a patient with a binding agent that is capable of binding to one of the above polypeptides; and (b) detecting in the sample an amount of polypeptide that binds to the binding agent; and (c) comparing the amount of polypeptide with a predetermined cut-off value, and therefrom determining the presence or absence of a cancer in a patient. In preferred embodiments, the binding agent is an antibody, most preferably a monoclonal antibody. The cancer may be breast cancer.

In related aspects, methods are provided for monitoring the progression of a cancer in a patient, comprising: (a) contacting a biological sample obtained from a patient with a binding agent that is capable of binding to one of the above polypeptides; (b) detecting in the sample an amount of a polypeptide that binds to the binding agent; (c) repeating steps (a) and (b) using a biological sample obtained from the patient at a subsequent point in time; and (d) comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT 19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6.

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20A6.

SEQ ID NO: 45 is the determined cDNA sequence of SYN21G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21 G10-2.

SEQ ID NO: 51 is the determined cDNA sequence of SYN21 G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6.

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095

SEQ ID NO: 127 is the determined cDNA sequence of 13096

SEQ ID NO: 128 is the determined cDNA sequence of 13099

SEQ ID NO: 129 is the determined cDNA sequence of 13100

SEQ ID NO: 130 is the determined cDNA sequence of 13103

SEQ ID NO: 131 is the determined cDNA sequence of 13106

SEQ ID NO: 132 is the determined cDNA sequence of 13107

SEQ ID NO: 133 is the determined cDNA sequence of 13108

SEQ ID NO: 134 is the determined cDNA sequence of 13121

SEQ ID NO: 135 is the determined cDNA sequence of 13126

SEQ ID NO: 136 is the determined cDNA sequence of 13129

SEQ ID NO: 137 is the determined cDNA sequence of 13130

SEQ ID NO: 138 is the determined cDNA sequence of 13134

SEQ ID NO: 139 is the determined cDNA sequence of 13141

SEQ ID NO: 140 is the determined cDNA sequence of 13142

SEQ ID NO: 141 is the determined cDNA sequence of 14376

SEQ ID NO: 142 is the determined cDNA sequence of 14377

SEQ ID NO: 143 is the determined cDNA sequence of 14383

SEQ ID NO: 144 is the determined cDNA sequence of 14384

SEQ ID NO: 145 is the determined cDNA sequence of 14387

SEQ ID NO: 146 is the determined cDNA sequence of 14392

SEQ ID NO: 147 is the determined cDNA sequence of 14394

SEQ ID NO: 148 is the determined cDNA sequence of 14398

SEQ ID NO: 149 is the determined cDNA sequence of 14401

SEQ ID NO: 150 is the determined cDNA sequence of 14402

SEQ ID NO. 151 is the determined cDNA sequence of 14405

SEQ ID NO: 152 is the determined cDNA sequence of 14409

SEQ ID NO: 153 is the determined cDNA sequence of 14412

SEQ ID NO: 154 is the determined cDNA sequence of 14414

SEQ ID NO: 155 is the determined CDNA sequence of 14415

SEQ ID NO: 156 is the determined cDNA sequence of 14416

SEQ ID NO: 157 is the determined cDNA sequence of 14419

SEQ ID NO: 158 is the determined cDNA sequence of 14426

SEQ ID NO: 159 is the determined cDNA sequence of 14427

SEQ ID NO: 160 is the determined cDNA sequence of 14375

SEQ ID NO: 161 is the determined cDNA sequence of 14378

SEQ ID NO: 162 is the determined cDNA sequence of 14379

SEQ ID NO: 163 is the determined cDNA sequence of 14380

SEQ ID NO: 164 is the determined cDNA sequence of 14381

SEQ ID NO: 165 is the determined cDNA sequence of 14382

SEQ ID NO: 166 is the determined cDNA sequence of 14388

SEQ ID NO: 167 is the determined cDNA sequence of 14399

SEQ ID NO: 168 is the determined cDNA sequence of 14406

SEQ ID NO: 169 is the determined cDNA sequence of 14407

SEQ ID NO: 170 is the determined cDNA sequence of 14408

SEQ ID NO: 171 is the determined cDNA sequence of 14417

SEQ ID NO: 172 is the determined cDNA sequence of 14418

SEQ ID NO: 173 is the determined cDNA sequence of 14423

SEQ ID NO: 174 is the determined cDNA sequence of 14424

SEQ ID NO: 175 is the determined cDNA sequence of B726P-20

SEQ ID NO: 176 is the predicted amino acid sequence of B726P-20

SEQ ID NO: 177 is a PCR primer

SEQ ID NO: 178 is the determined cDNA sequence of B726P-74

SEQ ID NO: 179 is the predicted amino acid sequence of B726P-74

SEQ ID NO: 180 is the determined cDNA sequence of B726P-79

SEQ ID NO: 181 is the predicted amino acid sequence of B726P-79

SEQ ID NO: 182 is the determined cDNA sequence of 19439.1, showing homology to the mammaglobin gene SEQ ID NO: 183 is the determined cDNA sequence of 19407.1, showing homology to the human keratin gene SEQ ID NO: 184 is the determined cDNA sequence of 19428.1, showing homology to human chromosome 17 clone SEQ ID NO: 185 is the determined cDNA sequence of B808P (19408), showing no significant homology to any known gene SEQ ID NO: 186 is the determined cDNA sequence of 19460.1, showing no significant homology to any known gene SEQ ID NO: 187 is the determined cDNA sequence of 19419.1, showing homology to Ig kappa light chain SEQ ID NO: 188 is the determined cDNA sequence of 19411.1, showing homology to human alpha-1 collagen SEQ ID NO: 189 is the determined cDNA sequence of 19420.1, showing homology to mus musculus proteinase-3

SEQ ID NO: 190 is the determined cDNA sequence of 19432.1, showing homology to human high motility group box SEQ ID NO: 191 is the determined cDNA sequence of 19412.1, showing homology to the human plasminogen activator gene SEQ ID NO: 192 is the determined cDNA sequence of 19415.1, showing homology to mitogen activated protein kinase SEQ ID NO: 193 is the determined cDNA sequence of 19409.1, showing homology to the chondroitin sulfate proteoglycan protein SEQ ID NO: 194 is the determined cDNA sequence of 19406.1, showing no significant homology to any known gene SEQ ID NO: 195 is the determined cDNA sequence of 19421.1, showing homology to human fibronectin SEQ ID NO: 196 is the determined cDNA sequence of 19426.1, showing homology to the retinoic acid receptor responder 3

SEQ ID NO: 197 is the determined cDNA sequence of 19425.1, showing homology to MyD88 mRNA SEQ ID NO: 198 is the determined cDNA sequence of 19424.1, showing homology to peptide transporter (TAP-1) mRNA SEQ ID NO: 199 is the determined cDNA sequence of 19429.1, showing no significant homology to any known gene SEQ ID NO: 200 is the determined cDNA sequence of 19435.1, showing homology to human polymorphic epithelial mucin SEQ ID NO: 201 is the determined cDNA sequence of B813P (19434.1), showing homology to human GATA-3 transcription factor SEQ ID NO: 202 is the determined cDNA sequence of 19461.1, showing homology to the human AP-2 gene SEQ ID NO: 203 is the determined cDNA sequence of 19450.1, showing homology to DNA binding regulatory factor SEQ ID NO: 204 is the determined cDNA sequence of 19451.1, showing homology to Na/H exchange regulatory co-factor SEQ ID NO: 205 is the determined cDNA sequence of 19462.1, showing no significant homology to any known gene SEQ ID NO: 206 is the determined cDNA sequence of 19455.1, showing homology to human mRNA for histone HAS.Z SEQ ID NO: 207 is the determined cDNA sequence of 19459.1, showing homology to PAC clone 179N16

SEQ ID NO: 208 is the determined cDNA sequence of 19464.1, showing no significant homology to any known gene SEQ ID NO: 209 is the determined cDNA sequence of 19414.1, showing homology to lipophilin B SEQ ID NO: 210 is the determined cDNA sequence of 19413.1, showing homology to chromosome 17 clone hRPK.209_J_20

SEQ ID NO: 211 is the determined cDNA sequence of 19416.1, showing no significant homology to any known gene SEQ ID NO: 212 is the determined cDNA sequence of 19437.1, showing homology to human clone 24976 mRNA SEQ ID NO: 213 is the determined cDNA sequence of 19449.1, showing homology to mouse DNA for PG-M core protein SEQ ID NO: 214 is the determined cDNA sequence of 19446.1, showing no significant homology to any known gene SEQ ID NO: 215 is the determined cDNA sequence of 19452.1, showing no significant homology to any known gene SEQ ID NO: 216 is the determined cDNA sequence of 19483.1, showing no significant homology to any known gene SEQ ID NO: 217 is the determined cDNA sequence of 19526.1, showing homology to human lipophilin C SEQ ID NO: 218 is the determined cDNA sequence of 19484.1, showing homology to the secreted cement gland protein XAG-2

SEQ ID NO: 219 is the determined cDNA sequence of 19470.1, showing no significant homology to any known gene SEQ ID NO: 220 is the determined cDNA sequence of 19469.1, showing homology to the human HLA-DM gene SEQ ID NO: 221 is the determined cDNA sequence of 19482.1, showing homology to the human pS2 protein gene SEQ ID NO: 222 is the determined cDNA sequence of B805P (19468.1), showing no significant homology to any known gene SEQ ID NO: 223 is the determined cDNA sequence of 19467.1, showing homology to human thrombospondin mRNA SEQ ID NO: 224 is the determined cDNA sequence of 19498.1, showing homology to the CDC2 gene involved in cell cycle control SEQ ID NO: 225 is the determined cDNA sequence of 19506.1, showing homology to human cDNA for TREB protein SEQ ID NO: 226 is the determined cDNA sequence of B806P (19505.1), showing no significant homology to any known gene SEQ ID NO: 227 is the determined cDNA sequence of 19486.1, showing homology to type I epidermal keratin SEQ ID NO: 228 is the determined cDNA sequence of 19510.1, showing homology to glucose transporter for glycoprotein SEQ ID NO: 229 is the determined cDNA sequence of 19512.1, showing homology to the human lysyl hydroxylase gene SEQ ID NO: 230 is the determined cDNA sequence of 19511.1, showing homology to human palimotoyl-protein thioesterase SEQ ID NO: 231 is the determined cDNA sequence of 19508.1, showing homology to human alpha enolase SEQ ID NO: 232 is the determined cDNA sequence of B807P (19509.1), showing no significant homology to any known gene SEQ ID NO: 233 is the determined cDNA sequence of B809P (19520.1), showing homology to clone 102D24 on chromosome 11q13.31

SEQ ID NO: 234 is the determined cDNA sequence of 19507.1, showing homology toprosome beta-subunit SEQ ID NO: 235 is the determined cDNA sequence of 19525.1, showing homology to human pro-urokinase precursor SEQ ID NO: 236 is the determined cDNA sequence of 19513.1, showing no significant homology to any known gene SEQ ID NO: 237 is the determined cDNA sequence of 19517.1, showing homology to human PAC 128M19 clone SEQ ID NO: 238 is the determined cDNA sequence of 19564.1, showing homology to human cytochrome P450-IIB SEQ ID NO: 239 is the determined cDNA sequence of 19553.1, showing homology to human GABA-A receptor pi subunit SEQ ID NO: 240 is the determined cDNA sequence of B811P (19575.1), showing no significant homology to any known gene SEQ ID NO: 241 is the determined cDNA sequence of B810P (19560.1), showing no significant homology to any known gene SEQ ID NO: 242 is the determined cDNA sequence of 19588.1, showing homology to aortic carboxypetidase-like protein SEQ ID NO: 243 is the determined cDNA sequence of 19551. 1, showing homology to human BCL-1 gene SEQ ID NO: 244 is the determined cDNA sequence of 19567.1, showing homology to human proteasome-related mRNA SEQ ID NO: 245 is the determined cDNA sequence of B803P (19583.1), showing no significant homology to any known gene SEQ ID NO: 246 is the determined cDNA sequence of B812P (19587.1), showing no significant homology to any known gene SEQ ID NO: 247 is the determined cDNA sequence of B802P (19392.2), showing homology to human chromosome 17

SEQ ID NO: 248 is the determined cDNA sequence of 19393.2, showing homology to human nicein B2 chain SEQ ID NO: 249 is the determined cDNA sequence of 19398.2, human MHC class II DQ alpha mRNA SEQ ID NO: 250 is the determined cDNA sequence of B804P (19399.2), showing homology to human Xp22 BAC GSHB-184P14

SEQ ID NO: 251 is the determined cDNA sequence of 19401.2, showing homology to human ikB kinase-b gene SEQ ID NO: 252 is the determined cDNA sequence of 20266, showing no significant homology to any known gene SEQ ID NO: 253 is the determined cDNA sequence of B826P (20270), showing no significant homology to any known gene SEQ ID NO: 254 is the determined cDNA sequence of 20274, showing no significant homology to any known gene SEQ ID NO: 255 is the determined cDNA sequence of 20276, showing no significant homology to any known gene SEQ ID NO: 256 is the determined cDNA sequence of 20277, showing no significant homology to any known gene SEQ ID NO: 257 is the determined cDNA sequence of B823P (20280), showing no significant homology to any known gene SEQ ID NO: 258 is the determined cDNA sequence of B821P (20281), showing no significant homology to any known gene SEQ ID NO: 259 is the determined cDNA sequence of B824P (20294), showing no significant homology to any known gene SEQ ID NO: 260 is the determined cDNA sequence of 20303, showing no significant homology to any known gene SEQ ID NO: 261 is the determined cDNA sequence of B820P (20310), showing no significant homology to any known gene SEQ ID NO: 262 is the determined cDNA sequence of B825P (20336), showing no significant homology to any known gene SEQ ID NO: 263 is the determined cDNA sequence of B827P (20341), showing no significant homology to any known gene SEQ ID NO: 264 is the determined cDNA sequence of 20941, showing no significant homology to any known gene SEQ ID NO: 265 is the determined cDNA sequence of 20954, showing no significant homology to any known gene SEQ ID NO: 266 is the determined cDNA sequence of 20961, showing no significant homology to any known gene SEQ ID NO: 267 is the determined cDNA sequence of 20965, showing no significant homology to any known gene SEQ ID NO: 268 is the determined cDNA sequence of 20975, showing no significant homology to any known gene SEQ ID NO: 269 is the determined cDNA sequence of 20261, showing homology to Human p120 catenin SEQ ID NO: 270 is the determined cDNA sequence of B822P (20262), showing homology to Human membrane glycoprotein 4F2

SEQ ID NO: 271 is the determined cDNA sequence of 20265, showing homology to Human Na, K-ATPase Alpha 1

SEQ ID NO: 272 is the determined cDNA sequence of 20267, showing homology to Human heart HS 90, partial cds SEQ ID NO: 273 is the determined cDNA sequence of 20268, showing homology to Human mRNA GPI-anchored protein p137

SEQ ID NO: 274 is the determined cDNA sequence of 20271, showing homology to Human cleavage stimulation factor 77 kDa subunit SEQ ID NO: 275 is the determined cDNA sequence of 20272, showing homology to Human p190-B SEQ ID NO: 276 is the determined cDNA sequence of 20273, showing homology to Human ribophorin SEQ ID NO: 277 is the determined cDNA sequence of 20278, showing homology to Human ornithine amino transferase SEQ ID NO: 278 is the determined cDNA sequence of 20279, showing homology to Human S-adenosylmethionine synthetase SEQ ID NO: 279 is the determined cDNA sequence of 20293, showing homology to Human x inactivation transcript SEQ ID NO: 280 is the determined cDNA sequence of 20300, showing homology to Human cytochrome p450

SEQ ID NO: 281 is the determined cDNA sequence of 20305, showing homology to Human elongation factor-1 alpha SEQ ID NO: 282 is the determined cDNA sequence of 20306, showing homology to Human epithelial ets protein SEQ ID NO: 283 is the determined cDNA sequence of 20307, showing homology to Human signal transducer mRNA SEQ ID NO: 284 is the determined cDNA sequence of 20313, showing homology to Human GABA-A receptor pi subunit mRNA SEQ ID NO: 285 is the determined cDNA sequence of 20317, showing homology to Human tyrosine phosphatase SEQ ID NO: 286 is the determined cDNA sequence of 20318, showing homology to Human cathepsine B proteinase SEQ ID NO: 287 is the determined cDNA sequence of 20320, showing homology to Human 2-phosphopyruvate-hydratase-alpha-enolase SEQ ID NO: 288 is the determined cDNA sequence of 20321, showing homology to Human E-cadherin SEQ ID NO: 289 is the determined cDNA sequence of 20322, showing homology to Human hsp86

SEQ ID NO: 290 is the determined cDNA sequence of B828P (20326), showing homology to Human x inactivation transcript SEQ ID NO: 291 is the determined cDNA sequence of 20333, showing homology to Human chromatin regulator, SMARCA5

SEQ ID NO: 292 is the determined cDNA sequence of 20335, showing homology to Human sphingolipid activator protein 1

SEQ ID NO: 293 is the determined cDNA sequence of 20337, showing homology to Human hepatocyte growth factor activator inhibitor type 2

SEQ ID NO: 294 is the determined cDNA sequence of 20338, showing homology to Human cell ashesion molecule CD44

SEQ ID NO: 295 is the determined cDNA sequence of 20340, showing homology to Human nuclear factor (erythroid-derived)-like 1

SEQ ID NO: 296 is the determined cDNA sequence of 20938, showing homology to Human vinculin mRNA SEQ ID NO: 297 is the determined cDNA sequence of 20939, showing homology to Human elongation factor EF-1-alpha SEQ ID NO: 298 is the determined cDNA sequence of 20940, showing homology to Human nestin gene SEQ ID NO: 299 is the determined cDNA sequence of 20942, showing homology to Human pancreatic ribonuclease SEQ ID NO: 300 is the determined cDNA sequence of 20943, showing homology to Human transcobalamin I SEQ ID NO: 301 is the determined cDNA sequence of 20944, showing homology to Human beta-tubulin SEQ ID NO: 302 is the determined cDNA sequence of 20946, showing homology to Human HS 1 protein SEQ ID NO: 303 is the determined cDNA sequence of 20947, showing homology to Human cathepsin B SEQ ID NO: 304 is the determined cDNA sequence of 20948, showing homology to Human testis enhanced gene transcript SEQ ID NO: 305 is the determined cDNA sequence of 20949, showing homology to Human elongation factor EF-1-alpha SEQ ID NO: 306 is the determined cDNA sequence of 20950, showing homology to Human ADP-ribosylation factor 3

SEQ ID NO: 307 is the determined cDNA sequence of 20951, showing homology to Human IFP53 or WRS for tryptophanyl-tRNA synthetase SEQ ID NO: 308 is the determined cDNA sequence of 20952, showing homology to Human cyclin-dependent protein kinase SEQ ID NO: 308 is the determined cDNA sequence of 20957, showing homology to Human alpha-tubulin sioform 1

SEQ ID NO: 309 is the determined cDNA sequence of 20959, showing homology to Human tyrosine phosphatase-61bp deletion SEQ ID NO: 310 is the determined cDNA sequence of 20966, showing homology to Human tyrosine phosphatase SEQ ID NO: 311 is the determined cDNA sequence of B830P (20976), showing homology to Human nuclear factor NF 45

SEQ ID NO: 312 is the determined cDNA sequence of B829P (20977), showing homology to Human delta-6 fatty acid desaturase SEQ ID NO: 313 is the determined cDNA sequence of 20978, showing homology to Human nuclear aconitase SEQ ID NO: 314 is the determined cDNA sequence of 19465, showing no significant homology to any known gene.

SEQ ID NO: 315 is the determined cDNA sequence of clone 23176.

SEQ ID NO: 316 is the determined cDNA sequence of clone 23140.

SEQ ID NO: 317 is the determined cDNA sequence of clone 23166.

SEQ ID NO: 318 is the determined cDNA sequence of clone 23167.

SEQ ID NO: 319 is the determined cDNA sequence of clone 23177.

SEQ ID NO: 320 is the determined cDNA sequence of clone 23217.

SEQ ID NO: 321 is the determined cDNA sequence of clone 23169.

SEQ ID NO: 322 is the determined cDNA sequence of clone 23160.

SEQ ID NO: 323 is the determined cDNA sequence of clone 23182.

SEQ ID NO: 324 is the determined cDNA sequence of clone 23232.

SEQ ID NO: 325 is the determined cDNA sequence of clone 23203.

SEQ ID NO: 326 is the determined cDNA sequence of clone 23198.

SEQ ID NO: 327 is the determined cDNA sequence of clone 23224.

SEQ ID NO: 328 is the determined cDNA sequence of clone 23142.

SEQ ID NO: 329 is the determined cDNA sequence of clone 23138.

SEQ ID NO: 330 is the determined cDNA sequence of clone 23147.

SEQ ID NO: 331 is the determined cDNA sequence of clone 23148.

SEQ ID NO: 332 is the determined cDNA sequence of clone 23149.

SEQ ID NO: 333 is the determined cDNA sequence of clone 23172.

SEQ ID NO: 334 is the determined cDNA sequence of clone 23158.

SEQ ID NO: 335 is the determined cDNA sequence of clone 23156.

SEQ ID NO: 336 is the determined cDNA sequence of clone 23221.

SEQ ID NO: 337 is the determined cDNA sequence of clone 23223.

SEQ ID NO: 338 is the determined cDNA sequence of clone 23155.

SEQ ID NO: 339 is the determined cDNA sequence of clone 23225.

SEQ ID NO: 340 is the determined cDNA sequence of clone 23226.

SEQ ID NO: 341 is the determined cDNA sequence of clone 23228.

SEQ ID NO: 342 is the determined cDNA sequence of clone 23229.

SEQ ID NO: 343 is the determined cDNA sequence of clone 23231.

SEQ ID NO: 344 is the determined cDNA sequence of clone 23154.

SEQ ID NO: 345 is the determined cDNA sequence of clone 23157.

SEQ ID NO: 346 is the determined cDNA sequence of clone 23153.

SEQ ID NO: 347 is the determined cDNA sequence of clone 23159.

SEQ ID NO: 348 is the determined cDNA sequence of clone 23152.

SEQ ID NO: 349 is the determined cDNA sequence of clone 23161.

SEQ ID NO: 350 is the determined cDNA sequence of clone 23162.

SEQ ID NO: 351 is the determined cDNA sequence of clone 23163.

SEQ ID NO: 352 is the determined cDNA sequence of clone 23164.

SEQ ID NO: 353 is the determined cDNA sequence of clone 23165.

SEQ ID NO: 354 is the determined cDNA sequence of clone 23151.

SEQ ID NO: 355 is the determined cDNA sequence of clone 23150.

SEQ ID NO: 356 is the determined cDNA sequence of clone 23168.

SEQ ID NO: 357 is the determined cDNA sequence of clone 23146.

SEQ ID NO: 358 is the determined cDNA sequence of clone 23170.

SEQ ID NO: 359 is the determined cDNA sequence of clone 23171.

SEQ ID NO: 360 is the determined cDNA sequence of clone 23145.

SEQ ID NO: 361 is the determined cDNA sequence of clone 23174.

SEQ ID NO: 362 is the determined cDNA sequence of clone 23175.

SEQ ID NO: 363 is the determined cDNA sequence of clone 23144.

SEQ ID NO: 364 is the determined cDNA sequence of clone 23178.

SEQ ID NO: 365 is the determined cDNA sequence of clone 23179.

SEQ ID NO: 366 is the determined cDNA sequence of clone 23180.

SEQ ID NO: 367 is the determined cDNA sequence of clone 23181.

SEQ ID NO: 368 is the determined cDNA sequence of clone 23143

SEQ ID NO: 369 is the determined cDNA sequence of clone 23183.

SEQ ID NO: 370 is the determined cDNA sequence of clone 23184.

SEQ ID NO: 371 is the determined cDNA sequence of clone 23185.

SEQ ID NO: 372 is the determined cDNA sequence of clone 23186.

SEQ ID NO: 373 is the determined cDNA sequence of clone 23187.

SEQ ID NO: 374 is the determined cDNA sequence of clone 23190.

SEQ ID NO: 375 is the determined cDNA sequence of clone 23189.

SEQ ID NO: 376 is the determined cDNA sequence of clone 23202.

SEQ ID NO: 378 is the determined cDNA sequence of clone 23191.

SEQ ID NO: 379 is the determined cDNA sequence of clone 23188.

SEQ ID NO: 380 is the determined cDNA sequence of clone 23194.

SEQ ID NO: 381 is the determined cDNA sequence of clone 23196.

SEQ ID NO: 382 is the determined cDNA sequence of clone 23195.

SEQ ID NO: 383 is the determined cDNA sequence of clone 23193.

SEQ ID NO: 384 is the determined cDNA sequence of clone 23199.

SEQ ID NO: 385 is the determined cDNA sequence of clone 23200.

SEQ ID NO: 386 is the determined cDNA sequence of clone 23192.

SEQ ID NO: 387 is the determined cDNA sequence of clone 23201.

SEQ ID NO: 388 is the determined cDNA sequence of clone 23141.

SEQ ID NO: 389 is the determined cDNA sequence of clone 23139.

SEQ ID NO: 390 is the determined cDNA sequence of clone 23204.

SEQ ID NO: 391 is the determined cDNA sequence of clone 23205.

SEQ ID NO: 392 is the determined cDNA sequence of clone 23206.

SEQ ID NO: 393 is the determined cDNA sequence of clone 23207.

SEQ ID NO: 394 is the determined cDNA sequence of clone 23208.

SEQ ID NO: 395 is the determined cDNA sequence of clone 23209.

SEQ ID NO: 396 is the determined cDNA sequence of clone 23210.

SEQ ID NO: 397 is the determined cDNA sequence of clone 23211.

SEQ ID NO: 398 is the determined cDNA sequence of clone 23212.

SEQ ID NO: 399 is the determined cDNA sequence of clone 23214.

SEQ ID NO: 400 is the determined cDNA sequence of clone 23215.

SEQ ID NO: 401 is the determined cDNA sequence of clone 23216.

SEQ ID NO: 402 is the determined cDNA sequence of clone 23137.

SEQ ID NO: 403 is the determined cDNA sequence of clone 23218.

SEQ ID NO: 404 is the determined cDNA sequence of clone 23220.

SEQ ID NO: 405 is the determined cDNA sequence of clone 19462.

SEQ ID NO: 406 is the determined cDNA sequence of clone 19430.

SEQ ID NO: 407 is the determined cDNA sequence of clone 19407.

SEQ ID NO: 408 is the determined cDNA sequence of clone 19448.

SEQ ID NO: 409 is the determined cDNA sequence of clone 19447.

SEQ ID NO: 410 is the determined cDNA sequence of clone 19426.

SEQ ID NO: 411 is the determined cDNA sequence of clone 19441.

SEQ ID NO: 412 is the determined cDNA sequence of clone 19454.

SEQ ID NO: 413 is the determined cDNA sequence of clone 19463.

SEQ ID NO: 414 is the determined cDNA sequence of clone 19419.

SEQ ID NO: 415 is the determined cDNA sequence of clone 19434.

SEQ ID NO: 416 is the determined extended cDNA sequence of B820P.

SEQ ID NO: 417 is the determined extended cDNA sequence of B821P.

SEQ ID NO: 418 is the determined extended cDNA sequence of B822P.

SEQ ID NO: 419 is the determined extended cDNA sequence of B823P.

SEQ ID NO: 420 is the determined extended cDNA sequence of B824P.

SEQ ID NO: 421 is the determined extended cDNA sequence of B825P.

SEQ ID NO: 422 is the determined extended cDNA sequence of B826P.

SEQ ID NO: 423 is the determined extended cDNA sequence of B827P.

SEQ ID NO: 424 is the determined extended cDNA sequence of B828P.

SEQ ID NO: 425 is the determined extended cDNA sequence of B829P.

SEQ ID NO: 426 is the determined extended cDNA sequence of B830P.

SEQ ID NO: 427 is the determined cDNA sequence of clone 266B4.

SEQ ID NO: 428 is the determined cDNA sequence of clone 22892.

SEQ ID NO: 429 is the determined cDNA sequence of clone 266G3.

SEQ ID NO: 430 is the determined cDNA sequence of clone 22890.

SEQ ID NO: 431 is the determined cDNA sequence of clone 264B4.

SEQ ID NO: 432 is the determined cDNA sequence of clone 22883.

SEQ ID NO: 433 is the determined cDNA sequence of clone 22882.

SEQ ID NO: 434 is the determined cDNA sequence of clone 22880.

SEQ ID NO: 435 is the determined cDNA sequence of clone 263G1.

SEQ ID NO: 436 is the determined cDNA sequence of clone 263G6.

SEQ ID NO: 437 is the determined cDNA sequence of clone 262B2.

SEQ ID NO: 438 is the determined cDNA sequence of clone 262B6.

SEQ ID NO: 439 is the determined cDNA sequence of clone 22869.

SEQ ID NO: 440 is the determined cDNA sequence of clone 21374.

SEQ ID NO: 441 is the determined cDNA sequence of clone 21362.

SEQ ID NO: 442 is the determined cDNA sequence of clone 21349.

SEQ ID NO: 443 is the determined cDNA sequence of clone 21309.

SEQ ID NO: 444 is the determined cDNA sequence of clone 21097.

SEQ ID NO: 445 is the determined cDNA sequence of clone 21096.

SEQ ID NO: 446 is the determined cDNA sequence of clone 21094.

SEQ ID NO: 447 is the determined cDNA sequence of clone 21093.

SEQ ID NO: 448 is the determined cDNA sequence of clone 21091.

SEQ ID NO: 449 is the determined cDNA sequence of clone 21089.

SEQ ID NO: 450 is the determined cDNA sequence of clone 21087.

SEQ ID NO: 451 is the determined cDNA sequence of clone 21085.

SEQ ID NO: 452 is the determined cDNA sequence of clone 21084.

SEQ ID NO: 453 is a first partial cDNA sequence of clone 2BT1-40.

SEQ ID NO: 454 is a second partial cDNA sequence of clone 2BT1-40.

SEQ ID NO: 455 is the determined cDNA sequence of clone 21063.

SEQ ID NO: 456 is the determined cDNA sequence of clone 21062.

SEQ ID NO: 457 is the determined cDNA sequence of clone 21060.

SEQ ID NO: 458 is the determined cDNA sequence of clone 21053.

SEQ ID NO: 459 is the determined cDNA sequence of clone 21050.

SEQ ID NO: 460 is the determined cDNA sequence of clone 21036.

SEQ ID NO: 461 is the determined cDNA sequence of clone 21037.

SEQ ID NO: 462 is the determined cDNA sequence of clone 21048.

DETAILED DESCRIPTION OF THE INVENTION

As noted above, the present invention is generally directed to compositions and methods for the therapy and diagnosis of cancer, such as breast cancer. The compositions described herein may include breast tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a breast tumor protein or a variant thereof A "breast tumor protein" is a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human breast tumor proteins. Sequences of polynucleotides encoding specific tumor proteins are provided in SEQ ID NOS:1–175, 178, 180 and 182–462.

Breast Tumor Proitein Polynucleotides

Any polynucleotide that encodes a breast tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a breast tumor protein. More preferably, a polynucleotide encodes an immunogenic portion of a breast tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein, The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native breast tumor protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.o. (1978) A model of evolutionary change in proteins—Matrices for detecting distant relationships. In Dayhoff, M.O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof Such polynucleotide variants are capable of hybridizing under moderately stringent conditions to a naturally occurring DNA sequence encoding a native breast tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least five fold greater in a breast tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al.,

*Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nuel. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of breast tumor proteins are provided in SEQ ID NO: 1–175, 178, 180 and 182–462. The isolation of these sequences is described in detail below.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a breast tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a breast tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and *Carr, Molecular and Imminologic Approaches*, Futura Publishing Co. (Mt. Kisco, N.Y.; 1994)). Alternatively, an antisense molecule may be designed to hybridize with a control region of a gene (e.g, promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Breast Tumor Polypeptides

Within the context of the present invention, polypeptides may comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 19 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratoty Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Imminol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diphtheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ system, available from Nexell Therapeutics Inc., Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml–100 $\mu$g/ml, preferably 200 ng/ml–25 $\mu$g/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be $CD4^+$ and/or $CD8^+$. Breast tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Composotions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (N.Y., 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y Acad. Sci.* 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulztion* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999) In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as “immature” and “mature” cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as breast cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^-$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays. which may be performed using samples obtained from a patient before and after treatment.

Methods for Detecting Cancer

In general, a cancer may be detected in a patient based on the presence of one or more breast tumor proteins and/or polynucleotides encoding such proteins in a biological sample (for example, blood, sera, urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added, The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (I100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^-$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 μg/ml). It may be desirable to incubate another aliquot of a T cell sample in the absence of breast tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NOS:1–175, 178, 180 and 182–462. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N.Y., 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue .were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO. 63–87. Comparison of the sequences of SEQ ID NO: 74–87 with those in the gene bank as described above, revealed homology to previously identified human genes. No significant homologies were found to the sequences or SEQ ID NO: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [$\alpha$-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245 and 246, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO: 216) was over-expressed in a few breast tumors, with no over-expression in any normal tissues tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1

(SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clone 19587.1 (SEQ ID NO: 246) showed low level over-expression in some breast tumors and no significant over-expression in normal tissues.

Clone 19520.1 (SEQ ID NO: 233), showing homology to clone 102D24 on chromosome 11q13.31, was found to be over-expressed in breast tumors and in SCID tumors. Clone 19517.1 (SEQ ID NO: 237), showing homology to human PAC 128MI9 clone, was found to be slightly over-expressed in the majority of breast tumors tested. Clone 19392.2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO: 405–415. Comparison of these sequences to those in the public database, as outlined above, revealed homologies between the sequences of SEQ ID NO: 408, 411, 413 and 414 and previously isolated ESTs. The sequences of SEQ ID NO: 405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO: 315–404. Comparison of these sequences with those in the public database, as described above, revealed no significant homologies to the sequence of SEQ ID NO: 366. The sequences of SEQ ID NO: 320–324, 342, 353, 367, 368, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO: 427–439. The determined cDNA sequences of 22 clones identified using the modified Gemtools analysis are provided in SEQ ID NO: 440–462, wherein SEQ ID NO: 453 and 454 represent two partial, non-overlapping, sequences of the same cione.

Comparison of the clone sequences of SEQ ID NO: 436 and 437 (referred to as 263G6 and 262B2) with those in the public databases, as described above, revealed no significant homologies to previously identified sequences. The sequences of SEQ ID NO: 427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2BT1-59, 2BT1-52 and 2BT1-40, respectively) showed some homology to previously isolated expressed sequences tags (ESTs). The sequences of SEQ ID NO: 428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

Example 2

Isolation and Characterization of Breast Tumor Polypeptides Obtained by PCR-Based Subtraction Using Scid-passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659, filed Nov. 13 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–313, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO: 416–426, respectively.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide consisting of SEQ ID NO:181.

2. An isolated polypeptide consisting of a sequence having at least 90% identity to the entirety of SEQ ID NO:181 and comprising no more than 432 amino acid residues, wherein said polypeptide is useful in the detection of breast cancer.

3. An isolated polypeptide consisting of a sequence having at least 95% identity to the entirety of SEQ ID NO:181 and comprising no more than 432 amino acid residues, wherein said polypeptide is useful in the detection of breast cancer.

4. An isolated polypeptide consisting of an amino acid sequence that is encoded by the polynucleotide set forth in SEQ ID NO:180.

5. An isolated polypeptide consisting of an amino acid sequence that is encoded by a polynucleotide sequence having at least 90% identity to the entirety of SEQ ID NO:180 and comprising no more than 1681 nucleotides, wherein said polypeptide is useful in the detection of breast cancer.

6. An isolated polypeptide consisting of an amino acid sequence that is encoded by a polynucleotide sequence having at least 95% identity to the entirety of SEQ ID NO: 180 and comprising no more than 1681 nucleotides, wherein said polypeptide is useful in the detection of breast cancer.

7. A composition comprising a polypeptide according to any one of claims 1, 3, and 5, in combination with a physiologically acceptable carrier.

8. An immunogenic composition comprising a polypeptide according to any one of claims 1, 4, and 5, in combination with a non-specific immune response enhancer.

9. An immunogenic composition according to claim 8, wherein the non-specific immune response enhancer is an adjuvant.

10. An immunogenic composition according to claim 8, wherein the non-specific immune response enhancer induces a Type I response.

11. A fusion protein comprising at least one polypeptide according to any one of claims 2, 3, 4, and 5.

12. A fusion protein according to claim 11, wherein the fusion protein comprises an expression enhancer that increases expression of the fusion protein in a host cell transfected with a polynucleotide encoding the fusion protein.

13. A fusion protein according to claim 11 wherein the fusion protein comprises a T helper epitope that is not present within said polypeptide.

14. A fusion protein according to claim 11, wherein the fusion protein comprises an affinity tag.

15. A composition comprising a fusion protein according to claim 11, in combination with a physiologically acceptable carrier.

16. An immunogenic composition comprising a fusion protein according to claim 11, in combination with a non-specific immune response enhancer.

17. An immunogenic composition according to claim 16, wherein the non-specific immune response enhancer is an adjuvant.

18. An immunogenic composition according to claim 16, wherein the non-specific immune response enhancer induces a Type I response.

* * * * *

SEQUENCE LISTING

```
<160> NUMBER OF SEQ ID NOS: 463

<210> SEQ ID NO 1
<211> LENGTH: 281
<212> TYPE: DNA
<213> ORGANISM: Homo sapien

<400> SEQUENCE: 1

caatgacagt caatctctat cgacagcctg cttcatattt agctattgtt cgtattgcct     60

tctgtcctag gaacagtcat atctcaagtt caaatgccac aacctgagaa gcggtgggct    120

aagataggtc ctactgcaaa ccacccctcc atatttccgt acgcaattac aattcagttt    180

ctgtgacatc tctttacacc actggaggaa aaatgagata ttctctgatt tattctacta    240

taacactcta catagagcta tggtgagtgc taaccacatc g                        281
```

-continued

<210> SEQ ID NO 2
<211> LENGTH: 300
<212> TYPE: DNA
<213> ORGANISM: Homo sapien

<400> SEQUENCE: 2
gaggtcctgg gctaacctaa tggtttatta ttggtggaga gaaagatctg gaaatacttg 60
aggttattac atactagatt agcttctaat gtgaaccatt tttcttttaa cagtgataaa 120
ttattatttc cgaagttaac tgttcccttg gtcgtgatac acactcgatt aacaaacata 180
ctgttgtatt ttttccagtt ttgtttggct atgccaccac agtcatcccc agggtctata 240
catactatgt ctcaactgta ttatttgcca tttttggcat tagaatgctt cgggaaggct 300

<210> SEQ ID NO 3
<211> LENGTH: 302
<212> TYPE: DNA
<213> ORGANISM: Homo sapien

<400> SEQUENCE: 3
ggccgaggta attggttaag tctaaagaga ttattattcc ttgatgtttg ctttgtattg 60
gctacaaatg tgcagaggta atacatatgt gatgtcgatg tctctgtctt tttttttgtc 120
tttaaaaaat aattggcagc aactgtattt gaataaaatg atttcttagt atgattgtac 180
agtaatgaat gaaagtggaa catgtttctt tttgaaaggg agagaattga ccatttattg 240
ttgtgatgtt taagttataa cttatcgagc acttttagta gtgataactg tttttaaact 300
tg 302

<210> SEQ ID NO 4
<211> LENGTH: 293
<212> TYPE: DNA
<213> ORGANISM: Homo sapien

<400> SEQUENCE: 4
tgtaccaatc ctttggcaca agaatatgta agaactatag ttgtttttat tggtttttgt 60
tcttgagatt gttttcattc tgtttttgac tgtatctctt taggaggctg aggatggcat 120
tattgcttat gatgactgtg gggtgaaact gactattgct tttcaagcca aggatgtgga 180
aggatctact tctcctcaaa tacgagataa ggcaagataa ttctgctcat tcgagagagg 240
gttaagagtt gtcatcttaa tcataaatcc tgcaggatgg gttcttcaaa ttt 293

<210> SEQ ID NO 5
<211> LENGTH: 275
<212> TYPE: DNA
<213> ORGANISM: Homo sapien

<400> SEQUENCE: 5
cgaggtttgg aatcagactt ctgtgtccag taaaaaactc ctgcactgaa gtcattgtga 60
cttgagtagt tacagactga ttccagtgaa cttgatctaa tttcttttga tctaatgaat 120
gtgtctgctt accttgtctc cttttaattg ataagctcca agtagttgct aattttttga 180
caactttaaa tgagtttcat tcacttcttt tacttaatgt tttaagtata gtaccaataa 240
tttcattaac ctgttctcaa gtggtttagc tacca 275

<210> SEQ ID NO 6
<211> LENGTH: 301
<212> TYPE: DNA
<213> ORGANISM: Homo sapien

-continued

<400> SEQUENCE: 6
gaggtctggt ttcctgggta tgcctggact gttgcccagt gtaagatctg tgcaagccat 60
attggatgga agtttacggc caccaaaaaa gacatgtcac ctcaaaaatt ttggggctta 120
acgcgatctg ctctgttgcc cacgatccca gacactgaag atgaaataag tccagacaaa 180
gtaatacttt gcttgtaaac agatgtgata gagataaagt tatctaacaa attggttata 240
ttctaagatc tgctttggaa attattgcct ctgatacata cctaagtaaa cataacatta 300
a 301

<210> SEQ ID NO 7
<211> LENGTH: 301
<212> TYPE: DNA
<213> ORGANISM: Homo sapien

<400> SEQUENCE: 7
gtccagtttg tacacagtga ttccttatgc acgccgaaag ggtttccgta aaaatgacat 60
tatatacaaa tctgtacacc catccaccag agcgattctc cagctcccag agggagttat 120
caacttaaag caggatacct gaggtttcat gtctttagtt gccttatcat aatcccaaat 180
atacatttca gggtttgttt ttgtttttaa agacactttc ctggaatatg tgcactatgg 240
ttaaaattaa aaacaaaagt aataaaataa aatgatcgct ggaaggactg acctccccac 300
c 301

<210> SEQ ID NO 8
<211> LENGTH: 301
<212> TYPE: DNA
<213> ORGANISM: Homo sapien

<400> SEQUENCE: 8
ctgtcctcat ctctgcaaag ttcagcttcc ttccccaggt ctctgtgcac tctgtcttgg 60
atgctctggg gagctcatgg gtggaggagt ctccaccaga gggaggctca ggggactggt 120
tgggccaggg atgaatattt gagggataaa aattgtgtaa gagccaaaga attggtagta 180
gggggagaac agagaggagc tgggctatgg gaaatgattt gaataatgga gctgggaata 240
tggctggata tctggtacta aaaaagggtc tttaagaacc tacttcctaa tctcttcccc 300
a 301

<210> SEQ ID NO 9
<211> LENGTH: 301
<212> TYPE: DNA
<213> ORGANISM: Homo sapien

<400> SEQUENCE: 9
gaggtctgcc taagtagagg acaaagactt cctcctttca aaggagaact gagcccagga 60
ttggtaagtt taaggcactt aaccttgacc agctctgtag gtctggagca ttctggtccc 120
tggccgcttt caccaccagg cccttctcac ttatccacct cacatactgc cccagcattc 180
ctttggcatt gcgagctgtg acttgacaca ttttaatgac aagattgaag tagctacctt 240
gcaggataga ttttctgggg tataggggac aaaccaacag tgccatcagg tgtcttaaca 300
c 301

<210> SEQ ID NO 10
<211> LENGTH: 301
<212> TYPE: DNA

-continued

<213> ORGANISM: Homo sapien

<400> SEQUENCE: 10
ggcaggtcca acagttcttc cagttctggt cgagctttga atcgtccctt gaagtcttct 60
tcagtgtgct ccttcactga cagtctgact ccttcaggaa gactgctttg gattatttcc 120
aagaaaattt ctgcaaacgt agcactcaaa ccgctgatct gaaccactcg ctcatgggtg 180
gtaagcactg agtccaggag cattttgctg ccttggtcct gcaactgcaa cacttctatg 240
gttttggttg gcattgcata actttcctcg actttaatgg agagagattg cagaggttgt 300
g 301

<210> SEQ ID NO 11
<211> LENGTH: 301
<212> TYPE: DNA
<213> ORGANISM: Homo sapien

<400> SEQUENCE: 11
aggtctgtga ctttcaccca ggacccagga cgcagccctc cgtgggcact gccggcgcct 60
tgtctgcaca ctggaggtcc tccattacag aggcccagcg cacatcgctg gccccacaaa 120
cgttcagggg tacagccatg gcagctcctt cctctgccgt gagaaaagtg cttggagtac 180
ggtttgccac acacgtgact ggacagtgtc caattcaaat ctttcagggc agagtccgag 240
cagcgcttgg tgacagcctg tcctctcctg ctctccaaag gccctgctcc ctgtcctctc 300
t 301

<210> SEQ ID NO 12
<211> LENGTH: 301
<212> TYPE: DNA
<213> ORGANISM: Homo sapien

<400> SEQUENCE: 12
gaggtctggg attacaggca cgtgccacca cacctagcta atttttgagc atggggctca 60
aaggaactgc tctctggggc atgtcagatt tcggatttgg ggctgcacac tgatactctc 120
taagtggtgg aggaacttca tcccactgaa attcctttgg catttggggt tttgtttttc 180
tttttttcct tcttcatcct cctccttttt taaaagtcaa cgagagcctt cgctgactcc 240
accgaagaag tgcaccactg ggagccaccc cagtgccagg cgcccgtcca gggacacaca 300
c 301

<210> SEQ ID NO 13
<211> LENGTH: 256
<212> TYPE: DNA
<213> ORGANISM: Homo sapien

<400> SEQUENCE: 13 tttttggca taaaaaacac aatgatttaa tttctaaagc acttatatta ttatggcatg 60
gtttgggaaa caggttatta tattccacat aggtaattat gcagtgcttc tcatggaaaa 120
aatgcttagg tattggcctt ttctctggaa accatatttt tcctttttta ataatcaact 180
aaaatgtata tgttaaaaag cctcatcttt tgattttcaa tatacaaaat gctttcttta 240
aaagaacaag attcaa 256

<210> SEQ ID NO 14
<211> LENGTH: 301
<212> TYPE: DNA
<213> ORGANISM: Homo sapien -continued

<400> SEQUENCE: 14
ggtccttgat agaggaagag gaatatccaa ggcaaagcca ccaccacgtc caacctcctc 60
atcctctacc tttcctgtcc ccagaggtat gagatagacc ccctggcctg gttcctgcac 120
tgtgctaggc ccacagtgga cacttccacc ttaatggaga ataggcccca tggagtggag 180
gtccctcctc catggcctgc aacccaatga ctatgggggt gacacaagtg acctctgccc 240
tgtgatggct caacaccatc acacgcaact gtccagacaa gccccctcaa cgggctgctg 300
t 301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct 60
ctctttctgc ttttctgatc atcctaaagg ctgaatacat cctcctcctg tgtggaggac 120
acgaagcaat actaaaatca atacactcga tcaggtcttc atcagatacc acgtcactgt 180
gggtagagtg ctaattttca acaaatgtgg tgttcttagg gccccacaag gtagtccttt 240
ctcaaggtcg ctgggccac 259

<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc 60
agtgttattc agtgctatgc ctccttgtaa tgggtagtta ttaattattt tcagagcttt 120
ctggaaatac tgtcctaact ggctatgttt aggatctttg ttatctctga agacaaagaa 180
agaactagga ctcttaattt tggggtgctt cttgactctt agttgggaaa ctgaaaatat 240
ttccaacctt ttacccacgt caatggcata ttctgggaat caccaccacc accaccacta 300
c 301

<210> SEQ ID NO 17
<211> LENGTH: 301
<212> TYPE: DNA
<213> ORGANISM: Homo sapien

<400> SEQUENCE: 17
gcccgggcag gtctggggcc tagggtggct ctttgcaaag ctgaggggca agctaaggaa 60
gccaggcagg tcaggggccc tttcggcctt ctcaagcctc cacctgagtt ctcgtcaatg 120
ccagtctccc tggtatgatt ggggacatta tcagagaaac atctaatagc gcacatctgg 180
gcacccacac tctgcttcag ttgcatccat cctcccaccc caaattcaac tcctgaccca 240
atacaaaaga cttttttaac caggatttct tcttgcagga aagctgactt ggaaacacgg 300
g 301

<210> SEQ ID NO 18
<211> LENGTH: 301
<212> TYPE: DNA
<213> ORGANISM: Homo sapien -continued

<400> SEQUENCE: 18
attacaggca cgtgccacca cacctagcta atttttgagc atggggctca aaggaactgc 60
tctctggggc atgtcagatt tcggatttgg ggctgcacac tgatactctc taagtggtgg 120
aggaacttca tcccactgaa attcctttgg catttggggt tttgtttttc tttttttcct 180
tcttcatcct cctccttttt taaaagtcaa cgagagcctt cgctgactcc accgaagaag 240
tgcaccactg gggaccaccc agtgccaggc gcccgtccag ggacacacac agtcttcact 300
g 301

<210> SEQ ID NO 19
<211> LENGTH: 301
<212> TYPE: DNA
<213> ORGANISM: Homo sapien

<400> SEQUENCE: 19
agaatctctg cactgtcatc aggtacaaca aaagatcaaa cccctgtccc gatgttaact 60
ttttaactta aaagaatgcc agaaaaccca gatcaacact ttccagctac gagccgtcca 120
caaaggccac ccaaaggcca gtcagactcg tgcagatctt attttttaat agtagtaacc 180
acaatacaca gctctttaaa gctgttcata ttcttccccc attaaacacc tgccccgggc 240
ggccaagggc gaattctgca gatatccatc acactggcgg ccgctcgagc atgcatctag 300
a 301

<210> SEQ ID NO 20
<211> LENGTH: 290
<212> TYPE: DNA
<213> ORGANISM: Homo sapien

<400> SEQUENCE: 20
aggttttttt tttttttttt tttttttttt tttttccctt tcaattcatt taatttcaac 60
aatctgtcaa aaaacagcca ataaacaaat actgaattac attctgctgg gtttttttaaa 120 ggctctaaac tataaaaaca tcttgtgtct cccaccctga ccaccctgct acttttccat 180
ataccacagg ccacccataa acacaaagcc agggggtgaa gctgacatgg tctatttgga 240
gccagtaaac aggagggcga taagtcctga taagcactta tggacaatat 290

<210> SEQ ID NO 21
<211> LENGTH: 301
<212> TYPE: DNA
<213> ORGANISM: Homo sapien

<400> SEQUENCE: 21
agaaaggtaa ctgccagcca ggcttgcatt gtttagccag aaattgctgc ttggttctag 60
actctttaaa aaaaaaaaat acccagggtt tgtcatcatt ttcagaggca gagtgccaaa 120
tatcacccaa agctcttgtg tcttttttttt accccttat tttattttta tttattaatt 180
ttttgtgcaa acatcaaatg tcactggtgt tcacagaagg cttttttgac tagccttaaa 240
ttcctgagtc aaaagattaa tcagattttc aggcagtgtt taatcaggtg ctttgtcctg 300
t 301

<210> SEQ ID NO 22
<211> LENGTH: 301
<212> TYPE: DNA
<213> ORGANISM: Homo sapien

<400> SEQUENCE: 22

-continued

```
gacgccatgc accctccggt aaccagcagc cgcctgtcca tcccccaaga ccggaaaggc     60

agcagcagcc cccgggagcc cagggctgtc ctcggtgcat ctggctgcag agggaaattg    120

atgaccttac acagcaacta gcggccatgc agtccttcac tgacaagttc caggaccttt    180

gaagttggag ccagcgtccg gagctgcagc caagcgagtt tcctccttat cctccttagc    240

cagggctttt tctcttccgc tgcatttgcc cccttcccaa cgcaattcaa agcagttgtg    300

a                                                                    301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac     60

attatttgtc tgtcacagaa gagagctgct tatgattttg aaggggtcag ggagggtggg    120

agttggtaaa gagtagggta tttctataac agatattatt cagtcttatt tcctaagatt    180

ttgttgtaac ttaaggtatc ttgctacagt agacagaatt ggtaatagca acttttaaaa    240

ttgtcattag ttctgcaata ttagctgaaa tgtagtacag aaaagaatgt acatttagac    300

atttgggttc agttgcttgt agtctgtaaa tttaaaacag cttaatttgg tacaggttac    360

acatatggac ctcccgggcg g                                              381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg     60

caaagggtct cattggtcct gatgaataat cttgtgactg tacatattcc tgggtgcatg    120

tccacaaata ctgaggtata gcctgcatgc cactaaaaat aacaaaggtt tcaggggtgg    180

aaacattgtc caccacactg tcatgaccat cttt                                214
```

<210> SEQ ID NO 25
<211> LENGTH: 302
<212> TYPE: DNA
<213> ORGANISM: Homo sapien

<400> SEQUENCE: 25

```
gggggcactg agaactccct ctggaattct tggggggtgt tggggagaga ctgtgggcct     60

ggagataaaa cttgtctcct ctaccaccac cctgtaccct agcctgcacc tgtcctcatc    120

tctgcaaagt tcagcttcct tccccaggtc tctgtgcact ctgtcttgga tgctctgggg    180

agctcatggg tggaggagtc tccaccagag ggaggctcag ggactggtt gggccaggga     240

tgaatatttg agggataaaa attgtgtaag aagccaaaga aattggtagt agggggggaga   300

ac                                                                   302
```

<210> SEQ ID NO 26
<211> LENGTH: 301
<212> TYPE: DNA
<213> ORGANISM: Homo sapien

<400> SEQUENCE: 26

-continued

```
ttggagaacg cgctgacata ctgctcggcc acagtcagtg aagctgctgc atctccatta      60

tgttgtgtca gagctgcagc caggattcga atagcttcag ctttagcctt ggccttcgcc     120

agaactgcac tggcctctcc tgctgcctga tttatctgtg cagccttttc tgcttcggag     180

gccaggatct gggcctgttt cttcccttct gccacattga tggccgactc tcgggtcccc     240

tcagactcta gaactgtggc ccgtttccgc cgctctgcct ccacctgcat ctgcatagac     300

t                                                                     301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg      60

accattttat tagacaccct ctattagtgt taacagacaa agatgaaggt taagttgaaa     120

tcaaattgaa atcatcttcc ctctgtacag attgcaatat ctgataatac cctcaacttt     180

cttggtgcaa attaattgcc tggtactcac agtccagtgt taacaggcaa taatggtgtg     240

attccagagg agaggactag gtggcaggaa aataaatgag attagcagta tttgacttgg     300

a                                                                     301
```

<210> SEQ ID NO 28
<211> LENGTH: 286
<212> TYPE: DNA
<213> ORGANISM: Homo sapien

<400> SEQUENCE: 28

```
tttttttttg cacaggatgc acttattcta ttcattctcc cccacccttc ccatatttac      60

atccttagag gaagagaggg gtaaggtgat aaagtaactg aaggaccgca agacgggtat     120

gtcccttgtt caccaaatgg tcaaagggtc aaagatcgga ggaggtcagg gggtaacgca     180

ggaacaggtg agggcgtttc gccctctctc cctctcccct tttcaacctc ttaatcactg     240

gctaactcgc gacctcatgg gttaattcgt aagcttacac gcgttg                    286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga      60

ttttcctttg ttcaaaggat ttattcctac catttcacaa atccgaaaat aattgaggaa     120

acaggttaca tcattccaat tttgccttgg gtttgaagag tctctcatgg tggcacagtc     180

ctccagggta gctatgttgt tgggctcccc tacatcccag aagctcagag actttgtcaa     240

aggtgtgccg tccacccatt gccactgacc ctcgacaacc tggtctgaca gtccaataaa     300

a                                                                     301
```

<210> SEQ ID NO 30
<211> LENGTH: 332
<212> TYPE: DNA
<213> ORGANISM: Homo sapien

<400> SEQUENCE: 30

```
gagcagaatt gatgcctatg gctccaagtc aaatactgct aatctcattt attttcctgc      60
```

-continued

```
cacctagtcc tctcctctgg aatcacacca ttattgcctg ttaacactgg actgtgagta    120

ccaggcaatt aatttgcacc aagaaagttg agggtattat cagatattgc aatctgtaca    180

gagggaagat gatttcaatt tgatttcaac ttaaccttca tctttgtctg ttaacactaa    240

tagagggtgt ctaataaaat ggtcaaattt gtgatctcat ttgttataac tagcactctt    300

ttcacagatg tgatgactga tttccagcag ac                                  332
```

<210> SEQ ID NO 31
<211> LENGTH: 141
<212> TYPE: DNA
<213> ORGANISM: Homo sapien

<400> SEQUENCE: 31

```
aaaggctatc aagtactttg aaggacagga aggaatgaac acacccaggt ggacgtttgg     60

tttcatttgc aggggttcag ggagggttgc aggggttcag ggagggctct tgtcccacaa    120

ccgggggaag ggagagggca c                                              141
```

<210> SEQ ID NO 32
<211> LENGTH: 201
<212> TYPE: DNA
<213> ORGANISM: Homo sapien

<400> SEQUENCE: 32

```
gagctgatct cacagcacat acagaatgat gctactatgt agaccctcac tcccttggga     60

aatctgtcat ctaccttaaa gagagaaaaa agatggaaca taggcccacc tagtttcatc    120

catccaccta cataaccaac atagatgtga ggtccactgc actgatagcc agactgcctg    180

gggtaaacct tttcagggag g                                              201
```

<210> SEQ ID NO 33
<211> LENGTH: 181
<212> TYPE: DNA
<213> ORGANISM: Homo sapien

<400> SEQUENCE: 33

```
tttcaaaaca ctcatatgtt gcaaaaaaca catagaaaaa taaagtttgg tgggggtgct     60

gactaaactt caagtcacag acttttatgt gacagattgg agcagggttt gttatgcatg    120

tagagaaccc aaactaattt attaaacagg atagaaacag gctgtctggg tgaaatggtt    180

c                                                                    181
```

<210> SEQ ID NO 34
<211> LENGTH: 151
<212> TYPE: DNA
<213> ORGANISM: Homo sapien

<400> SEQUENCE: 34

```
atgtcctgca cagtatagct tggacctctg ggcctgaacc agggtgagca tcaaggcccc     60

catttctcct caccacgggg tcgcttgtca gctccaagaa ccagtctggc cccactgaga    120

acttttcagt cgagggcctg atgaatcttg g                                   151
```

<210> SEQ ID NO 35
<211> LENGTH: 291
<212> TYPE: DNA
<213> ORGANISM: Homo sapien

<400> SEQUENCE: 35

-continued

```
tctttagggc aaaatcatgt ttctgtgtac ctagcaatgt gttcccattt tattaagaaa     60

agctttaaca cgtgtaatct gcagtcctta acagtggcgt aattgtacgt acctgttgtg    120

tttcagtttg tttttcacct ataatgaatt gtaaaaacaa acatacttgt ggggtctgat    180

agcaaacata gaaatgatgt atattgtttt ttgttatcta tttattttca tcaatacagt    240

attttgatgt attgcaaaaa tagataataa tttatataac aggttttctg t             291


<210> SEQ ID NO 36
<211> LENGTH: 201
<212> TYPE: DNA
<213> ORGANISM: Homo sapien

<400> SEQUENCE: 36

ctgatacaat tataataacg gttccctgaa ccttttagag tgcaattaag aacaaaaact     60

aaattttgtt tacatgaata tggaataaat acaataatca aaatatgact ctccctaaaa    120

gtgaaacaca caagccaatc cggaactgct gtgcgaaaga taaaatcgag aaaggcaagg    180

tttcggtagg aggacgcgat g                                              201


<210> SEQ ID NO 37
<211> LENGTH: 121
<212> TYPE: DNA
<213> ORGANISM: Homo sapien

<400> SEQUENCE: 37

catcacactg gcggccgctc gagcatgcat ctagagggcc caattcgccc tataatgagt     60

cgtattacaa ttcactggcc gtcgttttac aacgtcgtga ctgggaaaac cctggcgtta    120

c                                                                    121


<210> SEQ ID NO 38
<211> LENGTH: 200
<212> TYPE: DNA
<213> ORGANISM: Homo sapien

<400> SEQUENCE: 38

aaacatgtat tactctatat ccccaagtcc tagagcatga cctgcatgtt ggagatgttg     60

tacagcaatg tatttatcca gacatacata tatgatattt agagacacag tgattctttt    120

gataacacca cacatagaac attataatta cacacaaatt tatggtaaaa gaattaatat    180

gctgtctggt gctgctgtta                                                200


<210> SEQ ID NO 39
<211> LENGTH: 760
<212> TYPE: DNA
<213> ORGANISM: Homo sapien

<400> SEQUENCE: 39

gcgtggtcgt cggccgaggt cctgggctag acctaatggt ttattattgg tggagagaaa     60

gatctggaaa tacttgaggt tattacatac tagattagct tctaatgtga accatttttc    120

ttttaacagt gatcaaatta ttatttcgaa gttaatcgtt cccttggtgg ctgcatacac    180

atcgcattaa caaacatact gttgtatttt ttcccagttt tgtttggcta tgccaccaca    240

gtcatcccca gggtctatac atactatgtt tcaactgtat tatttgccat ttttggcatt    300

agaatgcttc gggaaggctt aaagatgagc cctgatgagg gtcaagagga actggaagaa    360

gttcaagctg aattaaagaa gaaagatgaa gaagtaagcc atggcactgt tgatctggac    420

caaaaaggca ctcaactagg aataaacact ctacagaggt ttctcagtgg ccccatctgt    480
```

-continued gtgatatgcg gggctacaca aaaatagctt cttttgcttt gttctgttct tatacctgtc 540
tgtgatctga cttggggttg gtgtgaatgt agtagagaaa ggaagctgac agatgaatac 600
tgaacacagg taatcagttt ccttaattag gttgattata agctcctgaa aagcaggaac 660
tgtattttat aattttacct gtttctcccg tggtgtctag gatagtaagt gagcagagca 720
gtaaatactg tttggtttgt tcagacctgc ccgggcggcc 760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgtttttct 60
tttattaaca ggaattttga ttcttcaagg aagtggctca atttcaattt caggtgacca 120
ggtttatcgt gacttttcct tcttgtttac ttttcgctag gaaggggagt tgtaggggca 180
gattcaggta ttggaatagg aaaattacgt ctaaaccatg gaaatcttgg aaatggaatt 240
ggtggaagtg ggcgaaatgg atatgggtaa gggaacacaa aaaaccctga agctaattca 300
tcgctgtcac tgatacttct tttttctcgt tcctggtctt gagagactgg gaaaccaaca 360
gccactgcca agatggctgt gatcaggagg agaactttct tcatctcaaa cgtttcagtc 420
agttctttct ctcacctcgg ccgcgaccac gc 452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc 60
aagatacata gcaatgatag caggtttctt tttaaagctt agtattaata ttaaatattt 120
ttccccattt aaattttaca ttacttgcca agaaaaaaaa aaaattaaaa ctcaagttac 180
ttgaagcctg gacacacttc catgattagc cgggctaggt aaaagttggt ggctttattc 240
ttcctgctct ataagcagat ccaggcccta gaaagatggg accagggtat ataattgttt 300
ttgaaaagtg tgctacaaaa atggatggcc tgttataagc caggatacaa agttaaggat 360
gggggtaagg gagggacatt ttcttccaga agaaaagaca gaatttctga agagtcccag 420
tccataattt tcccaaaatg gttggaggag agggtaaaat ctcaacatga gtttcaaagt 480
actgtctctg tgaggggccg gtagatgcct tgctgaggag ggatggctaa tttggaccat 540
gccccatccc cagctaggag aatggaaatg gaaactttaa ttgcccagtg ggtgtgaaag 600
tgggctgaag cttggttggt actgaattct ctaagaggtt tcttctagaa acagacaact 660
cagacctgcc cgggcg 676

<210> SEQ ID NO 42
<211> LENGTH: 468
<212> TYPE: DNA
<213> ORGANISM: Homo sapien

<400> SEQUENCE: 42
agcgtggtcg cggccgaggt ttggccggga gcctgatcac ctgccctgct gagtcccagg 60
ctgagcctca gtctccctcc cttggggcct atgcagaggt ccacaacaca cagatttgag 120

-continued

```
ctcagccctg gtgggcagag aggtagggat ggggctgtgg ggatagtgag gcatcgcaat    180
gtaagactcg ggattagtac acacttgttg attaatggaa atgtttacag atccccaagc    240
ctggcaaggg aatttcttca actccctgcc ccccagccct ccttatcaaa ggacaccatt    300
ttggcaagct ctatgaccaa ggagccaaac atcctacaag acacagtgac catactaatt    360 aaaacccccct gcaaagccca gcttgaaacc ttcacttagg aacgtaatcg tgtcccctat    420
cctacttccc cttcctaatt ccacagacct gcccgggcgg ccgctcga                 468

<210> SEQ ID NO 43
<211> LENGTH: 408
<212> TYPE: DNA
<213> ORGANISM: Homo sapien

<400> SEQUENCE: 43
atcatatcaa aacactatct tcccatctgt ttctcaatgc ctgctacttc ttgtagatat     60
ttcatttcag gagagcagca gttaaacccg tggattttgt agttaggaac ctgggttcaa    120
acctctttcc actaattggc tatgtctctg gacagttttt tttttttttt tttttttaa    180 accctttctg aactttcact ttctatggct acctcaaaga attgttgtga ggcttgagat    240
aatgcatttg taaagggtct gccagatagg aagatgctag ttatggattt acaaggttgt    300
taaggctgta agagtctaaa acctacagtg aatcacaatg catttacccc cactgacttg    360
gacataagtg aaaactagcc cgaagtctct ttttcaaatt acttacag                 408

<210> SEQ ID NO 44
<211> LENGTH: 160
<212> TYPE: DNA
<213> ORGANISM: Homo sapien

<400> SEQUENCE: 44
tggtcgcggc cgaggtcttg tgtgccctgt ggtccagggg accaagaaca acaagatcca     60
ctctctgtgc tacaatgatt gcaccttctc acgcaacact ccaaccagga ctttcaacta    120
caacttctcc gctttggcaa acaccgtcac tcttgctgga                         160

<210> SEQ ID NO 45
<211> LENGTH: 231
<212> TYPE: DNA
<213> ORGANISM: Homo sapien

<400> SEQUENCE: 45
cgagcggccg cccgggcagg tctggggagg tgattccatc cagagtcata tctgttgtca     60
ccccaataag tcgatcagca aggctgacag gctgtgagga aaccccggcc ttgtagcctg    120
tcacctctgg ggggatgatg actgcctggc agacgtaggc tgtgatagat ttgggagaaa    180
acctgactca ccctcaggaa tccggaggtc ggtgacattg tcggtgcaca c             231

<210> SEQ ID NO 46
<211> LENGTH: 371
<212> TYPE: DNA
<213> ORGANISM: Homo sapien

<400> SEQUENCE: 46
cccgggcagg tctgtgtaac atgccaaggc tttgcacttt ctgcagagca gttttttatt     60
ttccttatca ggtacaggtt ttggtttttc ttgactatct ctgatgaatt tttcatgagt    120
ctgtatatgc agaatctttt ccctaaatac tgcttcgtcc catgtctgaa ggcgtaaaat    180
aaagtcattc atcatttttt ctttgtacat gtttatttgt tctttttcaa ttacaccaag    240
```

-continued cattactagt cagaaggaag cacttgctac ctcttgctct tcctctgcct ctggtttgga 300
tcattttgat gacattgccc acattactca tgaaggatga caagattgca ctgtgcaatg 360
tcaattgcct t 371

<210> SEQ ID NO 47
<211> LENGTH: 261
<212> TYPE: DNA
<213> ORGANISM: Homo sapien

<400> SEQUENCE: 47
gccctgtttt tatacacttc acatttgcag aaatataatg atgccctcat tatcagtgag 60
catgcacgaa tgaaagatgc tctggattac ttgaaagact tcttcagcaa tgtccgagca 120
gcaggattcg atgagattga gcaagatctt actcagagat ttgaagaaaa gctgcaggaa 180
ctagaaagtg tttccaggga tcccagcaat gagaatccta aacttgaaga cctctgcttc 240
atcttacaag aagagtacca c 261

<210> SEQ ID NO 48
<211> LENGTH: 701
<212> TYPE: DNA
<213> ORGANISM: Homo sapien

<400> SEQUENCE: 48
cgagcggccc ccgggcaggt ccaattagta caagtctcat gatataatca ctgcctgcat 60
acatatgcac agatccagtt agtgagtttg tcaagcttaa tctaattggt taagtctcaa 120
agagattatt attcttgatg tttgctttgt attggctaac aaatgtgcag aggtaataca 180
tatgtgatgt ccgatgtctc tgtctttttt tttgtcttta aaaaataatt ggcagcaact 240
gtatttgaat aaaatgattt cttagtatga ttgtaccgta atgaatgaaa gtggaacatg 300
tttctttttg aaagggagag aattgaccat ttattattgt gatgtttaag ttataactta 360
ttgagcactt ttagtagtga taactgtttt taaacttgcc taataccttt cttgggtatt 420
gtttgtaatg tgacttattt aaccccettt tttgtttgtt taagttgctg ctttaggtta 480
acagcgtgtt ttagaagatt taaatttttt tcctgtctgc acaattagtt attcagagca 540
agagggcctg attttataga agccccttga aaagaggtcc agatgagagc agagatacag 600
tgagaaatta tgtgatctgt gtgttgtggg aagagaattt tcaatatgta actacggagc 660
tgtagtgcca ttagaaactg tgaatttcca aataaatttg a 701

<210> SEQ ID NO 49
<211> LENGTH: 270
<212> TYPE: DNA
<213> ORGANISM: Homo sapien

<400> SEQUENCE: 49
agcggccgcc cgggcaggtc tgatattagt agctttgcaa ccctgataga gtaaataaat 60
tttatgggcg ggtgccaaat actgctgtga atctatttgt atagtatcca tgaatgaatt 120
tatggaaata gatatttgtg cagctcaatt tatgcagaga ttaaatgaca tcataatact 180
ggatgaaaac ttgcatagaa ttctgattaa atagtgggtc tgtttcacat gtgcagtttg 240
aagtatttaa attaaccact cctttcacag 270

<210> SEQ ID NO 50
<211> LENGTH: 271
<212> TYPE: DNA

-continued

<213> ORGANISM: Homo sapien

<400> SEQUENCE: 50
atgcatttat ccatatgaac ttgattattc tgaattactg actataaaaa ggctattgtg 60
aaagatatca cactttgaaa cagcaaatga attttcaatt ttacatttaa ttataagacc 120
acaataaaaa gttgaacatg cgcatatcta tgcatttcac agaagattag taaaactgat 180
ggcaacttca gaattatttc atgaagggta caaacagtct ttaccacaat tttcccatgg 240
tcttatcctt caaaataaaa ttccacacac t 271

<210> SEQ ID NO 51
<211> LENGTH: 241
<212> TYPE: DNA
<213> ORGANISM: Homo sapien

<400> SEQUENCE: 51
tggtcgcggc cgaggtgtga ggagatgaac tttgtgttaa tggggggcac tttaaatcga 60
aatggcttat ccccaccgcc atgtaagtta ccatgcctgt ctcctccctc ctacacattt 120
ccagctcctg ctgcagttat tcctacagaa gctgccattt accagccctc tgtgattttg 180
aatccacgag cactgcaggc cctccacagc gttactaccc agcaggcact cagctcttca 240
t 241

<210> SEQ ID NO 52
<211> LENGTH: 271
<212> TYPE: DNA
<213> ORGANISM: Homo sapien

<400> SEQUENCE: 52
tccaagactt aaaacttagg aaacacctat gatgccactt taactggaag taatggagac 60
atctgattcc aaattcacat tttaaatgcc tatttgcaat cagcaaagag ccaggtatgc 120
tgcatgctgc ttgctgtaag ttacgatttg gcttcactag ctcaaatttt ttcactccac 180
caaaagataa ggcacaggcc cgtttgtcca atcaagtttg ctgaaaatac tgcagcctga 240
gtgtagacaa acttcccctg aatttgctag a 271

<210> SEQ ID NO 53
<211> LENGTH: 493
<212> TYPE: DNA
<213> ORGANISM: Homo sapien

<400> SEQUENCE: 53
ttagcgtggt cgcggtccga ggtctggcct gactagctca ctctgaagag tgtctttcac 60
atggattaac caaaaaatgc attactgcct ttggcacact gtcttgaata ttctttctga 120
caatgagaaa atatgattta atggagtcgt tcaataacct cacaatctcg ctgttccgag 180
cagatagttt tcgtgccaac aggaactggc acatctagca ggttcacggc atgacctttt 240
tgtggactgg ctggcataat tggaatgggt tttgattttt cttctgctaa taactcttca 300
agcttttgaa gttttcaagc attcctctcc agttgcctgt ggttggttct tgaacaccat 360
ctccaacccc accacctcca gatgcaacct tgtctcgtga tacagacctg cccgggcggc 420
cctcaagggc gaattctgca gatatccatc acactggcgg ccgctcgagc atgcatctag 480
agggcccaat tcg 493

<210> SEQ ID NO 54
<211> LENGTH: 321

-continued

<212> TYPE: DNA
<213> ORGANISM: Homo sapien

<400> SEQUENCE: 54
cgtggtcgcg gccgaggtct gtttgcttgt tggtgtgagt ttttcttctg gagactttgt 60
actgaatgtc aataaactct gtgattttgt taggaagtaa aactgggatc tatttagcca 120
ctggtaagct tctgaggtga aggattcagg gacatctcgt ggaacaaaca ctccccactg 180
gactttctct ctggagatac ccttttgaat atacaatggc cttggctcac taggtttaaa 240
tacaaacaag tctgaaaccc actgaagact gagagattgc agcaatattc tctgaattag 300
gatcgggttc cataactcta a 321

<210> SEQ ID NO 55
<211> LENGTH: 281
<212> TYPE: DNA
<213> ORGANISM: Homo sapien

<400> SEQUENCE: 55
ttgcaaatga aactgtggat gtataataag aaaacacaag ggtttattct taacactaaa 60
attaacatgc cacacgaaga ctgcattaca gctctctgtt tctgtaatgc agaaaaatct 120
gaacagccca ccttggttac agctagcaaa gatggttact tcaaagtatg gatattaaca 180
gatgactctg acatatacaa aaaagctgtt ggctggacct gtgactttgt tggtagttat 240
cacaagtatc aagcaactaa ctgttgtttc tccgaagatg g 281

<210> SEQ ID NO 56
<211> LENGTH: 612
<212> TYPE: DNA
<213> ORGANISM: Homo sapien

<400> SEQUENCE: 56
gcgtggtcgc ggccgaggtc ctgtccgggg gcactgagaa ctccctctgg aattcttggg 60
gggtgttggg gagagactgt gggcctggag ataaaacttg tctcctctac caccaccctg 120
taccctagcc tgcacctgtc ctcatctctg caaagttcag cttccttccc caggtctctg 180
tgccactctg tcttggatgc tctggggagc tcatgggtgg aggagtctcc accagaggga 240
ggctcagggg actggttggg ccagggatga atatttgagg gataaaaatt gtgtaagagc 300
caaagaattg gtagtagggg gagaacagag aggagctggg ctatgggaaa tgatttgaat 360
aatggagctg ggaatatggc tggatatctg gtactaaaaa agggtcttta agaacctact 420
tcctaatctc ttccccaatc caaaccatag ctgtctgtcc agtgctctct tcctgcctcc 480
agctctgccc caggctcctc ctagactctg tccctgggct agggcagggg aggagggaga 540
gcagggttgg gggagaggct gaggagagtg tgacatgtgg ggagaggacc agacctgccc 600
gggcggccgt cg 612

<210> SEQ ID NO 57
<211> LENGTH: 363
<212> TYPE: DNA
<213> ORGANISM: Homo sapien

<400> SEQUENCE: 57
gtcgcggccg aggtcctgag cgtcacccta gttctgcccc tttttagctg tgtagacttg 60
gacaagacat ttgacttccc tttctccttg tctataaaat gtggacagtg gacgtctgtc 120
acccaagaga gttgtgggag acaagatcac agctatgagc acctcgcacg gtgtccagga 180

-continued tgcacagcac aatccatgat gcgttttctc cccttacgca ctttgaaacc catgctagaa 240
aagtgaatac atctgactgt gctccactcc aacctccagc gtggatgtcc ctgtctgggc 300 ccttttttctg ttttttattc tatgttcagc accactggca ccaaatacat tttaattcac 360
cga 363

<210> SEQ ID NO 58
<211> LENGTH: 750
<212> TYPE: DNA
<213> ORGANISM: Homo sapien

<400> SEQUENCE: 58
cgtggtcgcg gccgaggtct aattccacct gactggcaga acctgcgccc ctcgcctaac 60
ctgcgccctt ctcccaactc gcgtgcctca cagaacccag gtgctgcaca gccccgagat 120
gtggcccttc ttcaggaaag agcaaataag ttggtccaag tacttgatgc ttaaggaata 180
cacaaaggtg cccatcaagc gctcagaaat gctgagagat atcatccgtg aatacactga 240
tgtttatcca gaaatcattg aacgtgcatg ctttgtccta gagaagaaat ttgggattca 300
actgaaagaa attgacaaag aagaacacct gtatattctc atcagtaccc ccgagtccct 360
ggctggcata ctgggaacga ccaaagacac acccaagctc ggtctcttct tggtgattct 420
gggtgtcatc ttcatgaatg gcaaccgtgc cagtgaggct gtcttttggg aggcactacg 480
caagatggga ctgcgtcctg ggtgagaca tcccctccct tggagatcta aggaaacttc 540
tcacctatga gtttgtaaag cagaaatacc tggactacag acgagtgccc aacagcaacc 600
ccccggagta tgagttcctc tggggcctcc gtccctacca tgagactagc aagatgaaaa 660
tgctgagatt cattgcagag gttcagaaaa gagaccctcg tgactggact gcacagttca 720
tggaggctgc agatgaggac ctgcccgggc 750

<210> SEQ ID NO 59
<211> LENGTH: 505
<212> TYPE: DNA
<213> ORGANISM: Homo sapien

<400> SEQUENCE: 59
tggccgcccg ggcaggtcca gtctacaagc agagcactct catggggagc accagatgag 60
ttccagccgc agttctttta taagctttaa gtgcctcatg aagacgcgag gatctcttcc 120
aagtgcaacc tggtcacatc agggcacatt cagcagcaga agtctgtttc cagtatagtc 180
cttggtatgg ctaaattcca ctgtcccttt ctcagcagtc aataatccat gataaattct 240
gtacaacact gtagtcaata acagcagcac cagacagcat attaattctt ttaccataaa 300
tttgtgtgta attataatgt tctatgtgtg gtgttatcaa aagaatcact gtgtctctaa 360
atatcatata tgtatgtctg gataaataca ttgctgtaca acatctccaa catgcaggtc 420
atgctctaag acttggggat atagagtaat acatgtttcg tggacctcgg ccgcgaccac 480
gctaagggcg aattctgcag atatc 505

<210> SEQ ID NO 60
<211> LENGTH: 520
<212> TYPE: DNA
<213> ORGANISM: Homo sapien

<400> SEQUENCE: 60
cgtggtcgcg gccgaggtcc tcaggacaag gaaacaggta tcagcatgat ggtagcagaa 60
accttatcac caaggtgcag gagctgactt cttccaaaga gttgtggttc cgggcagcgg 120

-continued

```
tcattgcctg cccttgctgg agggctgatt ttagtgttgc ttattatgtt ggccctgagg    180

atgcttcgaa gtgaaaataa gaggctgcag gatcagcggc aacagatgct ctcccgtttg    240

cactacagct ttcacggaca ccattccaaa aaggggcagg ttgcaaagtt agacttggaa    300

tgcatggtgc cggtcagtgg gcacgagaac tgctgtctga cctgtgataa aatgagacaa    360

gcagacctca gcaacgataa gatcctctcg cttgttcact ggggcatgta cagtgggcac    420

gggaagctgg aattcgtatg acggagtctt atctgaacta cacttactga acagcttgaa    480

ggacctgccc gggcggccgc tcgaaagggg cgaattctgc                          520
```

```
<210> SEQ ID NO 61
<211> LENGTH: 447
<212> TYPE: DNA
<213> ORGANISM: Homo sapien

<400> SEQUENCE: 61

agagaggtgt ttttattctt tggggacaaa gccgggttct gtgggtgtag gattctccag     60

gttctccagg ctgtagggcc cagaggctta atcagaattt tcagacaaaa ctggaacctt    120

tctttttttcc cgttggttta tttgtagtcc ttgggcaaac caatgtcttt gttcgaaaga    180

gggaaaataa tccaaacgtt tttcttttaa cttttttttt aggttcaggg gcacatgtgt    240

aggcttgcta tataggtaaa ttgcatgtca ccagggtttg ttgtacagat tatttcatca    300

tccagataaa aagcatagta ccagataggt agttttttga tcctcaccct ccttccatgc    360

tccgacctca ggtaggcccc agtgtctgac ctgcccggcg gcccgctcga aagggccaat    420

tctgcagata tccatcacac tggccgg                                        447
```

```
<210> SEQ ID NO 62
<211> LENGTH: 83
<212> TYPE: PRT
<213> ORGANISM: Homo sapien

<400> SEQUENCE: 62

Lys Lys Val Leu Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys
```

```
<210> SEQ ID NO 63
<211> LENGTH: 683
<212> TYPE: DNA
<213> ORGANISM: Homo sapien

<400> SEQUENCE: 63

acaaagattg gtagctttta tattttttta aaaatgctat actaagagaa aaaacaaaag     60

accacaacaa tattccaaat tataggttga gagaatgtga ctatgaagaa agtattctaa    120

ccaactaaaa aaaatattga aaccactttt gattgaagca aaatgaataa tgctagattt    180

aaaaacagtg tgaaatcaca ctttggtctg taaacatatt tagctttgct tttcattcag    240
```

-continued atgtatacat aaacttattt aaaatgtcat ttaagtgaac cattccaagg cataataaaa 300
aaagwggtag caaatgaaaa ttaaagcatt tattttggta gttcttcaat aatgatrcga 360
gaaactgaat tccatccagt agaagcatct ccttttgggt aatctgaaca agtrccaacc 420
cagatagcaa catccactaa tccagcacca attccttcac aaagtccttc cacagaagaa 480
gtgcgatgaa tattaattgt tgaattcatt tcagggcttc cttggtccaa ataaattata 540
gcttcaatgg gaagaggtcc tgaacattca gctccattga atgtgaaata ccaacgctga 600
cagcatgcat ttctgcattt tagccgaagt gagccactga acaaaactct tagagcacta 660
tttgaacgca tctttgtaaa tgt 683

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64
ctgttcattt gtccgccagc tcctggactg gatgtgtgaa aggcatcaca tttccatttt 60
cctccgtgta aatgttttat gtgttcgcct actgatccca ttcgttgctt ctattgtaaa 120
tatttgtcat ttgtatttat tatctctgtg ttttccccct aaggcataaa atggtttact 180
gtgttcattt gaacccattt actgatctct gttgtatatt tttcatgcca ctgctttgtt 240
ttctcctcag aagtcgggta gatagcattt ctatcccatc cctcacgtta ttggaagcat 300
gcaacagtat ttattgctca gggtcttctg cttaaaactg aggaaggtcc acattcctgc 360
aagcattgat tgagacattt gcacaatcta aaatgtaagc aaagtaagtc attaaaaata 420
caccctctac ttgggcttta tactgcatac aaatttactc atgagccttc ctttgaggaa 480
ggatgtggat ctccaaataa agatttagtg tttattttga gctctgcatc ttancaagat 540
gatctgaaca cctctccttt gtatcaataa atagccctgt tattctgaag tgagaggacc 600
aagtatagta aaatgctgac atctaaaact aaataaatag aaaacaccag gccagaacta 660
tagtcatact cacacaaagg gagaaattta aactcgaacc aagcaaaagg cttcacggaa 720
atagcatgga aaaacaatgc ttccagtgg 749

<210> SEQ ID NO 65
<211> LENGTH: 612
<212> TYPE: DNA
<213> ORGANISM: Homo sapien

<400> SEQUENCE: 65
acagcagcag tagatggctg caacaacctt cctcctaccc cagcccagaa aatatttctg 60
ccccacccca ggatccggga ccaaaataaa gagcaagcag gccccccttca ctgaggtgct 120 gggtagggct cagtgccaca ttactgtgct ttgagaaaga ggaaggggat ttgtttggca 180
ctttaaaaat agaggagtaa gcaggactgg agaggccaga gaagatacca aaattggcag 240
ggagagacca tttggcgcca gtcccctagg agatgggagg agggagatag gtatgagggt 300
aggcgctaag aagagtagga ggggtccact ccaagtggca gggtgctgaa atgggctagg 360
accaacagga cactgactct aggtttatga cctgtccata cccgttccac agcagctggg 420
tgggagaaat caccattttg tgacttctaa taaaataatg ggtctaggca acagttttca 480

-continued atggatgcta aaacgattag gtgaaaagtt gatggagaat tttaattcag gggaattagg 540
ctgataccat ctgaaaccat ttggcatcat taaaaatgtg acaacctggt ggctgccagg 600
gaggaagggg ag 612

<210> SEQ ID NO 66
<211> LENGTH: 703
<212> TYPE: DNA
<213> ORGANISM: Homo sapien

<400> SEQUENCE: 66
tagcgtggtc gcggccgagg tacattgatg ggctggagag cagggttggc agcctgttct 60
gcacagaacc aagaattaca gaaaaaagtc caggagctgg agaggcacaa catctccttg 120
gtagctcagc tccgccagct gcagacgcta attgctcaaa cttccaacaa agctgcccag 180
accagcactt gtgttttgat tcttcttttt tccctggctc tcatcatcct gcccagcttc 240
agtccattcc agagtcgacc agaagctggg tctgaggatt accagcctca cggagtgact 300
tccagaaata tcctgaccca caaggacgta acagaaaatc tggagaccca agtggtagag 360
tccagactga gggagccacc tggagccaag gatgcaaatg gctcaacaag gacactgctt 420
gagaagatgg gagggaagcc aagacccagt gggcgcatcc ggtccgtgct gcatgcagat 480
gagatgtgag ctggaacaga ccttcctggc ccacttcctg atcacaagga atcctgggct 540
tccttatggc tttgcttccc actgggattc ctacttaggt gtctgccctc aggggtccaa 600
atcacttcag gacaccccaa gagatgtcct ttagtctctg cctgaggcct agtctgcatt 660
tgtttgcata tatgagaggg tacctgcccg ggcggccgct cga 703

<210> SEQ ID NO 67
<211> LENGTH: 1022
<212> TYPE: DNA
<213> ORGANISM: Homo sapien

<400> SEQUENCE: 67
cttgagaaag caggattgtt ttaagttcca agatttaaca aacttactgt tcagcatcat 60
attcaagcct aaaaggaaga taggattttc aagatatatt tccaacttct ttaacatggc 120
accatggatg aactgtttct cagcactgtg ctgcttcact tggaattaag gatgaattgg 180
gaggagacag tatgacatag gtgggtaggt tgggtggtga ggggaaccag ttctaatagt 240
cctcaactcc actccagctg ttcctgttcc acacggtcca ctgagctggc ccagtccctt 300
tcactcagtg tgtcaccaaa ggcagcttca aggctcaatg gcaagagacc acctataacc 360
tcttcacctt ctgctgcctc tttctgctgc cactgactgc catggccatc tgctatagcc 420
gcattgtcct cagtgtgtcc aggccccaga caaggaaggg gagccatggt gagactccaa 480
ttcccaggcc ttaatcctta accctagacc tgttgcctct agcatcattt atttatctac 540
ctacctaata gctatctacc agtcattaaa ccatggtgag attctaacca tgtctagcac 600
ctgatgctag agataatttt gttgaatccc ttcaattata aacagctgag ttagctggac 660
aaggactagg gaggcaatca gtattattta ttcttgaaca ccatcaagtc tagacttggt 720
ggcttcatat ttctatcata atccctgggg gtaagaaatc atatagcccc aggttgggaa 780
ggggaaaacg gtttgcaaca ttctcctcct tgtaggaggc gagctctgtc tcactagcta 840
tgcccctcca tcaattcacc ctatactcag atcagaagct gagtgtctga attacagtat 900
attttctaaa ttcctagccc ctgctggtga atttgccctc ccccgctcct ttgacaattg 960
tccccgtgtt cgtctccggg ccctgagact ggccctgctt atcttgctga ccttcatcct 1020

-continued ct 1022

<210> SEQ ID NO 68
<211> LENGTH: 449
<212> TYPE: DNA
<213> ORGANISM: Homo sapien

<400> SEQUENCE: 68
ccagatccat tttcagtggt ctggatttct ttttattttc ttttcaactt gaaagaaact 60
ggacattagg ccactatgtg ttgttactgc cactagtgtt caagtgcctc ttgttttccc 120
agagatttcc tgggtctgcc agaggcccag acaggctcac tcaagctctt taactgaaaa 180
gcaacaagcc actccaggac aaggttcaaa atggttacaa cagcctctac ctgtcgcccc 240
agggagaaag gggtagtgat acaagtctca tagccagaga tggttttcca ctccttctag 300
atattcccaa aaagaggctg agacaggagg ttattttcaa ttttattttg gaattaaata 360 ctttttttccc tttattactg ttgtagtccc tcacttggat atacctctgt tttcacgata 420
gaaataaggg aggtctagag cttctattc 449

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69
gcccttagcg tgggtcgcgg cncgangtct ggagcntatg tgatncctat ggtncncagg 60
cnnatactgc tantctcatt tattctcctg cnacctantc ctctnctctg gaatcacacc 120
attattgcct gttaacactg gactgtgagt accangcaat taatttgcac caanaaagtt 180
gagggtatta tcanatattg caatctgtac agagggaaga tgatttcaat ttgatttcaa 240
cttaaccttc atctttgtct gttaacacta atagagggtg tctaataaaa tggcaaattt 300
gngatctcat tnggtataac tacactcttt ttcacagatg tgatgactga atttccanca 360
acctgcccgg gcggncgntc naagggc 387

<210> SEQ ID NO 70
<211> LENGTH: 836
<212> TYPE: DNA
<213> ORGANISM: Homo sapien

<400> SEQUENCE: 70
tattccattt acaaaataaa ttcagccctg cactttcttt agatgccttg atttccagaa 60
tggagcttag tgctactgaa taccctggcc acagagccac ctcaggatat tcttttctcc 120
accctagttt atttatttat agatatctgt ttacaaagtc tgtagtaaat cctgatgctg 180
accatctgaa atgtactttt tttctgaatg ctgtttcaat ctaaaatagc agcttttgag 240
aaaacaatga tgtaaattcc ttatgataaa aggatgattc tatatattct ttaatgatat 300
taaatatgcc gaagccaagc acacagtctt tctaaagtgt gtgtatgttt gtgtgaatgt 360
gaatgatact gatcttatat ctgttaaaag ttgttttaaa aagctgtggc atcccattgt 420
tcatatttgc caagtcttct gtaaagatgt ctaggacgaa atattttatg tgctaatgca 480
tgtatttgta aaccagattt gtttaccact caaaattaac ttgttttctt catccaaaaa 540

-continued agtttatttc ttccacgtac ttaaattttc tgtgtgggta taatatagct ttctaatttt 600
tttctttcac aaaggcaggt tcaaaattct gttgaaagaa aaatgctttc tgaaactgag 660
gtataacacc agagcttgct gtttaaagga ttatatgatg tacatcagtt ctataaatgt 720
gctcagcagt ttaacatgtg aatcctgttt taaagtgctc agatttcaac tgtgtaagcc 780
attgatataa cgctgtaatt aaaaatgttt atatgaaaaa aaaaaaaaaa aaaaaa 836

<210> SEQ ID NO 71
<211> LENGTH: 618
<212> TYPE: DNA
<213> ORGANISM: Homo sapien

<400> SEQUENCE: 71
gttgcagtga gctcaagtgt tgggtgtatc agctcaaaac accatgtgat gccaatcatc 60
tccacaggag caatttgttt accttttttt tctgatgctt tactaacttc atcttttaga 120
tttaaatcat tagtagatcc tagaggagcc agtttcagaa aatatagatt ctagttcagc 180
accacccgta gttgtgcatt gaaataatta tcattatgat tatgtatcag agcttctggt 240
tttctcattc tttattcatt tattcaacaa ccacgtgaca aacactggaa ttacaggatg 300
aagatgagat aatccgctcc ttggcagtgt tatactatta tataacctga aaaaacaaac 360
aggtaatttt cacacaaagt aatagatatc atgacacatt taaaataggg cactactgga 420
acacacagat aggacatcca ggttttgggt caatattgta gactttttgg tggatgagat 480
atgcaggttg atrccagaag gacaacaaaa acatatgtca gatagaaggg aggagcaaat 540
gccaagagct ggagctgagg aagatcactg tgaaattcta tgtagtctag ttggctggat 600
gctagagcaa agaggtgg 618

<210> SEQ ID NO 72
<211> LENGTH: 806
<212> TYPE: DNA
<213> ORGANISM: Homo sapien

<400> SEQUENCE: 72
tctacgatgg ccatttgctc attgtctttc ctctgtgtgt agtgagtgac cctggcagtg 60
tttgcctgct cagagtggcc cctcagaaca acagggctgg ccttggaaaa accccaaaac 120
aggactgtgg tgacaactct ggtcaggtgt gatttgacat gagggccgga ggcggttgct 180
gacggcagga ctggagaggc tgcgtgcccg gcactggcag cgaggctcgt gtgtccccca 240
ggcagatctg ggcactttcc caacccaggt ttatgccgtc tccagggaag cctcggtgcc 300
agagtggtgg gcagatctga ccatccccac agaccagaaa caaggaattt ctgggattac 360
ccagtccccc ttcaacccag ttgatgtaac cacctcattt tttacaaata cagaatctat 420
tctactcagg ctatgggcct cgtcctcact cagttattgc gagtgttgct gtccgcatgc 480
tccgggcccc acgtggctcc tgtgctctag atcatggtga ctcccccgcc ctgtggttgg 540
aatcgatgcc acggattgca ggccaaattt cagatcgtgt ttccaaacac ccttgctgtg 600
ccctttaatg ggattgaaag cacttttacc acatggagaa atatattttt aatttgtgat 660
gcttttctac aaggtccact atttctgagt ttaatgtgtt tccaacactt aaggagactc 720
taatgaaagc tgatgaattt tcttttctgt ccaaacaagt aaaataaaaa taaaagtcta 780
tttagatgtt gaaaaaaaaa aaaaaa 806

<210> SEQ ID NO 73
<211> LENGTH: 301

-continued

<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73
actctggtaa gcttgttgtt gtccaagtga agctccctca gatgaggcgt gttggccana 60
gagccattgt caacagcaga gatgctgttg aaactcaatc ccaacttagc caaattattc 120
agtcctttca ggctagctgc atcaactctg ctgattttgt tgccatcaag atgtaattcc 180
gtaagggaag gaggaagacc ttgaggaatg ctggygatat tggyatcagc aatgcggatg 240
tasgaagagc ttcttcmttc cctggaaagc cccattttca atyccttgag ctcttcakcg 300
g 301

<210> SEQ ID NO 74
<211> LENGTH: 401
<212> TYPE: DNA
<213> ORGANISM: Homo sapien

<400> SEQUENCE: 74
agtttacatg atccctgtaa cagccatggt ctcaaactca gatgcttcct ccatctgcca 60
agtgtgttct ggatacagag cacatcgtgg cttctggggt cacactcagc ttaggctgtg 120
ggtccacaga gcactcatct ggctgggcta tggtggtggt ggctctactc aagaagcaaa 180
gcagttacca gcacattcaa acagtgtatt gaacatcttt taaatatcaa agtgagaaac 240
aagaaggcaa cataataatg ttatcagaaa gatgttagga agtaaggaca gctgtgtaaa 300
gcttgaggct gaaaagtagc ttgccagctt catttctttg gtttcttggg tagtgggccg 360
ccggaacagc aagatgtgag gttctggttc atggatcata t 401

<210> SEQ ID NO 75
<211> LENGTH: 612
<212> TYPE: DNA
<213> ORGANISM: Homo sapien

<400> SEQUENCE: 75
ttatttttca atttttattt tggttttctt acaaaggttg acattttcca taacaggtgt 60
aagagtgttg aaaaaaaaat tcaaattttt ggggagcgag ggaaggagtt aatgaaactg 120
tattgcacaa tgctctgatc aatccttctt tttctctttt gcccacaatt taagcaagta 180
gatgtgcaga agaaatggaa ggattcagct ttcagttaaa aaagaagaag aagaaatggc 240
aaagagaaag ttttttcaaa tttctttctt ttttaattta gattgagttc atttatttga 300
aacagactgg gccaatgtcc acaaagaatt cctggtcagc accaccgatg tccaaaggtg 360
caatatcaag gaagggcagg cgtgatggct tatttgtttt gtattcaatg attgtctttc 420
cccattcatt tgtcttttta gagcagccat ctacaagaac agtgtaagtg aacctgctgt 480
tgccctcagc aacaagttca acatcattag agccctgtag aatgacagcc tttttcaggt 540
tgccagtctc ctcatccatg tatgcaatgc tgttcttgca gtggtaggtg atgttctgag 600
aggcatagtt gg 612

<210> SEQ ID NO 76
<211> LENGTH: 844
<212> TYPE: DNA
<213> ORGANISM: Homo sapien -continued

<400> SEQUENCE: 76

```
ggctttcgag cggccgcccg ggcaggtctg atggttctcg taaaaacccc gctagaaact     60
gcagagacct gaaattctgc catcctgaac tcaagagtgg agaatactgg gttgacccta    120
accaaggatg caaattggat gctatcaagg tattctgtaa tatggaaact ggggaaacat    180
gcataagtgc caatcctttg aatgttccac ggaaacactg gtggacagat tctagtgctg    240
agaagaaaca cgtttggttt ggagagtcca tggatggtgg ttttcagttt agctacggca    300
atcctgaact tcctgaagat gtccttgatg tgcagcykgc attccttcga cttctctcca    360
gccgagcttc ccagaacatc acatatcact gcaaaaatag cattgcatac atggatcagg    420
ccagtggaaa tgtaaagaag gccctgaagc tgatggggtc aaatgaaggt gaattcaagg    480
ctgaaggaaa tagcaaattc acctacacag ttctggagga tggttgcacg aaacacactg    540
gggaatggag caaaacagtc tttgaatatc gaacacgcaa tgctgttcct tgacattgca    600
ccaccaatgt ccagaggtgc aatgtcaagg aacggcaggc gagatggctt atttgttttg    660
tattcaatga ttgtcttgcc ccattcattt gtctttttgg agcagccatc gactaggaca    720
gagtaggtga acctgctgtt gccctcagca acaagttcca catcgttgga accctgcaga    780
agcacagcct tgttcaarct gcccgtctcc tcatccagat acctcggccg cgaccacgct    840
aatc                                                                 844
```

<210> SEQ ID NO 77
<211> LENGTH: 314
<212> TYPE: DNA
<213> ORGANISM: Homo sapien

<400> SEQUENCE: 77

```
ccagtcctcc acttggcctg atgagagtgg ggagtggcaa gggacgtttc tcctgcaata     60
gacacttaga tttctctctt gtgggaagaa accacctgtc catccactga ctcttctaca    120
ttgatgtgga aattgctgct gctaccacca cctcctgaag aggcttccct gatgccaatg    180
ccagccatcc tggcatcctg gccctcgagc aggctgcggt aagtagcgat ctcctgctcc    240
agccgtgtct ttatgtcaag cagcatcttg tactcctggt tctgagcctc catctcgcat    300
cggagctcac tcag                                                      314
```

<210> SEQ ID NO 78
<211> LENGTH: 548
<212> TYPE: DNA
<213> ORGANISM: Homo sapien

<400> SEQUENCE: 78

```
accaagagcc aagtgttaca caggatattt taaaaataaa atgtttttgg aatcctcacc     60
tcccatgcta tcttctaaga taactacaaa tattcttcaa agatttaact gagttctgcc    120
aaggacctcc caggactcta tccagaatga ttattgtaaa gctttacaaa tcccaccttg    180
gccctagcga taattaggaa atcacaggca aacctcctct ctcggagacc aatgaccagg    240
ccaatcagtc tgcacattgg ttttgttaga tactttgtgg agaaaaacaa aggctcgtga    300
tagtgcagct ctgtgcctac agagagcctc ccttttggtt ctgaaattgc tgatgtgaca    360
gagacaaagc tgctatgggt ctaaaacctt caataaagta actaatgaca ctcaaggtcc    420
tgggactctg agacagacgg tggtaaaacc cacagctgcg attcacattt ccaatttatt    480
ttgagctctt tctgaagctg ttgcttccta cctgagaatt cccatttaga gagctgcaca    540
gcacagtc                                                             548
```

<210> SEQ ID NO 79
<211> LENGTH: 646
<212> TYPE: DNA
<213> ORGANISM: Homo sapien

<400> SEQUENCE: 79

| | | | | | |
|---|---|---|---|---|---|
| accccgtcac | tatgtgaata | aaggcagcta | gaaaatggac | tcaattctgc | aagccttcat | 60 |
| ggcaacagcc | catattaaga | cttctagaac | aagttaaaaa | aaatcttcca | tttccatcca | 120 |
| tgcatgggaa | aagggcttta | gtatagttta | ggatggatgt | gtgtataata | ataaaatgat | 180 |
| aagatatgca | tagtgggga | ataaagcctc | agagtccttc | cagtatgggg | aatccattgt | 240 |
| atcttagaac | cgagggattt | gtttagattg | ttgatctact | aatttttttc | ttcacttata | 300 |
| tttgaatttt | caatgatagg | acttattgga | aattggggat | aattctgttg | tggtattaaa | 360 |
| taatattcat | tttttaaaaa | ctcatcttgg | tattgagtta | gtgcattgac | ttccaatgaa | 420 |
| ttgacataag | cccatatttc | attttaacca | gaaacaaaaa | ctagaaaatg | ttactcccta | 480 |
| aataggcaac | aatgtatttt | ataagcactg | cagagattta | gtaaaaaaca | tgtatagtta | 540 |
| ctttagaaac | aacttctgac | acttgagggt | tacccaatgg | tctccttccc | attctttata | 600 |
| tgaggtaaat | gcaaaccagg | gagccaccga | ataaacagcc | ctgagt | | 646 |

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80

| | | | | | |
|---|---|---|---|---|---|
| gtctgaatga | gcttcnctgc | gagatgganc | ancataaccc | agaantccaa | aancntanng | 60 |
| aacgnnaaaa | cccgntngaa | caagnaaacn | gcaactnacg | gccgcctgnt | gnagggcgag | 120 |
| gacgcccacc | tctcctcctc | ccagttctcc | tctggatcgc | agncatccan | agatgtgacc | 180 |
| tcttccagcc | gccaaatccg | caccaaggtc | atggatgtgc | acgatggcaa | ggtgggtgtc | 240 |
| cacccacgaa | caggtccttc | gcaccaagaa | ctgagg | | | 276 |

<210> SEQ ID NO 81
<211> LENGTH: 647
<212> TYPE: DNA
<213> ORGANISM: Homo sapien

<400> SEQUENCE: 81

| | | | | | |
|---|---|---|---|---|---|
| gtcctgcctt | tcatcttttc | tttaaaaaaa | ataaatgttt | acaaaacatt | tccctcagat | 60 |
| tttaaaattc | atggaagtaa | taaacagtaa | taaaatatgg | atactatgaa | aactgacaca | 120 |
| cagaaaaaca | taaccataaa | atattgttcc | aggatacaga | tattaattaa | gagtgacttc | 180 |
| gttagcaaca | cgtagacatt | catacatatc | cggtggaaga | ctggtttctg | agatgcgatt | 240 |
| gccatccaaa | cgcaaatgct | tgatcttgga | gtaggrtaat | ggccccagga | tcttgcagaa | 300 |
| gctctttatg | tcaaacttct | caagttgatt | gacctccagg | taatagtttt | caaggttttc | 360 |
| attgacagtt | ggtatgtttt | taagcttgtt | ataggacaga | tccagctcaa | ccagggatga | 420 |
| cacattgaaa | gaatttccag | gtattccact | atcagccagt | tcgttgtgag | ataaacgcag | 480 |
| atactgcaat | gcattaaaac | gcttgaaata | ctcatcaggg | atgttgctga | tcttattgtt | 540 |

-continued

```
gtctaagtag agagttagaa gagagacagg gagaccagaa ggcagtctgg ctatctgatt    600

gaagctcaag tcaaggtatt cgagtgattt aagaccttta aaagcag                  647


<210> SEQ ID NO 82
<211> LENGTH: 878
<212> TYPE: DNA
<213> ORGANISM: Homo sapien

<400> SEQUENCE: 82

ccttctttcc ccactcaatt cttcctgccc tgttattaat taagatatct tcagcttgta     60

gtcagacaca atcagaatya cagaaaaatc ctgcctaagg caaagaaata taagacaaga    120

ctatgatatc aatgaatgtg ggttaagtaa tagatttcca gctaaattgg tctaaaaaag    180

aatattaagt gtggacagac ctatttcaaa ggagcttaat tgatctcact tgttttagtt    240

ctgatccagg gagatcaccc ctctaattat ttctgaactt ggttaataaa agtttataag    300

atttttatga agcagccact gtatgatatt ttaagcaaat atgttattta aaatattgat    360

ccttcccttg gaccaccttc atgttagttg ggtattataa ataagagata caaccatgaa    420

tatattatgt ttatacaaaa tcaatctgaa cacaattcat aaagatttct cttttatacc    480

ttcctcactg gccccctcca cctgcccata gtcaccaaat tctgttttaa atcaatgacc    540

taagatcaac aatgaagtat tttataaatg tatttatgct gctagactgt gggtcaaatg    600

tttccatttt caaattattt agaattctta tgagtttaaa atttgtaaat ttctaaatcc    660

aatcatgtaa aatgaaactg ttgctccatt ggagtagtct cccacctaaa tatcaagatg    720

gctatatgct aaaaagagaa aatatggtca agtctaaaat ggctaattgt cctatgatgc    780

tattatcata gactaatgac atttatcttc aaaacaccaa attgtcttta gaaaaattaa    840

tgtgattaca ggtagagaac ctcggccgcg accacgct                            878


<210> SEQ ID NO 83
<211> LENGTH: 645
<212> TYPE: DNA
<213> ORGANISM: Homo sapien

<400> SEQUENCE: 83

acaaacattt tacaaaaaag aacattacca atatcagtgg cagtaagggc aagctgaaga     60

ataaatagac tgagtttccg ggcaatgtct gtcctcaaag acatccaaac tgcgttcagg    120

cagctgaaac aggcttcttt cccagtgaca agcatatgtg gtcagtaata caaacgatgg    180

taaatgaggc tactacatag gcccagttaa caaactcctc ttctcctcgg gtaggccatg    240

atacaagtgg aactcatcaa ataatttaaa cccaaggcga taacaacgct atttcccatc    300

taaactcatt taagccttca caatgtcgca atggattcag ttacttgcaa acgatcccgg    360

gttgtcatac agatacttgt ttttacacat aacgctgtgc catcccttcc ttcactgccc    420

cagtcaggtt tcctgttgtt ggaccgaaag gggatacatt ttagaaatgc ttccctcaag    480

acagaagtga gaaagaaagg agaccctgag gccaggatct attaaacctg gtgtgtgcgc    540

aaaagggagg gggaaggcag gaatttgaaa ggataaacgt ctcctttgcg ccgaggaatc    600

aggaagcgtg actcacttgg gtctgggacg ataccgaaat ccggt                    645


<210> SEQ ID NO 84
<211> LENGTH: 301
<212> TYPE: DNA
<213> ORGANISM: Homo sapien
<220> FEATURE:
<221> NAME/KEY: misc_feature
```

-continued

<222> LOCATION: (1)...(301)
<223> OTHER INFORMATION: n = A,T,C or G

<400> SEQUENCE: 84

```
tctgatgtca atcacaactt gaaggatgcc aatgatgtac caatccaatg tgaaatctct     60

cctcttatct cctatgctgg agaaggatta gaaggttatg tggcagataa agaattccat    120

gcacctctaa tcatcgatga gaatggagtt catgggctgg tgaaaaatgg tatttgaacc    180

agataccaag ttttgtttgc cacgatagga atagctttta tttttgatag accaactgtg    240

aacctacaag acgtcttgga caactgaagn ttaaatatcc acangggttt attttgcttg    300

g                                                                   301
```

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

```
agcgtgggtc gcggcncgan gtagagaacc gactgaaacg tttgagatga agaaagttct     60

cctcctgatc acagccatct tggcagtggc tgttggtttc ccagtctctc aagaccagga    120

acgagaaaaa agaagtatca gtgacagcga tgaattagct tcagggtttt ttgtgttccc    180

ttacccatat ccatttcgcc cacttccacc aattccattt ccaagatttc catggtttan    240

acgtaatttt cctattccaa tacctgaatc tgcccctaca actccccttc ctagcg        296
```

<210> SEQ ID NO 86
<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300

agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctccccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                         806
```

<210> SEQ ID NO 87
<211> LENGTH: 620
<212> TYPE: DNA

-continued

<213> ORGANISM: Homo sapien

<400> SEQUENCE: 87
tttttgcatc agatctgaaa tgtctgagag taatagtttc tgttgaattt ttttttgttc 60
atttttctgc acagtccatt ctgtttttat tactatctag gcttgaaata tatagtttga 120
aattatgaca tccttcctct ttgttatttt cctcatgatt gctttggcta ttcaaagttt 180
attttagttt catgtaaatt tttgaattgt attttccatt attgtgaaaa tagtaccact 240
gcaattttaa taggaagttt attgaatcta tagattactt tggataatat ggcacttcaa 300
taatattcat gttttcaatt catagacaaa atattttaaa atttatttgt atcttttcta 360
atttttcctt tttttattgt aaagatttac ctccttggtt aatattttcc tcagaaattt 420
attatttaag gtatagtcaa taaaattttc ttcctctatt ttgtcagata gtttaagtgt 480
atgaaaccat agatatactt gtatgttaat tttatatttt gctaatttac tgagtgtatt 540
tattagttta gagaggtttt aatgtactgt ttatggtttt ttaaatataa gattacttat 600
tttttaaaaa aaaaaaaaaa 620

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88
tagctgtgnt cagcaggccg aggttttttt tttttttgag atggagtctc gccctgtcac 60
ccaggctgga gtgcagtggc ctgatctcag ctcactgcaa gctccacctc ctggattcac 120
gctattctcc tgcctcagcc tcccaagtag ctgggactac aggcgcccgc caccacgccc 180
agctaattnt ttgnattttt agtacnagat gcggtttcat cgtgttagcc agcatggnct 240
cgatctcctg acctcgtgaa ctgcccgcct cggcctccca aagacctgcc cgggcnggcc 300
gctcgaaa 308

<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89
agcggccgcc cgggcaggtc tgttaagtaa catacatatc accttaataa aaatcaagat 60
gaaatgtttt agaaactatt ttatcaaaag tggctctgat acaaagactt gtacatgatt 120
gttcacagca gcactattaa tgccaaaaag tagacaaaac ctaaatgtcc attaactgat 180
aagcaaaatg tggtatatcc atacaatgga atattatgta gcccacaaca tggcatggag 240
tactacaaca tggatgagcc tcaaaaacgt tatgctaaat gaaaaaagtc agatatagga 300
aaccacatgt catatgatcc catttatatg aaatagccag aaaaggcaag tcatagaaac 360
aagatagatc ggaaaatggg ttggaggact acaaatggca ccagggatct ttgaagttga 420
tggaaatggt ctaaaatcag actgtggntg tggttgaaca agtctgtaaa tttaccaaaa 480
tgcgttaata ca 492

-continued

<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90
tcgagcggcc gcccgggcag gtacaagctt tttttttttt tttttttttt ttttctaaca 60
gttctctgtt ttattgcaat acagcaaagt ctggttaata ttaagngata tcaacataaa 120
gtattggtga ggagtctttt gtgacatttt ttaccatccc accttaaata tttctgtgca 180
aaanaatcca catcattgtt tggtancana ggatctctta aaaagttccc taanacactg 240
agggcataaa accaaacaaa ataaaataag gagtgatagg ctaaagcagt atcttcccct 300
ccatccacat ttgncaagca ttatattcta accaaaaaat gatcacacca ggccatgcaa 360
aactgtccaa tattaccgag aaaaaaccct 390

<210> SEQ ID NO 91
<211> LENGTH: 192
<212> TYPE: DNA
<213> ORGANISM: Homo sapien

<400> SEQUENCE: 91
agcgtggtcg cggccgaggt ctgtcaatta atgctagtcc tcaggattta aaaaataatc 60
ttaactcaaa gtccaatgca aaaacattaa gttggtaatt actcttgatc ttgaattact 120
tccgttacga aagtccttca catttttcaa actaagctac tatatttaag gcctgcccgg 180
gcggccgctc ga 192

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92
agcgtggtcg cggccgaggt ctgacaacta acaaagaagc aaaaactggc atcttggaca 60
tcctagtatt acacttgcaa gcaattagaa cacaaggagg gccaaggaaa aagtttagct 120
ttgaatcact tccaaatcta ctgattttga ggttccgcag tagttctaac aaaacttttc 180
agacaatgtt aactttcgat taagaaagaa aaaaacccca aacatcttca ggaattccat 240
gccaggttca gtctcttcca gtgagcccgc ttgctaaaag tccacgtgca ccattaatta 300
gctgggctgg cagcaccatg taaaaagaag cctattcacc accaaccaca cagactagac 360
atgtaaagta ggatcaagta atggatgaca accatggtcg tggaatatgg tcaatgagag 420
tcagaaaagt acaggcacca gtacaagcag cagataacag aattgacggg ccaaaggata 480
aaaataggct tatttaaata ggatgctaca gaacacatnc acttctaatt ggaagctgct 540
ttacactggg tggcattgna ccatatgcat 570

<210> SEQ ID NO 93
<211> LENGTH: 446
<212> TYPE: DNA

-continued

<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93
tcgagcggcc gcccgggcag gtccaggttt ttatttagtt gtgtaatctt ggacaagtta 60
cctaactttt ttgagtctga atatatttaa tctgcaaaat gagaatcatg ataatacgtc 120
ataggcttaa ttaggaggat taaatgaaat aatttatagg tggtgccatg gttacataca 180
agtattagta gttaattctt ttcctttgtt tacttttata gtataggttg gatgaaggtt 240
ccagtatagg caaaaatact acttgggggt aaagtagagt gtgatacttt atttgaaatg 300
ttccctgaat ctgatcttta ctttttgnta ctgctgcact acccaaatcc aaattttcat 360
cccaacattc ttggatttgt gggacagcng tagcagcttt tccaatataa tctatactac 420
atcttttctt actttggtgc tttttg 446

<210> SEQ ID NO 94
<211> LENGTH: 409
<212> TYPE: DNA
<213> ORGANISM: Homo sapien

<400> SEQUENCE: 94
cgagcggccg cccgggcagg tccatcagct cttctgctta gaatacgagg cagacagtgg 60
agaggtcaca tcagttatcg tctatcaggg tgatgaccca agaaaggtga gtgagaaggt 120
gtcggcacac acgcctctgg atccacccat gcgagaagcc ctcaagttgc gtatccagga 180
ggagattgca aagcgccaga gccaacactg accatgttga aggcgttctc tccaggctgg 240
attcactgca ctcggaagaa ttctgcccag ggaatttagt gtgggggtac caggaccagt 300
ttgtcttgat cttgagaccc ccagagctgc tgcatccata gggtgttgca ggactacacc 360
tggcctgcct tgcagtcatt ctttcttata tgttgaccca tttgcccaa 409

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95
tcgagcggcc gcccgggcag gtcctacttg tttgcagctt ccacacactg cacctaccta 60
ctacctctct tccatgctta actgggttta gaaaggtgag ctatgcgtag aagaactact 120
tgggatattc aagtgctgta tttgaacgat aagcctatag ataacagtct gaagctgcaa 180
gggagacttt gttagtacac tactataaac aggtaaacta cctgtttgta cttgatatag 240
tgcatatgaa atgactgatt taatacaaaa ctacagaaca tgcaaaattt tttctgagat 300
gttaagtatt acttcagtgg agaacaaaac ttacttaacc tttcgctaat gcatgtagta 360
ccagaaagca aacatggttt tagcttcctt tactcaaaat atgaacatta agtggttgtg 420
aattttgtct gccaagtggt tcagaaaata cattataaat aacctaagtt aaaaaaaaga 480 aactgngaac 490

<210> SEQ ID NO 96
<211> LENGTH: 223

-continued

<212> TYPE: DNA
<213> ORGANISM: Homo sapien

<400> SEQUENCE: 96
agcgtggtcg cggccgaggt ctggaagccc accctaggac ttgaatggca ccttgtcctt 60
tctctgccag taatgcaatc caacacaata tgctacaggg aaaacagaat ttccacggtg 120
ccgccctctg gtacaaggga aacagcacgc aaagcaaaag gccacagagg gctccctgag 180
aatccagtac aactaagcga ggacctgccc gggcggccgc tcg 223

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97
tcgagcggcc gcccgggcag gtctgtgcag gagacactga agtgggtagt gtccataatc 60
tttttagcct gttgctgaaa ttccagttgt actccttcaa accaaaatgc ttacaggatc 120
atgggaaagc ctcggttgca gaaatcaaga caggcaagtg ggaagataac tcggctttga 180
ggttaaacag atctgggttc aaagcatagt ttcactctct gtcttgtgaa gtgtcctggg 240
tgaagtcatt tcctctcttg aatttcagag aggatgaaaa tataaaaagt ataataacta 300
tcttcataat ctttgtgagg attaaagaag acgaagtgtg tgaaaagcta agcacagagc 360
aggcattcta caataagtag ttattatttt tggaaccatc ccgnccctag ccccagccca 420
attaccttct cttagnctct tcatatcgaa ngccgtaatc ttgaccttct cttgcnactg 480
gattggtgct ggttgatgcc caaacttccc gagatgctgt ctgggaa 527

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98
tcgagcggcc gcccgggcag gtctggctcc catggccctt ggggtggcct gactctgtca 60
ctattcctaa aaccttctag gacatctgct ccaggaagaa ctttcaacac caaaattcat 120
ctcaatttta cagatgggaa aagtgattct gagaccagac cagggtcagg ccaaggtcat 180
ccagcatcag tggctgggct gagactgggc ccagggaacc ctgtctgctc ctctttttcc 240
cagagctgtg agttctctag ccaaggctgc actcttgagg gagagccagg aagcatagct 300
gaggccatga caacctcact cttcacctga aaatttaacc cgtggcagag gatccaggca 360
catataggct tcggagccaa acaggacctc ggccgcgacc acgctaagcc gaattccagc 420
acactggcgg ccgttactag tggatcccga gcttnggtac caagcttggc gtaatcatgg 480
gcatagctgg ttcctggggt gaaaatggta tccg 514

<210> SEQ ID NO 99
<211> LENGTH: 530
<212> TYPE: DNA
<213> ORGANISM: Homo sapien
<220> FEATURE:

-continued

<221> NAME/KEY: misc_feature
<222> LOCATION: (1)...(530)
<223> OTHER INFORMATION: n = A,T,C or G

<400> SEQUENCE: 99
tcgagcggcc gcccgggcag gtctgaagaa acaggtataa atttggcagc cagtaatttt 60
gacagggaag ttacagcttg catgacttta aatatgtaaa tttgaaaata ctgaatttcg 120
agtaatcatt gtgctttgtg ttgatctgaa aaatataaca ctggctgtcg aagaagcatg 180
ttcaaaaata tttaattcac ttcaaaatgt catacaaatt atggtggttt ctatgcaccc 240
ctaaagcttc aagtcattta gctcaggtac atactaaagt aatatattaa ttcttccagt 300
acagtggtgt ttcataccat tgacatttgc ataccctaga ataatttaag aaagacatgt 360
gtaatattca caatgttcag aaaagcaagc aaaaggtcaa ggaacctgct ttggttcttc 420
tggagatggn ctcatatcag cttcataaac attcattcta caaaatagta agctaaccat 480
ttgaacccca atttccagat taagcatatt ttctcataaa tnatgaagcc 530

<210> SEQ ID NO 100
<211> LENGTH: 529
<212> TYPE: DNA
<213> ORGANISM: Homo sapien

<400> SEQUENCE: 100
agcgtggtcg cggccgaggt ccaggcacgg tggcttatgt gtgtaatccc agcacttggg 60
gaggctgagg gaggtggatc acttgagtcc aggagtttga gaccagtctg ggcaacatgg 120
cgaaacttca tcactaccaa agaagaaaaa aattagccag gtgtggtggt gtatgcctgt 180
agtcccagat actctggtgg ctgaggtgag aggatagctt gagcccagga aattgaggct 240
gcagtgaact atgattgcac tactgtgctc cagcttgggc aacagagtga gatcttgtct 300
ccaaaagtcc ttgaaggatt ttaggaagtt gttaaaagtc ttgaaacgat gtttgggggc 360
atgttagggt tcttgaatgt ttaattcctc taataactgc ttattcaaga gaagcatttc 420
tgactgggtg cggggcagtg gcttcatgcc ccataatccc agtactttgg gaggctgaag 480
caggaacatt gcttgagccc aggacttcaa gaacagcctg ggtaacata 529

<210> SEQ ID NO 101
<211> LENGTH: 277
<212> TYPE: DNA
<213> ORGANISM: Homo sapien

<400> SEQUENCE: 101
tcgagcggcc gcccgggcag gtcgcaggaa gaggatggaa actgaggagt ccaggaagaa 60
gagggaacga gatcttgagc tggaaatggg agatgattat attttggatc ttcagaagta 120
ctgggattta atgaatttgt ctgaaaaaca tgataagata ccagaaatct gggaaggcca 180
taatatagct gattatattg atccagccat catgaagaaa ttggaagaat tagaaaaaga 240
agaagagctg agaacagacc tcggccgcga ccacgct 277

<210> SEQ ID NO 102
<211> LENGTH: 490
<212> TYPE: DNA
<213> ORGANISM: Homo sapien

<400> SEQUENCE: 102
gcgtggtcgc ggccgaggtc tgacggcttt gctgtcccag agccgcctaa acgcaagaaa 60
agtcgatggg acagttagag gggatgtgct aaagcgtgaa atcagttgtc cttaattttt 120

-continued agaaagattt tggtaactag gtgtctcagg gctgggttgg ggtccaaagt gtaaggaccc 180
cctgccctta gtggagagct ggagcttgga gacattaccc cttcatcaga aggaattttc 240
ggatgttttc ttgggaagct gttttggtcc ttggaagcag tgagagctgg gaagcttctt 300
ttggctctag gtgagttgtc atgtgggtaa gttgaggtta tcttgggata aagggtcttc 360
tagggcacaa aactcactct aggtttatat tgtatgtagc ttatattttt tactaaggtg 420
tcaccttata agcatctata aattgacttc tttttcttag ttgtatgacc tgccccgggc 480
ggccgctcga 490

<210> SEQ ID NO 103
<211> LENGTH: 490
<212> TYPE: DNA
<213> ORGANISM: Homo sapien

<400> SEQUENCE: 103
gagcggccgc ccgggcaggt ccaaaccagc ttgctcataa gtcattaacc aaatccatta 60
taggtaattt gttcagttca atgtttacaa ttcttatgga aaaaattagc aacacacaca 120
tttaaaacgt gtgcatttac ctttgcgtga gtgcttaaaa tacatatttc tatttcaaga 180
tgacatttaa aaattattct aatatatcag cagcaaaaat ataatttgca attacaaaaa 240
actaaactag aatccttaag ttattctcat gtttacagtt gtgattcttt aataaatact 300
attatgcagc tctattgttt aagctttctg gatttggttt aaacacatgc atatatattg 360
tcaattgtgg gaagctttac aagttatatt ccatgcactt tttggacaga gttctaacag 420
agccagccag tccacaaaac aggcaagaca aaagttgaat taactggggc aaaataggac 480
tcttatgcaa 490

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct 60
cggcctccca aagtgttggg attacaggca tgagccactg cgcccgaccg agttgaacat 120
ttaatgtcag actaggccag agtttctcaa tctttttatt ctcacttccc aaaggagccg 180
ttggagattt tcccctcaat ctctctcctt catgaaattt cataccacaa atatagtatg 240
ttttatttat gtactgtgac cctttgaagg atcacaaacc aatataatag tttttctttt 300
taacccgtca aggaccaagt ttttgcccct gttggaaatg cataaactgg actgatgaat 360
tggtatagat ggcttttatc atgaggatca gaaaaacttg aaattccttg gctacgacac 420
tccatattta tcaccgtata gggaggacct tggtatgggg aagtagaaac acttctacac 480
tttacagca 489

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105

-continued

```
gcgtggtcgc ggccgaggtc tgactggctt cagccccaga agttgagctg gcctttagac     60

aaaataattg cacctccctc tgctgcttat tcccttccgt ttttcatttg agtgtgaaca    120

gttagataaa atctgtggct gnctcttcca ccttgctcta gtttccattg ctgtgagcag    180

gccctcctat gccccgcatt tagctacaat gctgtggact cacttgattc tttttctccg    240

agctttgtct agaaatatgt gaaggtgagg ttaagtgctt ctctgtgtag atccacttag    300

ccctgtctgc tgtctcgatg ggcgttgctt cgtctctcct ctcttccatc ctttccattt    360

gcttctcacc accttctggc ttctttttctt aatgcaataa aggcagtttc taacaaagaa    420

agaatgtggg ctttggagtt agacagacct ggntttaaat tctgcttctg gctctccaa     479
```

<210> SEQ ID NO 106
<211> LENGTH: 511
<212> TYPE: DNA
<213> ORGANISM: Homo sapien

<400> SEQUENCE: 106

```
tcgcggccga ggtccaaaac gtggattcca atgacctgcc ttgagcccgc ggttgccagg     60

agttggacct gcagtagtat gggaagctca cggcctaaat accgactgcc ctctgacccc    120

accgtccagc gattctagaa catttctagt aggaaagaca tagcaaggga ttttcatgat    180

tgggaaatac tgggagacaa gctgaagatt tgttaagggc tatgcttctg tcatctttta    240

ggtatttaag gctactcctt tagctagcta ctttgagctg tttaaagtga ctatctccct    300

acacagagtt acacaatgag catctctgaa agagaatatt accctggatt tccaaagatg    360

tactctaaca ggatgaccag gcaaaaggtg acccggggga ggagtctgtt ataacactcg    420

gacccacatg ttctcaaggc acttcagaac tttgggaaat cattttgtac cggatcctca    480

gaaagcattt atggaaatac acatccttta g                                   511
```

<210> SEQ ID NO 107
<211> LENGTH: 451
<212> TYPE: DNA
<213> ORGANISM: Homo sapien

<400> SEQUENCE: 107

```
ggccgcccgg gcaggtccag aatatcaaat caaaaggtca caaatgttca cttcctcctc     60

caccctctta catattggat cttcaattgc aatagggagt gtaagatggg cattttagag    120

acgtagttgc atcagcagaa gcaaacccat cttatacaaa tgggttttgg ggataggaaa    180

aggctgctaa aaattcacaa gtcaccattc cccagaagca atgaatagcc gtagaagacc    240

aaggaagatc aacaagtttc caaagtgcta aagccagaga tttggccctt ccaaaatacc    300

accaggacgc ctggacccgt gggctctccg catgtcacca ctgactgcca ggatgctgct    360

gcacctccct tccttgagac acaacagaga gacagtgaag tcacccaaga ctgggatcat    420

cagaggctcc tcatgcttgc tacagagaag c                                   451
```

<210> SEQ ID NO 108
<211> LENGTH: 461
<212> TYPE: DNA
<213> ORGANISM: Homo sapien

<400> SEQUENCE: 108

```
ccgcccgggc aggtcctgaa aacattcaga ctaatcaaaa tggtactact gtaacttctt     60

ataatacata atataaaagt ttttgaaaga tatagacaca attaacccct aaacaacaca    120

ctatctgatt ctcaaaagca atggctattt aacaagatgt aaaaggacaa taacatatca    180
```

-continued aagaactttc acacacctaa agatagcatt tagcagcaag ttagtcagac aaaacaaaca 240
caaatatttt cacatttcct atgtttgttt ttaactttac ttcataaagc cactgataat 300
tgaggtttct ttcaagtata agatttctaa aattaaaaac tgtttttgac atatttttat 360
aaagaaataa aaagcaaaac gcaatccaac tatttatatg agtccctctt ctccaacagc 420
tttagatggt tttctgagta cttttttaca cagaatattt t 461

<210> SEQ ID NO 109
<211> LENGTH: 441
<212> TYPE: DNA
<213> ORGANISM: Homo sapien

<400> SEQUENCE: 109
ggccgcccgg gcaggtctga ttataagaga aagaaatcca gtgacacgag ggcaggcagg 60
ccccgctctg ctctgatcga gaaaagcttc ctgatgtcag ggagatggaa ctgccaccat 120
cagaaccatg gcactttggg tgaaggtgtg tcagcgacca agggggcagg aaatgggcag 180
tgactaaggg ggcaggaaac aggcaggcac atggcaaggt tctcccagcc catcagccca 240
gtgatggcct cgattttgaa gctgcactac tgtctgaaaa gcacaattac tggtgactct 300
taacaaactt cagcatactg gggaaggaga ctgtcaagta actgaattgg aaagatgaaa 360
aagaaccatc tctaaaagtt gatgcttgtc agaagaataa cctcctttgt gcaagtcttg 420
caacatcttc attcaaccac a 441

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110
ggtcgcggcc gaggtctggg gaaggggtga gaatccctgg gccttgccca gtcctgagct 60
ctgggtgtct gcagggaagc acagtggtga gttagtgtta aagaaagcat ccagagaggt 120
aagaggggct tgggtagcac cctttgcctc tgtcacttcc gcaaaaactt cttgttgagg 180
aggaagatga gaaggttgac attgactttg gccttgttga agagtttcat gacagccaca 240
ccctcatact ggagctgcan gagatcctga tagtgaagct tgaaatcgct ccatgtccac 300
acccaggaac ttggcattta cttcaaactt tcctgcctca tctcccggcg tgatgtcaaa 360
natgacgttt cttgaagtga gaggcgggaa agatcttcaa tttccaccaa agacaccctt 420
tttccaggaa gcttgagcaa caagtgtaat g 451

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111
ggccgacgtt cgacctgact tctttngagc agntgncact acccgtcttg aggaatgccg 60
actgcagaca gtggcccang gcaaagagtg tgcgtcatcg atganattgg naagatggag 120

-continued

```
ctcttcagtc agnttttcat tcaagctgnt cgtcagacgc tgtctacccc agggactata    180

atcctnggca caatcccagt tcctanagga aagccactgn ctcttgtaga agaaatcana    240

cacanaaagg atgtgaacng tgtttaatgt caccaaggga aaacatgaaa ccaccttctg    300

ccagatatcg ggacgttgcg tgcagatcaa gcacgnaagt gaagacgcgt gcattccttg    360

ccttccgtga acgantgccc agntcaagaa gancctgatg gaaccct                  407
```

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

```
tcgcggccga ggtcggccga ggtctgacat ctgttgtctg tgataaccac ttctgtattg     60

cgtcttaacc acttctgtat tgtgtggttt taactgccta aggcggcaat gggcagtggg    120

cccctttccc ttaggatggg tatcaattca acaatattta taaggcattt actgtgtgct    180

aagcatttgg aagacccagg ctacaaaata agacatagtt cctgccctcc aggccagcag    240

agggaggcac aaatacccag gaatctctga tgggtgtgaa gtgcggtcgt gggccacaga    300

aaatgaccgt catggagacc ctgctaaagg tcggaccctg agcccaaagg ggtattcaga    360

agnggagatg attttggccc cactcataga tgggtggcaa a                        401
```

<210> SEQ ID NO 113
<211> LENGTH: 451
<212> TYPE: DNA
<213> ORGANISM: Homo sapien

<400> SEQUENCE: 113

```
gtcgcggccg aggtccatat taaaaagtcc atcataaaca aagactcctc ctcatggtat     60

gaatatgctc catatgccca taatggtgca taacggactt agaaattcca atgagtctta    120

gggttgaaat ttccaatgac ctgagcaagg cagctcccta tagcttctgg ataacatttt    180

acacccagag ttcaggctta aacagaccta tcaacacaat tattttcgga ttgtctgtct    240

agaaaacggc aatgctcaaa ggaatataaa taagggtggg gggacatatg cttccagcct    300

ggcctttctc catgtggtaa aaaacaatgg aatggctgtg ttaatttttt tttaatcttt    360

tctgaccttt actatgtttg gtaatggaaa taagtcaggg aaaacaaaat gaacaggtct    420

catcacttaa ttaatactgg gttttcttct t                                   451
```

<210> SEQ ID NO 114
<211> LENGTH: 441
<212> TYPE: DNA
<213> ORGANISM: Homo sapien

<400> SEQUENCE: 114

```
ggccgcccgg gcaggtccat cctgtcagag atgggagaag tcacagacgg aatgatggat     60

acaaagatgg ttcactttct tacacactat gctgacaaga ttgaatctgt tcatttttca    120

gaccagttct ctggtccaaa aattatgcaa gaggaaggtc agcctttaaa gctacctgac    180

actaagagga cactgttgtt tacatttaat gtgcctggct caggtaacac ttacccaaag    240

gatatggagg cactgctacc cctgatgaac atggtgattt attctattga taaagccaaa    300

aagttccgac tcaacagaga aggcaaacaa aaagcagata agaaccgtgc ccgagtagaa    360
```

-continued gagaacttct tgaaacttga cacatgtgca aagacaggaa gcagcacagt ctcggcggga 420
ggaagaaaaa aagaacagag a 441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaaggaaaag aagcaaagag actcagtcca 60
taatgctgat tagttagaag aaagggctag gattgagaaa gtaccaggaa cttttaatta 120
tttaaaagag aatgctgact gttaatgttt taaatcttac tgttcaaatg tactaatatg 180
aatttttacc ctttgtgcat gaatattcta aacaactaga agacctccac aatttagcag 240
ttatgaaagt taaacttttt attataaaaa ttctaaacct tactgctcct ttaccaggaa 300
catgacacac tatttancat cagttgcata cctcgccaat agtataattc aactgtcttg 360
cccgaacaat catctccatc tggaagacgt aagcctttag aaacacattt ttctattaat 420
ttctctagaa c 431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca aagaagacga 60
aggcagagtg gtgtcaaatc tttgacggca cagatgcctg tgtgactccg gttctgactt 120
ttgaggaggt tgttcatcat gatcacaaca aggaaccggg gctcgtttat caccagtgag 180
gagcaggacg tgagcccccg ccctgcacct ctgctgttaa acaccccagc catcccttct 240
ttcaaaaggg atcctttcat aggagaacac actgaggaga tacttgaaga atttggattc 300
agcccgcgaa gagatttatc aagcttaact cagataaaat cattgaaagt aataaggtaa 360
aagctaagtc tctaacttcc aggcccacgg ctcaagtgaa tttcgaatac tgcatttaca 420
g 421

<210> SEQ ID NO 117
<211> LENGTH: 489
<212> TYPE: DNA
<213> ORGANISM: Homo sapien

<400> SEQUENCE: 117
agcgtggtcg cggccgaggt aaggctgcga ggttgtggtg tctgggaaac tccgaggaca 60
gagggctaaa tccatgaagt ttgtggatgg cctgatgatc cacagcggag accctgttaa 120
ctactacgtt gacactgctg tgcgccacgt gttgctcaga cagggtgtgc tgggcatcaa 180
ggtgaagatc atgctgccct gggacccaac tggtaagatt ggccctaaga agcccctgcc 240
tgaccacgtg agcattgtgg aacccaaaga tgagatactg cccaccaccc ccatctcaga 300
acagaagggt gggaagccag agccgcctgc catgccccag ccagtcccca cagcataaca 360
gggtctcctt ggcagacctg cccgggcggc cgctcgaaag cccgaattcc agcacactgg 420

-continued cggccgttac tagtggatcc cagctcggta ccaagcttgg cgtaatcatg gtcatagctg 480
gtttcctgt 489

<210> SEQ ID NO 118
<211> LENGTH: 489
<212> TYPE: DNA
<213> ORGANISM: Homo sapien

<400> SEQUENCE: 118
tcgagcggcc gcccgggcag gtattgaata cagcaaaatt ctatatacaa agtgacctgg 60
acctgctgct tcaaaacatg atcctttctt actaatatct tgatagtcgg tccatagagc 120
attagaaagc aattgactct taaataaaca gaaaagtgcc taatgcacat taaatgaatg 180
gcctaactac tggaacttta gtagttctat aaggtgatta acataggtag gatccagttc 240
ctatgacagg ctgctgaaga acagatatga gcatcaagag gccattttgt gcactgccac 300
cgtgatgcca tcgtgtttct ggatcataat gttcccatta tctgattcta gacacaccac 360
aggaatatca gtggggtcag aggttagctt agctgcttgc tgggctagaa cagatatcac 420
tccagcatgc tcatctgaca gggtcccgcg gcaacccaga ttaagtcctt gtgaatctgt 480
gcacaggga 489

<210> SEQ ID NO 119
<211> LENGTH: 181
<212> TYPE: DNA
<213> ORGANISM: Homo sapien

<400> SEQUENCE: 119
taggttccag agacttttgg cccaggagga atatttactt ttagctctgg acatcattac 60
aaaaaggaat atttcccaaa cctcttcaga ccgagaatac atgggtaaaa ttattaaata 120
gttgtataat aaaaataatt ttttccttaa aaaaaaaaaa aacctcggcc gcgaccacgc 180
t 181

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120
gcgtggtcgc ggccgaggtc catttaaaac aaagaaaaat actaaagcca ctagtaaaca 60
tctgatgtgc aaaatacaac atcctctagt tggctttatg ccattattac ataagctcca 120
aatagctcat cttaaattaa aaagaaaaag tggctgtccc atctctgctg cataaatcag 180
attttttttt aaaggtttag agtactttaa ggaagggaag ttcaaaactg ccagtgaaat 240
tcacagagaa tacaaattta gcaatttaat ttcccaaagc tctttgaaga agcaagagag 300
tctctcttct taatgcagtg ttctcccaag aggaactgta attttgcttg gtacttatgc 360
tgggagatat gcaaaatgtg tttttcaatg tttgctagaa tataatggtt cctcttcagt 420
gnctggttca tcctggaact catgggttaa gaaggacttc ttggagccga actgcccggg 480 cgggccntt 489

<210> SEQ ID NO 121
<211> LENGTH: 531

-continued

<212> TYPE: DNA
<213> ORGANISM: Homo sapien

<400> SEQUENCE: 121
cgagcggccg cccgggcagg tggccagcgc tggtcccgca gacgccgaga tggaggaaat 60
atttgatgat gcgtcacctg gaaagcaaaa ggaaatccaa gaaccagatc ctacctatga 120
agaaaaaatg caaactgacc gggcaaatag attcgagtat ttattaaagc agacagaact 180
ttttgcacat ttcattcaac ctgctgctca gaagactcca acttcacctt tgaagatgaa 240
accagggcgc ccacgaataa aaaaagatga gaagcagaac ttactatccg ttggcgatta 300
ccgacaccgt agaacagagc aagaggagga tgaagagcta ttaacagaaa gctccaaagc 360
aaccaatgtt tgcactcgat ttgaagactc tccatcgtat gtaaaatggg gtaaactgag 420
agattatcag gtcccgagga ttaaactggc tcatttcttt gtatgagaat ggcatcaatg 480
gtatccttgc agatgaaatg ggcctaggaa agactcttca acaatttctc t 531

<210> SEQ ID NO 122
<211> LENGTH: 174
<212> TYPE: DNA
<213> ORGANISM: Homo sapien

<400> SEQUENCE: 122
tcgagcggcc gcccgggcag gtctgccaac agcagaggcg gggcctccgg catcttcaaa 60
gcacctctga gcaggctcca gccctctggc tgcgggaggg gtctggggtc tcctctgagc 120
tcggcagcaa agcagatgtt atttctctcc cgcgacctcg gccgcgacca cgct 174

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123
agcgtggtcg cggccgaggt cctcaaccaa gagggttgat ggcctccagt caagaaactg 60
tggctcatgc cagcagagct ctctcctcgt ccagcaggcg ccatgcaagg gcaggctaaa 120
agacctccag tgcatcaaca tccatctagc anagagaaaa ggggcactga agcagctatg 180
tctgccaggg gctaggggct cccttgcaga cagcaatgct acaataaagg acacagaaat 240
gggggaggtg ggggaagccc tatttttata acaaagtcaa acagatctgt gccgttcatt 300
cccccagaca cacaagtaga aaaaaaccaa tgcttgtggt ttctgccaag atggaatatt 360
cctccttcct aanttccaca catggccgtt tgcaatgctc gacagcattg cactgggctg 420
cttgtctctg tggtctgggc accagtagct tgggccccat atacacttct cagttcccac 480
anggcttatg gccnangggc angctccaat tttcaagcac cacgaaggaa g 531

<210> SEQ ID NO 124
<211> LENGTH: 416
<212> TYPE: DNA
<213> ORGANISM: Homo sapien

<400> SEQUENCE: 124
tcgagcggcc gcccgggcag gtccatctat actttctaga gcagtaaatc tcataaattc 60
acttaccaag cccaggaata atgactttta aagccttgaa tatcaactaa gacaaattat 120

-continued

```
gccaattctg atttctcaca tatacttaga ttacacaaag ataaagcttt agatgtgatc    180

attgtttaat gtagacttat ctttaaagtt tttaattaaa aactacagaa gggagtaaac    240

agcaagccaa atgatttaac caaatgattt aagagtaaaa ctcactcaga aagcattata    300

cgtaactaaa tatacatgag catgattata tacatacatg aaactgcaat tttatggcat    360

tctaagtaac tcatttaagt acatttttgg catttaaaca aagatcaaat caagct        416
```

```
<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

agcgtggtcg cggccgaggt gctttttttt tttttttttt tttttttttt gctattctaa     60

aggggaaggc cccttttat taaacttgta cattttactt tccttctttc anaatgctaa    120

taaaaaactt ttgtttatac ttaaaaaaac cataaatcan acaaacaaaa gaaacgattc    180

caacatcact tctgngatg                                                 199
```

```
<210> SEQ ID NO 126
<211> LENGTH: 490
<212> TYPE: DNA
<213> ORGANISM: Homo sapien

<400> SEQUENCE: 126

cgtggtcgcg gccgaggtcc agttgctcta agtggattgg atatggttgg agtggcacag     60

actggatctg ggaaaacatt gtcttatttg cttcctgcca ttgtccacat caatcatcag    120

ccattcctag agagaggcga tgggcctatt tgtttggtgc tggcaccaac tcgggaactg    180

gcccaacagg tgcagcaagt agctgctgaa tattgtagag catgtcgctt gaagtctact    240

tgtatctacg gtggtgctcc taagggacca caaatacgtg atttggagag aggtgtggaa    300

atctgtattg caacacctgg aagactgatt gactttttag agtgtggaaa aaccaatctg    360

agaagaacaa cctaccttgt ccttgatgaa gcagatagaa tgcttgatat gggctttgaa    420

ccccaaataa ggaagattgt ggatcaaata agacctgata ggcaaactct aatgtggagt    480

gcgacttggc                                                           490
```

```
<210> SEQ ID NO 127
<211> LENGTH: 490
<212> TYPE: DNA
<213> ORGANISM: Homo sapien

<400> SEQUENCE: 127

cgtggtcgcg gccgaggtcg gccgaggtct ggagatctga gaacgggcag actgcctcct     60

caagtgggtc cctgacccct gacccccgag cagcctaact gggaggcacc ccccagcagg    120

ggcacactga cacctcacac ggcagggtat tccaacagac ctgaagctga gggtcctgtc    180

tgttagaagg aaaactaaca agcagaaagg acagccacat caaaaaccca tctgtacatc    240

accatcatca aagaccaaaa gtaaataaaa ccacaaagat gggaaaaaaa cagaacagaa    300

aaactggaaa ctctaaaaag cagagcacct ctcctcttcc aaaggaacgc agttcctcac    360

cagcaatgga acaaagctgg atggagaatg actttgacga gctgagaaaa gaacgcttca    420

gacgatcaaa ttactctgag ctacgggagg acattcaaac caaaggcaaa gaagttgaaa    480
```

-continued actttgaaaa 490

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128
cgtggtcgcg gccgaggtgc tttttttttt tttttttttt tttttttttt tgctgattta 60
ttttttctnt ttattgttac atacaatgta taaacacata aaacanaaaa cagtagggat 120
cctctaggat ctctagggan acagtaaagt anaaagaggt ctcanaaaca ttttttttaaa 180 gtacaagaca ttcagngctc ggcccaaagg cgtaaaaggt ttanagccag canatagctg 240
nactaaaggc tccgtctntn tccccanagc caggacaacc ccagggagct ntccattagc 300
agccagtcca cgcaggcagg atgctgcgga aaaagctcta tgctganaac attccccttg 360
atggaaagaa gggcaacaca aaaggggtaa ctaanagctc cttcctctcg tgagggcgac 420
aactgaggaa cagaaaagga gtgtcccatg tcacttttga ccccctccc 469

<210> SEQ ID NO 129
<211> LENGTH: 419
<212> TYPE: DNA
<213> ORGANISM: Homo sapien

<400> SEQUENCE: 129
gcgtggtcgc ggccgaggtc tgattttcat ttaaatattt cagagctata gcatttgcct 60
ccatgctcaa atccacacca ttggggctta agccgctcat gccaacatta gcaaatgaca 120
tgcagtttaa tccagagatc actgcttctg ggctgatgca tgccaacaca ctggcgtgat 180
ccacgttatg tgcatttttc ttcactttag tgggagaatc aatttttact ccaaggcttc 240
ttagttgctt aagagttgca ttaaggacac aatctttgtc caccagtctt gaatgatgtg 300
tttttttctt tgtatggtaa acgttttggg ttctggtgca ttcatgactg ataattactg 360
ctttggtaga cggctgctca agtttccttg gaggaactat ttaataggtg ggttacttg 419

<210> SEQ ID NO 130
<211> LENGTH: 354
<212> TYPE: DNA
<213> ORGANISM: Homo sapien

<400> SEQUENCE: 130
agcgtggtcg cggccgaggt ccatctgagg agataaccac atcactaaca aagtgggagt 60
gaccccgcag agcacgctgt ggaattccat agttggtctc atccctggtc agtttccaca 120
tgatgatggt cttatctcga gaggcggaga ggatcatgtc cgggaactgc ggggtagtag 180
cgatctgggt tacccagccg ttgtggccct tgagggtgcc acgaagggtc atctgctcag 240
tcatggcggc ggcgagagcg tgtgtcgctg cagcgacgag gatggcactg gatggcttag 300
agaaactagc accacaacct ctcctgccgc acctgcccgg gcggcccgct cgaa 354

<210> SEQ ID NO 131
<211> LENGTH: 474
<212> TYPE: DNA
<213> ORGANISM: Homo sapien
<220> FEATURE:

-continued

<221> NAME/KEY: misc_feature
<222> LOCATION: (1)...(474)
<223> OTHER INFORMATION: n = A,T,C or G

<400> SEQUENCE: 131
cgagcggccg cccgggcagg tctggcagca gcttcctctg gaataattga cagctttgtg 60
ctgcctgact aaaatttgaa atgacaaccg ctgaatgtaa aatgatgtac ctacaatgag 120
agagatttag gaatactatc tgtcaatcca tagatgtaga aacaaaacaa actacagaat 180
gaaaacaaac ttattttaaa ccaaagaaac aaatgtatcc aaaatatagt ccatgatata 240
tttgattact agtataacca cagttgaaaa cttaaaaaaa aaaattgaca ttttttgtaa 300
tgggtactaa tggatttata aaaggtttct gtttccaaag atgttattgg ggtccacata 360
ttccttgaag acttcagcat cccaaagccc gacatcagag atactttcct ttagccattg 420
nttcccgtaa cttgcccact ccatggtgat gtgacaggct tcccttcatt agca 474

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132
ggccgaggtg gggaattcat gtggaggtca gagtggaagc aggtgtgaga gggtccagca 60
gaaggaaaca tggctgccaa agtgtttgag tccattggca agtttggcct ggccttagct 120
gttgcaggag gcgtggtgaa ctctgcctta tataatgtgg atgctgggca cagagctgtc 180
atctttgacc gattccgtgg agtgcaggac attgtggtag gggaagggac tcattttctc 240
atcccgtggg tacagaaacc aattatcttt gactgccgtt ctcgaccacg taatgtgcca 300
gtcatcactg gtagcaaaga tttacagaat gtcaacatca cactgcgcat cctcttccgg 360
cctgtcgcca gccagcttcc tcgcatcttc accagcatcg ganaggacta tgatgaaccg 420
tgtgctgccg tccatcacaa ctgagatcct caagtcagtg gtggctcgct ttga 474

<210> SEQ ID NO 133
<211> LENGTH: 387
<212> TYPE: DNA
<213> ORGANISM: Homo sapien

<400> SEQUENCE: 133
tgctcgagcg gccgccagtg tgatggatat ctgcagaatt cggcttagcg tggtcgcggc 60
cgaggtctgc gggcccctta gcctgccctg cttccaagcg acggccatcc cagtagggga 120
ctttcccaca ctgtgccttt acgatcagcg tgacagagta gaagctggag tgcctcacca 180
cacggcccgg aaacagcggg aagtaactgg aaagagcttt aggacagctt agatgccgag 240
tgggcgaatg ccagaccaat gatacccaga gctacctgcc gccaacttgt tgagatgtgt 300
gtttgactgt gagagagtgt gtgtttgtgt gtgtgttttg ccatgaactg tggccccagt 360
gtatagtgtt tcagtggggg agaactg 387

<210> SEQ ID NO 134
<211> LENGTH: 401
<212> TYPE: DNA
<213> ORGANISM: Homo sapien

<400> SEQUENCE: 134

```
ggccgcccgg gcaggtctga tgaagaacac gggtgtgatc cttgccaatg acgccaatgc     60

tgagcggctc aagagtgttg tgggcaactt gcatcggctg ggagtcacca acaccattat    120

cagccactat gatgggcgcc agttccccaa ggtggtgggg ggctttgacc gagtactgct    180

ggatgctccc tgcagtggca ctggggtcat ctccaaggat ccagccgtga agactaacaa    240

ggatgagaag gacatcctgc gcttgtgctc acctccagaa ggaagttgct cctgagtgct    300

attgactctt gtcaatgcga ccttcaagac aggaggctac ctggtttact gcacctgttc    360

tatcacagtg agacctctgc catggcagaa caggggaagc t                        401
```

<210> SEQ ID NO 135
<211> LENGTH: 451
<212> TYPE: DNA
<213> ORGANISM: Homo sapien

<400> SEQUENCE: 135

```
ggtcgcggcc gaggtctgtt cctgagaaca gcctgcattg gaatctacag agaggacaac     60

taatgtgagt gaggaagtga ctgtatgtgg actgtggaga aagtaagtca cgtgggccct    120

tgaggacctg gactgggtta ggaacagttg tactttcaga ggtgaggtgt cgagaaggga    180

aagtgaatgt ggtctggagt gtgtccttgg ccttggctcc acagggtgtg ctttcctctg    240

gggccgtcag ggagctcatc ccttgtgttc tgccagggtg gggtaccggg gtttgacact    300

gaggagggta acctgctggc tggagcggca gaacagtggc cttgatttgt cttttggaag    360

attttaaaaa ccaaaaagca taaacattct ggtccttcac aatgctttct ctgaagaaat    420

acttaacgga aggacttctc cattcaccat t                                   451
```

<210> SEQ ID NO 136
<211> LENGTH: 411
<212> TYPE: DNA
<213> ORGANISM: Homo sapien

<400> SEQUENCE: 136

```
ggccgcccgg gcaggtctga atcacgtaga atttgaagat caagatgatg aagccagagt     60

tcagtatgag ggttttcgac ctgggatgta tgtccgcgtt gagattgaaa atgttccctg    120

tgaatttgtg cagaactttg accccccttta ccccattatc ctgggtggct tgggcaacag    180

tgagggaaat gttggacatg tgcaggtggg tccctttgct gcgtatttgg tgcctgaggc    240

tctgtggatt tcccctccat caatcatctt accctctcat ccccctcaga tgcgtctgaa    300

gaaacatctc tggtataaga aaatcctcaa gtcccaagat ccaatcatat tttctgtagg    360

gtggaggaag tttcagacca tcctgctcta ttatatccga agaccacaat g             411
```

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

```
cggccgcccg ggcaggtcgg ttggtgcggc ctccattgtt cgtgttttaa ggcgccatga     60

ggggtgacag aggccgtggt cgtggtgggc gctttggttc cagaggaggc ccaggaggag    120

ggttcaggcc ctttgcacca catatcccat ttgacttcta tttgtgtgaa atggcctttc    180
```

-continued

```
cccggntcaa gccagcacct cgatgaaact t                                 211


<210> SEQ ID NO 138
<211> LENGTH: 471
<212> TYPE: DNA
<213> ORGANISM: Homo sapien

<400> SEQUENCE: 138

gccgcccggg caggtctggg ctggcgactg gcatccaggc cgtaactgca aatctatgct     60

aggcggggtc tcccttctgt gtgttcaagt gttctcgact tggattctta actattttaa    120

aaaatgcact gagtttgggt taaaaaccaa ccaccaaaat ggatttcaac acagctctaa    180

agccaagggc gtggccggct ctcccaacac agcgactcct ggaggccagg tgcccatggg    240

cctacatccc ctctcagcac tgaacagtga gttgattttt ctttttacaa taaaaaaagc    300

tgagtaatat tgcataggag taccaagaaa ctgcctcatt ggaaacaaaa actatttaca    360

ttaaataaaa agcctggccg caggctgcgt ctgccacatt tacagcacgg tgcgatgcac    420

acggtgacca aaccacggag gcaagcttct ggcactcaca ccacgacccg c             471


<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139

gtcgcggccg aggtctgttc tttagctcag atttaaacct gctgtctctt ctttatttgc     60

agaatgaatt cccagttcct gagcagttca agaccctatg gaacgggcag aagttggtca    120

ccacagtgac agaaattgct ggataagcga agtgccactg ggttctttgc cctcccttca    180

caccatggga taaatctgta tcaagacggt tcttttctag atttcctcta cctttttgct    240

cttaaaactg cttctctgct ctgagaagca cagctacctg ccttcactga aatatacctc    300

aggctgaaat ttggggtggg atagcaggtc agttgatctt ctgcaggaag gtgcagcttt    360

tccatatcag ctcaaccacg ccgncagtcc attcttaagg aactgccgac taggactgat    420

gatgcatttt agcttttgag cttttggggg gtattctacc aaccaacagt ccatttggaa    480

a                                                                    481


<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140

gtcgcggccg aggtttccca tttaagaaaa atagatcttg agattctgat tcttttccaa     60

acagtcccct gctttcatgt acagcttttt ctttacctta cccaaaattc tggccttgaa    120

gcagttttcc tctatggctt tgcctttctg attttctcag aggctcgagt ctttaatata    180

accccaaatg aaagaaccaa ggggaggggt gggatggcac tttttttgt tggtcttgtt     240

ttgttttgtt ttttggttgg ttgggttccg ttattttta agattagcca ttctctgctg     300

ctatttccct acataatgtc aatttttaac cataattttg acatgattga gatgtacttg    360
```

-continued aggctttttt gntttaattg agaaaagact ttgcaatttt ttttttagga tgagcctctc 420
c 421

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141
cgantngccc gcccgggcan gtctgtctaa ntttntcang gaccacgaac agaaactcgt 60
gcttcaccga anaacaatat cttaaacatc gaanaattta aatattatga aaaaaaacat 120
tgcaaaatat aaaataaata nnaaaaggaa aggaaacttt gaaccttatg taccgagcaa 180
atccaggtct agcaaacagt gctagtccta nattacttga tntacaacaa cacatgaata 240
ca 242

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142
agcgtggtcg cggcncgang tccacagggc anatattctt ttagtgtctg gaattaaaat 60
gtttgaggtt tangtttgcc attgtctttc caaaaggcca aataattcan atgtaaccac 120
accaagtgca aacctgtgct ttctatttca cgtactgttg tccatacagt tctaaataca 180
tgtgcagggg attgtagcta atgcattaca cagtcgttca gtcttctctg cagacacact 240
aagtgatcat accaacgtgt tatacactca actagaanat aataagcttt aatctgaggg 300
caagtacagt cctgacaaaa gggcaagttt gcataataga tcttcgatca attctctctc 360
caaggggccc gcaactaggc tattattcat aaaacacaac tgaanagggg attggtttta 420
ctggtaaatc atgtgntgct aaatcatttt ctgaacagtg gggtctaaat cantcattga 480
tttagtggca gccacctgcc cggcggccgn tcgaagccca attctgcaga tatccatcac 540
actggcggcc g 551

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143
cgagnggccc gcccgggcag gtatcttcac aaactcaaca aaggcactac atgagacttc 60
acattcccct agtccaatag ctgacaaatt tttgcaacgt tctgcaatgc gaattaactc 120
ttcatcaagt ggccgtaatc catttgcaca cactactagt tcaaccagtc tagggcatgt 180
cattcccaca cggccaagca catctttgct tactgatctc ccaaagtaca gatgggtggc 240

-continued

```
aggtatttca tagcgaaaga aggggtcaaa ttcttcttca tataanaaaa aatacatcac    300

taagttcact ttgggtgaat gtctgatgaa agcatcccag ctactcttct gaatagtatg    360

gaagtgtgtc tgtccaggat tctcactgac tacatcaatg cgcaaatgtt ctaatcgaac    420

atgtttttca gaagacaatg caagtaacaa ctcatcactc aataagtggt aagttcaggg    480

ctagttctct taagccgnga cactgatcag cacac                               515
```

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144

```
tgcattctct ntggatgcan acctgcccgt tggtagggac tntgctcaca cggaacatgg     60

acggttacac ctgtgccgtg ggtgacgtcc accagcttct ggatcatctc ggcgngggtg    120

ttgtggaagg gcagactatc cacctccatg cncacgatgc ccganacgcc actccggact    180

ntgtgctgca ccaanatgcc cagcattnta tcttcaagca nagcacttat cagggtcctt    240

ggcacac                                                              247
```

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145

```
cgtgggtcgc ggcccgangt ctgctgtaac aaaacaccat agtctgggca gctcatagac     60

aatggaattt tatttctcac gcttctggag gctggattcc aagatcaagg ttccaggaga    120

ctcagtgtct ggcaaggtct cggtttctgc ctcanagatg gtgccatctg gctgtgtcct    180

cacaagtagg aaggtgcaag aagctcccct caggctctgt ctgtaagaca ctgatcccat    240

tcatganggg gaaacgtaat gacctaatca gcccccagag accccacttc taacaccatc    300

accttgggg                                                            309
```

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146

```
agcgtgggtc gcggcncgac gtcctgtcca tatttcacag cccgagaact aatacaagat     60

gctgacatca tattttgtcc ctacaactat cttctanatg cacaaataag ggaaagtatg    120

gatttaaatc tgaaagaaca ggttgtcatt ttanatgaag ctcataacat cgaggactgt    180

gctcgggaat cagcaagtta cagtgtaaca gaagttcagc ttcggtttgc tcgggatgaa    240

ctanatagta tggtcaacaa taatataagg aaganagatc atgaacccct acgagctgtg    300

tgctgtagcc tcattaattg gntagaagca aacgctgaat atcttgnana angagantat    360
```

-continued

```
gaatcagctt gtaaaatatg gagtggaaat gaaatgctct taactttaca caaaatgggt    420

atcaccactg ctacttttcc cattttgcng gtaagatatn ttttctacct gngaaacgta    480

tttaag                                                                486


<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147

gccgcccggg cangttcgac attacntnga gttccatgat gtacaattct ttcacgaaaa     60

acaatgaatg caagaatttg aggatctcct tactcctccc ttttacagat ggtctctcaa    120

tcccttcttc ttcctcttca tcttcatctt cttctgaacg cgctgccggg taccacggct    180

ttctttgtct ttatcgtgag atgaaggtga tgcttctgtt tcttctacca taactgaaga    240

aatttcgctg caagtctctt gactggctgt ttctccgact tcgcctttnt gtcaaacgng    300

agtcttttta cctcatgccc ctcagcttca cagcatcttc atctggatgt tnatttctca    360

aagggctcac tgaggaaact tctgattcan atgtcgaana gcactgtgaa gttttctctt    420

cattttgctg                                                            430


<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148

cccgggcagg tctgtgttgn tttncaaccg gtgtcctccc cagcgtccag aananggaaa     60

tgtggagcgg gtgatgatga cccctcgctg tcctgtcacc tcctgcacag cttcgtatgt    120

gggtctggtc tgggaccacc cgtacaggtt gtgcacgttg tagtgctcca cgggggagct    180

gtccggcagg atctgctgac tctccatgca cagagtcttg ctgctcaggc ccttgtccct    240

agattccaaa tatggcatat agggtggggt tatttagcat ttcattgctg cagcccctga    300

cagatccatc cacaaaattt gatggctcat tcatatcaat ccacaatcca tcaaacttca    360

agctcttctc tggntctcga nggtttgcat agaactcttc tatctctttc ttccaccacg    420

canacctcgg ncgcgaccac gctaagccga attctgcana tatccatcac actggcggcc    480

gct                                                                   483


<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

ctttcacgaa nacaatgaat gcaagaattt gaggatctcc ttactcctcc cttttacaga     60
```

-continued

```
tggtctctca atcccttctt cttcctcttc atcttcatct tcttctgaac gcgctgccgg    120

gtaccacggc tttctttgtc tttatcgtga gatgaaggtg atgcttctgt ttcttctacc    180

ataactgaag aaatttcgct gcaagtctct tgactggctg tttctccgac ttcgcctttt    240

tgcaaacgtg agtcttttta cctcatgccc ctcagcttcc acagcatctt catctggatg    300

ttcatttctc aaagggctca ctgaggaaac ttctgactca catgtcgaag aagcactgng    360

agtttctctt catttgctgc aaanttgctc tttgctggct gngctctcag accacccatt    420

tggctgcatg ggggctgac                                                 439


<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

ggcncgcccg ggcangtcca ctccactttt gagctctgag ggaatacctt caggagggac     60

agggtcaggg agtcctggca gctccgcagc agagattcac attcattcag agacttgttg    120

tccagtgcaa tgccattgat cgcaacgatc ctgtctccca cagcaaggga cccttcttta    180

gcggcagggc ttccaggcag cacagcggca gcatacactc cattctccag actgatgcca    240

ctgtctttct gtccactgan gttgatgtgc agcggcgtga ccaccttccc acccagggac    300

ttcctccgcc gcacgaccat gttgatgggc cccctnccca ttgaggagcg ccttgatggc    360

ctgcttcttg nccttggtga tgaagtccac atcggtgatt ctcacagcca gtcattgacc    420

cttaagcggn catcagcaat gcttcctttg gccactttag ngacaaatat gccacagtcc    480

ccgggaaaca agggtcattc acaccttctg gcatatcaaa cacctcggcc gggancacta    540

agccgaattc tgcagatatc catcacactg gngggccg                            578


<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

cgagcggccc gcccgggcag gtctgggaga tcagcgactg ctgccacgtg cccagaaatg     60

gctcgtcctt tcactacagc ggaatgcaat gagggtgggt gagaagatga tgggtcggtt    120

atttcattcc ttttcttttt acaacttcac tttcagagac ttcagcgttc catgtctgct    180

gtgctgtgga acccagagtg ctcttgcctg gatggctgag aatcccttgg accctggaag    240

cacctactcc atgatggccc ggtatagtgc aggctcaata taatcttccc ggtatcttga    300

gttgataact cgttgccgtt tcttttcttg cttaacctct ttctctgtga aaatctcatt    360

gaagcgcatg tctgaagcta ctgacagtct anatttgact ctcttgggaa gctcttcatc    420

cagtgtgtat acatcatctc tcttaaccac aagttggagc catncttaaa cttcacctgg    480

tacatttgga tagggtggga ggc                                            503


<210> SEQ ID NO 152
<211> LENGTH: 553
```

-continued

<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152
agcgtggtcg cggcccgagg tccactgagc tccgccttcc ccgggctccc tgaggaagca 60
gagtcctgac ttccaggaag gacaggacac agaggcaaga actcagcctg tgaggctctg 120
ggtggctcct gaggccagag gacgccttcc gcgatccatg gctcagcatc gtccttctgg 180
cttcccagcc ccgggccgaa cgttcgggtt aataagcaga gcagttattc ggctcctggc 240
aggagctccc ccgttagttt ccacgttgtg agcacattca tacttaagac tgnttctctt 300
tgtgttttaa gcgtctgtct ctgtagtaaa ctgaaatgtt aacagaaatg cagacctgcc 360
cgggcggccg ctcgaaagcc gaattctgca gatatccatc acactggcgg ccgctcgagc 420
atgcatctag anggcccaat tcgccctata gtgagtcgna ttacaattca ctgggccgcg 480
ntttacaacg tcgtgactgg gaaaaccctg cggtacccac ttaatcgcct tgcagnacat 540 cccccttcg cca 553

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153
tcgagcggct cgcccgggca ggtccaccta gcatggctcc tctaaacacg caactcagcg 60
aggggacccc cttcacctct ggcaagagag ctgggtagat cagaaacttg gtgacacctg 120
gctagcacag agcaggctca cttgtcttgg tcccactacc cagattcctg cagacattgc 180
aaaccaaatg aaggttgntg aatgacccct gtccccagcc acttgttttg gtatcatctg 240
ctctgcagtg gaatgcctgt gtgtttgagt tcactctgca tctgtatatt tgagtataga 300
aaccgantca agtgatctgt gcatncagac acactggggc acctgancac agaacaaatc 360
accttaacga tctggaatga aactgnganc antgcccgcc tgggtgggtc tgganaaact 420
gccgncttct tgttggacct tggccgcacc acct 454

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154
agcgtggtcg cggcccgang gcggcctcct gantganggg aagggacgtg ggggcggcca 60
cggcaggatt aacctccatt tcagctaatc atgggagaga ttaaagtctc tcctgattat 120
aactggttta naggtacagt tccccttaaa aagattattg tggatgatga tgacagtaag 180
atatggtcgc tctatgacgc gggcccccga agtatcaggt gtcctctcat attcctgccc 240
cctgtcagtg gaactgcaga tgtctttttc cggcagattt tggctctgac tggatggggt 300

-continued

```
taccgggtta tcgctttgca gtatccagtt tattgggacc atctcgagtt cttgtgatgg    360

attcacaaaa cttttanacc atttacaatt ggataaagtt catctttttg gcgcttcttt    420

gggangcttt ttggcccana aatttgctga atacactcac aaatctccta gaagccattc    480

cctaatcctc tgcaattcct tcagngacac ctctatcttc aaccaacttg gactggaaac    540

agctttggct gatgcctgca tttatgctca aaaaatagtt cttggaaatt ttcatc        596


<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155

ctcganttgg cncgcccggg cangtctgcc tggtttttga ccgngcgagc tatttagnct     60

ctggctctgt ttccggagct caaggnaaaa atcttgaana actcgagcag cttctgtgga    120

tagccttggg tacacatact gccgagcata gccaatgtac tttctcaata gctggtgggg    180

aatgggatct attgtttctc caggaaccac ctttagtctt tctgataatg gcttctcaga    240

aactacttca agtacggaag tatttgaatc ttgactatnc atacgagcta ctgtggcact    300

gctaatgggn tctctgctnt ccagctctta ttgcaatcac atg                      343


<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156

tcgagcggcc cgcccgggca ggtctggcac cacncagatc gattaactgg ctcatctgat     60

ctcgtggccc ccaccctgga actgacttag cacaaaagga cacctcaatt ccttatgatt    120

tcatctccga cccaaccaat caacaccctt gactcactgg ccttccccct cccaccaaat    180

tatccttaaa aactctgatc cccgaatgct cagggagatc gatttgagta ctaataagac    240

tccagtctcc tgcacaagca gctctgtgta ctcttcctct attgcaattc ctgtcttgat    300

aaatcggctc tgtgtaggcg gcggaagaag tgaacctgtt gggcggttac cacctctgtc    360

gtgtgtgaca gttgntttga atctctaatt gctcagtaca gatccacatg caggttaagt    420

aagaagcttt tgaagaaaat ggaaagtctt aagtgatggc ttccaagaaa tcaaacctac    480

attaattagg gaacaacgga ctttacgtat cacaaatgaa gagactgacn aagtaaatca    540

acttggcctt ttctta                                                    556


<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157

ggtccacaaa aatatatnaa ataagctgga tatataaaan caaacactta acatngncan     60
```

-continued

```
cattccttca gttattcaaa ctcactgata nctaacnggg agnagttggn attctggaag    120

acttcctaag ctaaaagtat atttacatat ttacaacaca ngtaaatata acngaagaac    180

tacttcaaat aangnngaaa ttccagaatt ctanagattt atagctatag ntnacaanta    240

tcaccaattg gtttgcaatc aannngnccag cactacttat gannaangtt taactannaa   300

accaaaaggg gagaaaacct ggnagggaaa nat                                 333
```

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

```
tcgagcggcc gcccgggcag gtctggtaca tttgtgcgag gtccggcact ctgttctcat     60

ccagtaagtg gtcgagccct ttctgcagaa ttgctgttaa atgttctcct aatagctgtt    120

tctccacaca agcaatcagt ggtttctgtg tgctgtggtc caagtaagtg attactctgt    180

ctccctcttc ttctaagcgt ttacttacat ggttaagata ttctggaacc tctctttcct    240

gcattaacct ttggccttcg gcagcatata agcaattagt ctcttccaaa aatttcagtt    300

caaatgaatc tttatacacc tgcaggtcag acagcatgcc caggnaggct ccgcaacagg    360

ctccggtcca cggcctcgcc gctcctctcg cgctcgatca gcagtaggat tccatcaatg    420

gttttactct gaaccatttt atcactaata atatgggttc taaacagttc taatcccata    480

tcccagatgg agggcagcgt ggagttctgc agcacatagg tgcggtccaa gaacaggaag    540

atgcttctga tcatgaatca tttgnctggc aatggtcctg ccagcacgtg gtaatctttc    600

ttttaaaaat aaacccttat ctaaacgtc                                      629
```

<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

```
tcgagcggcc gcccgggcag gttctagagg ganaatctgg ctgatttggg aataaaatat     60

aatcgaatat tcaacaccat gaagataaat cttattttgg aaatctactg accttaatac    120

cccaagcttg ccctgaatac tttgattgga attggaatat atcaaaaaag gttagtattt    180

ttgttgtagt taggatacta aaaggatatt agttacccaa gagatccaat ttgtttttct    240

gatgaatagt gttcagtaaa atgaagcagt cttaagagtg actaataatt tcaaagtgat    300

ttttcgtcta ttcttaatat tttttaatta tttattttta agagttttat accttgagca    360

gatacaatga tccgctttag tgagaggaca atttctgatt gattgttttc tcttcaggcc    420

atctcacctc ttcattctct tgttacattt gaagcagttg atataatggg tttatacttt    480

aaaagataga catggtgcca tgaagtttgg ggaagttggg tgaattatcc cattctagtt    540

acagangagc tttccttaaa tgccctttac ttctangttt ggtcaagaag tcattttctg    600

agtaaaagtt attttcatat atgttgggg                                      629
```

-continued

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160
tcgagcggcg cgcccgggca ggtctgctgg gattaatgcc aagttnttca gccataaggt 60
agcgaaatct agcagaatcc agattacatc cacttccaat cacgcggtgt ttgggtaatc 120
cacttagttt ccagataaca tacgtaagaa tgtccactgg gttggaaacc acaattatga 180
tgcaatcagg actgtacttg acgatctgag gaataatgaa tttgaagaca ttaacatttc 240
tctgcaccag attgagccga ctctcccctt cttgctgacg gactcctgca gttaccacta 300
caatcttana attgggcggg tcacagaata atctttatct gccacaattt taggtgctga 360
agaaataagc tcccatgctg cagatccatc atttctnctt taagcttatc ttccaaaaca 420
tccacaagan caangttcat cagccagaga ctttcccaga atgctgatag nacacgccat 480
accaacttgt ccaacancca ctacagcgat cttattggt 519

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161
cgagnggccc gcccgggcag gtccagtaag cntttnacga tgatgggaaa ggttatgcaa 60
ggtcccagcg gtacaacgag ctgtttctac atcatttgta ttctgcatgg tacgtacaat 120
agcagacacc atctgaggag aacgcatgat agcgtgtctg gaagcttcct ttttagaaag 180
ctgatggacc ataactgcag ccttattaac caccacctgg tcctcgtcat ttagcagttt 240
tgtcagttca gggattgcac gtgtggcang ttctgcatca tcttgatagt taatcaagtt 300
tacaactggc atgtttcagc atctgcgatg ggctcagcaa acgctggaca ttantgggat 360
gagcagcatc aaactgtgta natgggatct gcatgccctc atctaatgtc tcagggaaca 420
tagcagctcg taccctctga gctcga 446

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162
agcgtngtcg cggcccgang tcctgggaag cctttnttgc tgagcctcac agcctctgtc 60
aggcggctgc ggatccagcg gtccaccagg ctctcatggc ctccgggctg ggaggngggt 120
gagggcacaa aacccttccc aaggccacga anggcaaact tggtggcatt ccanagcttg 180
ttgcanaagt ggcggnaacc cagtatccgg ttcacatcca ggntgatgtc acgaccctgg 240
gacatgtang cacataatcc aaaccggaga gcatcggtgc cacattcacg aatccccgct 300

-continued

```
gggaagtcag ctttctgccc ttctttggcc ttctccacct cgctgggatc cagg          354


<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

tttttcncca agtcctcttg ccgngggatc tngactgcaa tttaagacac ttctaattag     60

ttatacccag gccctgcaaa attgctgggt ttatataata tattcttgct gcacgaagat    120

ttattattct gttggatgat tctattttaa ttntatttat tctggccaaa aaagaacctt    180

ctccgctcgt caagagangc caatntgtct tgaaggacaa gagaaagatg ctaacacaca    240

ctttcttctt cttgagga                                                  258


<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

ggaacatatt acttttaaat tacttgggtc aatgaaacat ttaataaaaa catttgcttc     60

tctatataat acgtatgtat aaaataagcc ttttcanaaa ctctggttct cataatcctc    120

tataaatcan atgatctgac ttctaagagg aacaaattac agnaaggggt atacattnat    180

gaatactggt agtactagag ganngacgct aaaccactct actaccactt gcggaactct    240

cacagggtaa atgacaaagc caatgactga ctctaaaaac aa                       282


<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165

gcccgggcan gtcctgtaat cccagctact cangangctg agtcatgana atcgcctgaa     60

tccgggaggt agaggccgca gcgagcaaag attaagccac tgcactccag tctgggtgac    120

agagtgagaa tctgtctgtt gctcctctgg cattggtctg aaatgggttt gtagaacatg    180

ccacagaagg accagcanca gcaacaaatg gatttgtgga angcgtagct ccaaatggag    240

cangcacact tgatgaagca cgctgtgtct gtgcagangc aaccactggc actgttccaa    300

aaacattgct gctagcatta cttgtggaag tatacgcatt actggaggtg gctgcanaac    360

tgaaaacgct gtctagttct gccanagctg catacttgnc tgaanatgca cttgactgac    420

tgggaactga accacanaac caacaggacc tttacctgtg ga                       462


<210> SEQ ID NO 166
<211> LENGTH: 365
<212> TYPE: DNA
```

-continued

<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166

```
cgtgggtcgc ggcncgangt ctgaaaccaa tccagaacta aacatcagca cacaaaaaat     60

accaggatag atggaatcaa aagactctga agccaaaagg aggctaggga gagcaactga    120

acttagcaag ctgaggactt cagtgtccat catccgatcc tgccctgtaa caacaggtct    180

atatgataga gatattccat ctgagctgga ggccattatc cttagcaaac taacacagaa    240

cagaaaacca aatacatgtt ctcatttaga agtaggagct aaatgatgag aactcaagga    300

cacaaagaaa ggaacaacag acactggggc ctacttgagg gtggagggtg ggaggaggga    360

gaaga                                                                365
```

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167

```
agcgtggtcg cggcgcgang tccagcccta gcttgcctgt gactccgcct tcactgggtg     60

ctctctctaa aagttgctga ctctttactg tatctcccaa ttcccactcc attggttcca    120

taaggggagg ggtgtctcac tcaacatggt gttcctggta ccaagaactg gctgacgaag    180

ctgggtgccg tggctcatgc ctgtaatccc agcacttttg ggaggccaag aagggcggat    240

cacctgaggt ctggagttca agatcagcct gaccaacatg atgaaaccaa gtctccacta    300

aaaatataaa acaattagcc aggcatggtg gtgggtgcct gnaatcccag ctactgggga    360

ngct                                                                 364
```

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168

```
cccgggcagg tcaaaaccca aaacctttca ttttagccca aaccagctca tgattaggta     60

tacaaggata acagaaccag ttgtcaggac gagcatttga caagtaaaag caattcttgc    120

aaagctgcag ttcatccagc tcatggcatg tgtctttata tagcatcctc gcaatgtcag    180

cttgctcact gtctgctcca tagaaaatca cggtattgtg gagaagcaat tgggcatcag    240

ctttgaactc ttcataactt cggtatttcc cttcattcac tttctcttga atggtgggaa    300

cgtccacaga cctcggccgc gaccacgcta agcccgaatt ctgcagatat ccatcacact    360

ggcggccgtt cgagcatggc atctagaagg cccaattcgc ctatagngag tcgnattacc    420

aattcactgg ccgtcgnttt acaacgc                                        447
```

<210> SEQ ID NO 169
<211> LENGTH: 524

-continued

<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169
cgantngcgc gcccgggcag gtctgagcag cctttctgnn tgctggacta ttgggattgg 60
gttcatccaa cagagactgt atggatgtta gaatggaaga cacatcatag gttggactcc 120
aacggttctg aagtatgtcc agacatatac taccatctgc atagactaag aacaaagaag 180
taggtacatt aaacgtaaca agaccactaa ggttttaaca ttatagacaa aacanaaata 240
gtcaaganta ctttgctttt gaagtttaaa gattcctatg ttgcttccca gttaactgcc 300
taaaaagata agncataacc accactagtg aaataatcan gatgatcaga gaatgtcana 360
tgtgatcagt ataaaactgg angatattna gtgtcatcct ttggaaaagg ctgccctatn 420
atccaggaaa tcanaaacat tnttgaacag ggnccctagc tatccacaga catgtgggaa 480
attcattccc caaatngtag gctggatccc ctatctgaaa taac 524

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgancggcn cgcccgggca ggtgacaaac ctgttattga agatgttggt tctgatgagg 60
aanaanatca gaagggatgg tgacaagaan aanaanaaga agattaagga aaagtacatc 120
gatcaagaag agctcaacaa aacaaagccc atctggacca gaaatcccga cgatattact 180
aatgangagt acggagaatt ctataanagc ttgaccaatg actgggaaga tcacttggca 240
gtgaagcatt tttcagttga nggacagttg gaattcagag cccttctatn tgtcccacga 300
cgtgctcctt ttgatctgtt tganancaga aa 332

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171
cgagnggcnc gcccgggcag gtctgttgat agcgacttaa cagaaaagtc tagacaaaca 60
taagcataaa aaattacagt ctttctaccc ttgggaatgg ggagaaaaag gaatctctac 120
cccaagacca gaaataataa gtcctgtttc tggtcctgaa catccagaat tatggaggct 180
ttggcctgac accacattan aatttggtct ggaaatcaaa ctttaganac angagatcgt 240
aagccatttt atactatcga cctaaattcc agtctaacgg ttcctttaca aagttgcgga 300
aagccctctt atatgctagc tgtaggaaat atag 334

<210> SEQ ID NO 172
<211> LENGTH: 439
<212> TYPE: DNA

-continued

<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172
agcgtggtcg cggcccgang tctgcctata aaactagact tctgacgctg ggctccagct 60
tcattctcac aggtcatcat cctcatccgg gagagcagtt gtctgagcaa cctctaagtc 120
gtgctcatac tgtgctgcca aagctgggtc catgacaact tctggtgggg cgagagcagg 180
catggcaaca aattccaagt tagggtctcc aatgagcttc ctagcaagcc agaggaaggg 240
cttttcaaag ttgtagttac ttttggcaga aatgtcgtag tactgaagat tcttctttcg 300
gtggaagaca atggatttcg ccttcacttt ctgccttaat atccactttg gtgccacaca 360
acacaatggg gatgntttca cacacttngn accanatctc tatgccagnt aggccatttt 420
ggaagnactt cganggtac 439

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173
cgatnggccg cccgggcagg tcctgtaaaa naggaaattc agacatcgta cgactcgtaa 60
ttgaatgtgg agctgactgc aatattttgt caaagcacca gaatagtgcc ctgcactttg 120
cgaagcagtc taacaatgtg cttgtgtacg acttgctgaa gaaccattta gagacacttt 180
caagagtagc agaagagaca ataaaggatt actttgaagc tcgccttgct ctgctagaac 240
cagtttttcc aatcgcatgt catcgactct gtgagggtcc agatttttca acagatttca 300
attaccaacc cccacagaac ataccagaag gctctggcat cctgctgttt atcttccatg 360
caaacttttt gggtaaagaa gttattgctc ggctctgtgg accgtgtagt gtacaagctg 420
tagttctgaa tgataaattt cagcttcctg tttttctggg tctcgctctg ttgtccaggc 480
tggagtgcag tggcgcggat tacagctcac tggagtcttg acttcccagg cacaagcaat 540
cctcccacct cagcctccta actacctggg actaaaaatg caccgccacc acattccgg 599

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174
tcgatttggc cgcccgggca ggtccatgcn gnttntgccc attcccatgg ngcccgacaa 60
ncccatcccc gaggccgaca tccccatgtt catgttcatg cccaccatgc cctggctcat 120
ccctgcgctg ttccccagag gggccattcc catggtgccc gtcattacac cgggcatgtt 180
cataggcatg ggtcccccca ggagagggtt agnttgaggc cggacaggaa gcatgtttga 240
tggagaactg aggttcacag nctccaaaac tttgagtcat cacattcata ggctgctgca 300
tattctgtct gctgaatcca ttgtatncag tgatggcctg ctggggnttt ggaaggctng 360

-continued cataccaggt agtaagntcg tctaggctga tgtttacacc tggggtcaga ccaagtanga 420
gggcaaggtt ttgctgactg attttctgga cccatatc 458

<210> SEQ ID NO 175
<211> LENGTH: 1206
<212> TYPE: DNA
<213> ORGANISM: Homo sapien

<400> SEQUENCE: 175
ggcacgagga agttttgtgt actgaaaaag aaactgtcag aagcaaaaga aataaaatca 60
cagttagaga accaaaaagt taaatgggaa caagagctct gcagtgtgag gtttctcaca 120
ctcatgaaaa tgaaaattat ctcttacatg aaaattgcat gttgaaaaag gaaattgcca 180
tgctaaaact ggaaatagcc acactgaaac accaatacca ggaaaaggaa aataaatact 240
ttgaggacat taagatttta aaagaaaaga atgctgaact tcagatgacc ctaaaactga 300
aagaggaatc attaactaaa agggcatctc aatatagtgg gcagcttaaa gttctgatag 360
ctgagaacac aatgctcact tctaaattga aggaaaaaca agacaaagaa atactagagg 420
cagaaattga atcacaccat cctagactgg cttctgctgt acaagaccat gatcaaattg 480
tgacatcaag aaaaagtcaa gaacctgctt tccacattgc aggagatgct tgtttgcaaa 540
gaaaaatgaa tgttgatgtg agtagtacga tatataacaa tgaggtgctc catcaaccac 600
tttctgaagc tcaaaggaaa tccaaaagcc taaaaattaa tctcaattat gccggagatg 660
ctctaagaga aaatacattg gtttcagaac atgcacaaag agaccaacgt gaaacacagt 720
gtcaaatgaa ggaagctgaa cacatgtatc aaaacgaaca agataatgtg aacaaacaca 780
ctgaacagca ggagtctcta gatcagaaat tatttcaact acaaagcaaa aatatgtggc 840
ttcaacagca attagttcat gcacataaga aagctgacaa caaaagcaag ataacaattg 900
atattcattt tcttgagagg aaaatgcaac atcatctcct aaaagagaaa aatgaggaga 960
tatttaatta caataaccat ttaaaaaacc gtatatatca atatgaaaaa gagaaagcag 1020
aaacagaagt tatataatag tataacactg ccaaggagcg gattatctca tcttcatcct 1080
gtaattccag tgtttgtcac gtggttgttg aataaatgaa taaagaatga gaaaaccaga 1140
agctctgata cataatcata atgataatta tttcaatgca caactacggg tggtgctgct 1200
cgtgcc 1206

<210> SEQ ID NO 176
<211> LENGTH: 317
<212> TYPE: PRT
<213> ORGANISM: Homo sapien

<400> SEQUENCE: 176

Met Gly Thr Arg Ala Leu Gln Cys Glu Val Ser His Thr His Glu Asn
1 5 10 15

Glu Asn Tyr Leu Leu His Glu Asn Cys Met Leu Lys Lys Glu Ile Ala
20 25 30

Met Leu Lys Leu Glu Ile Ala Thr Leu Lys His Gln Tyr Gln Glu Lys
35 40 45

Glu Asn Lys Tyr Phe Glu Asp Ile Lys Ile Leu Lys Glu Lys Asn Ala
50 55 60

Glu Leu Gln Met Thr Leu Lys Leu Lys Glu Glu Ser Leu Thr Lys Arg
65 70 75 80

Ala Ser Gln Tyr Ser Gly Gln Leu Lys Val Leu Ile Ala Glu Asn Thr

-continued

```
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile
305                 310                 315
```

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177

```
ccaatcatct ccacaggagc                                                20
```

<210> SEQ ID NO 178
<211> LENGTH: 1665
<212> TYPE: DNA
<213> ORGANISM: Homo sapien

<400> SEQUENCE: 178

```
gcaaactttc aagcagagcc tcccgagaag ccatctgcct tcgagcctgc cattgaaatg     60

caaaagtctg ttccaaataa agccttggaa ttgaagaatg aacaaacatt gagagcagat    120

cagatgttcc cttcagaatc aaaacaaaag aaggttgaag aaaattcttg ggattctgag    180

agtctccgtg agactgtttc acagaaggat gtgtgtgtac ccaaggctac acatcaaaaa    240

gaaatggata aaataagtgg aaaattagaa gattcaacta gcctatcaaa aatcttggat    300

acagttcatt cttgtgaaag agcaagggaa cttcaaaaag atcactgtga acaacgtaca    360

ggaaaaatgg aacaaatgaa aaagaagttt tgtgtactga aaaagaaact gtcagaagca    420

aaagaaataa aatcacagtt agagaaccaa aaagttaaat gggaacaaga gctctgcagt    480
```

-continued

```
gtgaggtttc tcacactcat gaaaatgaaa attatctctt acatgaaaat tgcatgttga    540

aaaaggaaat tgccatgcta aaactggaaa tagccacact gaaacaccaa taccaggaaa    600

aggaaaataa atactttgag gacattaaga ttttaaaaga aaagaatgct gaacttcaga    660

tgaccctaaa actgaaagag gaatcattaa ctaaaagggc atctcaatat agtgggcagc    720

ttaaagttct gatagctgag aacacaatgc tcacttctaa attgaaggaa aaacaagaca    780

aagaaatact agaggcagaa attgaatcac accatcctag actggcttct gctgtacaag    840

accatgatca aattgtgaca tcaagaaaaa gtcaagaacc tgctttccac attgcaggag    900

atgcttgttt gcaaagaaaa atgaatgttg atgtgagtag tacgatatat aacaatgagg    960

tgctccatca accactttct gaagctcaaa ggaaatccaa aagcctaaaa attaatctca   1020

attatgccgg agatgctcta agagaaaata cattggtttc agaacatgca caaagagacc   1080

aacgtgaaac acagtgtcaa atgaaggaag ctgaacacat gtatcaaaac gaacaagata   1140

atgtgaacaa acacactgaa cagcaggagt ctctagatca gaaattattt caactacaaa   1200

gcaaaaatat gtggcttcaa cagcaattag ttcatgcaca taagaaagct gacaacaaaa   1260

gcaagataac aattgatatt cattttcttg agaggaaaat gcaacatcat ctcctaaaag   1320

agaaaaatga ggagatattt aattacaata accatttaaa aaaccgtata tatcaatatg   1380

aaaaagagaa agcagaaaca gaaaactcat gagagacaag cagtaagaaa cttcttttgg   1440

agaaacaaca gaccagatct ttactcacaa ctcatgctag gaggccagtc ctagcattac   1500

cttatgttga aaatcttacc aatagtctgt gtcaacagaa tacttatttt agaagaaaaa   1560

ttcatgattt cttcctgaag cctgggcgac agagcgagac tctgtctcaa aaaaaaaaaa   1620

aaaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160
```

-continued

Val Arg Phe Leu Thr Leu Met Lys Met Lys Ile Ile Ser Tyr Met Lys
                165                 170                 175

Ile Ala Cys

<210> SEQ ID NO 180
<211> LENGTH: 1681
<212> TYPE: DNA
<213> ORGANISM: Homo sapien

<400> SEQUENCE: 180
gatacagtca ttcttgtgaa agagcaaggg aacttcaaaa agatcactgt gaacaacgta 60
caggaaaaat ggaacaaatg aaaaagaagt tttgtgtact gaaaaagaaa ctgtcagaag 120
caaaagaaat aaaatcacag ttagagaacc aaaaagttaa atgggaacaa gagctctgca 180
gtgtgagatt gactttaaac caagaagaag agaagagaag aaatgccgat atattaaatg 240
aaaaaattag ggaagaatta ggaagaatcg aagagcagca taggaaagag ttagaagtga 300
aacaacaact tgaacaggct ctcagaatac aagatataga attgaagagt gtagaaagta 360
atttgaatca ggtttctcac actcatgaaa atgaaaatta tctcttacat gaaaattgca 420
tgttgaaaaa ggaaattgcc atgctaaaac tggaaatagc cacactgaaa caccaatacc 480
aggaaaagga aaataaatac tttgaggaca ttaagatttt aaaagaaaag aatgctgaac 540
ttcagatgac cctaaaactg aaagaggaat cattaactaa aagggcatct caatatagtg 600
ggcagcttaa agttctgata gctgagaaca caatgctcac ttctaaattg aaggaaaaac 660
aagacaaaga aatactagag gcagaaattg aatcacacca tcctagactg gcttctgctg 720
tacaagacca tgatcaaatt gtgacatcaa gaaaaagtca agaacctgct ttccacattg 780
caggagatgc ttgtttgcaa agaaaaatga atgttgatgt gagtagtacg atatataaca 840
atgaggtgct ccatcaacca ctttctgaag ctcaaaggaa atccaaaagc ctaaaaatta 900
atctcaatta tgccggagat gctctaagag aaaatacatt ggtttcagaa catgcacaaa 960
gagaccaacg tgaaacacag tgtcaaatga aggaagctga acacatgtat caaaacgaac 1020
aagataatgt gaacaaacac actgaacagc aggagtctct agatcagaaa ttatttcaac 1080
tacaaagcaa aaatatgtgg cttcaacagc aattagttca tgcacataag aaagctgaca 1140
acaaaagcaa gataacaatt gatattcatt ttcttgagag gaaaatgcaa catcatctcc 1200
taaaagagaa aaatgaggag atatttaatt acaataacca tttaaaaaac cgtatatatc 1260
aatatgaaaa agagaaagca gaaacagaaa actcatgaga gacaagcagt aagaaacttc 1320
ttttggagaa acaacagacc agatctttac tcacaactca tgctaggagg ccagtcctag 1380
cattacctta tgttgaaaaa tcttaccaat agtctgtgtc aacagaatac ttattttaga 1440
agaaaaattc atgatttctt cctgaagcct acagacataa aataacagtg tgaagaatta 1500
cttgttcacg aattgcataa aagctgccca ggatttccat ctaccctgga tgatgccgga 1560
gacatcattc aatccaacca gaatctcgct ctgtcactca ggctggagtg cagtgggcgc 1620
aatctcggct cactgcaact ctgcctccca ggttcacgcc attctctggc acagcctccc 1680
g 1681

<210> SEQ ID NO 181
<211> LENGTH: 432
<212> TYPE: PRT
<213> ORGANISM: Homo sapien

<400> SEQUENCE: 181

-continued

```
Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
```

-continued 420 425 430

<210> SEQ ID NO 182
<211> LENGTH: 511
<212> TYPE: DNA
<213> ORGANISM: Homo sapiens

<400> SEQUENCE: 182
gaagtttcat gaggtttagc ttttctgggc tggggagtgg agagaaagaa gttgcagggc 60
ttacaggaaa tcccagagcc tgaggttttc tcccagattt gagaactcta gattctgcat 120
cattatcttt gagtctatat tctcttgggc tgtaagaaga tgaggaatgt aataggtctg 180
ccccaagcct ttcatgcctt ctgtaccaag cttgtttcct tgtgcatcct tcccaggctc 240
tggctgcccc ttattggaga atgtgatttc caagacaatc aatccacaag tgtctaagac 300
tgaatacaaa gaacttcttc aagagttcat agacgacaat gccactacaa atgccataga 360
tgaattgaag gaatgttttc ttaaccaaac ggatgaaact ctgagcaatg ttgaggtgtt 420
tatgcaatta atatatgaca gcagtctttg tgatttattt taactttctg caagaccttt 480
ggctcacaga actgcagggt atggtgagaa a 511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt 60
cttctctgcc atcttctcat actggtcacg catctcgttc agaatgcggc tcaggtccac 120
gccaggtgca gcgtccatct ccacattgac atctccaccc acctggcctc tcagggcatt 180
catctcctcc tcgtggttct tcttcaggta ggccagctcc tccttcaggc tctcaatctg 240
catctccagg tcagctctgg 260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag 60
agggcctttt ctagctgtat gactgttact tgaccttctt tgaaaagcat tcccaaaatg 120
ctctatttta gatagattaa cattaaccaa cataattttt tttagatcga gtcagcataa 180
atttctaagt cagcctctag tcgtggttca tctctttcac ctgcatttta tttggtgttt 240
gtctgaagaa aggaaagagg aaagcaaata cgaattgtac tatttgtacc aaatctttgg 300
gattcattgg caaataattt cagtgtggtg tattattaaa tagaaaaaaa aaattttgtt 360
tcctaggttg aaggtctaat tgataccgtt tgacttatga tgaccattta tgcactttca 420
aatgaatttg ctttcaaaat aaatgaagag cagacctcgg c 461

<210> SEQ ID NO 185
<211> LENGTH: 531
<212> TYPE: DNA
<213> ORGANISM: Homo sapiens

<400> SEQUENCE: 185
tctgatttta tttccttctc aaaaaaagtt atttacagaa ggtatatatc aacaatctga 60

-continued caggcagtga acttgacatg attagctggc atgatttttt cttttttttc ccccaaacat 120
tgtttttgtg gccttgaatt ttaagacaaa tattctacac ggcatattgc acaggatgga 180
tggcaaaaaa aagtttaaaa acaaaaaccc ttaacggaac tgccttaaaa aggcagacgt 240
cctagtgcct gtcatgttat attaaacata catacacaca atctttttgc ttattataat 300
acagacttaa atgtacaaag atgttttcca ctttttttcaa tttttaaaca caacagctat 360
aaacctgaac acatatgcta tcatcatgcc ataagactaa aacaattata tttagcgaca 420
agtagaaagg attaaatagt caaatacaag aatgaaaaac gcagtacata gtgtcgcgaa 480
ctcaaatcgg catttagata gatccagtgg tttaaacggc acgtttttgc t 531

<210> SEQ ID NO 186
<211> LENGTH: 441
<212> TYPE: DNA
<213> ORGANISM: Homo sapiens

<400> SEQUENCE: 186
cattcctttc ctcgcgttgg ggtttctctg tgtcagcgag cctcggtaca ctgatttccg 60
atcaaaagaa tcatcatctt taccttgact tttcagggaa ttactgaact ttcttctcag 120
aagatagggc acagccattg ccttggcctc acttgaaggg tctgcatttg ggtcctctgg 180
tctcttgcca agtttcccaa ccactcgagg gagaaatatc gggaggtttg acttcctccg 240
gggctttccc gagggcttca ccgtgagccc tgcggccctc agggctgcaa tcctggattc 300
aatgtctgaa acctcgctct ctgcctgctg gacttctgag gccgtcactg ccactctgtc 360
ctccagctct gacagctcct catctgtggt cctgttgtac tggacggggt ccccagggtc 420
ctgggggctt ttttcctgtc t 441

<210> SEQ ID NO 187
<211> LENGTH: 371
<212> TYPE: DNA
<213> ORGANISM: Homo sapiens

<400> SEQUENCE: 187
aaaagtgaat gagtaactat tatattgttg gcaataataa gttgcaaaat catcaggctg 60
caggctgctg atggtgagag tgaactctgt cccagatcca ctgccgctga accttgatgg 120
gaccccagat tctaaactag acgccttatg gatcaggagc tttggggctt tccctggttt 180
ctgttgatac caggccaacc aactactaac actctgactg gcccggcaag tgatggtgac 240
tctgtctcct acagttgcag acagggtgga aggagactgg gtcatctgga tgtcacattt 300
ggcacctggg agccagagca gcaggagccc caggagctga gcggggaccc tcatgtccat 360
gctgagtcct g 371

<210> SEQ ID NO 188
<211> LENGTH: 226
<212> TYPE: DNA
<213> ORGANISM: Homo sapiens

<400> SEQUENCE: 188
ggtatataaa ttgagatgcc cccccaggcc agcaaatgtt cctttttgtt caaagtctat 60
ttttattcct tgatattttt cttttttttt tttttgtgga tggggacttg tgaatttttc 120
taaaggtgct atttaacatg ggaggagagc gtgtgcggct ccagcccagc ccgctgctca 180
ctttccaccc tctctccacc tgcctctggc ttctcaggac ctgccc 226

-continued

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189
tgggtgaagt ttattctgtt ttcacatcta ggttgttggg ganagtgata gacaaagttc 60
tggattctgg gcatcgtcgg cgcatgcttg taatcctact tgggaggttg anacaggaga 120
cctcggccgc naccacgcta agggcgaatt ctgcanatat ccatcacact ggcggccgct 180
cgagcatgca tctanagggc ccaattcncc ctatagtgag ncgtattaca attcactggc 240
cgtcgtttta caacgtcgtg actgggaaaa ccctggcgtt acccaactta atcgccttgc 300
agcacatccc cctttcncca gctggcttaa tancgaagag gcccgcaccg atcgcccttc 360
ccaacanttg cgcagcctga atggcgaatg g 391

<210> SEQ ID NO 190
<211> LENGTH: 501
<212> TYPE: DNA
<213> ORGANISM: Homo sapiens

<400> SEQUENCE: 190
catcttggcc tttttgagct gtttccgctt cttctcatcc cggtcactgt caccctcatt 60
actggaggag ctggcagagg cgttgctgtc aaactcctct gccacatctt cctcctcttc 120
acctgggttg aatgactcat cggtttcttc tcctgagtca tcgctgctgt cattggcatt 180
ctcctcccgg atcttgcctt cctccttcat cctctccaag taggcatcat gctggtcctc 240
atcagagtca gcatattcat cgtagcttgg gttcatgccc tctttcaatc ctcggttttt 300
gatgttgagc tttttcgcgt tgacaaaatc aaacagtttc ccgtactcct ccctctcaat 360
gctgctgaag gtatactgag tgccctgctt ggtctcaatt tcaaagtcaa aggaacgagt 420
agtagtggta ccacgagcaa agttgacaaa ggagatctca tcgaagcgga tgtgcacagg 480
tggcttgtgg acgtagatga a 501

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191
ggaaaaactg tgaaaaatat atctgaattt attaagtaca gtataaaana gggttgtggc 60
aacagaaagt aaaaactaac atggattgct ataaatatgc tgaagcctag ttgttcaaat 120
gatacaattc tctcatgcta ctctaaagtt tataaagaaa aaggatttac actttacaca 180
ctgtacacaa aaggaatacc ttctgagagc cagggagtgg ggaaagggga aggagacttg 240
a 241

<210> SEQ ID NO 192
<211> LENGTH: 271
<212> TYPE: DNA
<213> ORGANISM: Homo sapiens -continued
<220> FEATURE:
<221> NAME/KEY: misc_feature
<222> LOCATION: (1)...(271)
<223> OTHER INFORMATION: n=A,T,C or G

<400> SEQUENCE: 192
tggtcntgga ttcacanata aantanatcg actaaaactg gcagaaattg tgaagcaggt 60
gatagaagan caaaccacgt cccacgaatc ccaataatga cagcttcaga ctttgctttt 120
ttaacaattt gaaaaattat tctttaatgt ataaagtaat tttatgtaaa ttaataaatc 180
ataatttcat ttccacattg attaaagctg ctgtatagat ttagggngca ggacttaata 240 atagngggaaa tgaaattatg atttattaat c 271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc 60
taacttcctg tgcctttcct atcacctcga gaagtaatta tcagttggtt tggatttttg 120
gaccaccgtt cagtcatttt gggttgccgt gctcccaaaa cattttaaat gaaagtattg 180
gcattcaaaa agacagcaga caaaatgaaa gaaaatgaga gcagaaagta agcatttcca 240
gcctatctaa tttctttagt tttctatttg cctccagtgc agtccatttc ctaatgtata 300
ccagcctact gtactattta aaatgctcaa tttcagcacc gatggacctg c 351

<210> SEQ ID NO 194
<211> LENGTH: 311
<212> TYPE: DNA
<213> ORGANISM: Homo sapiens

<400> SEQUENCE: 194
ctgagacaca gaggcccact gcgaggggga cagtggcggt gggactgacc tgctgacagt 60
caccctccct ctgctgggat gaggtccagg agccaactaa aacaatggca gaggagacat 120
ctctggtgtt cccaccaccc tagatgaaaa tccacagcac agacctctac cgtgtttctc 180
ttccatccct aaaccacttc cttaaaatgt ttggatttgc aaagccaatt tggggcctgt 240
ggagcctggg gttggatagg gccatggctg gtcccccacc atacctcccc tccacatcac 300
tgacacagac c 311

<210> SEQ ID NO 195
<211> LENGTH: 381
<212> TYPE: DNA
<213> ORGANISM: Homo sapiens

<400> SEQUENCE: 195
tgtcagagtg gcactggtag aagttccagg aaccctgaac tgtaagggtt cttcatcagt 60
gccaacagga tgacatgaaa tgatgtactc agaagtgtcc tggaatgggg cccatgagat 120
ggttgtctga gagagagctt cttgtcctgt ctttttcctt ccaatcaggg gctcgctctt 180
ctgattattc ttcagggcaa tgacataaat tgtatattcg gttcccggtt ccaggccagt 240
aatagtagcc tctgtgacac cagggcgggg ccgagggacc acttctctgg gaggagaccc 300
aggcttctca tacttgatga tgtagccggt aatcctggca cgtggcggct gccatgatac 360
cagcagggaa ttgggtgtgg t 381

-continued

<210> SEQ ID NO 196
<211> LENGTH: 401
<212> TYPE: DNA
<213> ORGANISM: Homo sapiens

<400> SEQUENCE: 196

```
cacaaacaag aggagcacca gacctcctct tggcttcgag atggcttcgc cacaccaaga     60
gcccaaacct ggagacctga ttgagatttt ccgccttggc tatgagcact gggccctgta    120
tataggagat ggctacgtga tccatctggc tcctccaagt gagtaccccg gggctggctc    180
ctccagtgtc ttctcagtcc tgagcaacag tgcagaggtg aaacgggagc gcctggaaga    240
tgtggtggga ggctgttgct atcgggtcaa caacagcttg gaccatgagt accaaccacg    300
gcccgtggag gtgatcacca gttctgcgaa ggagatggtt ggtcagaaga tgaagtacag    360
tattgtgagc aggaactgtg agcactttgt cacccagacc t                        401
```

<210> SEQ ID NO 197
<211> LENGTH: 471
<212> TYPE: DNA
<213> ORGANISM: Homo sapiens

<400> SEQUENCE: 197

```
ctgtaatgat gtgagcaggg agccttcctc cctgggccac ctgcagagag ctttcccacc     60
aactttgtac cttgattgcc ttacaaagtt atttgtttac aaacagcgac catataaaag    120
cctcctgccc caaagcttgt gggcacatgg gcacatacag actcacatac agacacacac    180
atatatgtac agacatgtac tctcacacac acaggcacca gcatacacac gtttttctag    240
gtacagctcc caggaacagc taggtgggaa agtcccatca ctgagggagc ctaaccatgt    300
ccctgaacaa aaattgggca ctcatctatt cctttctct tgtgtcccta ctcattgaaa     360
ccaaactctg gaaaggaccc aatgtaccag tatttatacc tctagtgaag cacagagaga    420
ggaagagagc tgcttaaact cacacaacaa tgaactgcag acacagacct g             471
```

<210> SEQ ID NO 198
<211> LENGTH: 201
<212> TYPE: DNA
<213> ORGANISM: Homo sapiens

<400> SEQUENCE: 198

```
ggtccattga ggctctgtcg gccatgccca cagttcgaag ctttgccaac gaggagggcg     60
aagcccagaa gtttagggaa aagctgcaag aaataaagac actcaaccag aaggaggctg    120
tggcctatgc agtcaactcc tggaccacta gtatttcagg tatgctgctg aaagtgggaa    180
tcctctacat tggtgggcag a                                              201
```

<210> SEQ ID NO 199
<211> LENGTH: 551
<212> TYPE: DNA
<213> ORGANISM: Homo sapiens

<400> SEQUENCE: 199

```
tctggcacag atcttcaccc acacggcggt ccacgtgctg atcatcttcc gggtctcacc     60
gggcctggaa cacaccatct tccccatgag cccggtgccc agtctggtga cttccatctt    120
ggcccctggc cttatgtccc agttatgacc cctgacttca actctggctc ttaccctgta    180
actccagtcc atctctgaca tttttaacac ccggccttgt gaccgtggac atagctcctg    240
acctcgattc ccatcttgag cccagtgtta gtccatgaga tcatgacctg actcctggtc    300
```

-continued tccaaccttg tgatcctaat tctgggacct caatcctagc ctctgaactt gggaccctgg 360
agctcctgac cttagtcctg accgctaccc ttgattctga cctttgatcc tgtaacttag 420
gggtggcccc tgaccttatt actgtcattt agctccttga ccttgccact tcaatcctgg 480
ctttatgacc tcctactctc aattttaact ttaaccaaat gaccaaattt gtgacactaa 540
atgaccacaa t 551

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200
cagctcancg ggcgacatgc ccctacaagt tggcanaagn ggctgccact gctgggtttg 60
tgtaagagag gctgctgnca ccattacctg cagaaacctt ctcatagggg ctacgatcgg 120
tactgctagg gggcacatag cgcccatggg tgtggtaggt ggggnactcn ntnataggat 180
ggtaggtatc ccgggctgga aanatgnnca g 211

<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttc t 60 taatttccac actatttctc ccatattcct taaacttctt ggcatccacc t 111

<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga 60
ggagagagag agagaggaaa attccctaac ccttggttta aagacaatat tcatttattg 120
ctcaaatgat gcttttaagg gaggacagtg gaataaaata aacttttttt ttctccctac 180
aatacataga agggttatca aaccactcaa gtttcaaaat ctttccaggg tccaatatca 240 cttttttttct ttcggttcaa tgaaaagcta aatgtaataa tactaattat agataaaatt 300
ttattttact ttttaaaaat ttgtccagac c 331

<210> SEQ ID NO 203
<211> LENGTH: 491
<212> TYPE: DNA
<213> ORGANISM: Homo sapiens

<400> SEQUENCE: 203
agtcacccag tctacttagt acctggttgc tgcctctgac cttttcagct tgataccctg 60
ggctttagtg taaccaataa atctgtagtg accttacctg tattccctgt gctatcctgt 120
gggaaggtag gaatgggcta agtatgatga atgtataggt tagggatctt ttggttttaa 180
atcacagaaa acctaattca aactggctta aaataaaaag gatttattgg ttcatgtaac 240

-continued

```
tagaaagtcc ataggtagtg ctggctccag gtgaagactt gacccagtag ttcagtatgt    300

ctctaaatac cggactgact tttttctcac tgttgcatct tctgtaggac catttaagtc    360

tgggccactt aatggctgcc agcattccta agattacact tttccccatt tatgtccaat    420

cagaaaaaga aggcatcttt gtaccagaaa tctcagcaaa agccctaata ttcacactga    480

ttaggacctg c                                                         491
```

<210> SEQ ID NO 204
<211> LENGTH: 361
<212> TYPE: DNA
<213> ORGANISM: Homo sapiens

<400> SEQUENCE: 204

```
tcccttcctc ccccatgtga taaatgggtc cagggctgat caaagaactc tgactgcaga     60

actgccgctc tcagtggaca gggcatctgt tatcctgaga cctgtggcag acacgtcttg    120

ttttcatttg atttttgtta agagtgcagt attgcagagt ctagaggaat tttgtttcc     180

ttgattaaca tgattttcct ggttgttaca tccagggcat ggcagtggcc tcagccttaa    240

acttttgttc ctactcccac cctcagcgaa ctgggcagca cggggagggt ttggctaccc    300

ctgcccatcc ctgagccagg taccaccatt gtaaggaaac actttcagaa attcagacct    360

c                                                                    361
```

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<220> FEATURE:
<221> NAME/KEY: misc_feature
<222> LOCATION: (3)
<223> OTHER INFORMATION: n=A,T,C or G

<400> SEQUENCE: 205

```
cnngtacagt tcttcctgga tggccgacac agatcctggg gaaaggcaat cctggcactg     60

ctctgaaacc agagctcctc ctccctcccc gggcagggtg gagctgagaa gggctgctct    120

agcgttggga ctccacctcc atacacctga tattttgata gggcaggtcc ctgctatggg    180

ccactgttct gggcagtata gtatgcttga cagcatcctt ggcatctatc caccagatcc    240

cagagcaccc gctactagct gtgacaacat cctccaaaca ttgcaaaatt tcccctggga    300

ggcaagattg cctcagatgg gagaatcacg ctctagggaa atctgctggt atgagaaccc    360

caactcccca ctccactgag cctccagatg gcgagcaggc tgcagctcca gcacagacac    420

gaagctccct ccagccactg acggtccatg gctggggtta cccaggacct c             471
```

<210> SEQ ID NO 206
<211> LENGTH: 261
<212> TYPE: DNA
<213> ORGANISM: Homo sapiens

<400> SEQUENCE: 206

```
tagagtattt agagtcctga gataacaagg aatccaggca tcctttagac agtcttctgt     60

tgtcctttct tcccaatcag agatttgtgg atgtgtggaa tgacaccacc accagcaatt    120

gtagccttga tgagagaatc caattcttca tctccacgaa tagcaagttg caagtgacga    180

ggggtaatac gctttacctt taagtctttt gatgcatttc ctgccagttc aagtacctct    240
```

-continued gcggtgaggt actccaggat g 261

<210> SEQ ID NO 207
<211> LENGTH: 361
<212> TYPE: DNA
<213> ORGANISM: Homo sapiens

<400> SEQUENCE: 207
gctctccggg agcttgaaga agaaactggc tacaaagggg acattgccga atgttctcca 60
gcggtctgta tggacccagg cttgtcaaac tgtactatac acatcgtgac agtcaccatt 120
aacggagatg atgccgaaaa cgcaaggccg aagccaaagc caggggatgg agagtttgtg 180
gaagtcattt ctttacccaa gaatgacctg ctgcagagac ttgatgctct ggtagctgaa 240
gaacatctca cagtggacgc cagggtctat tcctacgctc tagcactgaa acatgcaaat 300
gcaaagccat ttgaagtgcc cttcttgaaa ttttaagccc aaatatgaca ctggacctgc 360
c 361

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208
agaggagatn tttgccatgc ctgaatnctt tcctatncca ccctancact taacatatta 60
cttagtctgc tttgntaaaa gcaagtatta ccttnaactt gnctcttact ctttgccctt 120
tagctaacta ataaagnttg atntaggcat tattatataa ttctgagtca ttcatggtat 180
ctctcatgtt tgatgtattt tncaaactaa gatctatgat agttttttttt ccanagttcc 240 attaaatcat ttatttcctt tactttctca cctctgtnga aacatttaga aactggattt 300
gggaacccan ttttggaaaa ccagattcat agtcatgaaa atggaaactt ncatattctg 360
tttttgaaaa gatgtggacc t 381

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209
gtggagagca agtgatttat taaagcaaga cgttgaaacc tttacattct gcagtgaaga 60
tcagggtgtc attgaaagac agnggaaacc aggatgaaag tttttacatg tcacacacta 120
catttcttca atattttcac caggacttcc gcaatgaggc ttcgtttctg aagggacatc 180
tgatccgtgc atctcttcac tcctaacttg gctgcaacag cttccacctg c 231

<210> SEQ ID NO 210
<211> LENGTH: 371
<212> TYPE: DNA
<213> ORGANISM: Homo sapiens

<400> SEQUENCE: 210

-continued

```
tccatcctgg ttttgcagag atcaggttgt tgacagttcc tggttgaccc acagctaccc     60

atgtcagtta tctccactaa catatccaag aatctttgta ggacaatttc tccacctgca    120

aggtttttta ggtagaactc ttcttttaag gcaattagcc cattgccaaa aggttttact    180

gtcttaaagc tgtctttctg agatctaatt ccaaggactt ctccacagct aagtgagatg    240

cctcacacca ttaggtgatg ctttggacag aacagagtat tttcatcttg tgtttaaagc    300

aattccttgg cttcggctcc tcaccacttt ctatgccagt ctcccattta tgtccctagt    360

aatgcctatg c                                                          371
```

<210> SEQ ID NO 211
<211> LENGTH: 471
<212> TYPE: DNA
<213> ORGANISM: Homo sapiens

<400> SEQUENCE: 211

```
tttattttaa aagaaaaaaa ttaaaataga gccaacaaat gcaattaaga aaaaaaaagt     60

attgagacac aaggggacct acatgttctg gtctaagaag catgcaagta ttacaaagca    120

ttccagatac agtatgacag aggaacagtg aacaagcatt ggaacgatgc tctttctttc    180

agaaacggga agtctaacag ttatgttttc acaatggtag tgattaaacc atctttattt    240

ttaaggaatt ttataggaag aattttagca ccatcattaa aggaaaaata ataatacctt    300

tttagccctg cctatctcca gtcttggaat aataacagaa gcatagcacc tttcagtatc    360

taaaatataa acaagaatag taagtccatc ccagcttcta gagatgaggt agctcatgct    420

aagaaatgtt gggtcatttt tcctatgaaa gttcaaaggc caaatggtca c             471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat     60

atattttggg ttcaaaaaaa gtaaaaagat aatgtagctg catttctttg gttattttgg    120

gccccaaata tttcctcatc tttttgttgt tgtcatggat ggtggtgaca tggacttgtt    180

tatagaggac aggtcagctc tctggctcgg tgatctacat tctgaagttg tctgaaaatg    240

tcttcatgat taaattcagc ctaaacgttt tgccgggaac actgcagaga caatgctgtg    300

agtttccaac ctcagcccat ctgcgggcag agaaggtcta gtttgtccat caccattatg    360

atatcaggac tggttacttg gttaaggagg ggtctacctc g                        401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213

```
tgtgaagcat acataaataa atgaagtaag ccatactgat ttaatttatt ggatgttatt     60

ttccctaaga cctgaaaatg aacatagtat gctagttatt tttcagtgtt agccttttac    120

tttcctcaca caatttggaa tcatataata taggtacttt gtccctgatt aaataatgtg    180

acggatagaa tgcatcaagt gtttattatg aaaagagtgg aaaagtatat agcttttanc    240
```

-continued

```
aaaaggtgtt tgcccattct aagaaatgag cgaatatata gaaatagtgn gggcatttct    300

tcctgttagg tggagtgtat gtgttgacat ttctccccat ctcttcccac tctgtttnnt    360

ccccattatt tgaataaagt gactgctgaa nangactttg aatccttatc cacttaattt    420

aatgtttaaa gaaaaaccta taatggaaag tgagactcct t                        461

<210> SEQ ID NO 214
<211> LENGTH: 181
<212> TYPE: DNA
<213> ORGANISM: Homo sapiens

<400> SEQUENCE: 214

cctgagcttc tactcctttc ccttaagatt cctccaaagc accagctcca taaaatcctt     60

cagctcccca gacccacacc aagaacccca catgttaatt ggatcagcca aatctacaag    120

cagataagtc ctaaggagaa tgccgaagcg tttttcttct tcctcaagcc tagcatgaga    180

c                                                                    181

<210> SEQ ID NO 215
<211> LENGTH: 581
<212> TYPE: DNA
<213> ORGANISM: Homo sapiens

<400> SEQUENCE: 215

ctgctttaag aatggttttc caccttttcc ccctaatctc taccaatcag acacatttta     60

ttatttaaat ctgcacctct ctctatttta tttgccaggg gcacgatgtg acatatctgc    120

agtcccagca cagtgggaca aaaagaattt agaccccaaa agtgtcctcg gcatggatct    180

tgaacagaac cagtatctgt catggaactg aacattcatc gatggtctcc atgtattcat    240

ttattcactt gttcattcaa gtatttattg aatacctgcc tcaagctaga gagaaaagag    300

agtgcgcttt ggaaatttat tccagttttc agcctacagc agattatcag ctcggtgact    360

tttctttctg ccaccattta ggtgatggtg tttgattcag agatggctga atttctattc    420

ttagcttatt gtgactgttt cagatctagt ttgggaacag attagaggcc attgtcctct    480

gtcctgatca ggtggcctgg ctgtttcttt ggatccctct gtcccagagc cacccagaac    540

cctgactctt gagaatcaag aaaacaccca gaaaggacct c                        581

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216

ccgatgtcct gcttctgtgg accaggggct cctctgnngg tggcctcaac cacggctgag     60

atccctagaa gtccaggagc tgtggggaag agaagcactt agggccagcc agccgggcac    120

ccccacttgc gccccgaccc acgctcacgc accagacctg cccnggcggt cgctcnaaag    180

ggcgaattct gcagatatcc atcacactgg cggacgctcg agcatgcatc tagagggccc    240

aattcaccct atantgagtc gtattacaat tcactggccg t                        281

<210> SEQ ID NO 217
<211> LENGTH: 356
<212> TYPE: DNA
```

-continued

<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217
atagcaggtt tcaacaattg tcttgtagtt tgnagtaaaa agacataaga aagagaaggt 60
gtggtttgca gcaatccgta gttggtttct caccataccc tgcagttctg tgagccaaag 120
gtcttgcaga aagttaaaat aaatcacaaa gactgctgtc atatattaat tgcataaaca 180
cctcaacatt gctcagagtt tcatccgttt ggttaagaaa acattccttc aattcatcta 240
tggcatttgt agtggcattg tcgtctatga actcttgaag aagttctttg tattcagtct 300
tagacacttg tggattgatt gncttggaaa tcacattctc caataaggga cctcgg 356

<210> SEQ ID NO 218
<211> LENGTH: 321
<212> TYPE: DNA
<213> ORGANISM: Homo sapiens

<400> SEQUENCE: 218
ttgtccatcg ggagaaaggt gtttgtcagt tgtttcataa accagattga ggaggacaaa 60
ctgctctgcc aatttctgga tttctttatt ttcagcaaac actttcttta aagcttgact 120
gtgtgggcac tcatccaagt gatgaataat catcaagggt ttgttgcttg tcttggattt 180
atatagagct tcttcatatg tctgagtcca gatgagttgg tcaccccaac ctctggagag 240
ggtctggggc agtttgggtc gagagtcctt tgtgtccttt ttggctccag gtttgactgt 300
ggtatctctg gacctgcctg g 321

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219
ccggttaggt ccacgcgggg gcagtggagg cacaggctca nggtggccgg gctacctggc 60
accctatggc ttacaaagta gagttggccc agtttccttc cacctgaggg gagcactctg 120
actcctaaca gtcttccttg ccctgccatc atctggggtg gctggctgtc aagaaaggcc 180
gggcatgctt tctaaacaca gccacaggag gcttgtaggg catcttccag gtggggaaac 240
agtcttagat aagtaaggtg acttgtctaa g 271

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220
gtcctacgac gaggaccagc ttttcttctt cnacttttcc canaacactc gggtgcctcg 60
cctgcccgaa tttgctgact gggctcagga acagggagat gctcctgcca ttttatttga 120
caaagagttc tgcgagtgga tgatccagca aatagggcca aaacttgatg ggaaaatccc 180

-continued ggtgtccaga gggtttccta tcgctgaagt gttcacgctg aagcccctgg agtttggcaa 240
gcccaacact ttggtctgtt ttgtcagtaa tctcttccca cccatgctga cagtgaactg 300
gtagcatcat tccgtccctg tggaaggatt tgggcctact tttgtctcag a 351

<210> SEQ ID NO 221
<211> LENGTH: 371
<212> TYPE: DNA
<213> ORGANISM: Homo sapiens

<400> SEQUENCE: 221
gtctgcagaa gcgtgtctga ggtgtccggt ggaggtggca gccgagctct gggactaatc 60
accgtgctgg ggacggcacc gcgtcaggat gcaggcagat ccctgcagaa gtgtctaaaa 120
ttcacactcc tcttctggag ggacgtcgat ggtattagga tagaagcacc aggggacccc 180
acgaacggtg tcgtcgaaac agcagccctt atttgcacac tgggagggcg tgacaccagg 240
aaaaccacaa ttctgtcttt cacggggggc cactgtacac gtctctgtct gggcctcggc 300
cagggtgccg agggccagca tggacaccag gaccagggcg cagatcacct tgttctccat 360
ggtggacctc g 371

<210> SEQ ID NO 222
<211> LENGTH: 471
<212> TYPE: DNA
<213> ORGANISM: Homo sapiens

<400> SEQUENCE: 222
gtccatgttc catcattaat gttccaacat caccagggac acaaagctgc aaaaatgaga 60
agggaaataa ggttagagaa aggatccggg caatcttaag gactgaggaa gacatgttcc 120
ccaacccttg aactcacaaa ccctgaagct caaggattgc atccttcctc caaatctcac 180
tcaacataat aagtgcagaa caacatgcca aagcactgta tgaagcacta gggacaaaga 240
caaggtcaaa atccttgtaa ccaaatttaa tggtattgta atgcagtgtt aacacaggac 300
agtaacagaa cacccaagaa ccaaacagaa gagggtaggg ataagcataa atgaagtaac 360
atgaaataaa cttccaaatg gaaaacttgt ccataccccc agggcaagtc aactacagtc 420
tcccaaagga cataaattcc acttagggca cactagacag aaaacaatat t 471

<210> SEQ ID NO 223
<211> LENGTH: 411
<212> TYPE: DNA
<213> ORGANISM: Homo sapiens

<400> SEQUENCE: 223
agttgctcta caatgacaca caaatcccgt taaataaatt ataaacaagg gtcaattcaa 60
atttgaagta atgttttagt aaggagagat tagaagacaa caggcatagc aaatgacata 120
agctaccgat taactaatcg gaacatgtaa aacagttaca aaaataaacg aactctcctc 180
ttgtcctaca atgaaagccc tcatgtgcag tagagatgca gtttcatcaa agaacaaaca 240
tccttgcaaa tgggtgtgac gcggttccag atgtggattt ggcaaaacct catttaagta 300
aaaggttagc agagcaaagt gcggtgcttt agctgctgct tgtgccgctg tggcgtcggg 360
gaggctcctg cctgagcttc cttccccagc tttgctgcct gagaggaacc a 411

<210> SEQ ID NO 224
<211> LENGTH: 321
<212> TYPE: DNA

-continued

<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224
ggtctgaagt ttgataacaa agaaatatat ntaagacaaa aatagacaag agttaacaat 60
aaaaacacaa ctatctgttg acataacata tggaaacttt ttgtcagaaa gctacatctt 120
cttaatctga ttgtccaaat cattaaaata tggatgattc agtgccattt tgccagaaat 180
tcgtttggct ggatcataga ttaacatttt cgagagcaaa tccaagccat tttcatccaa 240
gtttttgaca tgggatgcta ggcttcctgg tttccatttg ggaaatgtat tcttatagtc 300
ctgtaaagat tccacttctg g 321

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225
atgtctgggg aaagagttca ttggcaaaag tgtnctccca agaatggttt acaccaagca 60
gagaggacat gtcactgaat ggggaaaggg aacccccgta tccacagtca ctgtaagcat 120
ccagtaggca ggaagatggc tttgggcagt ggctggatga aagcagattt gagataccca 180
gctccggaac gaggtcatct tctacaggtt cttccttcac tgagacaatg aattcagggt 240
gatcattctc t 251

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226
gttaggtccc aggccccccg ccaagnggtt accnnnntna ccactcctga cccaaaaatc 60
aggcatggca ttaaaacgtt gcaaattcct ttactgttat cccccccacc accaggacca 120
tgtagggtgc agtctttact ccctaacccg tttcccgaaa aaggtgctac ctcctttcca 180
gacagatgag agagggcagg acttcaggct ggatccacca ctgggctctc cctcccccag 240
cctggagcac gggaggggag gtgacggctg gtgactgatg gatgggtagt gggctgagaa 300
gaggggacta ggaagggcta ttccaggctc a 331

<210> SEQ ID NO 227
<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg 60
gctgaagcta gaagtgcaac cccctcctga tttctgcagc aagatgaact gccttatccc 120
cagcccgcag gaatgttcat atctgagcaa tcaatgggca ctgtgttcaa ccacgccatt 180

-continued

```
ttcaagattg gctccttaaa ccacccacaa ggcaccagct ctgggagaag ctgcagggag    240

aagagaacaa agccctcgct gtgatcagga tgggtgtctc ataccttttc tctggggtca    300

ttccaggtat gagacagagt tgaacctgcg catgagcgtg gaggccgaca tcaacggcct    360

gcgcagggtg ctggatgagc tgaccctgga c                                  391


<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228

gttgtccata gccacctcct gggatagaag ctttntagtt catagttcga ttagtgtgtc     60

cttaggacat aggtccagcc ctacagatta gctgggtgaa gaaggcaagt gtctcgacag    120

ggcttagtct ccaccctcag gcatggaacc attcagggtg aagcctggga tgtgggcaca    180

ggagactcag gctgatataa aaataacaaa atcagtaata aaaaaattat aaaacctgtt    240

gcttgtctga atagatttga gcaacagtct tgcttttgtt aaaatcctgg agccgttaag    300

tcctgaatat tcttctggac atcattgctg gctggagaaa ggagccccag gcccggctcg    360

gctgacatct gtcaggtttg gaagtctcat c                                  391


<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229

gtccatggct tctcacccag acagtctttc tgggcaactt ggggaagccc ctgttctgct     60

caagtctcac cccatggaag aggtggggga agggggcctt ggtttttcag gaagacgggt    120

tggagagcac gagtcactac aaagcagtaa aagtgaatgg tgtctccagg ggctgggtcc    180

agaacaccgc ggagagcccc anccataaag gtgtgttccg cctctggcct gcaggaatct    240

ctttgaatct ctttgattgg tggctccaag agcaatggga agtcaacagc caggaggctg    300

gactgggttc cctgggaccc cgaggtccca gaggctgctg g                        341


<210> SEQ ID NO 230
<211> LENGTH: 511
<212> TYPE: DNA
<213> ORGANISM: Homo sapiens

<400> SEQUENCE: 230

gtccaagcca aggaaaccat tcccttacag gagacctccc tgtacacaca ggaccgcctg     60

gggctaaagg aaatggacaa tgcaggacag ctagtgtttc tggctacaga aggggaccat    120

cttcagttgt ctgaagaatg gttttatgcc cacatcatac cattccttgg atgaaacccg    180

tatagttcac aatagagctc agggagcccc taactcttcc aaaccacatg ggagacagtt    240

tccttcatgc ccaagcctga gctcagatcc agcttgcaac taatccttct atcatctaac    300

atgccctact tggaaagatc taagatctga atcttatcct ttgccatctt ctgttaccat    360
```

-continued atggtgttga atgcaagttt aattaccatg gagattgttt tacaaacttt tgatgtggtc 420
aagttcagtt ttagaaaagg gagtctgttc cagatcagtg ccagaactgt gcccaggccc 480
aaaggagaca actaactaaa gtagtgagat a 511

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct 60
cccctcgtgt cagctcaggc agctcgaggc ccccgaccaa cacttgcagg ggtccctgct 120
agttagcgcc ccaccgccgt ggagttcgta ccgcttcctt agaacttcta cagaagccaa 180
gctccctgga gccctgttgg cagctctagc tttgcagtcg tgtaattggc ccaagtcatt 240
gtttttctcg cctcactttc caccaagtgt ctagagtcat gtgagcctcg tgtcatctcc 300
ggggtggacc t 311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt 60
ctaaaaagcg gttctgtaac tctcaatcca gagatgttaa aaatgtttct aggcacggta 120
ttagtaaatc aagtaaattt catgtcctct taaaggacaa acttccagag atttgaatat 180
aaatttttat atgtgttatt gattgtcgtg taacaaatgg cccccacaaa ttagtagctt 240
aaaatagcat ttatgatgtc actgttttct ttgccttttc attaatgttc tgtacagacc 300
tatgtaaaca acttttgtat atgcatatag gatagctttt ttgagggtat a 351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc 60
acagccaccc ccagtatgcc gctccaggac tctgggacta gggcgccaaa gtgtgcaaat 120
gaaaatacag gatacccagg gaactttgaa tttcagattg tgaaaagaaa acaaatcttg 180
agactccaca atcaccaagc taaaggaaaa agtcaagctg ggaactgctt agggcaaagc 240
tgcctcccat tctattcaca gtcatccccc tgaggctcac ctgcatagct gattgcttcc 300
tttcccctat cgcttctgta aaaatgcaga ctcactgagc cagactaaat tgtgtgttca 360
gtggaaggct gatcaagaac tcaaaagaat gcaacctttt gtctcttatc tactacaacc 420
aggaagcccc cacttaaggg ttgtcccacc ttactggact gaaccaaggt acatcttaca 480
cctactgatt gatgtctcat gtccccctaa g 511

<210> SEQ ID NO 234
<211> LENGTH: 221
<212> TYPE: DNA
<213> ORGANISM: Homo sapiens

<400> SEQUENCE: 234

-continued caggtccagc gaaggggctt cataggctac accaagcatg tccacataac cgaggaagct 60
ctctccatca gcatagcctc cgatgaccat ggtgttccac aaagggttca tcttcgagcg 120
ccggctgtac atggccctgg tcagccatga atgaatagct ctaggactat agctgtgtcc 180
atctcccaga agctcctcat caatcaccat ctggccgaga c 221

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235
ggtccaagaa agggacatct atgtgaaagt ganactgaga cagtgctggt cacaggtcat 60
gctgcagaat aatacattcc caggcactgt cacgtggggg acccaagagg ccccaggagt 120
gacctataac ctctccagaa agaccactct gtgtggcatc acagtccaca cagtttaagg 180
aaatatttag acttaacaat cagacaccag ctcttactca cacttacact cacagcccac 240
acacaagtgt gcaaacatac acacacatat atatttcctg atacattcat ggaatatcag 300
agccctgccc tgaagtcgtt agtgtctctg ctccccaaac cgctgctccc acattggcta 360
agctccctca agagacctca g 381

<210> SEQ ID NO 236
<211> LENGTH: 441
<212> TYPE: DNA
<213> ORGANISM: Homo sapiens

<400> SEQUENCE: 236
aggtcctgtt gcccctttct tttgcccaac ttcgccattt gggaattgga atatttaccc 60
aacacctgta ctgcattgaa tattggaagc aaataacttg gctttgatct tataggctca 120
cagatggagg aacgtacctt gaagttcaga tgagatttcg gacttttgag ttgatgctga 180
aacagcttga gatttttggg gactactgag agatgataat tgtattgtgc aatatgagaa 240
ggacatgaga tttggtgggc ataggtgtga aatgacattg tttggatgtg tttaccctcc 300
aaatctcttg ttgaatgtga tcttaaacgt tggtggtggg cctagtggaa ggtgttgaat 360
catgggggtg gactcttcat aatttgctta gctccatccc cttggtgatg agcaagtcct 420
tgctctgttg tgtcacatga g 441

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237
tcctaaaaaa ttagctgacc ttgttaaaaa tgttggcgtg agcagtatat tattacctat 60 cttttttat tgtgtgtgtg ngtgtgtgtn ttaaactaat tggctgaaat atctgcctgt 120
ttccctcttt acatttttct tgtttctttc cttatttatc tttgtccatc ttgagatcta 180
ctgtaaagtg aatnttttaa tgaaaacann nccaagttnt actctcactg ggnttgggac 240

-continued atcagatgta attgagaggc caacaggtaa gtcttcatgt c 281

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238
gtctgcctcc tcctactgtt tccctctatn aaaaagcctc cttggcgcag gttccctgag 60
ctgtgggatt ctgcactggt gcttnggatt ccctgatatg ttccttcaaa tccactgaga 120
attaaataaa catcgctaaa g 141

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239
aacaatctaa acaaatccct cggttctann atacaatgga ttccccatat tggaaggact 60
ctgangcttt attcccccac tatgcntatc ttatcatttt attattatac acacatccat 120
cctaaactat actaaagccc ttttcccatg catggatgga aatggaagat ttttttttaa 180
cttgttctag aagtcttaat atgggctgtt gccatgaagg cttgcagaat tgagtccatt 240
ttctagctgc ctttattcac atagtgatgg ggtactaaaa gtactgggtt gactcagaga 300
gtcgctgtca ttctgtcatt gctgctactc taacactgag caacactctc ccagtggcag 360
atcccctgta tcattccaag aggagcattc atccctttgc tctaatgatc aggaatgatg 420
cttattagaa aacaaactgc ttgacccagg aacaagtggc ttagcttaag naaacttggc 480
tttgctcana tccctgatcc t 501

<210> SEQ ID NO 240
<211> LENGTH: 451
<212> TYPE: DNA
<213> ORGANISM: Homo sapiens

<400> SEQUENCE: 240
tgtcctgaaa ggccattact aatagaaaca cagcctttcc aatcctctgg aacatattct 60
gtctgggttt ttaatgtctg tggaaaaaaa ctaaacaagt ctctgtctca gttaagagaa 120
atctattggt ctgaaggttt ctgaacctct ttctggttct cagcagaagt aactgaagta 180
gatcaggaag gggctgcctc aggaaaattc ctagatccta ggaattcagt gagaccctgg 240
gaaggaccag catgctaatc agtgtcagtg aatccacagt ctttacttcc tgcctcataa 300
agggccaggt ctccccagta ccaagtcctt tcctcatgaa gttgtgttgc ctcaggctgt 360
ttagggacca ttgcctgtct tggtcacatg agtctgtctc cttactttag tccctgggca 420
atccttgctt aatgcttttg ttgactcaac g 451

<210> SEQ ID NO 241
<211> LENGTH: 411
<212> TYPE: DNA
<213> ORGANISM: Homo sapiens -continued
<220> FEATURE:
<221> NAME/KEY: misc_feature
<222> LOCATION: (1)...(411)
<223> OTHER INFORMATION: n=A,T,C or G

<400> SEQUENCE: 241

```
aatctccagt gtgatggtat cggggttaga gcttcaatct ccagtgtgat ggtactgcag     60

cnagagcttc aatctccagt gngatggtat tagggttaga tcttcaatct ccagtgtgat    120

ggtatcaggg ttagagcttc agcctccagt gtgatggtat cagggttaga gcttcagcct    180

ccagtgtgat ggtatcgggg ttagatcttc aatccccagt ggtggtggtt agagcttcaa    240

tctccagtgt gatggtattg gggttagagc ttcaatctcc agtctgatgg tgtttcggga    300

tggggctttt aagatgtaat tagggtttaa gatcataagg gacctggtct gatggggatt    360

agtncgcttn tatgaagaga cacangaggg cttgctctat ctctgactct c             411
```

<210> SEQ ID NO 242
<211> LENGTH: 351
<212> TYPE: DNA
<213> ORGANISM: Homo sapiens

<400> SEQUENCE: 242

```
ttccccttca caacagtaga gacctacaca gtgaactttg gggacttctg agatcagcgt     60

cctaccaaga ccccagccca actcaagcta cagcagcagc acttcccaag cctgctgacc    120

acagtcacat cacccatcag cacatggaag gcccctggta tggacactga aaggaagggc    180

tggtcctgcc cctttgaggg ggtgcaaaca tgactgggac ctaagagcca gaggctgtgt    240

agaggctcct gctccacctg ccagtctcgt aagaaatggg gttgctgcag tgttggagta    300

ggggcagagg gagggagcca aggtcactcc aataaaacaa gctcatggca c             351
```

<210> SEQ ID NO 243
<211> LENGTH: 241
<212> TYPE: DNA
<213> ORGANISM: Homo sapiens

<400> SEQUENCE: 243

```
gtctgtgctt tatcaggaaa agcacaagaa tatgtttttc tacctaaaac cctcttctac     60

tttaaaaatg gtttgctgaa tttttctatg tttttaaaat gtttttatgc ttttttttaa    120

acacgtaaag gatggaacct aatcctctcc cgagacgcct cctttgtgtt aatgcctatt    180

cttacaacag agaaacaagt acattaatat aaaaacgagt tgattattgg ggtataaaat    240

a                                                                    241
```

<210> SEQ ID NO 244
<211> LENGTH: 301
<212> TYPE: DNA
<213> ORGANISM: Homo sapiens

<400> SEQUENCE: 244

```
ggtccagagc aatagcgtct gtggtgaagc gcctgcactc ctcgggagac atgcctggct     60

tatatgctgc atccacataa ccatagataa aggtgctgcc ggagccacca atggcaaaag    120

gctgtcgagt cagcattcct cccagggttc catatacctg acctccttca cgttggtccc    180

agccagctac catgagatgt gcagacaagt cctctcgata tttatagctg atatttctca    240

ccacatttgc agcagccaaa acaagtggag gttcctccag ttctatccca tggagctcca    300

g                                                                    301
```

<210> SEQ ID NO 245
<211> LENGTH: 391
<212> TYPE: DNA
<213> ORGANISM: Homo sapiens

<400> SEQUENCE: 245
ctgacactgc tgatgtgggc cggggggcgc cgaggcacaa ctggtggccg gaccattgag 60
gcacctggag ggtaggcagc ttgtggtgca gacaccacag agagagaaaa gttggatgga 120
gtggtgggaa taatcagggt ggcacactgt gcctagaagc ttccagggcc accaagagaa 180
tgggaaggga aactacaaca ttcacaacag aaataggagt caattcactt agacccagaa 240
ctccagaaag ggggagtgta ggaatctaca atttcaaagc cagctcgtgt ctacctagag 300
ccccaaactg cataagcacc aggattgtac accttagtcc ctcaagatag tttcaagtga 360
gcgtgcaatt cactcttaca gaggagggcc t 391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246
tcctccacag gggaagcagg aagttngacc agcttcaggc tggaacgtgc ccagggcaca 60
gagctggcaa ggtgcaaagn cntctgcaga atattcacca ggttgacaca gacctccaca 120
ttcagacata ttccaagctt ctggggtctt cagggcccca gaatttcctg gtcttgggca 180
tggtncacaa gtcatttgtc cttcctcatt ttggaaggtt ccatttggac ataaaatgca 240
agcgttctcg tgctncatna taataggtcc cagcctgcac tgacacattt g 291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
cactgagtga atgagtatat aatttatgaa aacagaaaag tgctttggaa aaaaaaaaag 60
acaacaggag tacatacagn gaaccaaaaa gagtgtacca ggaggagcan accctgaaca 120
gttanaacta tggaaatcgc tatgctttgt gttgtcacag gagttaaaat aggaataccc 180
tgcatacaat aaatatttat tggataaata actaagcctg atacccttt caatgcgtta 240 tacanactnt atcatcacac cactaatcta agttctcana agttaaacat tacaagactt 300
cagaacaaca taggcgtntt tggctccatt taacanaana aggaccatag tgatcattta 360
atctctatga gtctgtctta tcttctggaa aaggggccta acaccatttc cttttgcaaa 420
aaggtagctg ccttgcttcc agttctacca tcctntagca acccatcttt n 471

<210> SEQ ID NO 248
<211> LENGTH: 551
<212> TYPE: DNA
<213> ORGANISM: Homo sapiens

<400> SEQUENCE: 248

-continued

```
ccatgggatc aggaatgggg tcaggtcagt tgacctgagc atacccatta aacatgttca     60

aatgtcccca tcccacccac tcacatgaca tggctcccga gccctgagat ctgtatccca    120

agaacctcag ttgagaaata tttatggcag cttcactgtt gctcaagagc ctgggtattg    180

tagcagcctg ggggcaggtt gtccctaatg ttctccaagt tcttcacatc agccagaatc    240

ccatctatgc ttgtctccag caaatggagg tggcccctct gctgacgtgc cctctcttcc    300

agctctgaca tcatgggccg cagttggctg ttgatctggg tcttggctcg ggaaagcttc    360

tgctccagta agaccagccc ctcttcatct acactgagag gctggtccat cagatgcagg    420

aggccgtcta atgtgttgag tgtgtcttgg attgtaaccc cagcgttctt ggctctggta    480

tcaaccttct gggcttctgt aatcaccatc tgtactgcat ccatattcgt gtcgaactcc    540

agctccttcc t                                                         551


<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249

atntccagag ggaccgtaag actggtacaa gtttacacca taagaggcga cgtggtcagc     60

cacaatgtct tcacctccac aggggctcat cacggngggtc agggcaaggg cccccagcat   120

cagagctttg tttaggatca tcctcttccc aaggcagcct tagcagttgc tgacctgccc    180

g                                                                    181


<210> SEQ ID NO 250
<211> LENGTH: 551
<212> TYPE: DNA
<213> ORGANISM: Homo sapiens

<400> SEQUENCE: 250

tctgtagcta ggatgagctg gctctcaagc aaaagtttgt cttcctgggt ccatttgtgg     60

ttatcacttg ttattgaatg tacatcacaa attaaagtct gcattgttgg acgtaagaga    120

atgtgccgac tttggtaacc aggagatttc atgttactgg actgcctgta gtcacgtatt    180

tctgctatga cacatccgca atgaaaaata ttaacctgag atttttctag gagatcaacc    240

aaaataggag gtaattcttc tgcatccaaa tattcaagca actctccttc ttcatagggc    300

agtcgaatgg tctcggaatc tgatccgttt tttccccctga gcatcagaga atatccctca   360

tttcctgggt atagattgac cactaaacat gacaaagtct cttgcataac aagcttctct    420

aacaagttca catttcttct taatttctta acttcaggtt ctttttcaca ttcttcaata    480

tacaagtcat aaagtttttg aaatacagat tttcttccac ttgataggta tttcctttta    540

ggaggtctct g                                                         551


<210> SEQ ID NO 251
<211> LENGTH: 441
<212> TYPE: DNA
<213> ORGANISM: Homo sapiens

<400> SEQUENCE: 251

tgtctgctct cccatcctgg ttactatgag tcgctcttgg cagaaaggac cacagatgga     60
```

-continued

```
gagcttggca ctcgctccaa ctttgccgaa aagaggacaa ccaccaaagt agtaggtaaa    120

aacacaattt tagcagcagt gaaataaaaa gaggaagtga ggatggggcc aggccgcaac    180

tataattaaa ctgtctgttt aggagaagct gaatccagaa gaaacacaag ctgtaaagtg    240

agagaggaca gggagcaggg cctttggaga gcaggagagg acaggctgtc accaagcgct    300

gctcggactc tgccctgaaa gatttgaatt ggacactgtc cagtcacgtg tgtggcaaac    360

cgtactccaa gcacttttct cacggcagag gaaggagctg ccatggctgt acccctgaac    420

gtttgtgggg ccagcgatgt g                                              441


<210> SEQ ID NO 252
<211> LENGTH: 406
<212> TYPE: DNA
<213> ORGANISM: Homo sapiens

<400> SEQUENCE: 252

tttttttttg aacaagtaaa aatttcttta tttgctgaca ataagataac ctacagggaa     60

aacctgatga aatctattaa aaagttacta aaactaataa aagaatttag gaaggttata    120

gaatgtaaga ccaagacaca aaaatcaatt acatttctat ataatagcaa tgaacagata    180

ctgaaatttt aaaaactaaa tcattttaca aaagtatcac aatatgaaac actccgggat    240

aaattggata aaagatgtgc aagactgtac aaaagctaca aaacatttat gaaggaaatt    300

ggaagataga aacaagatag aaaatgaaaa tattgtcaag agtttcagat agaaaatgaa    360

aaacaagcta agacaagtat tggagaagta tagaagatag aaaaat                   406


<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253

gaaggagttc agtagcaaag tcacacctgt ccaattccct gagctttgct cactcagcta     60

atgggatggc aaaggtggtg gtgctttcat cttcaggcag aagcctctgc ccatccccct    120

caagggctgc aggcccagtt ctcatgctgc ccttgggtgg gcatctgtta acagaggaga    180

acgtctgggt ggcggcagca gctttgctct gagtgcctac aaanctaatg cttggtgcta    240

gaaacatcat cattattaaa cttcagaaaa gcagcagcca tgttcagtca ggctcatgct    300

gcctcactgc ttaagtgcct gcaggagccg cctgccaagc tcccettcct acacctggca    360

cactggggtc tgcacaaggc tttgtcaacc aaagacagct tccccctttt gattgcctgt    420

agactttgga gccaagaaac actctgtgtg actctacaca cacttcaggt ggtttgtgct    480

tcaaagtcat tgatgcaact tgaaaggaaa cagtttaatg gtggaaatga actaccattt    540

ataa                                                                 544


<210> SEQ ID NO 254
<211> LENGTH: 339
<212> TYPE: DNA
<213> ORGANISM: Homo sapiens

<400> SEQUENCE: 254

tggcattcag ggcagtgtct tctgcatctc ctaggaacct cgggagcggc agctccggcg     60

cctggtagcg agaggcgggt tccggagatc ccggcctcac ttcgtcccac tgtggttagg    120
```

-continued ggtgagtcct gcaaatgtta agtgatttgc tcaaggtgcc catttcgcag gaattggagc 180
ccaggccagt tctctgagcc tatcattagg gctaaaggag tgcgtgatca gaatggtgtc 240
tggacggttc tacttgtcct gcctgctgct ggggtccctg ggctctatgt gcatcctctt 300
cactatctac tggatgcagt actggcgtgg tggctttgc 339

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255
gaggtttttt nttttttttt tttttttttt caattaaana tttgatttat tcaagtatgt 60
gaaaacattn tacaatggaa acttttntta aatgctgcat gtnctgtgct atggaccacn 120
cacatacagc catgctgttt caaaaaactt gaaatgccat tgatagttta aaaactntac 180
ncccgatgga aaatcgagga aaacaattta atgtttcatn tgaatccana ggngcatcaa 240
attaaatgac agctccactt ggcaaataat agctgttact tgatggtatc caaaaaaaaa 300
tggttgggga tggataaatt caaaaatgct tccccaaagg ngggnggttt ttaaaaagtt 360
tcaggncaca acccttgcan aaaacactga tgcccaacac antga 405

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256
gggcangtct ggtcctctcc ccacatgtca cactctcctc agcctctccc ccaaccctgc 60
tctccctcct cccctgccct agcccaggga cagagtctag gaggagcctg gggcagagct 120
ggaggcagga agagagcact ggacagacag ctatggtttg gattggggaa gaggttagga 180
agtaggttct taaagaccct tttttagta 209

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257
tctggacacc ataatccctt ttaagtggct ggatggtcac acctctccca ttgacaagct 60
gggttaagtc aataggttga ctaggatcaa cacgacccaa atcaataaga tactgcagtc 120
tattgagact caaaggctta tactggcgtc tgaaactatg tccttcgtta aacccgtatt 180
ttgggattcg gatgtaaaat ggagtctggc ctccctcaaa gcccaagcgg ggccgggttc 240
ctctttgcct ttctccttta tggcctctgc cacattttct acctcttctc cgacctcttg 300
gtcttntctc nggtttcttg gagccgggat tcggctttaa gtn 343

-continued

<210> SEQ ID NO 258
<211> LENGTH: 519
<212> TYPE: DNA
<213> ORGANISM: Homo sapiens

<400> SEQUENCE: 258
gcggcttctg acttctagaa gactaaggct ggtctgtgtt tgcttgtttg cccacctttg 60
gctgataccc agagaacctg ggcacttgct gcctgatgcc cacccctgcc agtcattcct 120
ccattcaccc agcgggaggt gggatgtgag acagcccaca ttggaaaatc cagaaaaccg 180
ggaacaggga tttgcccttc acaattctac tccccagatc ctctcccctg gacacaggag 240
acccacaggg caggacccta agatctgggg aaaggaggtc ctgagaacct tgaggtaccc 300
ttagatcctt ttctacccac tttcctatgg aggattccaa gtcaccactt ctctcaccgg 360
cttctaccag ggtccaggac taaggcgttt tctccatagc ctcaacattt tgggaatctt 420
cccttaatca cccttgctcc tcctgggtgc ctggaagatg gactggcaga gacctctttg 480
ttgcgttttg tgctttgatg ccaggaatgc cgcctagtt 519

<210> SEQ ID NO 259
<211> LENGTH: 371
<212> TYPE: DNA
<213> ORGANISM: Homo sapiens

<400> SEQUENCE: 259
attgtcaact atatacacag tagtgaggaa taaaatgcac acaaaacaat ggatagaata 60
tgaaaatgtc ttctaaatat gaccagtcta gcatagaacc ttcttctctt ccttctcagg 120
tcttccagct ccatgtcatc taacccactt aacaaacgtg gacgtatcgc ttccagaggc 180
cgtcttaaca actccatttc caaaagtcat ctccagaaga catgtatttt ctatgatttc 240
ttttaaacaa atgagaattt acaagatgtg taactttcta actctatttt atcatacgtc 300
ggcaacctct ttccatctag aagggctaga tgtgacaaat gttttctatt aaaaggttgg 360
ggtggagttg a 371

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G

<400> SEQUENCE: 260
ttggattttt tgacttgcga tttcagtttt tttacttttt tttttttttt ttttganaaa 60
tactatattt attgtcaaag agtggtacat aggtgagtgt tcatcttccc tctcatgccg 120
gtatactctg cttcgctgtt tcagtaaaag ttttccgtag ttctgaacgt cccttgacca 180
caccataana caagcgcaag tcactcanaa ttgccactgg aaaactggct caactatcat 240
ttgaggaaag actganaaag cctatcccaa agtaatggac atgcaccaac atcgcggtac 300
ctacatgttc ccgtttttct gccaatctac ctgtgtttcc aagataaatt accacccagg 360
gagtcacttc ctgctatgtg aacaaaaacc cggtttcttt ctggaggtgc ttgactactc 420 tctcgngagc 430

<210> SEQ ID NO 261
<211> LENGTH: 365

-continued

<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261
tcctgacgat agccatggct gtaccactta actatgattc tattccaact gttcagaatc 60
atatcacaaa atgacttgta cacagtagtt tacaacgact cccaagagag gaaaaaaaaa 120
aaaaaagacg cctcaaaatt cactcaactt ttgagacagc aatggcaata ggcagcanag 180
aagctatgct gcaactgagg gcacatatca ttgaagatgt cacaggagtt taagagacag 240
gctggaaaaa atctcatact aagcaaacag tagtatctca taccaagcaa aaccaagtag 300
tatctgctca gcctgccgct aacagatctc acaatcacca actgtgcttt aggactgtca 360
ccaaa 365

<210> SEQ ID NO 262
<211> LENGTH: 500
<212> TYPE: DNA
<213> ORGANISM: Homo sapiens

<400> SEQUENCE: 262
cctagatgtc atttgggacc cttcacaacc attttgaagc cctgtttgag tccctgggat 60
atgtgagctg tttctatgca taatggatat tcggggttaa caacagtccc ctgcttggct 120
tctattctga atccttttct ttcaccatgg ggtgcctgaa gggtggctga tgcatatggt 180
acaatggcac ccagtgtaaa gcagctacaa ttaggagtgg atgtgttctg tagcatccta 240
tttaaataag cctattttat cctttggccc gtcaactctg ttatctgctg cttgtactgg 300
tgcctgtact tttctgactc tcattgacca tattccacga ccatggttgt catccattac 360
ttgatcctac tttacatgtc tagtctgtgt ggttggtggt gaataggctt ctttttacat 420
ggtgctgcca gcccagctaa ttaatggtgc acgtggactt ttagcaagcg ggctcactgg 480
aagagactga acctggcatg 500

<210> SEQ ID NO 263
<211> LENGTH: 413
<212> TYPE: DNA
<213> ORGANISM: Homo sapiens

<400> SEQUENCE: 263
ctcagagagg ttgaaagatt tgcctacgaa agggacagtg atgaagctaa gctctagatc 60
caggatgtct gacttcaaat tgaaactccc aaagtaatga gtttggaagg gtggggtgtg 120
gcctttccag gatgggggtc ttttctgctc ccagcggata gtgaaacccc tgtctgcacc 180
tggttgggcg tgttgctttc ccaaaggttt ttttttagg tccgtcgctg tcttgtggat 240
taggcattat tatctttact ttgtctccaa ataacctgga gaatggagag agtagtgacc 300
agctcagggc cacagtgcga tgaggaccat cttctcacct ctctaaatgc aggaagaaac 360
gcagagtaac gtggaagtgg tccacaccta ccgccagcac attgtgaatg aca 413

<210> SEQ ID NO 264
<211> LENGTH: 524
<212> TYPE: DNA
<213> ORGANISM: Homo sapiens

<400> SEQUENCE: 264

-continued

```
tccaatgggg ccctgagagc tgtgacagga actcacactc tggcactggc agcaaaacac     60

cattccaccc cactcatcgt ctgtgcacct atgttcaaac tttctccaca gttccccaat    120

gaagaagact catttcataa gtttgtggct cctgaagaag tcctgccatt cacagaaggg    180

gacattctgg agaaggtcag cgtgcattgc cctgtgtttg actacgttcc cccagagctc    240

attaccctct ttatctccaa cattggtggg aatgcacctt cctacatcta ccgcctgatg    300

agtgaactct accatcctga tgatcatgtt ttatgaccga ccacacgtgt cctaagcaga    360

ttgcttaggc agatacagaa tgaagaggag acttgagtgt tgctgctgaa gcacatcctt    420

gcaatgtggg agtgcacagg agtccaccta aaaaaaaaaa tccttgatac tgttgcctgc    480

ctttttagtc accccgtaac aagggcacac atccaggact gtgt                     524
```

```
<210> SEQ ID NO 265
<211> LENGTH: 344
<212> TYPE: DNA
<213> ORGANISM: Homo sapiens

<400> SEQUENCE: 265

tcctttcttc tacttcagga gatgattcaa agttacttgt ggacatttct ttaagttctg     60

aagacaaatg agacaggatt tggcctgcgg gttcttcaga cttctctacc acctccatta    120

actcttcatc ttggcttgac gtaggcaatg cactattttg ctcttttgtt tctggagatg    180

acccagcacc acttctttct cttggcgggg ttctaagtgt gtctttgaat accagtgaag    240

actcaggcct atcctgtact ggaaagggac taaatttgtc tttctgtcta ggaggtgatg    300

cagtagcatc ctcctgaggg ggtaaggcca ttttctcttt ttga                     344
```

```
<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

ccacaatgtc cataacttga gcaggctttg gcatcccacc accccccttca gaccaataca     60

cactatgttg gaggaacnac tttaaaatgt aaaatgagaa atgggcactg aacactccat    120

cctcactccc aacagcccac ccacacacct cttcaactgc tatccaaaca tggaggagct    180

cttgtggaag agaggctcaa caccaaataa                                     210
```

```
<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n=A,T,C or G

<400> SEQUENCE: 267

tcggncctcc caccctctna ctgaaattct ntgaaattct ccccctttggg atgaggatgg     60

caaccccagg catgtaccct cccaacctgg gacccgacct aataccctaa catcctgctg    120

acagtggctg ttctcgctgg gcaggcgtcc caaagcacat cgagccagat tcaggcagag    180

tggaactggc ccctcagcca tcagtggagg tggcctggga ggctctaccc tgaacggg      238
```

-continued

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268
tcctcaagga catgcccctt gatagaaact cagttcctgt ctccagttcc ctcctggacc 60
tgatccccca aatgcagggc ctgggactat atccagttcc ttattttcag aggcccatgc 120
acaagatgca cagcaaataa gtgctgaata aagacccagc tactgctagc ttaccctgct 180
ccaaacattc accaagtcct cagcaaagag ggccatccat tcacctcttc taaaaacaca 240
ctgagctccc cagtctatac cccaagatat gcttggctcc caactatccc tcctctctca 300
tctccaagcc agtttcccct ttctaagtat actgatatta ccaaagacac tgacaatctt 360
cttttcctac ctctccccag tgactaggtt tgcagcagga gctctataag tcctagtata 420
cagcagaagc tccataaatg tgtgctgacc taacattang c 461

<210> SEQ ID NO 269
<211> LENGTH: 434
<212> TYPE: DNA
<213> ORGANISM: Homo sapiens

<400> SEQUENCE: 269
ctgtgttggt gagcaccgat tcccactcaa tatggcgtgg cttacagtct tcattaggtt 60
cccgctccca accagaatga ggaatgatca cttcatctgt caaggcatgc agtgcatggt 120
ccacaatctc cattttgatt gagtcatggg atgaaagatt ccacagggtt ccggtaataa 180
cttcagtaag gtccatatca cgagcctttc gaagcaatcg cacaagggca ggcacaccat 240
cacagttttt tatggcaatc ttgttatcct ggtcacgtcc aaaagagata ttcttgagag 300
ctccacaggc tccaaggtgc acttcctttt tgggatggtc taacaatccc accagtactg 360
ggatgccctt gagcttccgc acgtcagtct tcaccttgtc attgcggtag cataagtgtt 420
gcaggtatgc aaga 434

<210> SEQ ID NO 270
<211> LENGTH: 156
<212> TYPE: DNA
<213> ORGANISM: Homo sapiens

<400> SEQUENCE: 270
ctgcaccagc gattaccagt ggcattcaaa tactgtgtga ctaaggattt tgtatgctcc 60
ccagtagaac cagaatcaga caggtatgag ctagtcaaca gcaagtcttt gttggattcg 120
agtaggctca ggatctgctg aaggtcggag gagtta 156

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271
ccactgtcac ggtctgtctg acacttactg ccaaacgcat ggcaaggaaa aactgcttag 60

-continued

```
tgaagaactt agaagctgtg gagaccttgg ggtccacgtn caccatctgc tctgataaaa    120

ctggaactct gactcanaac cggatgacag tggcccacat gtggtttgac aatcaaatcc    180

atgaagctga tacgacagag aatcagagtg gtgtctcttt tgacaagact tcagctacct    240

ggcttgctct gtccagaatt gcaggtcttt gtaacagggc agtgtttcag gctaaccagg    300

aaaacctacc tattcttaag cgggcagttg caggagatgc ctctgagtca gcactcttaa    360

agtgcataga gctgtgctgt ggntncgtga aggagatgag agaaagatac nccaaaatcg    420

tcgagatacc cttcaactcc accaacaagt accagttgtc tattcataag aaccccaaca    480

catcggagcc ccaacacctg ttggtgatga agggcgcccc agaaaggatc cta           533
```

<210> SEQ ID NO 272
<211> LENGTH: 630
<212> TYPE: DNA
<213> ORGANISM: Homo sapiens

<400> SEQUENCE: 272

```
tggtattttt ctttttcttt tggatgtttt atactttttt ttcttttttc ttctctattc     60

ttttcttcgc cttcccgtac ttctgtcttc cagttttcca cttcaaactt ctatcttctc    120

caaattgttt catcctacca ctcccaatta atctttccat tttcgtctgc gtttagtaaa    180

tgcgttaact aggctttaaa tgacgcaatt ctccctgcgt catggatttc aaggtctttt    240

aatcaccttc ggtttaatct ctttttaaaa gatcgccttc aaattatttt aatcacctac    300

aacttttaaa ctaaacttta agctgtttaa gtcaccttca ttttaatcta aaagcattgc    360

ccttctattg gtattaattc ggggctctgt agtcctttct ctcaattttc ttttaaatac    420

attttttact ccatgaagaa gcttcatctc aacctccgtc atgttttaga aaccttttat    480

cttttccttc ctcatgctac tcttctaagt cttcatattt tctcttaaaa tcttaagcta    540

ttaaaattac gttaaaaact taacgctaag caatatctta gtaacctatt gactatattt    600

tttaagtagt tgtattaatc tctatctttc                                     630
```

<210> SEQ ID NO 273
<211> LENGTH: 400
<212> TYPE: DNA
<213> ORGANISM: Homo sapiens

<400> SEQUENCE: 273

```
tctggtttgc cctccagttc attctgaatc tagacttgct cagcctaatc aagttcctgt     60

acaaccagaa gcgacacagg ttcctttggt atcatccaca agtgaggggt acacagcatc    120

tcaacccttg taccagcctt ctcatgctac agagcaacga ccacagaagg aaccaattga    180

tcagattcag gcaacaatct ctttaaatac agaccagact acagcatcat catcccttcc    240

tgctgcgtct cagcctcaag tatttcaggc tgggacaagc aaacctttac atagcagtgg    300

aatcaatgta aatgcagctc cattccaatc catgcaaacg gtgttcaata tgaatgcccc    360

agttcctcct gttaatgaac cagaaacttt aaaacagcaa                          400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274

-continued

```
tntgagtatg tcccagagaa ggtgaagaaa gcggaaaaga aattagaaga gaatccatat     60

gaccttgatg cttggagcat tctcattcga gaggcacaga atcaacctat agacaaagca    120

cggaagactt atgaacgcct tgttgcccag ttccccagtt ctggcagatt ctggaaactg    180

tacattgaag cagaggttac tattttattt tattttttct tatatcagta ttgcagcatt    240

cactgtagtg atagaaaaca agttaggaac atagccaatt aggacaagga ggatttaaat    300

gtgtcttacc tttattttgt aaaataggta taaaggagta attaaaatga a             351
```

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

```
gcgnggtcgc nnncgaggtc tgagaagccc ataccactat ttgttgagaa atgtgtggaa     60

tttattgaag atacagggtt atgtaccgaa ggactctacc gtgtcagcgg gaataaaact    120

gaccaagaca atattcaaaa gcagtttgat caagatcata atatcaatct agtgtcaatg    180

gaagtaacag taaatgctgt agctggagcc cttaaagctt tctttgcaga tctgccagat    240

cctttaattc catattctct tcatccagaa ctattggaag cagcaaaaat cccggataaa    300

acagaacgtc ttcatgcctt gaaagaaatt gttaagaaat ttcatcctgt aaactatgat    360

gtattcagat acgtgataac a                                              381
```

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

```
gctcngactc cggcgggacc tgctcggagg aatggcgccg ccgggttcaa gcactgtctt     60

cctgttggcc ctgacaatca tagccagcac ctgggctctg acgcccactc actacctcac    120

caagcatgac gtggagagac taaaagcctc gctggatcgc cctttcacaa atttggaatc    180

tgccttctac tccatcgtgg gactcagcag ccttggtgct caggtgccag atgcaaagaa    240

agcatgtacc tacatcagat ctaaccttga tcccagcaat gtggattccc tcttctacgc    300

tgcccaggcc agccaggccc tctcaggatg tgagatctct atttcaaatg agaccaaaga    360

tctgcttctg gcagacctcg gccgcgacca                                     390
```

<210> SEQ ID NO 277
<211> LENGTH: 378
<212> TYPE: DNA
<213> ORGANISM: Homo sapiens

<400> SEQUENCE: 277

```
tgggaacttc tggggtagga cgttgtctgc tatctccagt tccacagacc caaccagtta     60

cgatggtttt ggaccattta tgccgggatt cgacatcatt ccctataatg atctgcccgc    120

actggagcgt gctcttcagg atccaaatgt ggctgcgttc atggtagaac caattcaggg    180
```

-continued

```
tgaagcaggc gttgttgttc cggatccagg ttacctaatg ggagtgcgag agctctgcac    240

caggcaccag gttctcttta ttgctgatga aatacagaca ggattggcca gaactggtag    300

atggctggct gttgattatg aaaatgtcag acctgatata gtcctccttg gaaaggccct    360

ttctgggggc ttataccc                                                  378
```

<210> SEQ ID NO 278
<211> LENGTH: 366
<212> TYPE: DNA
<213> ORGANISM: Homo sapiens

<400> SEQUENCE: 278

```
ggagggcaca ttccttttca cctcagagtc ggtcggggaa ggccacccag ataagatttg     60

tgaccaaacc agtgatgctg tccttgatgc ccaccttcag caggatcctg atgccaaagt    120

agcttgtgaa actgttgcta aaactggaat gatccttctt gctggggaaa ttacatccag    180

agctgctgtt gactaccaga aagtggttcg tgaagctgtt aaacacattg gatatgatga    240

ttcttccaaa ggttttgact acaagacttg taacgtgctg gtagccttgg agcaacagtc    300

accagatatt gctcaaggtg ttcatcttga cagaaatgaa gaagacattg gtgctggaga    360

ccaggg                                                               366
```

<210> SEQ ID NO 279
<211> LENGTH: 435
<212> TYPE: DNA
<213> ORGANISM: Homo sapiens

<400> SEQUENCE: 279

```
cctaagaact gagacttgtg acacaaggcc aacgacctaa gattagccca gggttgtagc     60

tggaagacct acaacccaag gatggaaggc ccctgtcaca aagcctacct agatggatag    120

aggacccaag cgaaaaagat atctcaagac taacggccgg aatctggagg cccatgaccc    180

agaacccagg aaggatagaa gcttgaagac ctggggaaat cccaagatga gaaccctaaa    240

ccctacctct tttctattgt ttacacttct tactcttaga tatttccagt tctcctgttt    300

atctttaagc ctgattcttt tgagatgtac tttttgatgt tgccggttac ctttagattg    360

acaagtatta tgcctggcca gtcttgagcc agctttaaat cacagctttt acctatttgt    420

taggctatag tgttt                                                     435
```

<210> SEQ ID NO 280
<211> LENGTH: 435
<212> TYPE: DNA
<213> ORGANISM: Homo sapiens

<400> SEQUENCE: 280

```
tctggatgag ctgctaactg agcacaggat gacctgggac ccagcccagc caccccgaga     60

cctgactgag gccttcctgg caaagaagga gaaggccaag ggggagccctg agagcagctt    120

caatgatgag aacctgcgca tagtggtggg taacctgttc cttgccggga tggtgaccac    180

ctcgaccacg ctggcctggg gcctcctgct catgatccta cacctggatg tgcagcgtga    240

gcccagacct gtccgggcgg ccgctcgaaa ttccagcaca ctggcggccg ttactagtgg    300

atccgagctc ggtaccaagc ttggcgtaat catggtcata gctgtttcct gtgtgaaatt    360

gttatccgct cacaattcca cacaacatac gagccggaag cataaagtgt aaagcctggg    420

gtgcctaatg agtga                                                     435
```

-continued

<210> SEQ ID NO 281
<211> LENGTH: 440
<212> TYPE: DNA
<213> ORGANISM: Homo sapiens

<400> SEQUENCE: 281
catctgatct ataaatgcgg tggcatcgac aaaagaacca ttgaaaaatt tgagaaggag 60
gctgctgaga tgggaaaggg ctccttcaag tatgcctggg tcttggataa actgaaagct 120
gagcgtgaac gtggtatcac cattgatatc tccttgtgga aatttgagac cagcaagtac 180
tatgtgacta tcattgatgc cccaggacac agagacttta tcaaaaacat gattacaggg 240
acatctcagg ctgactgtgc tgtcctgatt gttgctgctg gtgttggtga atttgaagct 300
ggtatctcca agaatgggca gacccgagag catgcccttc tggcttacac actgggtgtg 360
aaacaactaa ttgtcggtgt taacaaaatg gattccactg agccccctac agccagaaga 420
gatatgagga aattgttaag 440

<210> SEQ ID NO 282
<211> LENGTH: 502
<212> TYPE: DNA
<213> ORGANISM: Homo sapiens

<400> SEQUENCE: 282
tctgtggcgc aggagccccc tcccccggca gctctgacgt ctccaccgca gggactggtg 60
cttctcggag ctcccactcc tcagactccg gtggaagtga cgtggacctg gatcccactg 120
atggcaagct cttccccagc gatggttttc gtgactgcaa gaagggggat cccaagcacg 180
ggaagcggaa acgaggccgg ccccgaaagc tgagcaaaga gtactgggac tgtctcgagg 240
gcaagaagag caagcacgcg cccagaggca cccacctgtg ggagttcatc cgggacatcc 300
tcatccaccc ggagctcaac gagggcctca tgaagtggga gaatcggcat gaaggcgtct 360
tcaagttcct gcgctccgag gctgtggccc aactatgggg ccaaaagaaa aagaacagca 420
acatgaccta cgagaagctg agccgggcca tgaggtacta ctacaaacgg gagatcctgg 480
aacgggtgga tggccggcga ct 502

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283
ccatattaga ttactggaac atctaagcat cagtgtgtga ccatgcgaac aaaagacttc 60
ggggagtgtc tatttttaaa aaggtttatg tgtgtcgagg cagttgtaaa agatttactg 120
cagaatcaan cccactttta ggcttangac caggttctaa ctatctaaaa atattgactg 180
ataacaaaaa gtgttctaaa tgtggctatt ctgatccata nttgnttttt aaagaaaaaa 240
antgtntata cagaaagagt ntaaaagttc tgtgaattna atgcaaatta gncnccantc 300
ttgacttccc aaanacttga ttnatacctt tnactcctnt cnnttcctgn ncttcnttaa 360
nntcaatnat tnggnagtnn anggccntcn gnanaacacc nttncncgnt ccncgcaatc 420
canccgcctt nan 433

<210> SEQ ID NO 284

-continued

<211> LENGTH: 479
<212> TYPE: DNA
<213> ORGANISM: Homo sapiens

<400> SEQUENCE: 284
tctggaagga tcagggatct gagcaaagcc aagtttactt aagctaagcc acttgttcct 60
gggtcaagca gtttgttttc taataagcat cattcctgat cattagagca aagggatgaa 120
tgctcctctt ggaatgatac aggggatctg ccactgggag agtgttgctc agtgttagag 180
tagcagcaat gacagaatga cagcgactct ctgagtcaac ccagtacttt tagtaccccg 240
tcactatgtg aataaaggca gctagaaaat ggactcaatt ctgcaagcct tcatggcaac 300
agcccatatt aagacttcta gaacaagtta aaaaaaaatc ttccatttcc atccatgcat 360
gggaaaaggg ctttagtata gtttaggatg gatgtgtgta taataataaa atgataagat 420
atgcatagtg ggggaataaa gcctcagagt ccttccagta tggggaatcc attgtatct 479

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285 ttttttttt ttttttttt tcaatanaaa tgccataatt tattccattg tataaaaaag 60
tcatccttat gtaacaaaat gtnttcttan aanaanaaat atattatttc aggtcataaa 120
taatcagcaa acatacaact gttggcaact aaaaaaaaac ccaacactgg tattttccat 180
cagngctgaa aacaaacctg cttaaanata tatttacagg gatagtncag tnctcaaaaa 240
caaaaattga ggtattttgg ttcttctagg agtagacaat gacattttgg gangggcaga 300
cccctnnccc aaaaaataaa ataagggnat nttcttcant atngaanann gggggcgccc 360
cggggaaaan naaaccttgg gnngggggtt tggcccaagc ccttgaaaaa aaantttntt 420
tcccaaaaaa aacng 435

<210> SEQ ID NO 286
<211> LENGTH: 301
<212> TYPE: DNA
<213> ORGANISM: Homo sapiens

<400> SEQUENCE: 286
cctggtttct ggtggcctct atgaatccca tgtagggtgc agaccgtact ccatccctcc 60
ctgtgagcac cacgtcaacg gctcccggcc cccatgcacg ggggagggag atacccccaa 120
gtgtagcaag atctgtgagc ctggctacag cccgacctac aaacaggaca agcactacgg 180
atacaattcc tacagcgtct ccaatagcga gaaggacatc atggccgaga tctacaaaaa 240
cggccccgtg gagggagctt tctctgtgta ttcggacttc ctgctctaca agtcaggagt 300
g 301

<210> SEQ ID NO 287
<211> LENGTH: 432
<212> TYPE: DNA
<213> ORGANISM: Homo sapiens

<400> SEQUENCE: 287
tccagcttgt tgccagcatg agaaccgcca ttgatgacat tgaacgccgg gactggcagg 60

-continued

```
atgacttcag agttgccagc caagtcagcg atgtggcggt acagggggac ccccttctca    120

acggcaccag ctttgcagac ggcaagggac acccccagaa tggcgttcgc accaaactta    180

gatttatttt ctgttccatc catctcgatc atcagtttgt caatcttctc ttgttctgtg    240

acgttcagtt tcttgctaac cagggcaggc gcaatagttt tattgatgtg ctcaacagcc    300

tttgagacac ccttccccat atagcgagtc ttatcattgt cccggagctc tagggcctca    360

tagataccag ttgaagcacc actgggcaca gcagctctga agagaccttt tgaggtgaag    420

agatcaacct ca                                                        432


<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

tctggctcaa gtcaaagtcc tggtcctctt ctccgcctcc ttcttcatca tagtaataaa     60

cgttgtcccg ggtgtcatcc tctgggggca gtaagggctc tttgaccacc gctctcctcc    120

gaagaaacag caagagcagc agaatcagaa ttagcaaagc aagaattcct ccaagaatcc    180

ccagaatggc aggaatttgc aatcctgctt cgacaggctg tgccttccta cagacgccgg    240

cggccccttc acantcacac acgctgacct ctaaggtggt cacttggtct ttattctggt    300

tatccatgag cttgagattg attttg                                         326


<210> SEQ ID NO 289
<211> LENGTH: 451
<212> TYPE: DNA
<213> ORGANISM: Homo sapiens

<400> SEQUENCE: 289

gtcccggtgt ggctgtgccg ttggtcctgt gcggtcactt agccaagatg cctgaggaaa     60

cccagaccca agaccaaccg atggaggagg aggaggttga gacgttcgcc tttcaggcag    120

aaattgccca gttgatgtca ttgatcatca atactttcta ctcgaacaaa gagatctttc    180

tgagagagct catttcaaat tcatcagatg cattggacaa aatccggtat gaaagcttga    240

cagatcccag taaattagac tctgggaaag agctgcatat taaccttata ccgaacaaac    300

aagatcgaac tctcactatt gtggatactg gaattggaat gaccaaggct gacttgatca    360

ataaccttgg tactatcgcc aagtctggga ccaaagcgtt catggaagct ttgcaggctg    420

gtgcagatat ctctatgatt ggacctcggc c                                   451


<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

tttttttttt tcaaaacagt atattttatt ttacaatagc aaccaactcc ccagtttgtt     60

tcaattgtga catctagatg gcttaagatt actttctggt ggtcacccat gctgaacaat    120
```

-continued

```
atttttcaat cttccaaaca gcaaagactc aaaagagatt ctgcatttca catcagttca    180

caagttcaag agtcttccat ttatcttagc ttttggaata aattatcttt gaggtagaag    240

gacaatgacg aagccactta attccttgtg tctgcataaa agcagattta ttcatcacaa    300

cttcatttat gtgaataaag cagatgatga taaaatgttc tcttattctt gtttaatcag    360

tagtggtagt gatgccagaa acttgtaaat gcacttcaaa ccaattgtgg ctcaagtgta    420

ngtggttccc caaggctggt accaatgaga ctggggtttg ggaattagtt ggtcatcatc    480

cctcctgctg ccca                                                      494
```

<210> SEQ ID NO 291
<211> LENGTH: 535
<212> TYPE: DNA
<213> ORGANISM: Homo sapiens

<400> SEQUENCE: 291

```
tcgcgtgctt aacatgaaaa caaactttgt gctgtttggt tcattgtatg cattgatgga     60

gtcttgtctc tcatcatggg gtgtctgacc atccaacctg cagtactcat aatttctcca    120

catgcaataa tcttccaaaa tgtccaatac ccttgtcatt tgactgaaga ttagtactcg    180

tgaaccttgt tcttttaact tagggagcag cttgtctaaa accaccattt tgccactgtt    240

ggttactaga tgcatatctg ttgtataagg tggaccaggt tctgctccat caaagagata    300

tggatgatta caacattttc tcaactgcat taggatgttc aataacctca ttttgtccat    360

cttgcctgct gagttgagta tatctatatc cttcattaat atccgagtat accattccct    420

ttgcattttg ctgaggccca catagatttt tacttccttc tttggaggca aactcttttc    480

aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

```
tacnagcccg tgctgatcga gatcctggtg gaggtgatgg atccttcctt cgtgtgcttg     60

aaaattggag cctgcccctc ggcccataag cccttgttgg gaactgagaa gtgtatatgg    120

ggcccaagct actggtgcca gaacacagag acagcagccc agtgcaatgc tgtcgagcat    180

tgcaaacgcc atgtgtggaa ctaggaggag gaatattcca tcttggcaga aaccacagca    240

ttggtttttt tctacttgtg tgtctggggg aatgaacgca cagatctgtt tgactttgtt    300

ataaaaatag ggctccccca cctcccccat ttttgtgtcc tttattgnag cattgctgtc    360

tgcaagggag ccccta                                                    376
```

<210> SEQ ID NO 293
<211> LENGTH: 320
<212> TYPE: DNA
<213> ORGANISM: Homo sapiens

<400> SEQUENCE: 293

```
tcggctgctt cctggtctgg cggggatggg tttgctttgg aaatcctcta ggaggctcct     60

cctcgcatgg cctgcagtct ggcagcagcc ccgagttgtt tcctcgctga tcgatttctt    120

tcctccaggt agagttttct ttgcttatgt tgaattccat tgcctctttt ctcatcacag    180
```

-continued aagtgatgtt ggaatcgttt cttttgtttg tctgatttat ggttttttta agtataaaca 240
aaagtttttt attagcattc tgaaagaagg aaagtaaaat gtacaagttt aataaaaagg 300
ggccttcccc tttagaatag 320

<210> SEQ ID NO 294
<211> LENGTH: 359
<212> TYPE: DNA
<213> ORGANISM: Homo sapiens

<400> SEQUENCE: 294
ctgtcataaa ctggtctgga gtttctgacg actccttgtt caccaaatgc accatttcct 60
gagacttgct ggcctctccg ttgagtccac ttggctttct gtcctccaca gctccattgc 120
cactgttgat cactagcttt ttcttctgcc cacaccttct tcgactgttg actgcaatgc 180
aaactgcaag aatcaaagcc aaggccaaga gggatgccaa gatgatcagc cattctggaa 240
tttggggtgt ccttatagga ccagaggttg tgtttgctcc accttcttga ctcccatgtg 300
agtgtccatc tgattcagat ccatgagtgg tatgggaccc cccactgggg tggaatgtg 359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295
cctgagttgg gctgactgcc agagacagac ccctctgggt ctcggtgaac cagccaggca 60
tttacctcag tggttggcac ctggaacctg tccagggccc tcacctgact gaggagccgc 120
cgggcagtga agtaattgtc caggtctatg ctcttggggt ggataccata gccatccaag 180
gtattcctca ggttgtggaa ctgggtctga gtataggcag aactgggccc caggatgatc 240
tcccggagtg ggggaagctg tgaggtcagg taagtatcca cgtccacccg taccccaatc 300
aaactcagca gaatggtgaa ctggagaagt ccttccgtta agtatttctt cagagaaagc 360
attgctgaag gaccagaatg tttatgcttt ttggttttta aaatcttcca aaagacaaat 420
caaggccact gctctgccgc tccagccagc aggttaccct cctcagtgtc aaaccccgta 480
ccccaccctg gcagaacaca agggatgagc tccctgacgg ccccagagga aagcacaccc 540
tgtggagcca aggccaanga cacactccag accacattca cttt 584

<210> SEQ ID NO 296
<211> LENGTH: 287
<212> TYPE: DNA
<213> ORGANISM: Homo sapiens

<400> SEQUENCE: 296
ccttatcatt cattcttagc tcttaattgt tcattttgag ctgaaatgct gcattttaat 60
tttaaccaaa acatgtctcc tatcctggtt tttgtagcct tcctccacat cctttctaaa 120
caagatttta aagacatgta ggtgtttgtt catctgtaac tctaaaagat cctttttaaa 180
ttcagtccta agaaagagga gtgcttgtcc cctaagagtg tttaatggca aggcagccct 240
gtctgaagga cacttcctgc ctaagggaga gtggtatttg cagacta 287

<210> SEQ ID NO 297

-continued

<211> LENGTH: 457
<212> TYPE: DNA
<213> ORGANISM: Homo sapiens

<400> SEQUENCE: 297
ccaattgaaa caaacagttc tgagaccgtt cttccaccac tgattaagag tggggtggca 60
ggtattaggg ataatattca tttagccttc tgagctttct gggcagactt ggtgaccttg 120
ccagctccag cagccttctt gtccactgct ttgatgacac ccaccgcaac tgtctgtctc 180
atatcacgaa cagcaaagcg acccaaaggt ggatagtctg agaagctctc aacacacatg 240
ggcttgccag gaaccatatc aacaatggca gcatcaccag acttcaagaa tttagggcca 300
tcttccagct ttttaccaga acggcgatca atcttttcct tcagctcagc aaacttgcat 360
gcaatgtgag ccgtgtggca atccaataca ggggcatagc cggcgcttat ttggcctgga 420
tggttcagga taatcacctg agcagtgaag ccagacc 457

<210> SEQ ID NO 298
<211> LENGTH: 469
<212> TYPE: DNA
<213> ORGANISM: Homo sapiens

<400> SEQUENCE: 298
tctttgactt tccttgtcta cctcctctgg agatctcaaa ttctccaggt tccatgctcc 60
cagagatctc aatgattcct gattctcctc ttccaggagt ctgaatgtct cttggttcac 120
ttccacagac tccagtggtt cttgaatttc cttttctaga ggattcattg ccccctgatt 180
tatttcttct ggagtccaca gtggtgcttg agtttctgga gatttcagtg tttccaggtt 240
ctcttgtccc gcagacttca gtgattctag gatctctgtt tctaaagatt ttactgcctc 300
tatgctctct tctttgagtg actttaagaa ctcttgattc tcattttcaa gaggtctagc 360
tatctcctgg tcaagagact tcagtggttc tagatccact ttttctgggg gtcttaatgt 420
catctgatcc tgttccccta gagacctccg tcgctgttga gtctctttt 469

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299
tctgtggaga ggatgaggtt gagggaggtg gggtatntcg ctgctctgac cttaggtaga 60
gtcctccaca gaagcatcaa antggactgg cacatatgga ctcccttcac aggccacaat 120
gatgtgtctc tccttcgggc tggnccggta tgcacagttg gggta 165

<210> SEQ ID NO 300
<211> LENGTH: 506
<212> TYPE: DNA
<213> ORGANISM: Homo sapiens

<400> SEQUENCE: 300
tctgaggaaa gtttgggctt attagtattt gctccagcga acctccaagt tttctccatt 60
gcggacaacg taactaccag ctccttggct cagtggttcg cctccactca gaagttccca 120
gtaggttctg tcattattgt tggcacatag gccctgaata caggtgatat agggccccca 180
tgagcgctcc tccattgtga aaccaaatat agtatcattc attttctggg ctttctccat 240

-continued

```
cacactgagg aagacagaac catttagcac agtgacattg gtgaaatatg tttcattgat    300

tctcacagag taattgacgg agatatatga ttgtgagtca ggaggtgtca cagttatagg    360

ctcatcagcg gagatgttga agttacctga agcagagacg caagaagagt ctttgttaat    420

atccaagaag gtctttccca tcagggcagg taagacctgg gctgcagcgt ttggattgct    480

gaatgctcct tgagaaattt ccgtga                                          506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301

```
tcctaaggca gagcccccat cacctcaggc ttctcagttc ccttagccgt cttactcaac     60

tgcccctttc ctctccctca gaatttgtgt ttgctgcctc tatcttgttt tttgtttttt    120

cttctggggg gggtctagaa cagtgcctgg cacatagtag gcgctcaata aatacttgtt    180

tgttgaatgt ctcctctctc tttccactct gggaaaccta ngnttctgcc attctgggtg    240

accctgtatt tntttctggt gcccattcca tttgnccagn taatacttcc tcttaaaaat    300

ctcc                                                                  304
```

<210> SEQ ID NO 302
<211> LENGTH: 492
<212> TYPE: DNA
<213> ORGANISM: Homo sapiens

<400> SEQUENCE: 302

```
ttttcagtaa gcaacttttc catgctctta atgtattcct ttttagtagg aatccggaag     60

tattagattg aatggaaaag cacttgccat ctctgtctag gggtcacaaa ttgaaatggc    120

tcctgtatca catacggagg tcttgtgtat ctgtggcaac agggagtttc cttattcact    180

ctttatttgc tgctgtttaa gttgccaacc tcccctccca ataaaaattc acttacacct    240

cctgcctttg tagttctggt attcacttta ctatgtgata gaagtagcat gttgctgcca    300

gaatacaagc attgcttttg gcaaattaaa gtgcatgtca tttcttaata cactagaaag    360

gggaaataaa ttaaagtaca caagtccaag tctaaaactt tagtactttt ccatgcagat    420

ttgtgcacat gtgagagggt gtccagtttg tctagtgatt gttatttaga gagttggacc    480

actattgtgt gt                                                         492
```

<210> SEQ ID NO 303
<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg     60

gcagcggtgg ctcacatggc ctgtctgcac tgtaaccaca ggctgggatg tagccaggac    120

ttggtctcct tggaagacag gtctgatgtt tggccaatcc agtccttcag accctgcctg    180

aaacttgtat cttacgtgaa cttaaagaat aaaatgcatt tctaccccga tctcgccccc    240

aggactggca cgacaggccc acggcagatt agatcttttc ccagtactga tcggtgcgtg    300
```

-continued

```
gaattccagc caccacttct gattcgattc cacagtgatc ctgtcctctg agtattttaa    360

agaagccatt gtcaccccag tcagtgttcc aggagttggc aaccagccag tagggtgtgc    420

cattctccac tccccagccc aggatgcgga tggcatggac ctcggccgcg                470
```

<210> SEQ ID NO 304
<211> LENGTH: 79
<212> TYPE: DNA
<213> ORGANISM: Homo sapiens

<400> SEQUENCE: 304

```
tgtcccattg ttaactcagc ctcaaatctc aactgtcagg ccctacaaag aaaatggaga     60

gcctcttctg gtggatgcg                                                  79
```

<210> SEQ ID NO 305
<211> LENGTH: 476
<212> TYPE: DNA
<213> ORGANISM: Homo sapiens

<400> SEQUENCE: 305

```
tcactgagcc accctacagc cagaagagat atgaggaaat tgttaaggaa gtcagcactt     60

acattaagaa aattggctac aaccccgaca cagtagcatt tgtgccaatt tctggttgga    120

atggtgacaa catgctggag ccaagtgcta acgtaagtgg ctttcaagac cattgttaaa    180

aagctctggg aatggcgatt tcatgcttac acaaattggc atgcttgtgt ttcagatgcc    240

ttggttcaag ggatggaaag tcacccgtaa ggatggcaat gccagtggaa ccacgctgct    300

tgaggctctg gactgcatcc taccaccaac tcgtccaact gacaagccct tgcgcctgcc    360

tctccaggat gtctacaaaa ttggtggtaa gttggctgta aacaaagttg aatttgagtt    420

gatagagtac tgtctgcctt cataggtatt tagtatgctg taaatatttt taggta        476
```

<210> SEQ ID NO 306
<211> LENGTH: 404
<212> TYPE: DNA
<213> ORGANISM: Homo sapiens

<400> SEQUENCE: 306

```
tctgtctcgg agctcagggc gcagccagca cacacaggag cccacaggac agccacgtct     60

tcacagaaac tacagaagtc aggacccagg cgaggacctc aggaacaagt gccccctgca    120

gacagagaga cgcagtagca acagcttctg aacaactaca taataatgcg gggagaatcc    180

tgaagaccac tgcatcccac aagcactgac aaccacttca ggattttatt tcctccactc    240

taacccccag atccatttat gagaagtgag tgaggatggc aggggcatgg agggtgaagg    300

gacagcaagg atggtctgag ggcctggaaa caatagaaaa tcttcgtcct ttagcatatc    360

ctggactaga aaacaagagt tggagaagag gggggttgat acta                     404
```

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307

```
tcctgcctan acatctgtga gggcctcaag ggctgctgcc tcgactttct ccctagctaa     60

gtccacccgt ccagggacac agccagggca ctgctctgtg ctgacttcca ctgcagccaa    120
```

-continued gggtcaaaat gaagcatctg cggaggccag gactccttgg catcggacac agtcagggga 180
aaagccaccc tgactctgca ggacagaggg tctagggtca tttggcagga gaacactggt 240
gtgccaaggg aagcnancat 260

<210> SEQ ID NO 308
<211> LENGTH: 449
<212> TYPE: DNA
<213> ORGANISM: Homo sapiens

<400> SEQUENCE: 308
tctgtgctcc cgactcctcc atctcaggta ccaccgactg cactgggcgg ggccctctgg 60
ggggaaaggc tccacggggc agggatacat ctcgaggcca gtcatcctct ggaggcagcc 120
caatcaggtc aaagattttg cccaactggt cggcttcaga gtttccacag aagagaggct 180
ttcgacgaaa catctctgca aagatacagc caacactcca catgtccaca ggtgttgcat 240
atgtggactg cagaagaact tcgggagctc ggtaccagag tgtaacaacc ttgatcgttt 300
cggctggcaa gcctggtggg ggtgccttgt ccagatatgt ccttaggtcc tggtctacat 360
gctcaaacac cagggttacc ttgatctccc ggtcagttcg ggatgtggca cagacgtcca 420
tcagccggac aacattggga tgctcaaaa 449

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309
ctgtggaaac ctggggtgcc gggtaaatgg agaactccag cttggatttc ttgccataat 60
caactgagag acgttccatg agcagggagg tgaacccaga accagttccc ccaccaaagc 120
tgtggaaaac caagaagccc tgaagaccgg tgcactggtc agccagcttg cgaattcggt 180
ccaacacaag gtcaatgatc tccttgccaa tggtgtagtg ccctcgggca tagttattgg 240
cagcatcttc cttgcctgtg atgagctgct cagggtggaa gagctggcgg taggtgccag 300
tgcgaacttc atcaatgact gtgggttcca agtctacaaa cacagcccgg ggcacgtgct 360
tgccagcgcc cgtctcactt gaanaagggt gtttgaagga agtcatctcc t 411

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310
tcctcgtcca gcttgactcg attagtcctc ataaggtaag caaggcagat ggtggctgac 60
cgggaaatgc ctgcctggca gtggacaaac acccttcctc cagcattctt gatggagtct 120
atgaagtcaa tggcctcgtt gaaccaggag ctgatgtctg ccttgtggtt gtcctccaca 180
gggatgctct tgtactggta gtgaccctca aaatggttgg gacaattggc tgagacgttg 240
atcaaggcan ttatgcccaa ggcatccagc atgtccttgc gggaagcgtg atacgcactg 300

-continued

```
cccaggtaca gaaagggcag                                                320


<210> SEQ ID NO 311
<211> LENGTH: 539
<212> TYPE: DNA
<213> ORGANISM: Homo sapiens

<400> SEQUENCE: 311

tctggcccat gaagctgaag ttgggagaga tgatgcttcg cctctgcttc acaaactcaa     60

aggcctcgtc cagcttgact cgattagtcc tcataaggta agcaaggcag atggtggctg    120

accgggaaat gcctgcctgg cagtggacaa acacccttcc tccagcattc ttgatggagt    180

ctatgaagtc aatggcctcg ttgaaccagg agctgatgtc tgccttgtgg ttgtcctcca    240

cagggatgct cttgtactgg tagtgaccct caaaatggtt gggacaattg gctgagacgt    300

tgatcaaggc agttatgccc aaggcatcca gcatgtcctt gcgggaagcg tgatacgcac    360

tgcccaggta cagaaagggc aggatttcca ccgggccacc ctgaaatcca gaaatatcca    420

acattcatca agcttgctca aagccaaggc cagtgcccat acccacaaaa actttctgct    480

ggaaaagtca atttcagata ccgagtgaac tcagttctgt tgctggagga taaataaat     539


<210> SEQ ID NO 312
<211> LENGTH: 475
<212> TYPE: DNA
<213> ORGANISM: Homo sapiens

<400> SEQUENCE: 312

tcaaggatct tcctaaagcc accatgtgag aggattcgga cgagagtctg agctgtatgg     60

cagaccatgt cctgctgttc tagggtcatg actgtgtgta ctctaaagtt gccactctca    120

caggggtcag tgatacccac tgaacctggc aggaacagtc ctgcagccag aatctgcaag    180

cagcgcctgt atgcaacgtt tagggccaaa ggctgtctgg tggggttgtt catcacagca    240

taatggccta gtaggtcaag gatccagggt gtgaggggct caaagccagg aaaacgaatc    300

ctcaagtcct tcagtagtct gatgagaact ttaactgtgg actgagaagc attttcctcg    360

aaccagcggg catgtcggat ggctgctaag gcactctgca atactttgat atccaaatgg    420

agttctggat ccagttttcg aagattgggt ggcactgttg taatgagaat cttca         475


<210> SEQ ID NO 313
<211> LENGTH: 456
<212> TYPE: DNA
<213> ORGANISM: Homo sapiens

<400> SEQUENCE: 313

tccacttaaa gggtgcctct gccaactggt ggaatcatcg ccacttccag caccacgcca     60

agcctaacat cttccacaag gatcccgatg tgaacatgct gcacgtgttt gttctgggcg    120

aatggcagcc catcgagtac ggcaagaaga agctgaaata cctgccctac aatcaccagc    180

acgaatactt cttcctgatt gggccgccgc tgctcatccc catgtatttc cagtaccaga    240

tcatcatgac catgatcgtc cataagaact gggtggacct ggcctgggcc gtcagctact    300

acatccggtt cttcatcacc tacatccctt tctacggcat cctgggagcc ctccttttcc    360

tcaacttcat caggttcctg gagagccact ggtttgtgtg ggtcacacag atgaatcaca    420

tcgtcatgga gattgaccag gaggacctcg gcccgc                              456


<210> SEQ ID NO 314
<211> LENGTH: 477
```

-continued

<212> TYPE: DNA
<213> ORGANISM: Homo sapiens

<400> SEQUENCE: 314
tgcgtgggct tctggaagcc tggatctgga atcattcacc agattattct ggaaaactat 60
gcgtaccctg gtgttcttct gattggcact gactcccaca cccccaatgg tggcggcctt 120
gggggcatct gcattggagt tgggggtgcc gatgctgtgg atgtcatggc tgggatcccc 180
tgggagctga agtgccccaa ggtgattggc gtgaagctga cgggctctct ctccggttgg 240
tcctcaccca aagatgtgat cctgaaggtg gcaggcatcc tcacggtgaa aggtggcaca 300
ggtgcaatcg tggaatacca cgggcctggt gtagactcca tctcctgcac tggcatggcg 360
acaatctgca acatgggtgc agaaattggg gccaccactt ccgtgttccc ttacaaccac 420
aggatgaaga agtatctgag caagaccggc cgggaagaca ttgccaatct agctgat 477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315
caggtactgg atgtcaggtc tgcgaaactt cttanatttt gacctcagtc cataaaccac 60
actatcacct cggccatcat atgtgtctac tgtggggaca actggagtga aaacttcggt 120
tgctgcaggt ccgtgggaaa atcagtgacc agttcatcag attcatcaga atggtgagac 180
tcatcagact ggtgagaatc atcagtgtca tctacatcat cagagtcgtt cgagtcaatg 240
g 241

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316
nttntgtgat agtgtggttt atggactgag gncaaaatnt aagaagtttc gcagacctga 60
catccaancc tgcccgngcg gncgctcgaa aggncgaatt ctgcagatat ccatcacact 120
ggcggccgct cgagcatgca tctagagggc ccaattcgcc ctatantgag tnatattaca 180
attcactggc cgtcnnttta caacgtcgtg actgggaaaa ccctggcgtt acccaactta 240
a 241

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317
aggtaccctg ctcancagcc tgggngcctg ggttgtctcc ttgtccatcc actggtccat 60

-continued tctgctctgc atttttttgt tcctcttttg gaggttccac tttgggtttg ggctttgaaa 120
ttatagggct acaantacct cggccgaaac cacnctaagg gcgaattctg cagatatcca 180
tcacactggc ggncgctcga gcatgcatct agagggccca attcgcccta tagtgagtcg 240
t 241

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318
cgngnacaan ntacattgat gganggtntg nggntctgan tntttantta cantggagca 60
ttaatatttt cttnaacgtn cctcaccttc ctgaantaaa nactctgggt tgtagcgctc 120
tgtgctnana accacntnaa ctttacatcc ctcttttgga ttaatccact gcgcggccac 180
ctctgccgcg accacgctaa gggcnaattc tgcagatatc catcacactg gcggccgctc 240 n 241

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319
caggtactga tcggtgcgtg gaantccagc caccanttnt gattcgattc cacagtgatc 60
ctgtcctctg agtattttaa agaagccatt gtcaccccag tcagtgttcc aggagttggc 120
aaccagccag tagggtgtgc cattctccac tccccagccc aggatgcgga tggcatggcc 180
acccatcatc tctccggtga cgtgttggta cctcggccgc gaccacgcta agggcgaatt 240
c 241

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc 60
taaacaagtg actatactag cataaatcat tctagtaaaa cagctaaggt atagacattc 120
taataatttg ggaaaaccta tgattacaag tgaaaactca gaaatgcaaa gatgttggtt 180
ttttgtttct cagtctgctt tagcttttaa ctctnnnaan cncatgcaca cttgnaactc 240
t 241

<210> SEQ ID NO 321
<211> LENGTH: 241
<212> TYPE: DNA
<213> ORGANISM: Homo sapiens -continued
<220> FEATURE:
<221> NAME/KEY: misc_feature
<222> LOCATION: (1)...(241)
<223> OTHER INFORMATION: n = A,T,C or G

<400> SEQUENCE: 321
angtaccaac agagcttagt aattnntaaa aagaaaaaat gatctttttc cgacttctaa 60
acaagtgact atactagcat aaatcattct agtaaaacag ctaaggtata gacattctaa 120
taatttggga aaacctatga ttacaagtga aaactcagaa atgcaaagat gttggttttt 180
tgtttctcag tctgctttag cttttaactc tggaagcgca tgcacacntg aactctgctc 240
a 241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atctttttcc gacttctaaa 60
caagtgacta tactagcata aatcattctt ctagtaaaac agctaaggta tagacattct 120
aataatttgg gaaaacctat gattacaagt aaaaactcag aaatgcaaag atgttggttt 180
tttgtttctc agtctgcttt agcttttaac tctggaagcg catgcacact gaactctgct 240
c 241

<210> SEQ ID NO 323
<211> LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta 60
ggtctcaagt tatgagaatc tccatggctt tcaggggcta aacttttctg ccattctttt 120
gctcttaccg ggctcagaag gacatgtcag gtgggatacg tgtttctctt tcagagctga 180
agaaagggtc tgagctgcgg aatcagtaga gaaagccttg gtctcagtga ctccttggct 240
t 241

<210> SEQ ID NO 324
<211> LENGTH: 241
<212> TYPE: DNA
<213> ORGANISM: Homo sapiens

<400> SEQUENCE: 324
aggtactgtc gtatcctcag ccttgttcta tttctttatt ttagctttac agagattagg 60
tctcaagtta tgagaatctc catggctttc aggggctaaa cttttctgcc attcttttgc 120
tcttaccggg ctcagaagga catgtcaggt gggatacgtg tttctctttc agagctgaag 180
aaagggtctg agctgcggaa tcagtagaga aagccttggt ctcagtgact ccttggcttt 240
c 241

<210> SEQ ID NO 325
<211> LENGTH: 241
<212> TYPE: DNA
<213> ORGANISM: Homo sapiens

<400> SEQUENCE: 325

-continued

```
ggcaggtaca tttgttttgc ccagccatca ctctttttttg tgaggagcct aaatacattc     60

ttcctggggt ccagagtccc cattcaaggc agtcaagtta agacactaac ttggcccttt    120

cctgatggaa atatttcctc catagcagaa gttgtgttct gacaagactg agagagttac    180

atgttgggaa aaaaaaagaa gcattaactt agtagaactg aaccaggagc attaagttct    240

g                                                                    241


<210> SEQ ID NO 326
<211> LENGTH: 241
<212> TYPE: DNA
<213> ORGANISM: Homo sapiens

<400> SEQUENCE: 326

gcaggtacat ttgttttgcc cagccatcac tctttttttgt gaggagccta aatacattct     60

tcctggggtc cagagtcccc attcaaggca gtcaagttaa gacactaact tggccctttc    120

ctgatggaaa tatttcctcc atagcagaag ttgtgttctg acaagactga gagagttaca    180

tgttgggaaa aaaaagaagc attaacttag tagaactgat ccaggagcat taagttctga    240

a                                                                    241


<210> SEQ ID NO 327
<211> LENGTH: 241
<212> TYPE: DNA
<213> ORGANISM: Homo sapiens

<400> SEQUENCE: 327

ggtaccagac caagtgaatg cgacagggaa ttatttcctg tgttgataat tcatgaagta     60

gaacagtata atcaaaatca attgtatcat cattagtttt ccactgcctc acactagtga    120

gctgtgccaa gtagtagtgt gacacctgtg ttgtcatttc ccacatcacg taagagcttc    180

caaggaaagc caaatcccag atgagtctca gagagggatc aatatgtcca tgattatcag    240

g                                                                    241


<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 328

ggtacnagac caaatgaang ccacagggaa ttatttcctg tgttgataat tcatgaagta     60

gaacantata atcaaaatca attgtatcat cattagtttt ccactgcctc acactagtga    120

gctgtgccaa gtagtagtgt gacacctgtg ttgtcatttc ccacatcacg taagagcttc    180

caaggaaagc caaatcccag atgagtctca gagagggatc aatatgtcca tnatcatcan    240

g                                                                    241


<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329
```

-continued

```
ttcaggtcga gttggctgca gatttgtggt gcnttctgag ccgtctgtcc tgcgccaaaa     60

ngcttcaaag tattattaaa aacatatgga tccccatgaa gccctactac accaaagttt    120

accaggagat ttggatagga atggggctga tgggcttcat cgtttataaa atccgggctg    180

ctgataagaa gtaaggcttt gaaagcttca gcgcctgctn ctggtcanna ctaaccatan    240

n                                                                    241
```

<210> SEQ ID NO 330
<211> LENGTH: 241
<212> TYPE: DNA
<213> ORGANISM: Homo sapiens

<400> SEQUENCE: 330

```
ttttgtgcag atttgtggtg cgttctgagc cgtctgtcct gcgccaagat gcttcaaagt     60

attattaaaa acatatggat ccccatgaag ccctactaca ccaaagttta ccaggagatt    120

tggataggaa tggggctgat gggcttcatc gtttataaaa tccgggctgc tgataaaaga    180

agtaaggctt tgaaagcttc agcgcctgct cctggtcatc actaaccaga tttacttgga    240

g                                                                    241
```

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331

```
nttttaggna ctttgggctc cagacttcac tggtcttagg nattgaaacc atcacctggn     60

ntgcattcct catgactgag gttaacttaa aacaaaaatg gtaggaaagc tttcctatnc    120

ttcnggtaag anacaaatnt nctttaaaaa aangtggaag gcatgacnta cgtgagaact    180

gcacaaactg gccactgaca aaaatgaccc ccatttgtgt gacttcattg agacacatta    240

c                                                                    241
```

<210> SEQ ID NO 332
<211> LENGTH: 241
<212> TYPE: DNA
<213> ORGANISM: Homo sapiens

<400> SEQUENCE: 332

```
tgtgaggaga gggaacatgc tgagaaactg atgaagctgc agaaccaacg aggtggccga     60

atcttccttc aggatatcaa gaaaccagac tgtgatgact gggagagcgg gctgaatgca    120

atggagtgtg cattacattt ggaaaaaaat gtgaatcagt cactactgga actgcacaaa    180

ctggccactg acaaaaatga cccccatttg tgtgacttca ttgagacaca ttacctgaat    240

g                                                                    241
```

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G -continued

<400> SEQUENCE: 333
caggtacaag cttttttttt tttttttttt tttttttttt ttgnaaatac tntttattgn 60
aaatattcta tcctaaattc catatagcca attaattntt acanaatntt ttgttaattt 120
ttgngngtat aaattttaca aaaataaagg gtatgtttgt tgcacacaac ttacaaataa 180
taataaactn tttattgnaa atattnttta ttgnaaatat tctttatcct aaattccata 240
t 241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334
tacctgctgn aggggntgaa gncntctctg ctgccccagg catctgcanc ccctgctgct 60
ggttctgccc ctgctgcagc agaggagaag aaagatgaga agaaggagga gtctgaagag 120
tcagatgatg acatgggatt tggccttttt gattaaannc ctgctcccct gcaaataaag 180
cctttttaca caaaaaaaaa aaaaaaaaaa aaaaaaaaaa aagcttgtac ctgcccnggc 240
g 241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335
ctatgtgctg ggatgactat ggagacccaa atgtctcana atgtatgtcc cagaaacctg 60
tggctgcttc aaccattgac agttttgctg ctgctggctt ctgcagacag tcaagctgca 120
gctcccccaa aggctgtgct gaaacttgag cccccgtgga tcaacgtgct ccaggaggac 180
tctgtgactc tgacatgcca gggggctcgc agccctgaga gcgactccat tcagtggttc 240
c 241

<210> SEQ ID NO 336
<211> LENGTH: 241
<212> TYPE: DNA
<213> ORGANISM: Homo sapiens

<400> SEQUENCE: 336
taccaaccta tgcagccaag caacctcagc agttcccatc aaggccacct ccaccacaac 60
cgaaagtatc atctcaggga aacttaattc ctgcccgtcc tgctcctgca cctcctttat 120
atagttccct cacttgattt ttttaacctt ctttttgcaa atgtcttcag ggaactgagc 180
taatactttt ttttttcttg atgttttctt gaaaagcctt tctgttgcaa ctatgaatga 240
a 241

<210> SEQ ID NO 337
<211> LENGTH: 241
<212> TYPE: DNA
<213> ORGANISM: Homo sapiens -continued
<220> FEATURE:
<221> NAME/KEY: misc_feature
<222> LOCATION: (1)...(241)
<223> OTHER INFORMATION: n = A,T,C or G

<400> SEQUENCE: 337
ggtactgtat gtagctgcac tacaacagat tcttaccgtc tccacanagg tcatanattg 60
taaatggtna atactgactt ttttttatt cccttgactc aagacagcta acttcatttt 120
cagaactgtt ttaaaccttt gtgtgctggt ttataaaata atgtgtgtaa tccttgttgc 180
tttcctgata ccagactgtt tcccgtggtt ggttagaata tattttgntt tgatgcttat 240
a 241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt 60
ctcaaatgga gttttccact ttcctttgaa gtagacagca ttcaccagga tcatcctggt 120
atccccatct acagaacctt caggtaacaa gtttgggatt ttgcctttgg tttgagtctt 180
gacccaggaa ttaatctttt ttctagcttc ttctgcacat tctaggaagt ctactgcctg 240
g 241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg 60
aaagtgtctg caactccaaa gatcaaggcc ataacccagg agaccatcaa cggaagatta 120
gttctttgtc aagtgaatga aatccaaaag cacgcatgag accaatgaaa gtttccgcct 180
gttgtaaaat ctattttccc ccaaggaaag tccttgcaca gacaccagtg agtgagttct 240
a 241

<210> SEQ ID NO 340
<211> LENGTH: 241
<212> TYPE: DNA
<213> ORGANISM: Homo sapiens

<400> SEQUENCE: 340
gtagccctca cacacacatg cccgtaacag gatttatcac aagacacgcc tgcatgtaga 60
ccagacacag ggcgtatgga aagcacgtcc tcaagactgt agtattccag atgagctgca 120
gatgcttacc taccacggcc gtctccacca gaaaaccatc gccaactcct gcgatcagct 180
tgtgacttac aaaccttgtt taaaagctgc ttacatggac ttctgtcctt taaaagcttc 240
c 241

<210> SEQ ID NO 341
<211> LENGTH: 241
<212> TYPE: DNA
<213> ORGANISM: Homo sapiens

<400> SEQUENCE: 341

-continued

```
gtaccgccta ctttcgtctc atgtctccga acttcttgct gatggccgtt ccaacgttgc     60

tgaaagctgc agttgccttt tgccctgcgt gactcagggt ttcatgtgtt ttcttgtagg    120

cagtggtagt ctgcatgtca tgccagcttt tgctgaagtt ctgttttaat tcattcatca    180

ggttcatgcc gagttttgtt ttatctcaac tagatgcctt tctttcgctg acaaaacttg    240

t                                                                    241


<210> SEQ ID NO 342
<211> LENGTH: 241
<212> TYPE: DNA
<213> ORGANISM: Homo sapiens

<400> SEQUENCE: 342

gtacattggt gctataaata taaatgctac ttatgaagca tgaaattaag cttctttttt     60

cttcaagttt tttctcttgt ctagcaatct gttaggcttc tgaaccaaga ccaaatgttt    120

acgttcctct gctgcatacc aacgttactc caaacaataa aaatctatca tttctgctct    180

gtgctgagga atggaaaatg aaacccccac cccctgaccc ctaggactat acagtggaaa    240

c                                                                    241


<210> SEQ ID NO 343
<211> LENGTH: 241
<212> TYPE: DNA
<213> ORGANISM: Homo sapiens

<400> SEQUENCE: 343

gtacatgtgg tagcagtaat ttttttgaag caactgcact gacattcatt tgagttttct     60

ctcattatca gattctgttc caaacaagta ttctgtagat ccaaatggat taccagtgtg    120

ctacagactt cttattatag aacagcattc tattctacat caaaaatagt ttgtgtaagt    180

tagttttggt taccatctaa aatattttta aatgttcttt acataaaaat ttatgttgtg    240

t                                                                    241


<210> SEQ ID NO 344
<211> LENGTH: 241
<212> TYPE: DNA
<213> ORGANISM: Homo sapiens

<400> SEQUENCE: 344

ggtacaaaat tgttggaatt tagctaatag aaaaacatag taaatattta caaaaacgtt     60

gataacatta ctcaagtcac acacatataa caatgtagac aggtcttaac aaagtttaca    120

aattgaaatt atggagattt cccaaaatga atctaatagc tcattgctga gcatggttat    180

caatataaca tttaagatct tggatcaaat gttgtccccg agtcttctgc aatccagtcc    240

t                                                                    241


<210> SEQ ID NO 345
<211> LENGTH: 241
<212> TYPE: DNA
<213> ORGANISM: Homo sapiens

<400> SEQUENCE: 345

ggtacgaagc tgagcgcacg gggttgccc cagcgtggag cctggacctc aaacttcacg      60

gaaaatgctc tctctctttg acaggcttcc agctgtctcc taatttcctg gatgaactct    120

ccccggcgat ttaactgatc ctgaaaagtg gtgagaggac tgaggaagac aaccaggtca    180

gcgttagatc ggcctctgag ggtggtgccc ttgcctgagg agccaccctt taccaccttg    240
```

-continued g 241

<210> SEQ ID NO 346
<211> LENGTH: 241
<212> TYPE: DNA
<213> ORGANISM: Homo sapiens

<400> SEQUENCE: 346
caggtaccac tgagcctgag atggggatga gggcagagag aggggagccc cctcttccac 60
tcagttgttc ctactcagac tgttgcactc taaacctagg gaggttgaag aatgagaccc 120
ttaggtttta acacgaatcc tgacaccacc atctataggg tcccaacttg gttattgtag 180
gcaaccttcc ctctctcctt ggtgaagaac atcccaagcc agaaagaagt taactacagt 240
g 241

<210> SEQ ID NO 347
<211> LENGTH: 241
<212> TYPE: DNA
<213> ORGANISM: Homo sapiens

<400> SEQUENCE: 347
aggtacatct aaaggcatga agcactcaat tgggcaatta acattagtgt ttgttctctg 60
atggtatctc tgagaatact ggttgtagga ctggccagta gtgccttcgg gactgggttc 120
acccccaggt ctgcggcagt tgtcacagcg ccagccccgc tggcctccaa agcatgtgca 180
ggagcaaatg gcaccgagat attccttctg ccactgttct cctacgtggt atgtcttccc 240
a 241

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348
angtacttgg caagattnga tgctcttgng ctcantgaca tcattcataa cttgtnngtg 60
tgancagagg aggagnncat catcntgtcc tcattcgtca gnnncctctc ctctctgaat 120
ctcaaacaag ttgataatgg agaaaaattt gaattctcag gattgaggct ggactggttc 180
cgcctacang catacactag cgtggctaag gcccctctgc accctgcatg anaaccctga 240
c 241

<210> SEQ ID NO 349
<211> LENGTH: 241
<212> TYPE: DNA
<213> ORGANISM: Homo sapiens

<400> SEQUENCE: 349
gcaggtacca tttgtctgac ctctgtaaaa aatgtgatcc tacagaagtg gagctggata 60
atcagatagt tactgctacc cagagcaata tctgtgatga agacagtgct acagagacct 120
gctacactta tgacagaaac aagtgctaca cagctgtggt cccactcgta tatggtggtg 180
agaccaaaat ggtggaaaca gccttaaccc cagatgcctg ctatcctgac taatttaagt 240
c 241

-continued

<210> SEQ ID NO 350
<211> LENGTH: 241
<212> TYPE: DNA
<213> ORGANISM: Homo sapiens

<400> SEQUENCE: 350
aggtactgtg gatatttaaa atatcacagt aacaagatca tgcttgttcc tacagtattg 60
cgggccagac acttaagtga aagcagaagt gtttgggtga ctttcctact taaaattttg 120
gtcatatcat ttcaaaacat ttgcatcttg gttggctgca tatgctttcc tattgatccc 180
aaaccaaatc ttagaatcac ttcatttaaa atactgagcg gtattgaata cttcgaagca 240
g 241

<210> SEQ ID NO 351
<211> LENGTH: 241
<212> TYPE: DNA
<213> ORGANISM: Homo sapiens

<400> SEQUENCE: 351
tacagaaatc atttggagcc gttttgagac agaagtagag gctctgtcaa gtcaatactg 60
cattgcagct tggtccactg aagaagccac gcctgagata caaaagatgc actacacttg 120
acccgcttta tgttcgcttc ctctcccctt ctctctcatc aactttatta ggttaaaaca 180
ccacatacag gctttctcca aatgactccc tatgtctggg gtttggttag aattttatgc 240
c 241

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352
gtaccctgtn gagctgcacc aagattannt ggggccatca tgactgcanc cacnacgang 60
acgcaggcgt gnagtgcatc gtctgacccg gaaacccttt cacttctctg ctcccgaggt 120
gtcctcnggc tcatatgtgg gaaggcanan gatctctgan gagttncctg gggacaactg 180
ancagcctct ggagaggggc cattaataaa gctcaacatc attggcaaaa aaaaaaaaaa 240
a 241

<210> SEQ ID NO 353
<211> LENGTH: 241
<212> TYPE: DNA
<213> ORGANISM: Homo sapiens

<400> SEQUENCE: 353
aggtaccagt gcattaattt gggcaaggaa agtgtcataa tttgatactg tatctgtttt 60
ccttcaaagt atagagcttt tggggaagga aagtattgaa ctgggggttg gtctggccta 120
ctgggctgac attaactaca attatgggaa atgcaaaagt tgtttggata tggtagtgtg 180
tggttctctt ttggaatttt tttcaggtga tttaataata atttaaaact actataaaaa 240
c 241

<210> SEQ ID NO 354
<211> LENGTH: 241

-continued

<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 354
ngcaggtccg ggcaggtacc aagattcatt ctcatcaaaa actagaaaca gaagggcaaa 60
ttccagtttc cttctgggat tgaatacttt caagtaaggt cttcgacaaa caatcagggg 120
gccaattaat ccactgtaga ggtccttaac ttgatccaca gttgaataat aagcccatgg 180
aatacaagca gaatcctctg ttccagctcc agatctttct gggattttcc atacgtaagt 240
g 241

<210> SEQ ID NO 355
<211> LENGTH: 241
<212> TYPE: DNA
<213> ORGANISM: Homo sapiens

<400> SEQUENCE: 355
ggtacccacc ctaaatttga actcttatca agaggctgat gaatctgacc atcaaatagg 60
ataggatgga cctttttttg agttcattgt ataaacaaat tttctgattt ggacttaatt 120
cccaaaggat taggtctact cctgctcatt cactctttca aagctctgtc cactctaact 180
tttctccagt gtcatagata gggaattgct cactgcgtgc ctagtctttc ttcacttacc 240
t 241

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356
aggtactgta attgagcatc cggaatntgg agaagtaatt tagctacagg gtgaccaacg 60
caagaacata tgccagttcc tcgtagagat tggactggct aaggacgatc agctgaaggt 120
tcatgggttt taagtgcttg tggctcactg aagcttaagt gaggatttcc ttgcaatgag 180
tagaatttcc cttctctccc ttgtcacagg tttaaaaacc tcacagcttg tataatgtaa 240
c 241

<210> SEQ ID NO 357
<211> LENGTH: 241
<212> TYPE: DNA
<213> ORGANISM: Homo sapiens

<400> SEQUENCE: 357
ttttgtacca ccgatatgat caaggaaaat tctgcccatt tttatggctg aagttctaaa 60
aacctaattc aaagttcttc catgatccta cactgcctcc aagatggtcc aggctggcat 120
aaggcctgag cggcggtgag atccgcggct gccagcagct tgtcgctctt cagctggtat 180
gaagcccctc ggccacccga gtctccagga cctgcccggg cgccgctcga aagggcgaat 240
t 241

<210> SEQ ID NO 358

-continued

<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 358
aggtacgggg agtgggggtg aagcntgttc tctacatagg caacacagcc gcctaantca 60
caaagtcagt ggtcggccgc ttcgaccaac atgtggtgag cattccacgg gcgcatgaag 120
tctgggtgct gtgctcgagt ctctgaatat tttgatagga agcgacaaga aaattcaaac 180
tgctctttgc tgactactgg aaagtgaaaa gatgctcaag tttaccattc aaagaaacca 240
t 241

<210> SEQ ID NO 359
<211> LENGTH: 241
<212> TYPE: DNA
<213> ORGANISM: Homo sapiens

<400> SEQUENCE: 359
gaggtacaca aaaggaatac cttctgagag ccagggagtg aggaaagggg aaggagactt 60
gacgtcaagg gtgcttttga ggaacatgac gggccagcca gcctgcccca actttgaggc 120
cctgctgggc tcttgtgact ataaatatac tgtctatttc taatgcaatc cgtctttcct 180
gaaagatctt gttatctttt actattgaga catgctttca tttttgtggt cctgtttcca 240
a 241

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360
ngtactctat actaattctg cctttttata cttaattcta aatttctccc ctctaattta 60
caacaaattt tgtgattttt ataagaatct atgcctcccc aattctcaga ttcttctctt 120
ttctccttta tttctttgct taaattcagt ataagctttc ttggtatttt aggcttcatg 180
cacattctta ttcctaaaca ccagcagttc ttcagagacc taaaatccag tataggaata 240
a 241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc 60
ccactttgta cttttcttac tatcctgtct agaatcatgt cttatgattt taacagatat 120
agaaccactc ctagaaaatg ttctttcact ttctcgtttc ctttttaatc tatcatcctg 180
actactgaac ttaaaatctt tttcttccct tttttgtttc tcttttcttt tatcctgttc 240
a 241

-continued

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 362
aggtactttt atacctngct tangtcagtg acagatttac caatgacaac acaattttaa 60
aattccaaca catatattac tttgtcctat gaagggcaaa aagtcaatat attttaaatt 120
ttaaaaacag aatggatata atgacctttt tacacatcag tgatatttaa aagacttaaa 180
gagacaatac tatggttgag acactggctt cctattccag ccctaattaa agaaaaaata 240
g 241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363
ttangtacta aaaacaaaat cctaattctg ttttaaagag ctgggagatg ttaatcatat 60
gctcagtttt tccacgttat aatttcctaa atgcaaactt ttcaatcagg gcagttcaaa 120
ttcattacat cacagtaaat aacagtagcc aactttgatt ttatgcttat aggaaaaaaa 180
atcctgtaga tataaaaaca gcaaattttg acaaataaaa ctcaaaccat tcatccctaa 240
a 241

<210> SEQ ID NO 364
<211> LENGTH: 241
<212> TYPE: DNA
<213> ORGANISM: Homo sapiens

<400> SEQUENCE: 364
ggtacaagca gttagtcctg aaggcccctg ataagaatgt catcttctcc ccactgagca 60
tctccaccgc cttggccttc ctgtctctgg gggcccataa taccaccctg acagagattc 120
tcaaaggcct caagttcaac ctcacggaga cttctgaggc agaaattcac cagagcttcc 180
agcacctcct gcgcaccctc aatcagtcca gcgatgagct gcagctgagt atgggaaatg 240
c 241

<210> SEQ ID NO 365
<211> LENGTH: 241
<212> TYPE: DNA
<213> ORGANISM: Homo sapiens

<400> SEQUENCE: 365
cgaggtactg agattacagg catgagccac cacgcccggc caaaaacatt taaaaaatga 60
ctgtccctgc tcaaatactg cagtaggaaa tgtaatttga catatatcac ttccagaaaa 120
aaactttaaa tctttctata aaatgaattt gatacatcat cagcatgaag tgaagttaaa 180
atctcttaca aagtaaattc aggtatatca acaatgagat ccaaaagtat cggttcaaga 240
t 241

-continued

<210> SEQ ID NO 366
<211> LENGTH: 241
<212> TYPE: DNA
<213> ORGANISM: Homo sapiens

<400> SEQUENCE: 366
ggcaggtaca catcaaacac ttcattgcct aaatgcaggg acatgcttcc atctgaccac 60
ttgactatcc gagcattgct ttctttaatt tcatttcctt cttcatctcg gcgtatcctc 120
catcttatag tattttctac ctttaatttt aacctggttc taccttcttc atccagcatt 180
tcttcatctt caaattcatc ttcataatac tgggctctac acttgagaaa gttgggcagt 240
t 241

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367
gcaggtacaa ataattcctg ttgtnacatt tagtggacgc gattatctgt atacctcaaa 60
ttttaattta agaaagtatc acttaaagag catctcattt tctatagatt gaggcttaat 120
tactgaaaag tgactcaacc aaaaagcaca taacctttta aaggagctac acctaccgca 180
gaaagtcaga tgccctgtaa ataactttgg tctttcaaaa tagtggcaat gcttaagata 240
c 241

<210> SEQ ID NO 368
<211> LENGTH: 241
<212> TYPE: DNA
<213> ORGANISM: Homo sapiens

<400> SEQUENCE: 368
tttgtacatt gttaatagtg accctcggag gaaatggatt tctcttctat taaaaactct 60
atggtatata agcattacat aataatgcta cttaaccacc ttttgtctca agaattatca 120
ccaaagtttt ctggaaataa gtccacataa gaattaaata tttaaaaggt gaaatgttcc 180
ttattttaac tttagcaaga tcttttcttt ttcattaaga aacactttaa taattttaaa 240
g 241

<210> SEQ ID NO 369
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat 60
aaacaaaaca ccaaccagcc acagcagttg tgtcaagcat gacaattggt ctagtcttca 120
cattttatta gtaagtctat caagtaagag atgaagggtc tagaaaacta gacacaaagc 180
aaccagggtc caaatcacca aggtagatct gtgcttagct aaagggaaac acccgaagat 240
t 241

<210> SEQ ID NO 370
<211> LENGTH: 241

-continued

<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 370
ngttcacagt gcccctccgg cctcgccatg aggctcttcc tgtcgctccc ggtcctggtg 60
gtggttctgt cgatcgtctt ggaaggccca gccccagccc aggggacccc agacgtctcc 120
agtgccttgg ataagctgaa ggagtttgga aacacactgg aggacaaggc tcgggaactc 180
atcagccgca tcaaacagag tgaactttct gccaagatgc gggagtggtt ttcagaagac 240
a 241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 371
ggcaggtcat cttgagcctt gcacatgata ctcagattcc tcacccttgc ttaggagtaa 60
aacaatatac tttacagggt gataataatc tccatagtta tttgaagtgg cttgaaaaag 120
gcaagattga cttttatgac attggataaa atctacaaat cagccctcga gttattcaat 180
gataactgac aaactaaatt atttccctag aaaggaagat gaaaggnagt ggagtgtggt 240
t 241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 372
aggtacagca aagcgaccct tggtgnnata gatcagacgg aaattctctc ccgtcttgnc 60
aatgctgatg acatccatga atccagcagg gtaggttata tcagttcgga ccttgccatc 120
gattttaatg aaccgctgca tgcaaatctt ctttacttca tctcctgtca gggcatactt 180
aagtctgttc ctcaggaaaa tgatgagggg gagacactct ctcaacttgt ggggaccggt 240
g 241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca 60
gaagcagtag aaaatcttag cattccaatg gaaggcatgt atttgtaaaa tattctaaaa 120
tcagctctat agtttccttg tcctctttga taagggatca gacagagggt gtgtccccct 180
tcagcagcta cccttcttga caaactggtc tccaataata cctttcagaa acttacaaga 240

-continued

```
c                                                                 241


<210> SEQ ID NO 374
<211> LENGTH: 241
<212> TYPE: DNA
<213> ORGANISM: Homo sapiens

<400> SEQUENCE: 374

caggtactaa aacttacaat aaatatcaga gaagccgtta gtttttacag catcgtctgc    60

ttaaaagcta agttgaccag gtgcataatt tcccatcagt ctgtccttgt agtaggcagg   120

gcaatttctg ttttcatgat cggaatactc aaatatatcc aaacatcttt ttaaaacttt   180

gatttatagc tcctagaaag ttatgttttt taatagtcac tctactctaa tcaggcctag   240

c                                                                 241


<210> SEQ ID NO 375
<211> LENGTH: 241
<212> TYPE: DNA
<213> ORGANISM: Homo sapiens

<400> SEQUENCE: 375

aggtacaaag gaccagtatc cctacctgaa gtctgtgtgt gagatggcag agaacggtgt    60

gaagaccatc acctccgtgg ccatgaccag tgctctgccc atcatccaga agctagagcc   120

gcaaattgca gttgccaata cctatgcctg taaggggcta gacaggattg aggagagact   180

gcctattctg aatcagccat caactcagat tgttgccaat gccaaaggcg ctgtgactgg   240

g                                                                 241


<210> SEQ ID NO 376
<211> LENGTH: 241
<212> TYPE: DNA
<213> ORGANISM: Homo sapiens

<400> SEQUENCE: 376

ggtacatttt actttccttc tttcagaatg ctaataaaaa acttttgttt atacttaaaa    60

aaaccataaa tcagacaaac aaaagaaacg attccaacat cacttctgtg atgagaaaag   120

aggcaatgga attcaacata agcaaagaaa actctacctg gaggaaagaa atcgatcagc   180

gaagaaacaa ctcggggctg ctgccagact gcaggccatg cgaggaggag cctcctagag   240

g                                                                 241


<210> SEQ ID NO 377
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377

tcctttctgt ccaggtgatt cacagactag acctttctta tcctcctcct agagttttga    60

cttgggactc tagtgttaag atgatgagcc cgtgcatcag gtccttctgc actttggtgg   120

aagtctccca gggtaggttt cctatttgaa acagtggaat catgtttcca gtgataaagt   180

ttaatgacct catccttttt tttttttttc tcatctgcca tttgtgtgtc ttanatgggt   240

t                                                                 241
```

<210> SEQ ID NO 378
<211> LENGTH: 241
<212> TYPE: DNA
<213> ORGANISM: Homo sapiens

<400> SEQUENCE: 378

```
aggtcagcga tcaggtcctt tatgggcagc tgctgggcag ccccacaagc ccagggccag      60
ggcactatct ccgctgcgac tccactcagc ccctcttggc gggcctcacc cccagcccca     120
agtcctatga gaacctctgg ttccaggcca gcccttggg gaccctggta accccagccc     180
caagccagga ggacgactgt gtctttgggc cactgctcaa cttccccctc ctgcagggga    240
t                                                                    241
```

<210> SEQ ID NO 379
<211> LENGTH: 241
<212> TYPE: DNA
<213> ORGANISM: Homo sapiens

<400> SEQUENCE: 379

```
tacggagcaa tcgaagaggc atatccacac ttggggtggc tatagggctg gaaaatgctg      60
aagatgactg ctttcactga ggtcaaggat tgtaatattg ccagctttgt aaagccatta    120
aagcagaagt ttcttcagtg atcttctctc taagaaacac catcacctcc atgtgcctta    180
cagaggcccc ctgcgttctg ctgcattgct tttgcgcaat cccttgatga tgaagatggt    240
c                                                                    241
```

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380

```
acgtacacgc agaccgacat gggnnnttca ggcntnagat caaactcaaa acctgnaatg     60
atatccactc tcttttctt aagctcaggg aaatattcca agtagaagtc canaaagtca    120
tcggctaana tgcttcngaa tttgaattca tgcacatagg ccttgaaaaa actgtcaaac   180
tgannctgat cacccaccaa gtgggccntn tatgacacaa agcagaaacc tttctcntan   240
g                                                                    241
```

<210> SEQ ID NO 381
<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg     60
tctaaagaga gggtatttca tatggctttt agttcacttg tttgtatttc atcttgattt    120
ttttctttgg aaaataaagc attctatttg gttcagattt ctcagatttg aaaaaggctc    180
tatctcagat gtagtaaatt atttcctttc agtttgtgaa agcaggattt gactctgaaa    240
g                                                                    241
```

<210> SEQ ID NO 382
<211> LENGTH: 241
<212> TYPE: DNA

-continued

<213> ORGANISM: Homo sapiens

<400> SEQUENCE: 382
gtactgctat aatcaatacg tctgatagac aggtttatcc actatattga ccctacctct 60
aaaaggattg tcataattta tatgctttat gtttacacct atgatacagt tgccttggaa 120
cacaaaattt ttcattgtaa ttaaaaaaag aagagttgtg cagacagaag aaatcaaatc 180
taagaaaatc acaggagtag ataaatactc tagaattcat atacccttgg aagatgggtt 240
t 241

<210> SEQ ID NO 383
<211> LENGTH: 241
<212> TYPE: DNA
<213> ORGANISM: Homo sapiens

<400> SEQUENCE: 383
ggcaggtaca aagtcttctc tttgcttttt ataattttaa agcaaataac acatttaact 60
gtatttaagt ctgtgcaaat aatccttcag aagaaatatc caagattctg tttgcagagg 120
tcattttgtc tctcaaagat gattaaatga gtttgtcttc agataaagtg ctcctgtcca 180
gcagaactca aaaggccttc aagctgttca gtaagtgtag ttcagataag actccgtcat 240
a 241

<210> SEQ ID NO 384
<211> LENGTH: 241
<212> TYPE: DNA
<213> ORGANISM: Homo sapiens

<400> SEQUENCE: 384
ggtacacaaa atacacttgc aagcttgctt acagagacct gttaaacaaa gaacagacag 60
attctataaa atcagttata tcaacatata aaggagtgtg attttcagtt tgttttttta 120
agtaaatatg accaaactga ctaaataaga aggcaaaaca aaaaattatg cttccttgac 180
aaggcctttg gagtaaacaa aatgctttaa ggctcctggt gaatggggtt gcaaggatga 240
a 241

<210> SEQ ID NO 385
<211> LENGTH: 241
<212> TYPE: DNA
<213> ORGANISM: Homo sapiens

<400> SEQUENCE: 385
ggcaggtcta caatggctct gtcccttctg tggaatcgtt acaccaagag gtctcagtcc 60
tggtccctga ccccacagtg agctgtttag atgatccttc acatcttcct gatcaactgg 120
aagacactcc aatcctcagt gaagactctc tggagccctt caactctctg gcaccaggta 180
ggtttggagg ctatgtccct ttaacttatc catgcagagt agccaaactt tacctgaaag 240
a 241

<210> SEQ ID NO 386
<211> LENGTH: 241
<212> TYPE: DNA
<213> ORGANISM: Homo sapiens

<400> SEQUENCE: 386
aggtaccttt ttcctctcca aaggaacagt ttctaaagtt ttctgggggg aaaaaaaact 60
tacatcaaat ttaaaccata tgttaaactg catattagtt gtgttacacc aaaaaattgc 120

-continued

```
ctcagctgat ctacacaagt ttcaaagtca ttaatgcttg atataaattt actcaacatt    180

aaattatctt aaattattaa ttaaaaaaaa aactttctaa gggaaaaata aacaaatgta    240

g                                                                     241
```

<210> SEQ ID NO 387
<211> LENGTH: 241
<212> TYPE: DNA
<213> ORGANISM: Homo sapiens

<400> SEQUENCE: 387

```
accccactgg ccgctgtgga gtatctccac tctcccctcg tgagggccgc tcccaccgac     60

cagtcgaact ttcgtaaatg gagttaatgt gtttccactc cccttttccc ctttctggcc    120

ttttggtcca gaatttcctg gccttccggc atatcctggg agtcctcgac ttccaggaaa    180

gccaattgct ccccgatcac ctttaagacc cggaggacct attggacctg gaaatcctcg    240

t                                                                     241
```

<210> SEQ ID NO 388
<211> LENGTH: 241
<212> TYPE: DNA
<213> ORGANISM: Homo sapiens

<400> SEQUENCE: 388

```
tttgtactct tgtccacagc agagacattg agtataccat tggcatcaat gtcaaaagtg     60

acttcaatct gaggaacacc tcggggtgca ggaggtatgc ctgtgagttc aaacttgcca    120

agcaggttgt tatcctttgt catggcacgc tcgccttcat aaacctgaat aagtacacca    180

ggctggttgt cagaataggt agtgaaggtc tgtgtctgct tggtaggaat ggtggtatta    240

c                                                                     241
```

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389

```
tacctntgtt agtgagcacc ttgtcttntg tgcttatntc ttnaagataa atacatggaa     60

ggatgtgaaa atcggaacac caactatgtg tctcactgca tctaagtgaa gcagccacag    120

ctgtgagagt tttcaaagca gaaagatgct gatgtgacct ctggaattca gacatactga    180

gctatgggtc agaagtgttt tacttaaaaa gcaaacaatc cccaggaaat actgaatagg    240

a                                                                     241
```

<210> SEQ ID NO 390
<211> LENGTH: 241
<212> TYPE: DNA
<213> ORGANISM: Homo sapiens

<400> SEQUENCE: 390

```
gcaggtacat ccacatgttc ctccaaatga cgtttggggt cctgcttgcc aacattcttt     60

attgccagct gttcaggtgt catcttatct tcttcttcta cagccttatt gtaattcttg    120

gctaattcca acatctcttt taccactgat tcattgcgtt tacaatgttc actgtagtcc    180
```

-continued tgaagtgtca aaccttccat ccaactcttc ttatgcaaat ttagcaacat cttctgttcc 240
a 241

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391
cnggcacaan cttntgtttt tnntnttttt ttttttttn tctttatttn tttttantnt 60
taaanaaaaa nnntannnaa annngggttt aaatnctntn nncagancat taaaactgaa 120
ggggaaaaaa aaaccaaaaa cgagcttntt anttnacntg ggnttgggnn gntgctgatn 180
tnaagaagca anntttanan cnngcnnnat ganngagngn tcannttgaa atttnnaccc 240
t 241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gtttttteta 60 cattagaaat aagatgccac acaaggaact acattccaga tttaaagaaa tgaaaggata 120
ccattagtgt gtataacaga ttattgttca tacttgtaaa gcatcttatg tcattgagaa 180
tataaagaac agtgccttag aagacagtga aaggtaagct ctagcttaat gtctatgatt 240
t 241

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
ggcaggtaca taagcataat cagttatgga cagcttcttg tataaattgc tattcancaa 60
tacataaact gcctnaaaga tttatgctta caggtagaca ttcaatttac caataaaaca 120
gcatgttctg aaaatatggg cacattttaa aacatattaa gacagttctg ttaaccataa 180
tagtcccaca gtatgactga gtaataagaa tctacttcaa aagnaaaaaa aaaattaatc 240
a 241

<210> SEQ ID NO 394
<211> LENGTH: 241
<212> TYPE: DNA
<213> ORGANISM: Homo sapiens

<400> SEQUENCE: 394
aggtacagca gcagtagatg gctgcaacaa ccttcctcct accccagccc agaaaatatt 60
tctgccccac cccaggatcc gggaccaaaa taaagagcaa gcaggccccc ttcactgagg 120
tgctgggtag ggctcagtgc cacattactg tgctttgaga aagaggaagg ggatttgttt 180

-continued ggcactttaa aaatagagga gtaagcagga ctggagaggc cagagaagat accaaaattg 240
g 241

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395
nggcnggnnc caanatatga aatntnanta tnatacatga tnaaaagctt tatntatttt 60
agtgagtaat taagtttaca ctgtgaataa ggattaattc ccagatgacc atctacagtt 120
actaccacat agagggtata cacggatgga tcgattacaa gaatataaaa cttattttcc 180
ttcctgtatc cacatttctt tgcaatgtga atttgcaggc cctctcaaga agtggagtct 240
a 241

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396
gaggtacacc ttgaatgaca atgctnggag cccccctgtg gtcatcgacg cctccactgc 60
cattgatgca ccatccaacc tgcgtttcct ggccaccaca cccaattcct tgctggtatc 120
atggcagccg ccacgtgcca ggattaccgg ctacatcatc aagtatgaga agcctgggtc 180
tcctcccaga gaagtggtcc ctcggccccg ccctggtgtc acagaggcta ctattactgg 240
c 241

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 397
ggcaggtacc agcaggggga tgtgtttctg gggaattgtg gctctggaag cttcacggtt 60
tcccagaatg tggaaaatat atctgtgcan gatagaaatc ctgcccagag gctgtttctg 120
tctcatttga gctctccttc atgtggcaga gctgactgtg gcggtttagg agcctacatt 180
ttagaaaagc ttacctcaaa gttctgcatt gagcctgagc actggaaagg agataaaata 240
a 241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)

-continued

<223> OTHER INFORMATION: n = A,T,C or G

<400> SEQUENCE: 398
gangtgacca ngacatcacc tnacacntgg aaagcganga nttgaatggt gcntacaang 60
ccntacccnt tgcccannac ctgaacgcgc cttntgattg ggacagccgt gggaaggaca 120
gttatgaaac nantcanctg gatgaccana gtgntgaaac cnacanncac angcnntcna 180
cattatataa ncggaaagct aatgatgaga gcaatgatca ttccgatgtn attgatagtc 240
a 241

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399
cagagtgaga tgggagtggg agggccaatc tgatacagaa gggggtgaag ggtagggccc 60
ctgagcagcc caccccttac cctgacgaag gcaatcctcc tctggaatgt ctcttccctc 120
ttcagtctgg gttctgcctc agccacgaac tgggaaggag tgaggaacat cccaacggca 180
atgagagtat cccagtgact ccaaacagga angaatcagt gttcanaaag tcagggccct 240
t 241

<210> SEQ ID NO 400
<211> LENGTH: 241
<212> TYPE: DNA
<213> ORGANISM: Homo sapiens

<400> SEQUENCE: 400
ggtactcttg ctcttttagc tagagtgtat gtgaaaataa agaaatacat cattgtattc 60
acaaccatgt gtcttcattt ataacttttt gtttaaaaaa tttttagttc aagtttagtt 120
cattgatatt atcctctgaa tgcagttaag gctgggcaga aattctactc atgtgacatc 180
tgccacaggt ctattttgaa gcttttcttc taatgggcaa tgtttgtcct taccaggatt 240
t 241

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401
nncaggtact ttgtagagca gagagaggct ttggttcctc ctttcttcaa tcacgtggag 60
atgtgtcatc acctgggatt tcatctgggc cgccttttct gggtcaacag ccaacacatg 120
ctggtaatga cggatggtat gtaagcgatc tttgttctca gcacggacat aacgccgtaa 180
ggcctggaga atgcgatgag gccgtggcgg gtcagactgc aaggcagcca ggtagttctc 240
c 241

<210> SEQ ID NO 402
<211> LENGTH: 241

```
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 402

ggcaggtcca aaaaaaacct aaaaanngtt tcaggaatgt agagaaatat ccaacttaaa      60
tagcgaaaaa gtgcaccata attactgctg cactgcagtc atttctgcaa ttcccatgtt     120
tcttaaataa ctatcttgtc agataacaca caatataaag agcaattatg aaaaacagac     180
atttacatat acttctaaag tcttattggg aatatcctgt ttggccattg ggataaccaa     240
t                                                                    241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403

aggtgttaac tacccgctcc gagacgggat tgatgacgag tcctatgang ccattttcaa      60
gccggtcatg tccaaagtaa tggagatgtt ccagcctagt gcggtggtct tacagtgtgg     120
ctcagactcc ctatctgggg atcggttagg ttgcttcaat ctaactatca aaggacacgc     180
caagtgtgtg gaatttgtca agagctttaa cctgcctatg ctgatgctgg gaggcggtgg     240
t                                                                    241

<210> SEQ ID NO 404
<211> LENGTH: 241
<212> TYPE: DNA
<213> ORGANISM: Homo sapiens

<400> SEQUENCE: 404

caggtactgc aacccataaa atactgtttc ctcatatttc accttcctta atttggagtt      60
ttctgtcttc ttttcacggc attcaaagta ggaataaact ttgcttgtgt tgggtggata     120
ttgtttatag tgagtaacct tgtaggagtc ggtggccagg aggatgttga actcggcttc     180
tgccgcagga ttcatctcgg gccggaggac aaggggcccg cgcgccgcga gctccctgac     240
c                                                                    241

<210> SEQ ID NO 405
<211> LENGTH: 266
<212> TYPE: DNA
<213> ORGANISM: Homo sapiens

<400> SEQUENCE: 405

ttctgggctg gggagtggag agaaagaagt tgcagggctt acaggaaatc ccagagcctg      60
aggttttctc ccagatttga gaactctaga ttctgcatca ttatctttga gtctatattc     120
tcttgggctg taagaagatg aggaatgtaa taggtctgcc ccaagccttt catgccttct     180
gtaccaagct tgtttccttg tgcatccttc ccaggctctg gctgcccctt attggagaat     240
gtgatttcca agacaatcaa tccaca                                         266

<210> SEQ ID NO 406
```

-continued

<211> LENGTH: 231
<212> TYPE: DNA
<213> ORGANISM: Homo sapiens

<400> SEQUENCE: 406
ttggtgaaga accattcctc ggcatccttg cggttcttct ctgccatctt ctcatactgg 60
tcacgcatct cgttcagaat gcggctcagg tccacgccag gtgcagcgtc catctccaca 120
ttgacatctc cacccacctg gcctctcagg gcattcatct cctcctcgtg gttcttcttc 180
aggtaggcca gctcctcctt caggctctca atctgcatct ccaggtcagc t 231

<210> SEQ ID NO 407
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt 60
ttgtgccata atgcagcagt atggagggag gattttatgg agaaatgggg atagtcttca 120
tgaccacaaa taaataaagg aaaactaagc tgcattgtgg gttttgaaaa ggttattata 180
cttcttaaca attctttttt tcagggactt ttctagctgt atgactgtta cttgaccttc 240
tttgaaaagc attcccaaaa tgctct 266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg 60
acttttcagg gaattactga actttcttct cagaagatag ggcacagcca ttgccttggc 120
ctcacttgaa gggtctgcat ttgggtcctc tggtctcttg ccaagtttcc cagccactcg 180
agggagtaat atctggaggg caaagaagag acttatgtta ttgttgaacc tccagccaca 240
gggaggagca tgggcatggg t 261

<210> SEQ ID NO 409
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat 60
ctgtcccaga cccgctgcca ctgaatcggt cagggatccc ggattcccgg gtagatgccc 120
agtaaatgag cagtttagga ggctgtcctg gtttctgctg gtaccaagct aagtagttct 180
tattgttgga gctgtctaaa acactctggc tggtcttgca gttgatggtg gccctctcgc 240
ccagagacac agccagggag tgtgga 266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410

-continued

```
caaaaggtnc tttttgntca aaancnattt ttattccttg atatttttct tttttttttt     60

tttgnggatg gggacttgtg aatttttcta aaggggnnnn ttnannnngg aagaaaaccn    120

ngntccggtt ccagccaaac cngtngctna ctttccacct tntttccacc tccctcnggt    180

t                                                                    181


<210> SEQ ID NO 411
<211> LENGTH: 261
<212> TYPE: DNA
<213> ORGANISM: Homo sapiens

<400> SEQUENCE: 411

gcccctgcag tacttggccg atgtggacac ctctgatgag gaaagcatcc gggctcacgt     60

gatggcctcc caccattcca agcggagagg ccgggcgtct tctgagagtc agggtctagg    120

tgctggagtg cgcacggagg ccgatgtaga ggaggaggcc ctgaggagga agctggagga    180

gctggccagc aacgtcagtg accaggagac ctcgtccgag gaggaggaag ccaaggacga    240

aaaggcagag cccaacaggg a                                              261


<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

nttttntctt tacaattcag tcttcaacaa cttgagagct ttcttcatgt tgncaagcaa     60

cagagctgta tctgcaggnt cgtaagcata nagacngttt gaatatcttc cagngatatc    120

ggctctaact gncagagatg ggtcaacaaa cataatcctg gggacatact g             171


<210> SEQ ID NO 413
<211> LENGTH: 266
<212> TYPE: DNA
<213> ORGANISM: Homo sapiens

<400> SEQUENCE: 413

ttaggaccaa agatagcatc aactgtattt gaaggaactg tagtttgcgc attttatgac     60

atttttataa agtactgtaa ttctttcatt gaggggctat gtgatggaga cagactaact    120

cattttgtta tttgcattaa aattattttg ggtctctgtt caaatgagtt tggagaatgc    180

ttgacttgtt ggtctgtgta aatgtgtata tatatatacc tgaatacagg aacatcggag    240

acctattcac tcccacacac tctgct                                         266


<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 414

tttgccataa ttgagtgaaa agtggcagat ggcattaact ctgctccgct tcaagctggc     60

tccatgacca ctcaaggcct ccccancctg ttcgtcaagt tgtcctcaag tccaagcaat    120
```

-continued

```
ggaatccatg tgtttgcaaa aaaagtgtgc tanttttaag gnctttcgta taagaatnaa    180

tganacaatt ttcctaccaa aggangaaca aaaggataaa tataatacaa aatatatgta    240

tatggttgtt tgacaaatta tataac                                         266


<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415

cctccatcca gtctattaat tgttgccggg aagctanagt aagtagttcg ccagttaata     60

gtttgcgcaa cgttgttgcc attgctacag gcatcgtggt gtnacgctcg tcgattggta    120

tggcttcatt cagctccggt tcccaacgat caaggcgagt tacatgatcc cccatgttgt    180

gcaaaaaagc ggttagctcc ttcggtcctc cgatcgttgt canaagtaag ttggccgcag    240

tgttatcact catggttatg gcagca                                         266


<210> SEQ ID NO 416
<211> LENGTH: 878
<212> TYPE: DNA
<213> ORGANISM: Homo sapiens

<400> SEQUENCE: 416

cctgacgata gccatggctg taccacttaa ctatgattct attccaactg ttcagaatca     60

tatcacaaaa tgacttgtac acagtagttt acaacgactc ccaagagagg aaaaaaaaaa    120

aaaaagacgc ctcaaaattc actcaacttt tgagacagca atggcaatag gcagcagaga    180

agctatgctg caactgaggg cacatatcat tgaagatgtc acaggagttt aagagacagg    240

ctggaaaaaa tctcatacta agcaaacagt agtatctcat accaagcaaa accaagtagt    300

atctgctcag cctgccgcta acagatctca caatcaccaa ctgtgcttta ggactgtcac    360

caaagtcaga ttcggtgcta accaggtggc atctatgatc aacgtcgccc ctcttattta    420

acaaagggct ctgaaggagg tgttctccaa gcaacaagga gactgcttca gtacaagact    480

ttgcaccttg aattcaattg catcaagtgt ggatagcaaa ataagtatct taccattgaa    540

atatgtgttc agcctaagat tttacccacc agcagaacaa aagtgagggt gagagggatg    600

ggccagtgag gggatggggg agaaaaaaaa atcacaggat taccaccaaa gccttgtttt    660

aaaagggctc ccttcactat tcaggaaggg aagtggaagg agaaattaac caattcctgc    720

cacagcagcc ctttttggct gcttccacaa tagatacttt atggagtggc acagccaacc    780

ctatctgtga cctgccctgc ggataaacac agccaagcag gtttaattag atcaaagaca    840

caaagggcta ttccctcctt tcataacaac gcagacct                            878


<210> SEQ ID NO 417
<211> LENGTH: 514
<212> TYPE: DNA
<213> ORGANISM: Homo sapiens

<400> SEQUENCE: 417

ttctgacttc tagaagacta aggctggtct gtgtttgctt gtttgcccac ctttggctga     60

tacccagaga acctgggcac ttgctgcctg atgcccaccc ctgccagtca ttcctccatt    120

cacccagcgg gaggtgggat gtgagacagc ccacattgga aaatccagaa aaccgggaac    180
```

-continued

```
agggatttgc ccttcacaat tctactcccc agatcctctc ccctggacac aggagaccca    240

cagggcagga ccctaagatc tggggaaagg aggtcctgag aaccttgagg taccccttaga   300

tccttttcta cccactttcc tatggaggat tccaagtcac cacttctctc accggcttct    360

accagggtcc aggactaagg cgttttctcc atagcctcaa cattttggga atcttccctt    420

aatcaccctt gctcctcctg ggtgcctgga agatggactg gcagagacct ctttgttgcg    480

ttttgtgctt tgatgccagg aatgccgcct agtt                                514
```

<210> SEQ ID NO 418
<211> LENGTH: 352
<212> TYPE: DNA
<213> ORGANISM: Homo sapiens

<400> SEQUENCE: 418

```
ctgcaccagc gattaccagt ggcattcaaa tactgtgtga ctaaggattt tgtatgctcc     60

ccagtagaac cagaatcaga caggtatgag ctagtcaaca gcaagtcttt gttggattcg    120

agtaggctca ggatctgctg aaggtcggag gagttagtcc ccgcaatcaa gagcctgtct    180

tcctgaagcc cttggtgata ttttgccact cagccaagaa tgaggatgca tccttcagat    240

tctctatgtc ccgaacctgg aacccatcca cgccagcttg cagccaaaac tccagagcat    300

ccttcacctt ggtggaaaaa aaaaaaaaaa aaaaaaaaaa aaaaaaaaaa aa            352
```

<210> SEQ ID NO 419
<211> LENGTH: 344
<212> TYPE: DNA
<213> ORGANISM: Homo sapiens

<400> SEQUENCE: 419

```
ctggacacca taatcccttt taagtggctg gatggtcaca cctctcccat tgacaagctg     60

ggttaagtca ataggttgac taggatcaac acgacccaaa tcaataagat actgcagtct    120

attgagactc aaaggcttat actggcgtct gaaactatgt ccttcgttaa acccgtattt    180

tgggattcgg atgtaaaatg gagtctggcc tccctcaaag cccaagcggg gccgggttcc    240

tctttgcctt tctcctttat ggcctctgcc acattttcta cctcttctcc gacctcttgg    300

tcttctctcc ggtttcttgg agccgggatt cggctttaag ttgg                      344
```

<210> SEQ ID NO 420
<211> LENGTH: 935
<212> TYPE: DNA
<213> ORGANISM: Homo sapiens

<400> SEQUENCE: 420

```
cgaaagtcaa cgttaagggg ctcaggtgaa ccatgatgat gaccttctgt tgactttgaa     60

atattggctc ttgtgggtga caaaagccag acaagctgtg gctgtggtcc gattttaaga    120

cgaggttctc aaagatccaa aggagggaaa gggtattgga aacactgtgt atcatctgag    180

acacacgtgt cctcatgatc ttaaatgcct actttaaagc cacctaatac tgcccttcat    240

tgtggtcaga agagatttct acaaaagcac tcagaattct ggaggcagtt gtgattttgc    300

catgtggcag ttggtttgtg gagttgggca ggtgtgaaag ggtaaaactc cacttctgaa    360

tgctgcttct gccccctggg acccagcaca ttgttagacc atcttcttga ctgaaaattc    420

tctcctgatg ctgagccctg caccaccacc ttccttttcc taactatgaa ttgatggcaa    480

agtccactca aaacaaccag ttaagtgctc acgagagagt agtcaagcac ctccagaaag    540
```

-continued

```
aaaccgggtt tttgttcaca tagcaggaag tgactccctg ggtggtaatt tatcttggaa    600

acacaggtag attggcagaa aaacgggaac atgtaggtac cgcgatgttg gtgcatgtcc    660

attactttgg gataggcttt ctcagtcttt cctcaaatga tagttgagcc agttttccag    720

tggcaattct gagtgacttg cgcttgtctt atggtgtggt caagggacgt tcagaactac    780

ggaaaacttt tactgaaaca gcgaagcaga gtataccggc atgagaggga agatgaacac    840

tcacctatgt accactcttt gacaataaat atagtatttc tcaaaaaaaa aaaaaaaaaa    900

agtaaaaaaa ctgaaatcgc aagtcaaaaa atcca                                935


<210> SEQ ID NO 421
<211> LENGTH: 745
<212> TYPE: DNA
<213> ORGANISM: Homo sapiens

<400> SEQUENCE: 421

ggcttcgagc ggccgcccgg gcaggtccta gatgtcattt gggacccttc acaaccattt     60

tgaagccctg tttgagtccc tgggatatgt gagctgtttc tatgcataat ggatattcgg    120

ggttaacaac agtcccctgc ttggcttcta ttctgaatcc ttttctttca ccatggggtg    180

cctgaagggt ggctgatgca tatggtacaa tggcacccag tgtaaagcag ctacaattag    240

gagtggatgt gttctgtagc atcctattta aataagccta ttttatcctt tggcccgtca    300

actctgttat ctgctgcttg tactggtgcc tgtacttttc tgactctcat tgaccatatt    360

ccacgaccat ggttgtcatc cattacttga tcctacttta catgtctagt ctgtgtggtt    420

ggtggtgaat aggcttcttt ttacatggtg ctgccagccc agctaattaa tggtgcacgt    480

ggacttttag caagcgggct cactggaaga gactgaacct ggcatggaat tcctgaagat    540

gtttggggtt tttttctttc ttaatcgaaa gttaacattg tctgaaaagt tttgttagaa    600

ctactgcgga acctcaaaat cagtagattt ggaagtgatt caaagctaaa ctttttcctt    660

ggccctcctt gtgttctaat tgcttgcaag tgtaatacta ggatgtccaa gatgccagtt    720

tttgcttctt tgttagttgt cagac                                          745


<210> SEQ ID NO 422
<211> LENGTH: 764
<212> TYPE: DNA
<213> ORGANISM: Homo sapiens

<400> SEQUENCE: 422

gagttcagta gcaaagtcac acctgtccaa ttccctgagc tttgctcact cagctaatgg     60

gatggcaaag gtggtggtgc tttcatcttc aggcagaagc ctctgcccat ccccctcaag    120

ggctgcaggc ccagttctca tgctgccctt gggtgggcat ctgttaacag aggagaacgt    180

ctgggtggcg gcagcagctt tgctctgagt gcctacaaag ctaatgcttg gtgctagaaa    240

catcatcatt attaaacttc agaaaagcag cagccatgtt cagtcaggct catgctgcct    300

cactgcttaa gtgcctgcag gagccgcctg ccaagctccc cttcctacac ctggcacact    360

ggggtctgca caaggctttg tcaaccaaag acagcttccc ccttttgatt gcctgtagac    420

tttggagcca agaaacactc tgtgtgactc tacacacact tcaggtggtt tgtgcttcaa    480

agtcattgat gcaacttgaa aggaaacagt ttaatggtgg aaatgaacta ccatttataa    540

cttctgtttt tttattgaga aaatgattca cgaattccaa atcagattgc caggaagaaa    600

taggacgtga cggtactggg ccctgtgatt ctcccagccc ttgcagtccg ctaggtgaga    660

ggaaaagctc tttacttccg cccctggcag ggacttctgg gttatgggag aaaccagaga    720
```

-continued

```
tgggaatgag gaaaatatga actacagcag aagcccctgg gcag                   764


<210> SEQ ID NO 423
<211> LENGTH: 1041
<212> TYPE: DNA
<213> ORGANISM: Homo sapiens

<400> SEQUENCE: 423

ctcagagagg ttgaaagatt tgcctacgaa agggacagtg atgaagctaa gctctagatc    60

caggatgtct gacttcaaat tgaaactccc aaagtaatga gtttggaagg gtggggtgtg   120

gcctttccag gatgggggtc ttttctgctc ccagcggata gtgaaacccc tgtctgcacc   180

tggttgggcg tgttgctttc ccaaaggttt tttttttagg tccgtcgctg tcttgtggat   240

taggcattat tatctttact ttgtctccaa ataacctgga gaatggagag agtagtgacc   300

agctcagggc cacagtgcga tgaggaccat cttctcacct ctctaaatgc aggaagaaac   360

gcagagtaac gtggaagtgg tccacaccta ccgccagcac attgtgaatg acatgaaccc   420

cggcaacctg cacctgttca tcaatgccta caacaggtat tgggatgtag ttcagccaca   480

tcattgctat ttatgaggtg tcttctgtag atccgaaatg tgggacagat gagagggaga   540

gtataaaatg agcggaagag gcaggctctg agtttgagca aatagattaa taggacaggt   600

gtccccagga aggacacctg gcctgtaagc tggttcctgg cattcagctc gccttgcagg   660

gatctgaaca aacactccag accactgggg gtgcagacgt gagagggacg cagtcgcaca   720

ctcagagggt tgagagtaaa tatgtgtgcc cgctgctgac cttcacgaaa ggccaaatgt   780

aagaagagct aagtgagaga gcagcaaagc actcctggag gccggggata atccaggcag   840

gcttctggga gtttgtcatt ccaaggataa ggaggacctg aacatggcct ttgcctaagg   900

cgtggccctc tcaaccagca ctaggtgctt atctggagct cagctagggg aggagacagc   960

tcagggccat tggtgtcagc cagagactct gtaatcttcc agggagctcg ctcaacctgc  1020

tgagctcgct ctgccacgca c                                            1041


<210> SEQ ID NO 424
<211> LENGTH: 1288
<212> TYPE: DNA
<213> ORGANISM: Homo sapiens

<400> SEQUENCE: 424

ctaagaactg agacttgtga cacaaggcca acgacctaag attagcccag ggttgtagct    60

ggaagaccta caacccaagg atggaaggcc cctgtcacaa agcctaccta gatggataga   120

ggacccaagc gaaaaaggta tctcaagact aacggccgga atctggaggc ccatgaccca   180

gaacccagga aggatagaag cttgaagacc tggggaaatc ccaagatgag aaccctaaac   240

cctacctctt ttctattgtt tacacttctt actcttagat atttccagtt ctcctgttta   300

tctttaagcc tgattctttt gagatgtact ttttgatgtt gccggttacc tttagattga   360

cagtattatg cctgggccag tcttgagcca gctttaaatc acagctttta cctatttgtt   420

aggctatagt gttttgtaaa cttctgtttc tattcacatc ttctccactt gagagagaca   480

ccaaaatcca gtcagtatct aatctggctt ttgttaactt ccctcaggag cagacattca   540

tataggtgat actgtatttc agtcctttct tttgacccca gaagccctag actgagaaga   600

taaaatggtc aggttgttgg ggaaaaaaaa gtgccaggct ctctagagaa aaatgtgaag   660

agatgctcca ggccaatgag aagaattaga caagaaatac acagatgtgc cagacttctg   720
```

-continued

```
agaagcacct gccagcaaca gcttccttct ttgagcttag tccatccctc atgaaaaatg     780

actgaccact gctgggcagc aggagggatg atgaccaact aattcccaaa ccccagtctc     840

attggtacca gccttgggga accacctaca cttgagccac aattggtttt gaagtgcatt     900

tacaagtttc tggcatcact accactactg attaaacaag aataagagaa cattttatca     960

tcatctgctt tattcacata aatgaagttg tgatgaataa atctgctttt atgcagacac    1020

aaggaattaa gtggcttcgt cattgtcctt ctacctcaaa gataatttat tccaaaagct    1080

aagataaatg gaagactctt gaacttgtga actgatgtga aatgcagaat ctcttttgag    1140

tctttgctgt ttggaagatt gaaaaatatt gttcagcatg ggtgaccacc agaaagtaat    1200

cttaagccat ctagatgtca caattgaaac aaactgggga gttggttgct attgtaaaat    1260

aaaatatact gttttgaaaa aaaaaaac                                       1288
```

<210> SEQ ID NO 425
<211> LENGTH: 446
<212> TYPE: DNA
<213> ORGANISM: Homo sapiens

<400> SEQUENCE: 425

```
ccacttaaag ggtgcctctg ccaactggtg gaatcatcgc cacttccagc accacgccaa      60

gcctaacatc ttccacaagg atcccgatgt gaacatgctg cacgtgtttg ttctgggcga     120

atggcagccc atcgagtacg gcaagaagaa gctgaaatac ctgccctaca atcaccagca     180

cgaatacttc ttcctgattg ggccgccgct gctcatcccc atgtatttcc agtaccagat     240

catcatgacc atgatcgtcc ataagaactg ggtggacctg gcctgggccg tcagctacta     300

catccggttc ttcatcacct acatcccttt ctacggcatc ctgggagccc tccttttcct     360

caacttcatc aggttcctgg agagccactg gtttgtgtgg gtcacacaga tgaatcacat     420

cgtcatggag attgaccagg aggacc                                          446
```

<210> SEQ ID NO 426
<211> LENGTH: 874
<212> TYPE: DNA
<213> ORGANISM: Homo sapiens

<400> SEQUENCE: 426

```
tttttttttt tttttttttt ttttttcaat taaagatttg atttattcaa gtatgtgaaa      60

acattctaca atggaaactt ttattaaatg ctgcatgtac tgtgctatgg accacgcaca     120

tacagccatg ctgtttcaga agacttgaaa tgccattgat agtttaaaaa ctctacaccc     180

gatggagaat cgaggaagac aatttaatgt ttcatctgaa tccagaggtg catcaaatta     240

aatgacagct ccacttggca aataatagct gttacttgat ggtatccaag aagaaatggt     300

tggtgatgga taaattcaga aatgcttccc caaaggtggg tggtttttaa aaagttttca     360

ggtcacaacc cttgcagaaa acactgatgc ccaacacact gattcgcggt ccaggaaaca     420

cgggtcttcc aagttccaag gggctggggt tccccaacga tcaagttcct gtgctgtaat     480

caagagggtc ctttggactg gatagggagc acttgggagc tgtacaccat cagtcataat     540

ggatggcagt gtaaaagatg atccaaatga cctgagatgc tcctgaggag tggtgcacca     600

gacccaggag tgccactgta gggctgcttc tttgctttag tcatcacaca cacacacagc     660

tccagagcag caatggcctt tcctgtaaca ggaaaaaagc ctcctgctat tcccaagaac     720

cctcgtaatg gcaaaactcc ccaaatgaca cccaggacca cagcaatgat ctgtcggaac     780

cagtagatca catctaaaaa ttcatcctta tcctcccagg ccgcgtcgct ccgcagcacc     840
```

-continued ttactccaga cggagacttt gagggccccg ttgg 874

<210> SEQ ID NO 427
<211> LENGTH: 638
<212> TYPE: DNA
<213> ORGANISM: Homo sapiens

<400> SEQUENCE: 427
acttgtaatt agcacttggt gaaagctgga aggaagataa ataacactaa actatgctat 60
ttgatttttc ttcttgaaag agtaaggttt acctgttaca ttttcaagtt aattcatgta 120
aaaaatgata gtgattttga tgtaatttat ctcttgtttg aatctgtcat tcaaaggcca 180
ataatttaag ttgctatcag ctgatattag tagctttgca accctgatag agtaaataaa 240
ttttatgggc gggtgccaaa tactgctgtg aatctatttg tatagtatcc atgaatgaat 300
ttatggaaat agatatttgt gcagctcaat ttatgcagag attaaatgac atcataatac 360
tggatgaaaa cttgcataga attctgatta aatagtgggt ctgtttcaca tgtgcagttt 420
gaagtattta aataaccact cctttcacag tttattttct tctcaagcgt tttcaagatc 480
tagcatgtgg attttaaaag atttgccctc attaacaaga ataacattta aaggagattg 540
tttcaaaata tttttgcaaa ttgagataag gacagaaaga ttgagaaaca ttgtatattt 600
tgcaaaaaca agatgtttgt agctgtttca gagagagt 638

<210> SEQ ID NO 428
<211> LENGTH: 535
<212> TYPE: DNA
<213> ORGANISM: Homo sapiens

<400> SEQUENCE: 428
acaagatgat tcttcctcct caatttgaca gatcaaagaa gtatcccttg ctaattcaag 60
tgtatggtgg tccctgcagt cagagtgtaa ggtctgtatt tgctgttaat tggatatctt 120
atcttgcaag taaggaaggg atggtcattg ccttggtgga tggtcgagga acagctttcc 180
aaggtgacaa actcctctat gcagtgtatc gaaagctggg tgtttatgaa gttgaagacc 240
agattacagc tgtcagaaaa ttcatagaaa tgggtttcat tgatgaaaaa agaatagcca 300
tatggggctg gtcctatgga ggatacgttt catcactggc ccttgcatct ggaactggtc 360
ttttcaaatg tggtatagca gtggctccag tctccagctg ggaatattac gcgtctgtct 420
acacagagag attcatgggt ctcccaacaa aggatgataa tcttgagcac tataagaatt 480
caactgtgat ggcaagagca gaatatttca gaaatgtaga ctatcttctc atcca 535

<210> SEQ ID NO 429
<211> LENGTH: 675
<212> TYPE: DNA
<213> ORGANISM: Homo sapiens

<400> SEQUENCE: 429
actattttca accctgagca ttaacactgc ataccaaggg ggggtgggtc aagaagctgg 60
ttagatcgaa gcacaagcac aagccactga tattctctat gtgatcaggt ttttacaaaa 120
aaatacatag ttttcaataa ataatgctta attttacaac tttgatacag caatgtcata 180
caccgtttca acacactaca ctctgcatgc tagatagtct acgagaagac gaaactttgc 240
catgcatttt ctttcccccc tagtgctatc aaacacttca tcctccagcg cactgcctca 300
ggtagcttta ccttctctct gtttcacagc aataggccgt gcgctggcat gcaaactcta 360

-continued aaaaaggtcc cccccacaaa ccactcagac ttctacacaa aagggttttt cagcttttct 420
gctcccaaac ctggagtggc taagaaagta agtttcatgt ggccttggaa aatacacact 480
tgttaacagt gtcatgctga aaactgctct aaaacatcag gtggttctgt cctggtggcc 540
gtcacgaagc attatgggat gccataacca ctaggagtcc caaaccggaa aaaataggcc 600
tccgttttaa aacagtcaat tcaaaaaagg tgtcacagaa caaatgcaaa agactcttaa 660
acccacaaca tatgt 675

<210> SEQ ID NO 430
<211> LENGTH: 434
<212> TYPE: DNA
<213> ORGANISM: Homo sapiens

<400> SEQUENCE: 430
acctctgcca gaagtccagc gagaggacct cacagtagag cacaggccac tccgggagtg 60
catcagaaga ttcatcctca tggaggaaga aggcttcaaa cgtgaatggg taggagaagt 120
gagccacctt gtccattgcc agggacttgg tggtgcaggt ctgtgttact cctgagagct 180
gctggaatgc tgggcttgac cagtgagcag ttggcaattc tacaaagaag tggacgtaga 240
gattgtcata ctcatagcct tgggctgaaa cgacctctcc atttacaaag agccggaggg 300
cacctgggac agtcatctca aagtcggtgc ctacgaggct gctgagatac tccttgtgcc 360
ggccataaag atccttgaac actcgccgtt cccgctcctc ctcctccggc tgtgcgtggg 420
gggaaacatt gtcg 434

<210> SEQ ID NO 431
<211> LENGTH: 581
<212> TYPE: DNA
<213> ORGANISM: Homo sapiens

<400> SEQUENCE: 431
acacaagcct ccagcccgac ccagcggcct aatgaaactc tggcaaccta tcctgggcgt 60
ggccacgagt atccagctcc aagcccaagt gaggcgggga gtcaacttcc ccatgattgc 120
caagtgacca agaccagaag cagggacgat taggctagtt ctgcggcaag gtgaactgga 180
gaccctgtct ctgccctcct tccctggcct gtcccacaga catcccgttg tttaacccac 240
tgcctttgca aggacctgct ctgtccactc caaatcaaag gatacttgca tccttcttac 300
acagactccc atctctctgc tcatagtggt cccaggctgc ccgagaaaaa gaaacttggg 360
tcagtagaag gctcattagt gtgaaggagt gagaggccag gccttcctgt gacataatgc 420
ttctatgctt gtttcctaaa cacttggtcc acacacaata cctgggcagg aagagagaac 480
caagcaccac tggatggctc tggagccagg ggacttctat gcacatacaa ccaacatcac 540
cccactctgc tcatctgtgc ctccaccctg aacagcagag t 581

<210> SEQ ID NO 432
<211> LENGTH: 532
<212> TYPE: DNA
<213> ORGANISM: Homo sapiens

<400> SEQUENCE: 432
actccaactc aagtttacaa gttacacctt tgccacagcc ttggctaaat cttgaactag 60
tgcagaattc agctgtggta gagtgctgat cttagcatgc ttcgatgtgg catacttgtt 120
cttgacagtc atgtgctttg taagtccttg atttaccatg actacattct tagccaggtg 180
ctgcataact ggaagaagag attcttcagt atatgacagg taatgttgta gagttggtgt 240

-continued

```
ccattcacca ttatccagaa ttttcagtgc taagcaaaaa gctcctgctg caatttgaga    300

aggaggaaag tgcaccatgt catagtccaa catagttagt tccatcaggt atttggccaa    360

agtatgttgc tcgacatcaa cctctccaat cttagatgct ctccgaagga agtgcaaagg    420

tagaggccga cccagaccaa agtttaaagc tcttagaatc ttcatttcca tctgtctgat    480

ttggtgctta gtataagtgt tgtcagtcac aaaagcaaag tcaccaattt ct            532


<210> SEQ ID NO 433
<211> LENGTH: 531
<212> TYPE: DNA
<213> ORGANISM: Homo sapiens

<400> SEQUENCE: 433

acttggtttt acagctcctt tgaaaactct gtgtttggaa tatctctaaa aacatagaaa     60

acactacagt ggtttagaaa ttactaattt tacttctaag tcattcataa accttgtcta    120

tgaaatgact tcttaaatat ttagttgata gactgctaca ggtaataggg acttagcaag    180

ctcttttata tgctaaagga gcatctatca gattaagtta gaacatttgc tgtcagccac    240

atattgagat gacactaggt gcaatagcag ggatagattt tgttggtgag tagtctcatg    300

ccttgagatc tgtggtggtc ttcaaaatgg tggccagcca gatcaaggat gtagtatctc    360

atagttccca ggtgatattt ttcttattag aaaaatatta taactcattt gttgtttgac    420

acttatagat tgaaatttcc taatttattc taaattttaa gtggttcttt ggttccagtg    480

ctttatgttg ttgttgtttt tggatggtgt tacatattat atgttctaga a             531


<210> SEQ ID NO 434
<211> LENGTH: 530
<212> TYPE: DNA
<213> ORGANISM: Homo sapiens

<400> SEQUENCE: 434

acaagagaaa acccctaaaa aaaggatggc tttagatgac aagctctacc agagagactt     60

agaagttgca ctagctttat cagtgaagga acttccaaca gtcaccacta atgtgcagaa    120

ctctcaagat aaaagcattg aaaaacatgg cagtagtaaa atagaaacaa tgaataagtc    180

tcctcatatc tctaattgca gtgtagccag tgattattta gatttggata agattactgt    240

ggaagatgat gttggtggtg ttcaagggaa aagaaaagca gcatctaaag ctgcagcaca    300

gcagaggaag attcttctgg aaggcagtga tggtgatagt gctaatgaca ctgaaccaga    360

ctttgcacct ggtgaagatt ctgaggatga ttctgatttt tgtgagagtg aggataatga    420

cgaagacttc tctatgagaa aaagtaaagt taaagaaatt aaaaagaaag aagtgaaggt    480

aaaatcccca gtagaaaaga aagagaagaa atctaaatcc aaatgtaatg               530


<210> SEQ ID NO 435
<211> LENGTH: 677
<212> TYPE: DNA
<213> ORGANISM: Homo sapiens

<400> SEQUENCE: 435

accttatgat ctaattaata gatattagaa acagtagaaa gacaagttac acgtcaatgc     60

ccaatgacta gagtcaacat taaagagttg taatttaagt aatccaaact gacatctaat    120

tccaaaatca tttataaaat gtatttggct ttggaatcca caggacttca aacaagcaaa    180

gtttcactgc agatagtcac aaagatgcag atacactgaa atacttaaga gccttattaa    240
```

-continued

```
tgatttttgt tattttggat cttctgtttt tttcttatta tggtccgaag cctccttaat    300

accaatttat cagacagaag catgtcatct tgttgttcaa gataatccag taaattttca    360

gtccattcaa gtgccgcttt atggctaata cgcttctctg gattcagttc tgtttttcta    420

ctcttactgg aaggcttttg ctcagcagcc ttggtctggt cctcagcact ttcactgtca    480

gtcagcacct gacagcttga gtcactgctc cgagagtcga accactgatc aatattctca    540

atgtcaacat gttcacattc ttctgtgttc tgtaaaactg ttgctaaatt agctgctaaa    600

atggctcctt catcaatgtt catacctgaa ttctcttcat tgccagggaa aagtttttttc   660

catgctttgg ttatggt                                                   677


<210> SEQ ID NO 436
<211> LENGTH: 573
<212> TYPE: DNA
<213> ORGANISM: Homo sapiens

<400> SEQUENCE: 436

acctcttagg gtgggagaaa tggtgaagag ttgttcctac aacttgctaa cctagtggac     60

agggtagtag attagcatca tccggataga tgtgaagagg acggctgttt ggataataat    120

taaggataaa atttggccag ttgacagatt ctgtttccag cagtttttac agcaacagtg    180

gagtgcttca gtattgtgtt cctgtaaatt taattttgat ccgcaatcat ttggtataca    240

atgctgtttg aagttttgtc ctattggaaa agtcttgtgt tgcaggggtg cagttaagat    300

ctttgtgatg aggaatggga tggctaatt ttttgccgtt ttcttggaat tgggggcatg     360

gcaaatacag tagggtagtt tagttcttta cacagaacat gataaactac acctgttgat    420

gtcaccgtct gtcaatgaat attatagaag gtatgaaggt gtaattacca taataacaaa    480

acaccctgtc tttagggctg acctttcgtc ctttgacctc ctcagcctcc attcccatct    540

tcgctcagac tgcaagtatg tttgtattaa tgt                                 573


<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 437

acaattggta tccatatctt gttgaaattg taatgggaaa acaatatatt tcaatctcta     60

tgtagatagt gggtttttgt tttcataata tattctttta gtttactgta tgagttttgc    120

aggactgcat aatagatcac cacaatcata acatcttagg accacagaca tttatgagat    180

catggcttct gtgggttaga agtatgctca tgtcttaact gggtcctctg ctcagtctta    240

tctggctgca atcaaggtgt cagctgggct gaattttcat ttggaatctt gactgggaaa    300

gagtctgctt ccaaggtcat gaagtttgct ggcaaaatgt atgtttttat gacagtatga    360

ctgaaatccc aagctatctc ctgactttta gctgggtaat ctcaggccct aaatgttgcc    420

tacagttcct agaggctggt cacagttctt agccatgtgg atttcctcaa catggctgct    480

tgcttcatca agtcagcaag aatagcctgt catatcagtg tatatcaggc tcactcagga    540

taatttccct actgatgagc caaacactaa ctgattttag agcttaacta catctgcaaa    600

attcngttca ccagaggcaa gtcatattca gggaaggaga agtgt                    645
```

-continued

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat 60
atttctgatg aaaatgaagg aaaagaaatg tgtgttctgc gaatgactcg agctagacgt 120
tcccaggtag aacagcagca gctcatcact gttgaaaagg ctttggcaat tctttctcag 180
cctacaccct cacttgttgt ggatcatgag cgattaaaaa atcttttgaa gactgttgtt 240
aaaaaaagtc aaaactacaa catatttcag ttggaaaatt tgtatgcagt aatcagccaa 300
tgtatttatc ggcatcgcaa ggaccatgat aaaacatcac ttattcagaa aatggagcaa 360
gaggtagaaa acttcagttg ttccagatga tgatgtcatg gtatcgagta ttctttatat 420
tcagttccta tttaagtcat ttttgtcatg tccgcctaat tgatgtagta tgaaaccctg 480
catct 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc 60
aggttcaaca gtatggctcc aaatgatgaa atttcattct gattttctgg ctgaagacta 120
ttctgtttgt gtatgtccac cacagttact ttatcccttc atctgtggat gggcagaatg 180
aaacatatat ggaaatgttc tgtgcaataa aaacagcagt ggtaacacag atgtaggctc 240
tgagtgtctc actggagact gaagtccaca gatatgcaac aaagcctttg tctccctgat 300
gtttttgcct cctgctggtc atgtgctttc acacatcaag agaggacatt taacatttga 360
gccacagtgt catttgctgt tgtctgatgg ttggttggca gagaatttga actggagatg 420
aactttatta tccaggacgc tgagagtata acatgcatga cagagctttt agagcactgt 480
gatgtaacat gtcaagcaga aatagggagc atgtttacag ccattctatg aaa 533

<210> SEQ ID NO 440
<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca 60
cactctcaca ctcgcaccca gaattgtcaa agatacagat tgtaaaaatc tacgatccct 120
cagtctcact cacaaaaaat aaaatctcat gtccccaacg aacccagagt cagacgacag 180
ctggagcatt ggcagggaca gtcagaaagg agacaagtga aaacggtcag atggacacag 240
gcggaggaga aaagacagag ggagagagac catcgggaac aatcagaggg gccgagacga 300
tcagaaaagg gtcagcccga gacaggctga gccagagttt c 341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)

-continued

<223> OTHER INFORMATION: n = A,T,C or G

<400> SEQUENCE: 441
aagtttgggg ataatttatt atgcagcaag agataataca caggacttct canagcactt 60
aatatgttaa tataaatctc caanaaaaaa gatatacaat gaaacattcc tcttagttat 120
ctggccaagg anactttntt tttttganaa tattcttcaa aaagctgatc taatgatatg 180
gctctggtcc tacaattcca tgtaacttct aaccttgatt ttatctcatg agcaaatcat 240
ttatccttcc agaacctcaa cttttccctt ttacaaagta gaaataaacc atctgccttt 300
acataaatca ttaatacagc cctggatggg cagattctga gctatttttg gctggggggt 360
gggaaatagc ctgtggaggt cctaaaaaga tctacggggc tcgagatggt tctctgcaag 420
gtagcaggtg ggctcagggc ccatttcagt ctttgttccc caggccattt ccacaaaatg 480
gtgagaaata gtgtcttctt ttagcttgct cataactcaa agatgggggg catggacctg 540
ggcctttcta ggctagggca tgaacctcct cc 572

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442
tcccagctgc actgcttaca cgtcttcctt cgtnttcacc taccccgagg ctgactcctt 60
ccccagntgt gcagctgccc accgcaaggg cagcagcagc aatgagcctt cctctgactc 120
gctcagctca cccacgctgc tggccctgtg agggggcagg gaaggggagg cagccggcac 180
ccacaagtgc cactgcccga gctggtgcat tacagagagg agaaacacat cttccctaga 240
gggttcctgt agacctaggg aggaccttat ctgtgcgtga aacacaccag gctgtgggcc 300
tcaaggactt gaaagcatcc atgtgtggac tcaagtcctt acctcttccg gagatgtagc 360
aaaacgcatg gagtgtgta 379

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n = A,T,C or G

<400> SEQUENCE: 443
acatgccccc aaaggctcgc ttcattgcta cgattctcta cttaaatcca cattcacagc 60
tattgcctca gaccctctgg aggaggggcc aggggttagc tggctttgaa tagcatgtag 120
agcacaggca gtgtggccac aaatgtcaca caggtgacca gggtgctata gatggtgttc 180
ctgttgactt gggcttctag tctctgctcc gtgtctgaca gtgccaagat catgctcccc 240
tgctccagca agaagctggg catagccccg tctgctggtt ccaccaggcc tgggtgtgct 300
gcagacttta caagctgaac caccccagcc atttggctac aagtcttttc taggccatca 360
agctgctctc gtaagccttc tagacatgaa tggacttgcc tggaatgact aagctgctct 420
ttcaaggcag ctgaaaggac atcnacatct ctgtctctgg tcgggggact acctgcctgt 480
gacccagagt cctgccctgg cccagcagca t 511

-continued

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 444
acaggaagaa ttctacagtt aatctatcac agtgttccag caaagcatat gttgaaaact 60
acagttttca atctaacatc taaattttaa aaagtagcat ttcagcaaca aacaagctca 120
gagaggctca tggcaaaagt gaaataacag aactattgct cagatgtctg caaagtcaag 180
ctgctgccct cagctccgcc cacttgaagg cttaggcaga cacgtaaggt ggcggtggct 240
ccttggcagc accattcaca gtggcatcat catacggagg tagcagcacc gtagtgtcat 300
tgctggtaac ataaaccagg acatcagagg agttcctacc attgatgtat cggtagcagt 360
tccaaacaca gctaatcaag taacccttaa aagtcaagat aatgctaata aacagaagaa 420
taataaggac caaacaggta ggattcactg acatgacatc atctctgtag ggaaaattag 480
gaggcagttg ccgtatgtat tcctgaatgg agtttggata aataagcaca gtgattgcaa 540
ccaacanctt cagggcaaag tcaaagatct ggtaacagaa gaatgggatg atccaggctg 600
cgcgttgctt gt 612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445
accatcctgt tccaacagag ccattgccta ttcctaaatt gaatctgact gggtgtgccc 60
ctcctcggaa cacaacagta gaccttaata gtggaaacat cgatgtgcct cccaacatga 120
caagctgggc cagctttcat aatggtgtgg ctgctggcct gaagatagct cctgcctccc 180
agatcgactc agcttggatt gtttacaata agcccaagca tgctgagttg gccaatgagt 240
atgctggctt tctcatggct ctgggtttga atgggcacct taccaagctg gcgactctca 300
atatccatga ctacttgacc aagggccatg aaatgacaag cattggactg ctacttggtg 360
tttctgctgc aaaactaggc accatggata tgtctattac tcggcttgtt agcattcgca 420
ttcctgctct cttacccca acgtccacag agttggatgt tcctcacaat gtccaagtgg 480
ctgcagtggt tggcattggc cttgtatatc aagggacagc tcacagacat actgcagaag 540
tcctgttggc tgagatagga cggcctcctg gtcctgaaat ggaatactgc actgacagag 600
agtcatactc cttagctgct ggcttggccc tgggcatggt ctncttgggg catggcagca 660
atttgatagg tatgtntgat ctcaatgtgc ctgagcagct ctatcagt 708

<210> SEQ ID NO 446
<211> LENGTH: 612
<212> TYPE: DNA
<213> ORGANISM: Homo sapiens

<400> SEQUENCE: 446

-continued

```
acaagcaacg cgcagcctgg atcatcccat tcttctgtta ccagatcttt gactttgccc     60

tgaacatgtt ggttgcaatc actgtgctta tttatccaaa ctccattcag gaatacatac    120

ggcaactgcc tcctaatttt ccctacagag atgatgtcat gtcagtgaat cctacctgtt    180

tggtccttat tattcttctg tttattagca ttatcttgac ttttaagggt tacttgatta    240

gctgtgtttg gaactgctac cgatacatca atggtaggaa ctcctctgat gtcctggttt    300

atgttaccag caatgacact acggtgctgc tacccccgta tgatgatgcc actgtgaatg    360

gtgctgccaa ggagccaccg ccaccttacg tgtctgccta agccttcaag tgggcggagc    420

tgagggcagc agcttgactt tgcagacatc tgagcaatag ttctgttatt tcacttttgc    480

catgagcctc tctgagcttg tttgttgctg aaatgctact tttaaaatt tagatgttag    540

attgaaaact gtagttttca acatatgctt tgctggaaca ctgtgataga ttaactgtag    600

aattcttcct gt                                                        612


<210> SEQ ID NO 447
<211> LENGTH: 642
<212> TYPE: DNA
<213> ORGANISM: Homo sapiens

<400> SEQUENCE: 447

actgaaagaa ttaaagtcag aagtcttccc aaaacaaaaa gaactgccca cagagaaaat     60

cctttctgat acttttcatt gctaaaataa aacaggcggg aaatgtggaa aagaaattca    120

acaaaataat gtagcaccag aagaacaagt cctagatgat tcaagttcaa aaggtaagct    180

ccagcaatgt ggaagaggta aagaccaatg tagacaagct gacgaggaat atcttctttt    240

ttggttttct ggaagtagag ttcaggaaaa gcatgaagcc agtaagccag ctgtgatatg    300

tagaaaaact tcatttgaaa tgtcatcagg ttatggggat aagccctcca taagatagtt    360

gggtctgaga tgtagttttc agagatgaga atgaatgtgc cccaaacaca ggcaaaaagg    420

tagaacgcac taagctgacc agattcatta aacttgctgt gttttgtttt ggagaagtgc    480

attcgcctgt taattttatc caacatatac tcttgaatta cggcatgaat aattatcgcc    540

actagcatgt agaagaaaac agtagccaaa tctttgatgc catagtaata aagggacact    600

gattcagtag cttgttcttc tgttgctggg agggtgacat tg                       642


<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 448

accagaagac cttagaaaaa ggaggaaagg aggagaggca gataatttgg atgaattcct     60

caaagngttt gaaaatccag aggttcctag agaggaccag caacagcagc atcagcagcg    120

tgatgttatc gatgagccca ttattgaaga gccaagccgc ctccaggagt cagtgatgga    180

ggccagcaga acaaacatag atgagtcagc tatgcctcca ccaccacctc agggagttaa    240

gcgaaaagct ggacaaattg acccagagcc tgtgatgcct cctcagcagg tagagcagat    300

ggaaatacca cctgtagagc ttcccccaga agaacctcca aatatctgtc agctaatacc    360

agagttagaa cttctgccag aaaaagagaa ggag                               394
```

-continued

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: (1)...(494)
<223> OTHER INFORMATION: n = A,T,C or G

<400> SEQUENCE: 449
acaaaaaaca caaggaatac aacccaatag aaaatagtcc tgggaatgtg gtcagaagca 60
aaggcntgag tgtctttctc aaccgtgcaa aagccgtgtt cttcccggga aaccaggaaa 120
aggatccgct actcaaaaac caagaattta aaggagtttc ttaaatttcg accttgtttc 180
tgaagctcac ttttcagtgc cattgatgtg agatgtgctg gagtggctat taaccttttt 240
ttcctaaaga ttattgttaa atagatattg tggtttgggg aagttgaatt ttttataggt 300
taaatgtcat tttagagatg gggagaggga ttatactgca ggcagcttca gccatgttgt 360
gaaactgata aaagcaactt agcaaggctt cttttcatta ttttttatgt ttcacttata 420
aagtcttagg taactagtag gatagaaaca ctgtgtcccg agagtaagga gagaagctac 480
tattgattag agcc 494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct 60
tcatgactga ggttaactta aaacaaaaat ggtaggaaag ctttcctatg cttcgggtaa 120
gagacaaatt tgcttttgta gaattggtgg ctgagaaagg cagacagggc ctgattaaag 180
aagacatttg tcaccactag ccaccaagtt aagttgtgga acccaaaggt gacggccatg 240
gaaacgtaga tcatcagctc tgctaagtag ttaggggaag aaacatattc aaaccagtct 300
ccaaatggga tcctgtggtt acagtgaatg gccactcctg ctttattttt cctgagattg 360
ccgagaataa catggcactt atactgatgg gcagatgacc agatgaacat catcatccca 420
agaatatgga accaccgtgc ttgcatcaat agatttttcc ctgttatgta ggcattcctg 480
ccatccattg gcacttggct cagcacagtt aggccaacaa ggacataata gacaagtcca 540
aaacagt 547

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451
actacttnnt ggttaaaang ccactggtag agtcatctga ntgtaaacaa tgtccctgca 60
ctgctggaaa aatccactgg ctcccaagaa aagaaaatgg tctgaagcct ctgttgtggc 120
tctcacaact catctttccc taagtcatca agctccacat cactgaggtc aatgtcatcc 180
tccacgggaa gctcgccatc cctgccgtcc caaggctctc tctcaacgat ggtagggaaa 240
gccccgcctc ctacaggtgc cgtggagcca cgcccaaaag agagctccct gagaaactcg 300

-continued

```
ttgatgcctt gctcactgaa ggagcctttt agcagagcaa atttcatctt gcgtgcattg    360

atggcggcca tggcggggta ccca                                           384


<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452

actctaaagt tgccactctc acaggggtca gtgataccca ctgaacctgg caggaacagt     60

cctgcagcca gaatctgcaa gcagcgcctg tatgcaacgt ttagggccaa aggctgtctg    120

gtggggttgt tcatcacagc ataatggcct agtaggtcaa ggatccaggg tgtgaggggc    180

tcaaagccag gaaaacgaat cctcaagtcc ttcagtagtc tgatgagaac tttaactgtg    240

gactgagaag cattttcctc gaaccagcgg gcatgtcgga tggctgctaa ngcactctgc    300

aatactttga tatccaaatg gagttctgga tccagttttc naagattggg tggcactgtt    360

gtaatganaa tcttcactgt a                                              381


<210> SEQ ID NO 453
<211> LENGTH: 455
<212> TYPE: DNA
<213> ORGANISM: Homo sapiens

<400> SEQUENCE: 453

actgtgctaa acagcctata gccaagtttt aaagagttac aggaacaact gctacacatt     60

caaagaacag gcattcactg cagcctcctg atttgacctg atgggaggga caggagaatg    120

agtcactctg ccaccacttt tcctgccttg gatttgtaga ggatttgttt tgctctaatt    180

tgtttttcct atatctgccc tactaaggta cacagtctgg gcactttgaa aatgttaaag    240

tttttaacgt ttgactgaca gaagcagcac ttaaaggctt catgaatcta ttttccaaaa    300

aaagtatgct ttcagtaaaa cattttacca ttttatctaa ctatgcactg acatttttgt    360

tcttcctgaa aaggggattt atgctaacac tgtattttta atgtaaaaat atacgtgtag    420

agatatttta acttcctgag tgacttatac ctcaa                               455


<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454

acagagcanc tttacaagtt gtcacatttc tttataaatt tttttaaagc tacagtttaa     60

tacaaaatga attgcggttt tattacatta ataacctttc acctcagggt tttatgaaga    120

ggaaagggtt ttatgcaaaa gaaagtgcta caattcctaa tcattttaga cactttagga    180

gggggtgaag ttgtatgata aagcagatat tttaattatt tgttatcttt ttgtattgca    240

agaaatttct tgctagtgaa tcaagaaaac atccagattg acagtctaaa atggctactg    300

gtattttagt taattcaaaa atgaaacttt tcagtgattc actttactaa cattctattt    360

gagaaggctt attggtaaag ttt                                            383
```

-continued

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 455
actcctttan gacaaggaaa caggtatcag catgatggta gcagaaacct tatcaccaag 60
gtgcaggagc tgacttcttc caaagagttg tggttccggg cagcggtcat tgccgtgccc 120
attgctggag ggctgatttt agtgttgctt attatgttgg ccctgaggat gcttcgaagt 180
gaaaataaga ggctgcagga tcagcggcaa cagatgctct cccgtttgca ctacagcttt 240
cacggacacc attccaaaaa ggggcaggtt gcaaagttag acttggaatg catggtgccg 300
gtcagtgggc acgagaactg ctgtctgacc tgtgataaaa tgagacaagc agacctcagc 360
aacgataaga tcctctcgct tgt 383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456
acaaacattt tacaaaaaag aacattacca atatcagtgg cagtaagggc aagctgaaga 60
atangtagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacact atttcccatc 300
taaactcatt taagccttca caatgtcgca atggattcag ttacttgcaa acgatcccgg 360
gttgtcatac agatacttgt tttttacaca taacgctgtg ccatcccttc cttcactgcc 420
ccagtcaggt ttcctgttgt tggaccgaaa ggggatacat tttagaaatg cttccctcaa 480
gacagaagtg agaaagaaag gagaccctga ggccaggatc tattaaacct ggtgtgtgcg 540
caa 543

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 457
actggtgcca atattgncat ggtgagctcc tctctaatgt cttccagggc accaatatct 60
gcccatgtca cattagggac agtgacaaag ccttcccttt tggcagaggg ttggactgag 120
gatagagcaa caatgaaatc attcagttca atgcacagtc cttgcatctg ctcctctgag 180
aggggatctt ggtctcttag caaccccagc agcctttgta attcatcctg tgtttcagaa 240

-continued

```
gtgggctcag ttcccagcct ttcctcctgg actcctttag atggcaaatc ttccatttca    300

ggatttttct tctgctgttc ctgtagcttc attaagactc tattgactgc acacattgct    360

gcctctcggc acagtgccat gagatcagca ccaacaaagc ctggagttag gtgtgctaag    420

tgacagaaat caaaagcttg aggaagcctc agttttctgc acaatgtttg aagtattctt    480

tccctggatg cttcatctgg gatacctagg catatttctc ggtcgaacct tcccgcacgt    540

ctca                                                                 544


<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

acctntaggc tcaacggcag aancttcacc acaaaagcga aatgggcaca ccacagggag     60

aaaactggtt gtcctggatg tttgaaaagt tggtcgttgt catggtgtgt tacttcatcc    120

tatctatcat taactccatg gcacaaagtt atgccaaacg aatccagcag cggttgaact    180

cagaggagaa aactaaataa gtagagaaag ttttaaactg cagaaattgg agtggatggg    240

ttctgcctta aattgggagg actccaagcc gggaaggaaa attccctttt ccaacctgta    300

tcaattttta caacttttttt cctgaaagca gtttagtcca tactttgcac tgacatactt    360

tttccttctg tgctaaggta ag                                             382


<210> SEQ ID NO 459
<211> LENGTH: 168
<212> TYPE: DNA
<213> ORGANISM: Homo sapiens

<400> SEQUENCE: 459

ctcgtactct agccaggcac gaaaccatga agtagcctga tccttcttag ccatcctggc     60

cgccttagcg gtagtaactt tgtgttatga atcacatgaa agcatggaat cttatgaact    120

taatcccttc attaacagga gaaatgcaaa taccttcata tcccctca                 168


<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: (1)...(190)
<223> OTHER INFORMATION: n = A,T,C or G

<400> SEQUENCE: 460

acanctgcta ccagggagcc gagagctgac tatcccagcc tcggctaatg tattctacgc     60

catggatgga gcttcacacg atttcctcct gcggcagcgg cgaaggtcct ctactgctac    120

acctggcgtc accagtggcc cgtctgcctc aggaactcct ccgagtgagg gaggaggggg    180

ctcctttccc                                                           190


<210> SEQ ID NO 461
<211> LENGTH: 495
<212> TYPE: DNA
<213> ORGANISM: Homo sapiens

<400> SEQUENCE: 461
```

-continued

```
acagacaggc ttctctgcta tcctccaggc agtgtaatag tcaaggaaaa gggcaacagt     60

attggatcat tccttagaca ctaatcagct ggggaaagag ttcattggca aaagtgtcct    120

cccaagaatg gtttacacca agcagagagg acatgtcact gaatggggaa agggaacccc    180

cgtatccaca gtcactgtaa gcatccagta ggcaggaaga tggctttggg cagtggctgg    240

atgaaagcag atttgagata cccagctccg gaacgaggtc atcttctaca ggttcttcct    300

tcactgagac aatgaattca gggtgatcat tctctgaggg gctgagaggt gcttcctcga    360

ttttcactac cacattagct tggctctctg tctcagaggg tatctctaag actaggggct    420

tggtatatat gtggtcaaaa cgaattagtt cattaatggc ttccagcttg gctgatgacg    480

tccccactga cagag                                                      495


<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462

acactgaaac ataaatccgc aagtcaccac acatacaaca cccggcagga aaaaaacaaa     60

aacagggngt ttacatgatc cctgtaacag ccatggtctc aaactcagat gcttcctcca    120

tctgccaagt gtgttttgga tacagagcac atcgtggctt ctggggtcac actcagctta    180

ggctgtgggt ccacagagca ctcatctggc tgggctatgg tggtggtggc tctactcaag    240

aagcaaagca gttaccagca cattcaaaca gtgtattgaa catcttttaa atatcaaagt    300

gagaaacaag aaggcaacat aataatgtta tcagaaagat gttaggaagt aaggacagct    360

gtgtaaagct tgaggctgaa aagtagcttg ccagcttcat ttctttggtt tcttgggtag    420

tgggcgccgg aacagcaaga tgtgaggttc tggttcatgg atcatataat ggacccatcc    480

ctgactctgc tga                                                        493


<210> SEQ ID NO 463
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 463

ggtccattcc tttcctcgcg tnggggtttc tctgtgtcag cgagcctcgg tacactgatt     60

tccgatcaaa agaatcatca tctttacctt gacttttcag ggaattactg aactttcttc    120

tcagaagata gggcacagcc attgccttgg cctcacttga agggtctgca tttgggtcct    180

ctggtctctt gccaagtttc ccagccactc gagggagaaa t                         221
```